(12) United States Patent
Jones et al.

(10) Patent No.: US 7,115,708 B2
(45) Date of Patent: Oct. 3, 2006

(54) β-SUPERFAMILY CONOTOXINS

(75) Inventors: Robert M. Jones, Salt Lake City, UT (US); Baldomero M. Olivera, Salt Lake City, UT (US); Maren Watkins, Salt Lake City, UT (US); James E. Garrett, Salt Lake City, UT (US)

(73) Assignees: University of Utah Research Foundation, Salt Lake City, UT (US); Cognetix, Inc., Salt Lake City, UT (US)

( * ) Notice: Subject to any disclaimer, the term of this patent is extended or adjusted under 35 U.S.C. 154(b) by 0 days.

(21) Appl. No.: 11/198,847

(22) Filed: Aug. 8, 2005

(65) Prior Publication Data

US 2005/0271589 A1     Dec. 8, 2005

Related U.S. Application Data

(63) Continuation of application No. 10/838,226, filed on May 5, 2004, now abandoned, which is a continuation of application No. 10/058,053, filed on Jan. 29, 2002, now abandoned.

(60) Provisional application No. 60/264,323, filed on Jan. 29, 2001.

(51) Int. Cl.
*C07K 4/12*     (2006.01)
*A61K 51/08*    (2006.01)

(52) U.S. Cl. .................................. 530/324; 424/1.69
(58) Field of Classification Search ................ None
See application file for complete search history.

(56) References Cited

U.S. PATENT DOCUMENTS 5,595,972 A     1/1997   Olivera et al.

FOREIGN PATENT DOCUMENTS

WO     WO 00/20444 A1     4/2000

OTHER PUBLICATIONS

McIntosh, J. Michael et al., "*Conus* Peptides as Probes for Ion Channels," Methods in Enzymology, vol. 294, pp. 605-624, 1999.

*Primary Examiner*—Robert A. Wax
(74) *Attorney, Agent, or Firm*—Rothwell Figg Ernst & Manbeck

(57) ABSTRACT

The present invention is directed to β-superfamily conotoxin peptides, derivatives or pharmaceutically acceptable salts thereof. The present invention is further directed to the use of this peptide, derivatives thereof and pharmaceutically acceptable salts thereof for the treatment of disorders associated with voltage-gated ion channels, ligand gated channels and other receptors. The invention is further directed to nucleic acid sequences encoding the β-superfamily conotoxin peptides and encoding β-superfamily conotoxin propeptides, as well as the β-superfamily conotoxin propeptides.

20 Claims, No Drawings

```
                              SEQUENCE LISTING

<160> NUMBER OF SEQ ID NOS: 340

<210> SEQ ID NO 1
<211> LENGTH: 456
<212> TYPE: DNA
<213> ORGANISM: Conus flavidus
<220> FEATURE:
<221> NAME/KEY: CDS
<222> LOCATION: (7)..(255)

<400> SEQUENCE: 1 ggatcc atg cag acg gcc tac tgg gtg atg gtg atg atg atg gtg tgg         48
       Met Gln Thr Ala Tyr Trp Val Met Val Met Met Met Val Trp
         1               5                  10 att aca gcc cct ctg tct gaa ggt ggt aaa ttg aac gac gta att cgg        96
Ile Thr Ala Pro Leu Ser Glu Gly Gly Lys Leu Asn Asp Val Ile Arg
 15              20                  25                  30 ggt ttg gtg cca gat gac tta acc cca cag ctt att ttg caa agt ctg       144
Gly Leu Val Pro Asp Asp Leu Thr Pro Gln Leu Ile Leu Gln Ser Leu
                 35                  40                  45 gat tcc cgt cgt cat gat cac ggc att cgt ccg aag aga gtc gac ata       192
Asp Ser Arg Arg His Asp His Gly Ile Arg Pro Lys Arg Val Asp Ile
             50                  55                  60 tgt aac tgg agg ata tgt gca cca aac cca ttg aga cga cat gat ctt       240
Cys Asn Trp Arg Ile Cys Ala Pro Asn Pro Leu Arg Arg His Asp Leu
 65                  70                  75 aag aaa gga aac aat tgacgtcaga caaccgccac aacttgagta cgacatcgtt       295
Lys Lys Gly Asn Asn
         80 aatacgactt cagcaaatat gaaattttca gcatcactgt ggttgtgaag aaatcagttg     355 ctttaaaagg ttggatttgt ccttgtttaa gccgttgtac tgatgacatc tctgcactat     415 gaaataaagc tgatgtgaca aactaaaaaa aaaaaaaaaa a                         456

<210> SEQ ID NO 2
<211> LENGTH: 83
<212> TYPE: PRT
<213> ORGANISM: Conus flavidus

<400> SEQUENCE: 2

Met Gln Thr Ala Tyr Trp Val Met Val Met Met Met Val Trp Ile Thr
  1               5                  10                  15

Ala Pro Leu Ser Glu Gly Gly Lys Leu Asn Asp Val Ile Arg Gly Leu
                 20                  25                  30

Val Pro Asp Asp Leu Thr Pro Gln Leu Ile Leu Gln Ser Leu Asp Ser
             35                  40                  45

Arg Arg His Asp His Gly Ile Arg Pro Lys Arg Val Asp Ile Cys Asn
         50                  55                  60

Trp Arg Ile Cys Ala Pro Asn Pro Leu Arg Arg His Asp Leu Lys Lys
 65                  70                  75                  80

Gly Asn Asn

<210> SEQ ID NO 3
<211> LENGTH: 33
```

```
<212> TYPE: PRT
<213> ORGANISM: Conus flavidus
<220> FEATURE:
<221> NAME/KEY: PEPTIDE
<222> LOCATION: (1)..(33)
<223> OTHER INFORMATION: Xaa at residues 7, 20 and 22 may be Pro or
      hydroxy-Pro; Xaa at residue 15 may be Trp (Dor L) or bromo-Trp
      (Dor L)

<400> SEQUENCE: 3

His Asp His Gly Ile Arg Xaa Lys Arg Val Asp Ile Cys Asn Xaa Arg
1               5                   10                  15

Ile Cys Ala Xaa Asn Xaa Leu Arg Arg His Asp Leu Lys Lys Gly Asn
            20                  25                  30

Asn

<210> SEQ ID NO 4
<211> LENGTH: 374
<212> TYPE: DNA
<213> ORGANISM: Conus miles
<220> FEATURE:
<221> NAME/KEY: CDS
<222> LOCATION: (7)..(315)

<400> SEQUENCE: 4 ggatcc atg cag acg gcc tac tgg gtg atg gtg atg atg atg gtg gtg          48
       Met Gln Thr Ala Tyr Trp Val Met Val Met Met Met Val Val
       1               5                   10 ggg ctc acc gtc ggg agt cac gtc cat cgg tct cac agt cct aca tcg         96
Gly Leu Thr Val Gly Ser His Val His Arg Ser His Ser Pro Thr Ser
15                  20                  25                  30 cgc agc cat ggt gat gac tcc att cat gac aag acg att cat caa cat        144
Arg Ser His Gly Asp Asp Ser Ile His Asp Lys Thr Ile His Gln His
                35                  40                  45 ctg ttt gcc cgt ctt cct ctg gag aac aac gac gac cat cgt tct gtg        192
Leu Phe Ala Arg Leu Pro Leu Glu Asn Asn Asp Asp His Arg Ser Val
            50                  55                  60 gat ctt cct gca ggg aat ggt gca ggc aac acc aag caa caa gac caa        240
Asp Leu Pro Ala Gly Asn Gly Ala Gly Asn Thr Lys Gln Gln Asp Gln
65                  70                  75 agt cct cat cat gtg tgt tgt gct att ggt ccg gtt ctt cca ttc tgt        288
Ser Pro His His Val Cys Cys Ala Ile Gly Pro Val Leu Pro Phe Cys
        80                  85                  90 tgt gtc agt tgg ctg cac aaa ctc cat tgaactggcc aatgaaaata              335
Cys Val Ser Trp Leu His Lys Leu His
95                  100 actcaggaat agacagaaag gcaaaaaaaa aaaaaaaa                               374

<210> SEQ ID NO 5
<211> LENGTH: 103
<212> TYPE: PRT
<213> ORGANISM: Conus miles

<400> SEQUENCE: 5

Met Gln Thr Ala Tyr Trp Val Met Val Met Met Met Val Val Gly Leu
1               5                   10                  15

Thr Val Gly Ser His Val His Arg Ser His Ser Pro Thr Ser Arg Ser
            20                  25                  30

His Gly Asp Asp Ser Ile His Asp Lys Thr Ile His Gln His Leu Phe
        35                  40                  45

Ala Arg Leu Pro Leu Glu Asn Asn Asp Asp His Arg Ser Val Asp Leu
    50                  55                  60
```

```
Pro Ala Gly Asn Gly Ala Gly Asn Thr Lys Gln Gln Asp Gln Ser Pro
65                  70                  75                  80

His His Val Cys Cys Ala Ile Gly Pro Val Leu Pro Phe Cys Cys Val
                85                  90                  95

Ser Trp Leu His Lys Leu His
            100

<210> SEQ ID NO 6
<211> LENGTH: 29
<212> TYPE: PRT
<213> ORGANISM: Conus miles
<220> FEATURE:
<221> NAME/KEY: PEPTIDE
<222> LOCATION: (1)..(29)
<223> OTHER INFORMATION: Xaa at residue 1 is Gln or pyro-Glu; Xaa at
      residues 6, 15 and 18 may be Pro or hydroxy-Pro; Xaa at residue 24
      may be Trp (D or L) or bromo-Trp (D or L)

<400> SEQUENCE: 6

Xaa Gln Asp Gln Ser Xaa His His Val Cys Cys Ala Ile Gly Xaa Val
1               5                   10                  15

Leu Xaa Phe Cys Cys Val Ser Xaa Leu His Lys Leu His
            20                  25

<210> SEQ ID NO 7
<211> LENGTH: 359
<212> TYPE: DNA
<213> ORGANISM: Conus miles
<220> FEATURE:
<221> NAME/KEY: CDS
<222> LOCATION: (7)..(291)

<400> SEQUENCE: 7 ggatcc atg cag acg gcc tac tgg gtg atg gtg atg atg atg gtg gtg        48
       Met Gln Thr Ala Tyr Trp Val Met Val Met Met Met Val Val
       1               5                   10 ggg ttc acc gtc ggg ggt cac gtc cat cgg tct cac agt cct aca tcg      96
Gly Phe Thr Val Gly Gly His Val His Arg Ser His Ser Pro Thr Ser
15                  20                  25                  30 cgc agc cat ggt gat gac tcc att cat gac aag acg att cat caa cat     144
Arg Ser His Gly Asp Asp Ser Ile His Asp Lys Thr Ile His Gln His
                35                  40                  45 ctg ttt gcc cgt ctt cct cag gag aac aac gac gac cat cgt tct gtg     192
Leu Phe Ala Arg Leu Pro Gln Glu Asn Asn Asp Asp His Arg Ser Val
            50                  55                  60 gat ctt cct gca ggg act agc gca ggc gac atg aaa cca caa cgc caa     240
Asp Leu Pro Ala Gly Thr Ser Ala Gly Asp Met Lys Pro Gln Arg Gln
65                  70                  75 aga cgt ctc tgc tgc atc ttt gcc ccg att ctt tgg ttc tgt tgt cac     288
Arg Arg Leu Cys Cys Ile Phe Ala Pro Ile Leu Trp Phe Cys Cys His
    80                  85                  90 ggt taacagctca aattacactg cactggccga ttgaaagaac tgcaataaac           341
Gly
95 ggaaaaaaaa aaaaaaaa                                                   359

<210> SEQ ID NO 8
<211> LENGTH: 95
<212> TYPE: PRT
<213> ORGANISM: Conus miles

<400> SEQUENCE: 8
```

```
Met Gln Thr Ala Tyr Trp Val Met Val Met Met Val Val Gly Phe
1               5                   10                  15

Thr Val Gly Gly His Val His Arg Ser His Ser Pro Thr Ser Arg Ser
            20                  25                  30

His Gly Asp Asp Ser Ile His Asp Lys Thr Ile His Gln His Leu Phe
        35                  40                  45

Ala Arg Leu Pro Gln Glu Asn Asn Asp Asp His Arg Ser Val Asp Leu
    50                  55                  60

Pro Ala Gly Thr Ser Ala Gly Asp Met Lys Pro Gln Arg Gln Arg Arg
65              70                  75                  80

Leu Cys Cys Ile Phe Ala Pro Ile Leu Trp Phe Cys Cys His Gly
                85                  90                  95
```

<210> SEQ ID NO 9
<211> LENGTH: 14
<212> TYPE: PRT
<213> ORGANISM: Conus miles
<220> FEATURE:
<221> NAME/KEY: PEPTIDE
<222> LOCATION: (1)..(14)
<223> OTHER INFORMATION: Xaa at residue 7 may be Pro or hydroxy-Pro; Xaa
      at residue 10 may be Trp (D or L) or bromo-Trp (D or L)

<400> SEQUENCE: 9

```
Leu Cys Cys Ile Phe Ala Xaa Ile Leu Xaa Phe Cys Cys His
1               5                   10
```

<210> SEQ ID NO 10
<211> LENGTH: 351
<212> TYPE: DNA
<213> ORGANISM: Conus capitaneus
<220> FEATURE:
<221> NAME/KEY: CDS
<222> LOCATION: (7)..(291)

<400> SEQUENCE: 10

```
ggatcc atg cag acg gcc tac tgg gtg atg gtg atg atg atg gtg gtg         48
       Met Gln Thr Ala Tyr Trp Val Met Val Met Met Met Val Val
       1               5                   10 ggg ttc acc gtc ggg ggt cac gtc cat cgg tct cac agt cct aca tcg        96
Gly Phe Thr Val Gly Gly His Val His Arg Ser His Ser Pro Thr Ser
15              20                  25                  30 cgc agc cat ggt gat gac tcc att cat gac gag acg att cat caa cat       144
Arg Ser His Gly Asp Asp Ser Ile His Asp Glu Thr Ile His Gln His
                35                  40                  45 ctg ttt gcc cgt ctt cct cag gag aac aac gac gac cat cgt tct gtg       192
Leu Phe Ala Arg Leu Pro Gln Glu Asn Asn Asp Asp His Arg Ser Val
        50                  55                  60 gat ctt cct gca ggg act agc gca ggc gac atg aaa cca caa cgc caa       240
Asp Leu Pro Ala Gly Thr Ser Ala Gly Asp Met Lys Pro Gln Arg Gln
    65                  70                  75 aga ggt ttc tgc tgc gac ttt ccc ccg att ttt tgg ttc tgt tgt atc       288
Arg Gly Phe Cys Cys Asp Phe Pro Pro Ile Phe Trp Phe Cys Cys Ile
        80                  85                  90 ggt taacagcaca aattacactg cactggccga ttgaaagaac tgcaataaac             341
Gly
95 ggaaaaaaaa                                                             351
```

<210> SEQ ID NO 11
<211> LENGTH: 95
<212> TYPE: PRT

```
<213> ORGANISM: Conus capitaneus

<400> SEQUENCE: 11

Met Gln Thr Ala Tyr Trp Val Met Val Met Met Val Val Gly Phe
1               5                   10                  15

Thr Val Gly Gly His Val His Arg Ser His Ser Pro Thr Ser Arg Ser
            20                  25                  30

His Gly Asp Asp Ser Ile His Asp Glu Thr Ile His Gln His Leu Phe
            35                  40                  45

Ala Arg Leu Pro Gln Glu Asn Asn Asp Asp His Arg Ser Val Asp Leu
        50                  55                  60

Pro Ala Gly Thr Ser Ala Gly Asp Met Lys Pro Gln Arg Gln Arg Gly
65              70                  75                  80

Phe Cys Cys Asp Phe Pro Pro Ile Phe Trp Cys Cys Ile Gly
                85                  90                  95

<210> SEQ ID NO 12
<211> LENGTH: 15
<212> TYPE: PRT
<213> ORGANISM: Conus capitaneus
<220> FEATURE:
<221> NAME/KEY: PEPTIDE
<222> LOCATION: (1)..(15)
<223> OTHER INFORMATION: Xaa at residues 7 and 8 may be Pro or hydroxy-
      Pro; Xaa at residue 11 may be Trp (D or L) or bromo-Trp (D or L)

<400> SEQUENCE: 12

Gly Phe Cys Cys Asp Phe Xaa Xaa Ile Phe Xaa Phe Cys Cys Ile
1               5                   10                  15

<210> SEQ ID NO 13
<211> LENGTH: 348
<212> TYPE: DNA
<213> ORGANISM: Conus generalis
<220> FEATURE:
<221> NAME/KEY: CDS
<222> LOCATION: (7)..(222)

<400> SEQUENCE: 13 ggatcc atg cag acg gcc tac tgg gta atg gtg atg atg atg gtg tgg       48
       Met Gln Thr Ala Tyr Trp Val Met Val Met Met Met Val Trp
       1               5                   10 att aaa ggc cct gtg tct gaa ggt ggt aaa ttg aac gac gta att cgg      96
Ile Lys Gly Pro Val Ser Glu Gly Gly Lys Leu Asn Asp Val Ile Arg
15              20                  25                  30 ggt ttg gtg cca gac gac ttg acc cca gtg ttt gcc ttg cat cat ccg     144
Gly Leu Val Pro Asp Asp Leu Thr Pro Val Phe Ala Leu His His Pro
                35                  40                  45 gtt tcc cat cgt cgg tct cac agc agt agt ttg tgg tgt gta tgt cca     192
Val Ser His Arg Arg Ser His Ser Ser Ser Leu Trp Cys Val Cys Pro
            50                  55                  60 ttc agg gtg tgt cca cca tgc cat gga aga tgacctggtc ccaaaccaac       242
Phe Arg Val Cys Pro Pro Cys His Gly Arg
65                  70 aaaataacgt cagacaaccg ccacaacttt agtacgacat cccttaatac gacttcagca   302
agtattttaa catcactatg gtgtgatgaa atcagttgct ttaaaa                  348

<210> SEQ ID NO 14
<211> LENGTH: 72
<212> TYPE: PRT
<213> ORGANISM: Conus generalis
```

```
<400> SEQUENCE: 14

Met Gln Thr Ala Tyr Trp Val Met Val Met Met Val Trp Ile Lys
1               5                   10                  15

Gly Pro Val Ser Glu Gly Gly Lys Leu Asn Asp Val Ile Arg Gly Leu
                20                  25                  30

Val Pro Asp Asp Leu Thr Pro Val Phe Ala Leu His His Pro Val Ser
            35                  40                  45

His Arg Arg Ser His Ser Ser Ser Leu Trp Cys Val Cys Pro Phe Arg
        50                  55                  60

Val Cys Pro Pro Cys His Gly Arg
65                  70

<210> SEQ ID NO 15
<211> LENGTH: 19
<212> TYPE: PRT
<213> ORGANISM: Conus generalis
<220> FEATURE:
<221> NAME/KEY: PEPTIDE
<222> LOCATION: (1)..(19)
<223> OTHER INFORMATION: Xaa at residue 7 may be Trp (D or L) or bromo-
      Trp (D or L); Xaa at residues 11, 16 and 17 may be Pro or hydroxy-
      Pro

<400> SEQUENCE: 15

Ser His Ser Ser Ser Leu Xaa Cys Val Cys Xaa Phe Arg Val Cys Xaa
1               5                   10                  15

Xaa Cys His

<210> SEQ ID NO 16
<211> LENGTH: 405
<212> TYPE: DNA
<213> ORGANISM: Conus wittigi
<220> FEATURE:
<221> NAME/KEY: CDS
<222> LOCATION: (1)..(210)
<220> FEATURE:
<221> NAME/KEY: misc_feature
<222> LOCATION: (1)..(405)
<223> OTHER INFORMATION: n may be any base

<400> SEQUENCE: 16 atg atg ttg gtg tgg att aca gcc cct ctg cct gaa ggt ggt aaa ctg      48
Met Met Leu Val Trp Ile Thr Ala Pro Leu Pro Glu Gly Gly Lys Leu
1               5                   10                  15 aag cac gta att cgg ggt ttg gtg cca gac gac tta acc cca cag ctt      96
Lys His Val Ile Arg Gly Leu Val Pro Asp Asp Leu Thr Pro Gln Leu
                20                  25                  30 atc ttg cga agt ctg att tcc cgt cgt agt tct gac ggc agt gat ccg     144
Ile Leu Arg Ser Leu Ile Ser Arg Arg Ser Ser Asp Gly Ser Asp Pro
            35                  40                  45 aag gca aaa aaa cag tgt atg tgg aag aga tgt ata cca gac caa tcg     192
Lys Ala Lys Lys Gln Cys Met Trp Lys Arg Cys Ile Pro Asp Gln Ser
        50                  55                  60 aga cta gaa gaa gat gaa tgatgtcaga caaccgccat cactgtagta            240
Arg Leu Glu Glu Asp Glu
65                  70 tgacatcgtt aatacgactt aagcaaatat tttaacatca ctgtggttct gaagacatca   300
gttgctttaa aagattggat tcttccttgt ttaagagttg tactganatc attcctgccc   360
tgtgaaataa agctgatgtt gacanncaaa caaaaaaaaa aaaaa                   405

<210> SEQ ID NO 17
```

```
<211> LENGTH: 70
<212> TYPE: PRT
<213> ORGANISM: Conus wittigi
<220> FEATURE:
<221> NAME/KEY: misc_feature
<222> LOCATION: (1)..(405)
<223> OTHER INFORMATION: n may be any base

<400> SEQUENCE: 17

Met Met Leu Val Trp Ile Thr Ala Pro Leu Pro Glu Gly Gly Lys Leu
1               5                   10                  15

Lys His Val Ile Arg Gly Leu Val Pro Asp Asp Leu Thr Pro Gln Leu
            20                  25                  30

Ile Leu Arg Ser Leu Ile Ser Arg Ser Ser Asp Gly Ser Asp Pro
        35                  40                  45

Lys Ala Lys Lys Gln Cys Met Trp Lys Arg Cys Ile Pro Asp Gln Ser
    50                  55                  60

Arg Leu Glu Glu Asp Glu
65                  70

<210> SEQ ID NO 18
<211> LENGTH: 29
<212> TYPE: PRT
<213> ORGANISM: Conus wittigi
<220> FEATURE:
<221> NAME/KEY: PEPTIDE
<222> LOCATION: (1)..(29)
<223> OTHER INFORMATION: Xaa at residues 7 and 20 may be Pro or hydroxy-
      Pro; Xaa at residue 15 may be Trp (D or L) or bromo-Trp (D or L);
      Xaa at residues 26, 27 and 29 may be Glu or Gla

<400> SEQUENCE: 18

Ser Ser Asp Gly Ser Asp Xaa Lys Ala Lys Lys Gln Cys Met Xaa Lys
1               5                   10                  15

Arg Cys Ile Xaa Asp Gln Ser Arg Leu Xaa Xaa Asp Xaa
            20                  25

<210> SEQ ID NO 19
<211> LENGTH: 463
<212> TYPE: DNA
<213> ORGANISM: Conus consors
<220> FEATURE:
<221> NAME/KEY: CDS
<222> LOCATION: (7)..(222)

<400> SEQUENCE: 19 ggatcc atg cag acg gcc tac tgg gtg atg gtg atg atg atg gtg tgg        48
       Met Gln Thr Ala Tyr Trp Val Met Val Met Met Met Val Trp
       1               5                   10 att aca gcc cct ctg tct gaa ggt ggt aaa ttg aac gac gta att cgg      96
Ile Thr Ala Pro Leu Ser Glu Gly Gly Lys Leu Asn Asp Val Ile Arg
15                  20                  25                  30 ggt ttg gtg tca cac atc tta atc cca cag cat acc ttg cga agt ctg     144
Gly Leu Val Ser His Ile Leu Ile Pro Gln His Thr Leu Arg Ser Leu
                35                  40                  45 act tcc cgt gat cgt tct gac aac ggt ggt tcg agt gga gca caa ata     192
Thr Ser Arg Asp Arg Ser Asp Asn Gly Gly Ser Ser Gly Ala Gln Ile
        50                  55                  60 tgc atc tgg aag gta tgt cca cca tcc cca tagagacgac cacgaggaaa       242
Cys Ile Trp Lys Val Cys Pro Pro Ser Pro
65                  70 aagatgaacg gcgtcagaca accgccacaa ctgtagtacg acatcgttga tacgacttca   302
gcaactattt taacatcact gtggttgtga agaaatcagt cgctttaaaa gattggattt   362
```

```
ttccttgttt aagagttgta ctgatatcag ctctgcacta tgaaataaag ctgatgtgac      422
ataaaaaaaa aaaaaaaaag tactctgcgt tgttactcga g                          463
```

<210> SEQ ID NO 20
<211> LENGTH: 72
<212> TYPE: PRT
<213> ORGANISM: Conus consors

<400> SEQUENCE: 20

```
Met Gln Thr Ala Tyr Trp Val Met Val Met Met Val Trp Ile Thr
1               5                   10                  15

Ala Pro Leu Ser Glu Gly Gly Lys Leu Asn Asp Val Ile Arg Gly Leu
            20                  25                  30

Val Ser His Ile Leu Ile Pro Gln His Thr Leu Arg Ser Leu Thr Ser
        35                  40                  45

Arg Asp Arg Ser Asp Asn Gly Gly Ser Gly Ala Gln Ile Cys Ile
    50                  55                  60

Trp Lys Val Cys Pro Pro Ser Pro
65                  70
```

<210> SEQ ID NO 21
<211> LENGTH: 23
<212> TYPE: PRT
<213> ORGANISM: Conus consors
<220> FEATURE:
<221> NAME/KEY: PEPTIDE
<222> LOCATION: (1)..(23)
<223> OTHER INFORMATION: Xaa at residue 16 may be Trp (D or L) or bromo-Trp (D or L); Xaa at residues 20, 21 and 23 may be Pro or hydroxy-Pro

<400> SEQUENCE: 21

```
Asp Arg Ser Asp Asn Gly Gly Ser Ser Gly Ala Gln Ile Cys Ile Xaa
1               5                   10                  15

Lys Val Cys Xaa Xaa Ser Xaa
            20
```

<210> SEQ ID NO 22
<211> LENGTH: 470
<212> TYPE: DNA
<213> ORGANISM: Conus consors
<220> FEATURE:
<221> NAME/KEY: CDS
<222> LOCATION: (7)..(246)

<400> SEQUENCE: 22

```
ggatcc atg cag acg gcc tac tgg gtg atg gtg atg atg atg gtg tgg        48
       Met Gln Thr Ala Tyr Trp Val Met Val Met Met Met Val Trp
       1               5                   10 att aca gcc cct ctg tct gaa ggt ggt aaa ttg aac gac gca att cgg       96
Ile Thr Ala Pro Leu Ser Glu Gly Gly Lys Leu Asn Asp Ala Ile Arg
15                  20                  25                  30 ggt ttg gtg tca cac atc tta atc cca cag cat acc ttg cga agt ctg      144
Gly Leu Val Ser His Ile Leu Ile Pro Gln His Thr Leu Arg Ser Leu
            35                  40                  45 act tcc cgt gct cgt tct gac aac ggt ggt tcg agt gga gca caa ata      192
Thr Ser Arg Ala Arg Ser Asp Asn Gly Gly Ser Ser Gly Ala Gln Ile
            50                  55                  60 tgc atc tgg aag gta tgt cca cca tcc cca tgg aga cga cca caa gga      240
Cys Ile Trp Lys Val Cys Pro Pro Ser Pro Trp Arg Arg Pro Gln Gly
65                  70                  75
```

-continued

```
aaa aga tgaatgacgt cagacaaccg ccacaactgt agtacgacat cgttgatacg      296
Lys Arg
    80 acttcagcaa atattttaac atcactgtgg ttgtgaagaa atcagttgct ttaaaagatt   356 ggatttttcc ttgtttaaga gttgtactga tatcagctct gcactatgaa ataaagctga   416 tgtgacaaac aataaaaaag aaaaaaaaaa aagtactctg cgttgttact cgag          470
```

<210> SEQ ID NO 23
<211> LENGTH: 80
<212> TYPE: PRT
<213> ORGANISM: Conus consors

<400> SEQUENCE: 23

```
Met Gln Thr Ala Tyr Trp Val Met Val Met Met Val Trp Ile Thr
1               5                   10                  15

Ala Pro Leu Ser Glu Gly Gly Lys Leu Asn Asp Ala Ile Arg Gly Leu
            20                  25                  30

Val Ser His Ile Leu Ile Pro Gln His Thr Leu Arg Ser Leu Thr Ser
        35                  40                  45

Arg Ala Arg Ser Asp Asn Gly Gly Ser Ser Gly Ala Gln Ile Cys Ile
    50                  55                  60

Trp Lys Val Cys Pro Pro Ser Pro Trp Arg Arg Pro Gln Gly Lys Arg
65                  70                  75                  80
```

<210> SEQ ID NO 24
<211> LENGTH: 28
<212> TYPE: PRT
<213> ORGANISM: Conus consors
<220> FEATURE:
<221> NAME/KEY: PEPTIDE
<222> LOCATION: (1)..(28)
<223> OTHER INFORMATION: Xaa at residues 16 and 24 may be Trp (D or L)
      or bromo-Trp (D or L); Xaa at residues 20, 21, 23 and 27 may be
      Pro or hydroxy-Pro

<400> SEQUENCE: 24

```
Ala Arg Ser Asp Asn Gly Gly Ser Ser Gly Ala Gln Ile Cys Ile Xaa
1               5                   10                  15

Lys Val Cys Xaa Xaa Ser Xaa Xaa Arg Arg Xaa Gln
            20                  25
```

<210> SEQ ID NO 25
<211> LENGTH: 469
<212> TYPE: DNA
<213> ORGANISM: Conus consors
<220> FEATURE:
<221> NAME/KEY: CDS
<222> LOCATION: (7)..(228)

<400> SEQUENCE: 25

```
ggatcc atg cag acg gcc tac tgg gtg atg gtg atg atg atg gtg tgg     48
       Met Gln Thr Ala Tyr Trp Val Met Val Met Met Met Val Trp
       1               5                   10 att aca gcc cct ctg tct gaa ggt ggt aaa ttg aac gac gta att cgg    96
Ile Thr Ala Pro Leu Ser Glu Gly Gly Lys Leu Asn Asp Val Ile Arg
15                  20                  25                  30 ggt ttg gtg cca cac ttc tta acc cca cag cat atc ttg caa agt ctg    144
Gly Leu Val Pro His Phe Leu Thr Pro Gln His Ile Leu Gln Ser Leu
                35                  40                  45 act tcc cgt aat ggt tct ggc agc agt aat cag aaa gaa gca caa cta    192
Thr Ser Arg Asn Gly Ser Gly Ser Ser Asn Gln Lys Glu Ala Gln Leu
            50                  55                  60
```

```
tgc atc tgg aag gta tgt cca cca tcc cca tgg aga tgaccacaag         238
Cys Ile Trp Lys Val Cys Pro Pro Ser Pro Trp Arg
         65                  70 gaaaaagatg aacggcgtca gacaaccgcc acaactgtag tgggacatcg ttgatacgac  298
ttcagcaaat attttaacat cactgtggtt gtgaagaaat cagttgcttt aaaagattgg  358 attttttcctt gtttaagaat tgtactgata tcagctctgc actatgaaat aaagctgatg 418 tgacaaccca aaaaaaaaaa aaaaaaaaag tactctgcgt tgttactcga g           469
```

<210> SEQ ID NO 26
<211> LENGTH: 74
<212> TYPE: PRT
<213> ORGANISM: Conus consors

<400> SEQUENCE: 26

```
Met Gln Thr Ala Tyr Trp Val Met Val Met Met Val Trp Ile Thr
1               5                   10                  15

Ala Pro Leu Ser Glu Gly Gly Lys Leu Asn Asp Val Ile Arg Gly Leu
            20                  25                  30

Val Pro His Phe Leu Thr Pro Gln His Ile Leu Gln Ser Leu Thr Ser
        35                  40                  45

Arg Asn Gly Ser Gly Ser Ser Asn Gln Lys Glu Ala Gln Leu Cys Ile
    50                  55                  60

Trp Lys Val Cys Pro Pro Ser Pro Trp Arg
65                  70
```

<210> SEQ ID NO 27
<211> LENGTH: 25
<212> TYPE: PRT
<213> ORGANISM: Conus consors
<220> FEATURE:
<221> NAME/KEY: PEPTIDE
<222> LOCATION: (1)..(25)
<223> OTHER INFORMATION: Xaa at residue 10 may be Glu or Gla;  Xaa at
      residues 16 and 24 may be Trp (D or L) or bromo-Trp (D or L); Xaa
      at residues 20, 21 and 23 may be Pro or hydroxy-Pro

<400> SEQUENCE: 27

```
Asn Gly Ser Gly Ser Ser Asn Gln Lys Xaa Ala Gln Leu Cys Ile Xaa
1               5                   10                  15

Lys Val Cys Xaa Xaa Ser Xaa Xaa Arg
            20                  25
```

<210> SEQ ID NO 28
<211> LENGTH: 472
<212> TYPE: DNA
<213> ORGANISM: Conus tulipa
<220> FEATURE:
<221> NAME/KEY: CDS
<222> LOCATION: (7)..(231)
<220> FEATURE:
<221> NAME/KEY: misc_feature
<222> LOCATION: (1)..(472)
<223> OTHER INFORMATION: n may be any base

<400> SEQUENCE: 28

```
ggatcc atg cag acg gcc tac tgg gtg atg ctg atg atg atg gtg tgg    48
       Met Gln Thr Ala Tyr Trp Val Met Leu Met Met Met Val Trp
       1               5                   10 att aca gcc cct ctg tct gaa ggt ggt aaa ctg aac gac gta att cgg   96
Ile Thr Ala Pro Leu Ser Glu Gly Gly Lys Leu Asn Asp Val Ile Arg
15                  20                  25                  30
```

```
ggt ttg gtg cca cac gtc tta acc cca cag cat atc ttg caa agt ctg      144
Gly Leu Val Pro His Val Leu Thr Pro Gln His Ile Leu Gln Ser Leu
            35                  40                  45 gtt tcc cgt cgt cat ttt aac agc gtt gtt ccg acg gta tac ata tgc      192
Val Ser Arg Arg His Phe Asn Ser Val Val Pro Thr Val Tyr Ile Cys
        50                  55                  60 atg tgg aag gta tgt cca cca tcg cca tag aga cga cca taaggaaaaa       241
Met Trp Lys Val Cys Pro Pro Ser Pro     Arg Arg Pro
        65                  70 gatgaatgac gtcagacaac cgccacaact gtagtacgac atcgttaata cgacttcagc    301
aaatatttta acatcactgt ggttgtgaag aaatcagttg ctttaaaaga ttggattttt    361
ccttgtttca gagttgtact gatatcagct ctgcactatc aaataaagct gaagtgacaa    421
accnnaaaaa aaaaaaaaaa aaaaaaaaag tactctgcgt tgttactcga g             472
```

<210> SEQ ID NO 29
<211> LENGTH: 71
<212> TYPE: PRT
<213> ORGANISM: Conus tulipa
<220> FEATURE:
<221> NAME/KEY: misc_feature
<222> LOCATION: (1)..(472)
<223> OTHER INFORMATION: n may be any base

<400> SEQUENCE: 29

```
Met Gln Thr Ala Tyr Trp Val Met Leu Met Met Val Trp Ile Thr
1               5                   10                  15

Ala Pro Leu Ser Glu Gly Gly Lys Leu Asn Asp Val Ile Arg Gly Leu
            20                  25                  30

Val Pro His Val Leu Thr Pro Gln His Ile Leu Gln Ser Leu Val Ser
        35                  40                  45

Arg Arg His Phe Asn Ser Val Val Pro Thr Val Tyr Ile Cys Met Trp
    50                  55                  60

Lys Val Cys Pro Pro Ser Pro
65                  70
```

<210> SEQ ID NO 30
<211> LENGTH: 21
<212> TYPE: PRT
<213> ORGANISM: Conus tulipa
<220> FEATURE:
<221> NAME/KEY: PEPTIDE
<222> LOCATION: (1)..(21)
<223> OTHER INFORMATION: Xaa at residues 7, 18, 19 and 21 may be Pro or
      hydroxy-Pro; Xaa at residue 10 may be Tyr, 125I-Tyr, mono-iodo-
      Tyr, di-iodo-Tyr, O-sulpho-Tyr or O-phospho-Tyr; Xaa at residue 14
      may be Trp or bromo-Trp

<400> SEQUENCE: 30

```
His Phe Asn Ser Val Val Xaa Thr Val Xaa Ile Cys Met Xaa Lys Val
1               5                   10                  15

Cys Xaa Xaa Ser Xaa
            20
```

<210> SEQ ID NO 31
<211> LENGTH: 451
<212> TYPE: DNA
<213> ORGANISM: Conus tulipa
<220> FEATURE:
<221> NAME/KEY: CDS
<222> LOCATION: (1)..(279)

<400> SEQUENCE: 31

```
atg cag acg gcc tac tgg gtg atg ctg ttg atg atg gtg ggc att aca    48
Met Gln Thr Ala Tyr Trp Val Met Leu Leu Met Met Val Gly Ile Thr
1               5                   10                  15 gcc cct ctg cct gaa ggt ggt aaa ccg aac agc gta att cgg ggt ttg    96
Ala Pro Leu Pro Glu Gly Gly Lys Pro Asn Ser Val Ile Arg Gly Leu
            20                  25                  30 gtg cca aac gac tta act cca cag cat acc ttg cga agt ctg att tcc   144
Val Pro Asn Asp Leu Thr Pro Gln His Thr Leu Arg Ser Leu Ile Ser
        35                  40                  45 cgt cgt caa act gac gtt ctt ctg gag gct acc ctt ttg aca aca cca   192
Arg Arg Gln Thr Asp Val Leu Leu Glu Ala Thr Leu Leu Thr Thr Pro
50                  55                  60 gcc ccc gag cag aga ttg ttc tgc ttc tgg aag tca tgt tgg cca agg   240
Ala Pro Glu Gln Arg Leu Phe Cys Phe Trp Lys Ser Cys Trp Pro Arg
65              70                  75                  80 ccc tac cct tgg aga cga cgt gat ctt aat gga aaa cga tgaatgacgt   289
Pro Tyr Pro Trp Arg Arg Arg Asp Leu Asn Gly Lys Arg
                85                  90 cagacaaccg ccacaactgt agtacgacat cattaatacg acttcagcaa atattttaac   349
attactgtgg ttgtgaagaa atcacttgct ttaaaagatt ggttttttcc ttgtttcaga   409
gttgtactga tatcagctct gccctatgaa ataaagctga tg                     451
```

<210> SEQ ID NO 32
<211> LENGTH: 93
<212> TYPE: PRT
<213> ORGANISM: Conus tulipa

<400> SEQUENCE: 32

Met Gln Thr Ala Tyr Trp Val Met Leu Leu Met Met Val Gly Ile Thr
1               5                   10                  15

Ala Pro Leu Pro Glu Gly Gly Lys Pro Asn Ser Val Ile Arg Gly Leu
            20                  25                  30

Val Pro Asn Asp Leu Thr Pro Gln His Thr Leu Arg Ser Leu Ile Ser
        35                  40                  45

Arg Arg Gln Thr Asp Val Leu Leu Glu Ala Thr Leu Leu Thr Thr Pro
50                  55                  60

Ala Pro Glu Gln Arg Leu Phe Cys Phe Trp Lys Ser Cys Trp Pro Arg
65              70                  75                  80

Pro Tyr Pro Trp Arg Arg Arg Asp Leu Asn Gly Lys Arg
                85                  90

<210> SEQ ID NO 33
<211> LENGTH: 40
<212> TYPE: PRT
<213> ORGANISM: Conus tulipa
<220> FEATURE:
<221> NAME/KEY: PEPTIDE
<222> LOCATION: (1)..(40)
<223> OTHER INFORMATION: Xaa at residue 1 is Gln or pyro-Glu; Xaa at
      residue 7 and 17 may be Glu or Gla; Xaa at residue 14, 16, 29, 31
      and 33 may be Pro or hydroxy-Pro; Xaa at residues 24, 28 and 34
      may be Trp (D or L) or bromo-Trp (D or L)
<220> FEATURE:
<221> NAME/KEY: PEPTIDE
<222> LOCATION: (1)..(40)
<223> OTHER INFORMATION: Xaa at residue 32 may be Tyr, 125I-Tyr, mono-
      iodo-Tyr, di-iodo-Tyr, O-sulpho-Tyr or O-phospho-Tyr

<400> SEQUENCE: 33

Xaa Thr Asp Val Leu Leu Xaa Ala Thr Leu Leu Thr Thr Xaa Ala Xaa
1               5                   10                  15

```
        Xaa Gln Arg Leu Phe Cys Phe Xaa Lys Ser Cys Xaa Xaa Arg Xaa Xaa
                 20                  25                  30

Xaa Xaa Arg Arg Arg Asp Leu Asn
                 35                  40

<210> SEQ ID NO 34
<211> LENGTH: 414
<212> TYPE: DNA
<213> ORGANISM: Conus sulcatus
<220> FEATURE:
<221> NAME/KEY: CDS
<222> LOCATION: (1)..(285)

<400> SEQUENCE: 34 atg cag acg gcc tac tgg gtg atg gtg atg atg atg gtg tgg att aca        48
Met Gln Thr Ala Tyr Trp Val Met Val Met Met Met Val Trp Ile Thr
1               5                  10                  15 gcc cct ctg tct gaa ggt ggt aaa ccg aac gac gta att cgg ggt ttg        96
Ala Pro Leu Ser Glu Gly Gly Lys Pro Asn Asp Val Ile Arg Gly Leu
            20                  25                  30 gtg cca gac gac tta acc cca cag cgt gtc ttg cga agt ctg att tcc       144
Val Pro Asp Asp Leu Thr Pro Gln Arg Val Leu Arg Ser Leu Ile Ser
        35                  40                  45 cgt cgt caa tct ggc tgc aga gtc ccg ttt gaa ttg aaa tgc atc tgg       192
Arg Arg Gln Ser Gly Cys Arg Val Pro Phe Glu Leu Lys Cys Ile Trp
    50                  55                  60 aag ttc tgt aca ata tac cca tcg aga cca ttt gct tct ctg gaa gaa       240
Lys Phe Cys Thr Ile Tyr Pro Ser Arg Pro Phe Ala Ser Leu Glu Glu
65                  70                  75                  80 aaa gac gaa tgt cag aca gtc acc ata act gta aca tgg gat ttt           285
Lys Asp Glu Cys Gln Thr Val Thr Ile Thr Val Thr Trp Asp Phe
                85                  90                  95 taatacgtct ccagcaagta ttttaacatc actgtggttg tgaagaaatc agttgcttta     345
aaagattgga ttttttccttg tttaagagtt gtactgatat cagctctgcc ctgtgaaata    405
aagctgatg                                                             414

<210> SEQ ID NO 35
<211> LENGTH: 95
<212> TYPE: PRT
<213> ORGANISM: Conus sulcatus

<400> SEQUENCE: 35

Met Gln Thr Ala Tyr Trp Val Met Val Met Met Met Val Trp Ile Thr
1               5                  10                  15

Ala Pro Leu Ser Glu Gly Gly Lys Pro Asn Asp Val Ile Arg Gly Leu
            20                  25                  30

Val Pro Asp Asp Leu Thr Pro Gln Arg Val Leu Arg Ser Leu Ile Ser
        35                  40                  45

Arg Arg Gln Ser Gly Cys Arg Val Pro Phe Glu Leu Lys Cys Ile Trp
    50                  55                  60

Lys Phe Cys Thr Ile Tyr Pro Ser Arg Pro Phe Ala Ser Leu Glu Glu
65                  70                  75                  80

Lys Asp Glu Cys Gln Thr Val Thr Ile Thr Val Thr Trp Asp Phe
                85                  90                  95

<210> SEQ ID NO 36
<211> LENGTH: 45
<212> TYPE: PRT
<213> ORGANISM: Conus sulcatus
<220> FEATURE:
```

```
<221> NAME/KEY: PEPTIDE
<222> LOCATION: (1)..(45)
<223> OTHER INFORMATION: Xaa at residue 1 is Gln or pyro-Glu; Xaa at
      residues 7, 21 and 24 may be Pro or hydroxy-Pro; Xaa at residues
      9, 29, 30 and 33 may be Glu or Gla; Xaa at residues 14 and 43 may
      be Trp (D or L) or bromo-Trp (D or L)
<220> FEATURE:
<221> NAME/KEY: PEPTIDE
<222> LOCATION: (1)..(45)
<223> OTHER INFORMATION: Xaa at residue 20 may be Tyr, 125I-Tyr, mono-
      iodo-Tyr, di-iodo-Tyr, O-sulpho-Tyr or O-phospho-Tyr

<400> SEQUENCE: 36

Xaa Ser Gly Cys Arg Val Xaa Phe Xaa Leu Lys Cys Ile Xaa Lys Phe
1               5                  10                  15

Cys Thr Ile Xaa Xaa Ser Arg Ser Phe Ala Ser Leu Xaa Xaa Lys Asp
            20                  25                  30

Xaa Cys Gln Thr Val Thr Ile Thr Val Thr Xaa Asp Phe
            35                  40                  45

<210> SEQ ID NO 37
<211> LENGTH: 413
<212> TYPE: DNA
<213> ORGANISM: Conus sulcatus
<220> FEATURE:
<221> NAME/KEY: CDS
<222> LOCATION: (1)..(234)

<400> SEQUENCE: 37 atg cag acg gcc tac tgg gtg atg gtg atg atg atg gtg tgg att aca      48
Met Gln Thr Ala Tyr Trp Val Met Val Met Met Met Val Trp Ile Thr
1               5                   10                  15 gcc tct ctg tct gaa ggt ggt aaa ccg aac gac gtc att cgg ggt ttt      96
Ala Ser Leu Ser Glu Gly Gly Lys Pro Asn Asp Val Ile Arg Gly Phe
                20                  25                  30 gtg cca gac gac tta acc cca cag ctt atc ttg cga agt ctg att tcc     144
Val Pro Asp Asp Leu Thr Pro Gln Leu Ile Leu Arg Ser Leu Ile Ser
            35                  40                  45 cgt cgt cgt tct gac aag gat gtt ggg aag aga atg gaa tgt tac tgg     192
Arg Arg Arg Ser Asp Lys Asp Val Gly Lys Arg Met Glu Cys Tyr Trp
50                  55                  60 aag gca tgt aga ccc acg cta tcg aga cga cat gat ctt ggg             234
Lys Ala Cys Arg Pro Thr Leu Ser Arg Arg His Asp Leu Gly
65                  70                  75 taaaagatga atgacgtcag acaacagcca caactatagt atgacatcgt taatacgact   294
tcagcaaata ttttaacatc actgtggttg tgaagaaatc agttgcttta aaagattgga   354
tttttccgtg tttaagagtt gtactgatat cagctctgcc ctgtgaaata agctgatg     413

<210> SEQ ID NO 38
<211> LENGTH: 78
<212> TYPE: PRT
<213> ORGANISM: Conus sulcatus

<400> SEQUENCE: 38

Met Gln Thr Ala Tyr Trp Val Met Val Met Met Met Val Trp Ile Thr
1               5                   10                  15

Ala Ser Leu Ser Glu Gly Gly Lys Pro Asn Asp Val Ile Arg Gly Phe
                20                  25                  30

Val Pro Asp Asp Leu Thr Pro Gln Leu Ile Leu Arg Ser Le

```
Lys Ala Cys Arg Pro Thr Leu Ser Arg Arg His Asp Leu Gly
 65                  70                  75
```

```
<210> SEQ ID NO 39
<211> LENGTH: 27
<212> TYPE: PRT
<213> ORGANISM: Conus sulcatus
<220> FEATURE:
<221> NAME/KEY: PEPTIDE
<222> LOCATION: (1)..(27)
<223> OTHER INFORMATION: Xaa at residue 11 may be Glu or Gla; Xaa at
      residue 13 may be Pro or hydroxy-Pro; Xaa at residue 14 may be Trp
      (D or L) or bromo-Trp (D or L); Xaa at residue 19 may be Tyr,
      125I-Tyr, mono-iodo-Tyr, di-iodo-Tyr, O-sulpho-Tyr or O-phospho-
      Tyr

<400> SEQUENCE: 39

Arg Ser Asp Lys Asp Val Gly Lys Arg Met Xaa Cys Xaa Xaa Lys Ala
 1               5                   10                  15

Cys Arg Xaa Thr Leu Ser Arg Arg His Asp Leu
             20                  25
```

```
<210> SEQ ID NO 40
<211> LENGTH: 451
<212> TYPE: DNA
<213> ORGANISM: Conus magus
<220> FEATURE:
<221> NAME/KEY: CDS
<222> LOCATION: (1)..(279)

<400> SEQUENCE: 40
```

| | | | | | | | | | | | | | | | | |
|---|---|---|---|---|---|---|---|---|---|---|---|---|---|---|---|---|
| atg | cag | acg | gcc | tac | tgg | gtg | atg | ctg | atg | atg | atg | gtg | tgc | atc | aca | 48 |
| Met | Gln | Thr | Ala | Tyr | Trp | Val | Met | Leu | Met | Met | Met | Val | Cys | Ile | Thr | |
| 1 | | | | 5 | | | | | 10 | | | | | 15 | | |
| gcc | cct | ctg | cct | gaa | ggt | ggt | aaa | ccg | aac | agc | gga | att | cgg | ggt | ttg | 96 |
| Ala | Pro | Leu | Pro | Glu | Gly | Gly | Lys | Pro | Asn | Ser | Gly | Ile | Arg | Gly | Leu | |
| | | | 20 | | | | | 25 | | | | | 30 | | | |
| gtg | cca | aac | gac | tta | act | cca | cag | cat | acc | ttg | cga | agt | ctg | att | tcc | 144 |
| Val | Pro | Asn | Asp | Leu | Thr | Pro | Gln | His | Thr | Leu | Arg | Ser | Leu | Ile | Ser | |
| | | 35 | | | | | 40 | | | | | 45 | | | | |
| cgt | cgt | caa | act | gac | gtt | ctt | ctg | gat | gct | acc | ctt | ttg | aca | aca | cca | 192 |
| Arg | Arg | Gln | Thr | Asp | Val | Leu | Leu | Asp | Ala | Thr | Leu | Leu | Thr | Thr | Pro | |
| 50 | | | | | 55 | | | | | 60 | | | | | | |
| gcc | ccc | gag | cag | aga | ttg | ttc | tgc | ttc | tgg | aag | tca | tgt | tgg | cca | agg | 240 |
| Ala | Pro | Glu | Gln | Arg | Leu | Phe | Cys | Phe | Trp | Lys | Ser | Cys | Trp | Pro | Arg | |
| 65 | | | | 70 | | | | | 75 | | | | | 80 | | |
| ccc | tac | cct | tgg | aga | cga | cgt | aat | ctt | aat | gga | aaa | cga | tgaatgacgt | | | 289 |
| Pro | Tyr | Pro | Trp | Arg | Arg | Arg | Asn | Leu | Asn | Gly | Lys | Arg | | | | |
| | | | | 85 | | | | | 90 | | | | | | | |

```
cagacaaccg ccacaactgt agtacgacat cgttaatacg acttcagcaa atattttaac      349
ataactgtgg ttgtgaagaa atcggttgct ttaaaagatt ggattttttcc ttgtttcaga     409 gttgtactga tatgagctct gccctgtgaa ataaagctga tg                         451
```

```
<210> SEQ ID NO 41
<211> LENGTH: 93
<212> TYPE: PRT
<213> ORGANISM: Conus magus

<400> SEQUENCE: 41

Met Gln Thr Ala Tyr Trp Val Met Leu Met Met Met Val Cys Ile Thr
 1               5                   10                  15

Ala Pro Leu Pro Glu Gly Gly Lys Pro Asn Ser Gly Ile Arg Gly Leu
```

```
                20              25              30
Val Pro Asn Asp Leu Thr Pro Gln His Thr Leu Arg Ser Leu Ile Ser
            35              40              45

Arg Arg Gln Thr Asp Val Leu Leu Asp Ala Thr Leu Leu Thr Thr Pro
        50              55              60

Ala Pro Glu Gln Arg Leu Phe Cys Phe Trp Lys Ser Cys Trp Pro Arg
65              70              75              80

Pro Tyr Pro Trp Arg Arg Asn Leu Asn Gly Lys Arg
                85              90

<210> SEQ ID NO 42
<211> LENGTH: 40
<212> TYPE: PRT
<213> ORGANISM: Conus magus
<220> FEATURE:
<221> NAME/KEY: PEPTIDE
<222> LOCATION: (1)..(40)
<223> OTHER INFORMATION: Xaa at residue 1 is Gln or pyro-Glu; Xaa at
      residues 14, 16, 29, 31 and 33 may be Pro or hydroxy-Pro; Xaa at
      residue 17 may be Glu or Gla; Xaa at residues 24, 28 and 34 may be
      Trp (D or L) or bromo-Trp (D or L)
<220> FEATURE:
<221> NAME/KEY: PEPTIDE
<222> LOCATION: (1)..(40)
<223> OTHER INFORMATION: Xaa at residue 32 may be Tyr, 125I-Tyr, mono-
      iodo-Tyr, di-iodo-Tyr, O-sulpho-Tyr or O-phospho-Tyr

<400> SEQUENCE: 42

Xaa Thr Asp Val Leu Leu Asp Ala Thr Leu Leu Thr Thr Xaa Ala Xaa
1               5               10              15

Xaa Gln Arg Leu Phe Cys Phe Xaa Lys Ser Cys Xaa Xaa Arg Xaa Xaa
            20              25              30

Xaa Xaa Arg Arg Arg Asn Leu Asn
            35              40

<210> SEQ ID NO 43
<211> LENGTH: 423
<212> TYPE: DNA
<213> ORGANISM: Conus emaciatus
<220> FEATURE:
<221> NAME/KEY: CDS
<222> LOCATION: (1)..(249)

<400> SEQUENCE: 43 atg cag acg gcc tac tgg gtg atg gcg atg atg atg gtg tgg att aca      48
Met Gln Thr Ala Tyr Trp Val Met Ala Met Met Met Val Trp Ile Thr
1               5               10              15 gcc cct ctg tct gaa ggt ggt aaa ttg aac gac gta att cgg ggt ttg      96
Ala Pro Leu Ser Glu Gly Gly Lys Leu Asn Asp Val Ile Arg Gly Leu
            20              25              30 gtg cca gat gac tta acc cca cag ctt gtt ttg caa agt ctg gat tcc     144
Val Pro Asp Asp Leu Thr Pro Gln Leu Val Leu Gln Ser Leu Asp Ser
        35              40              45 cgt cgt cat act cac ggc att cgt ccg aag gga gac ggc ata tgt atc     192
Arg Arg His Thr His Gly Ile Arg Pro Lys Gly Asp Gly Ile Cys Ile
    50              55              60 tgg aag gta tgt cca cca gac cca tgg aga cga cat cgt ctt aag aaa     240
Trp Lys Val Cys Pro Pro Asp Pro Trp Arg Arg His Arg Leu Lys Lys
65              70              75              80 aga aac aat tgacgtcaga caaccgccac aacttgagta cgacatcgtt             289
Arg Asn Asn aatacgactt cagcaaatat gaattttca gcatcactgt ggttgtcaag aaatcagttg   349
```

```
ctttaaaaga ttggatttgt ccttgtttaa gagttgtact gatgtcagct ctgccctgtg        409
aaataaagct gatg                                                          423
```

<210> SEQ ID NO 44
<211> LENGTH: 83
<212> TYPE: PRT
<213> ORGANISM: Conus emaciatus

<400> SEQUENCE: 44

```
Met Gln Thr Ala Tyr Trp Val Met Ala Met Met Val Trp Ile Thr
1               5                   10                  15

Ala Pro Leu Ser Glu Gly Gly Lys Leu Asn Asp Val Ile Arg Gly Leu
            20                  25                  30

Val Pro Asp Asp Leu Thr Pro Gln Leu Val Leu Gln Ser Leu Asp Ser
        35                  40                  45

Arg Arg His Thr His Gly Ile Arg Pro Lys Gly Asp Gly Ile Cys Ile
    50                  55                  60

Trp Lys Val Cys Pro Pro Asp Pro Trp Arg Arg His Arg Leu Lys Lys
65                  70                  75                  80

Arg Asn Asn
```

<210> SEQ ID NO 45
<211> LENGTH: 33
<212> TYPE: PRT
<213> ORGANISM: Conus emaciatus
<220> FEATURE:
<221> NAME/KEY: PEPTIDE
<222> LOCATION: (1)..(33)
<223> OTHER INFORMATION: Xaa at residues 7, 19, 20 and 22 may be Pro or
      hydroxy-Pro; Xaa at residues 15 and 23 may be Trp (D or L) or
      bromo-Trp (D or L)

<400> SEQUENCE: 45

```
His Thr His Gly Ile Arg Xaa Lys Gly Asp Gly Ile Cys Ile Xaa Lys
1               5                   10                  15

Val Cys Xaa Xaa Asp Xaa Xaa Arg Arg His Arg Leu Lys Lys Arg Asn
            20                  25                  30

Asn
```

<210> SEQ ID NO 46
<211> LENGTH: 412
<212> TYPE: DNA
<213> ORGANISM: Conus circumcisus
<220> FEATURE:
<221> NAME/KEY: CDS
<222> LOCATION: (1)..(240)

<400> SEQUENCE: 46

```
atg cag acg gcc tac tgg gtg atg gtg atg atg gtg gtg tgg att aca        48
Met Gln Thr Ala Tyr Trp Val Met Val Met Met Val Val Trp Ile Thr
1               5                   10                  15 gcc cct ctg tct gaa ggt ggt aaa tcg aac gac gta att cgg ggt ttg        96
Ala Pro Leu Ser Glu Gly Gly Lys Ser Asn Asp Val Ile Arg Gly Leu
            20                  25                  30 gtg cca cac atc tta acc cca cag cat atc ttg caa agt ctg act tcc       144
Val Pro His Ile Leu Thr Pro Gln His Ile Leu Gln Ser Leu Thr Ser
        35                  40                  45 cgt ctt cgt tct gac agc agt ggt cag aaa gga gca caa ata tgc atc       192
Arg Leu Arg Ser Asp Ser Ser Gly Gln Lys Gly Ala Gln Ile Cys Ile
    50                  55                  60 tgg aag gta tgt cca cta tcc cca tgg aga cga cca caa gga aaa aga       240
Trp Lys Val Cys Pro Leu Ser Pro Trp Arg Arg Pro Gln Gly Lys Arg
```

```
Trp Lys Val Cys Pro Leu Ser Pro Trp Arg Arg Pro Gln Gly Lys Arg
 65                  70                  75                  80 tgaatgacgt cagacaaccg ctacaactgt agtacgacat cgttgatacg acttcagcaa      300
atattttaac atcactgtgg ttgtgaagaa atcagttgct ttaaaagatt ggattttcc      360 ttgtttaaga gttgtactga tatcagctct gccctgtgaa ataaagctga tg             412

<210> SEQ ID NO 47
<211> LENGTH: 80
<212> TYPE: PRT
<213> ORGANISM: Conus circumcisus

<400> SEQUENCE: 47

Met Gln Thr Ala Tyr Trp Val Met Val Met Met Val Val Trp Ile Thr
 1               5                  10                  15

Ala Pro Leu Ser Glu Gly Gly Lys Ser Asn Asp Val Ile Arg Gly Leu
                20                  25                  30

Val Pro His Ile Leu Thr Pro Gln His Ile Leu Gln Ser Leu Thr Ser
            35                  40                  45

Arg Leu Arg Ser Asp Ser Ser Gly Gln Lys Gly Ala Gln Ile Cys Ile
     50                  55                  60

Trp Lys Val Cys Pro Leu Ser Pro Trp Arg Arg Pro Gln Gly Lys Arg
 65                  70                  75                  80

<210> SEQ ID NO 48
<211> LENGTH: 28
<212> TYPE: PRT
<213> ORGANISM: Conus circumcisus
<220> FEATURE:
<221> NAME/KEY: PEPTIDE
<222> LOCATION: (1)..(28)
<223> OTHER INFORMATION: Xaa at residues 16 and 24 may be Trp (D or L)
      or bromo-Trp (D or L); Xaa at residues 20, 23 and 27 may be Pro or
      hydroxy-Pro

<400> SEQUENCE: 48

Leu Arg Ser Asp Ser Ser Gly Gln Lys Gly Ala Gln Ile Cys Ile Xaa
 1               5                  10                  15

Lys Val Cys Xaa Leu Ser Xaa Xaa Arg Arg Xaa Gln
                20                  25

<210> SEQ ID NO 49
<211> LENGTH: 410
<212> TYPE: DNA
<213> ORGANISM: Conus betulinus
<220> FEATURE:
<221> NAME/KEY: CDS
<222> LOCATION: (1)..(207)

<400> SEQUENCE: 49 atg cag acg gcc tac tgg gtg atg gtg atg atg atg gtg tgg att aca       48
Met Gln Thr Ala Tyr Trp Val Met Val Met Met Met Val Trp Ile Thr
 1               5                  10                  15 gcc cct ctg tcc gaa ggt ggt aaa ctg aac gat gta att cgg gct ttg       96
Ala Pro Leu Ser Glu Gly Gly Lys Leu Asn Asp Val Ile Arg Ala Leu
                20                  25                  30 gcg cca gac gac gta acc cca cag ttt atc ttg cga agt ctg att tcc      144
Ala Pro Asp Asp Val Thr Pro Gln Phe Ile Leu Arg Ser Leu Ile Ser
            35                  40                  45 cgt cgt cgt tct gac agc gat gtt cgg gag gta ccc gta tgt tcc tgg      192
Arg Arg Arg Ser Asp Ser Asp Val Arg Glu Val Pro Val Cys Ser Trp
     50                  55                  60
```

```
aag ata tgt cca cca tagccataga gacgacatga tcttaaggaa aaagagaaat         247
Lys Ile Cys Pro Pro
 65 gacgtcagac aaccgccaca actgtagtac ggcatcgtta atacgacttc agcaaatgtt        307 ttaacatcac tgtggttgtg aagaaatcag ctgctttaaa agattggatt tttccttaag        367 agttgcactg atgtcagttc tgccctgtga aataaagctg atg                          410

<210> SEQ ID NO 50
<211> LENGTH: 69
<212> TYPE: PRT
<213> ORGANISM: Conus betulinus

<400> SEQUENCE: 50

Met Gln Thr Ala Tyr Trp Val Met Val Met Met Val Trp Ile Thr
  1               5                  10                  15

Ala Pro Leu Ser Glu Gly Gly Lys Leu Asn Asp Val Ile Arg Ala Leu
               20                  25                  30

Ala Pro Asp Asp Val Th

```
tgg aag gta tgt cca cca gac cca tgg aga cga cat cat ctt aag aaa    240
Trp Lys Val Cys Pro Pro Asp Pro Trp Arg Arg His His Leu Lys Lys
 65              70                  75                  80 aga aac aat tgacgtcaga caaccgccac aacttgagta cgacatcgtt            289
Arg Asn Asn aatacgactt cagcaaatat gaaattttca gcatcactgt ggttgtcaag aaatcagttg  349
ctttaaaaga ttggatttgt ccttgtttaa gagttgtact gatgtcagct ctgccctatg  409
aaataaagct gatg                                                    423
```

<210> SEQ ID NO 53
<211> LENGTH: 83
<212> TYPE: PRT
<213> ORGANISM: Conus aurisiacus

<400> SEQUENCE: 53

```
Met Gln Thr Ala Tyr Trp Val Met Ala Met Met Val Trp Ile Thr
 1               5                  10                  15

Ala Pro Leu Ser Glu Gly Gly Lys Leu Asn Asp Val Ile Arg Gly Leu
                20                  25                  30

Val Pro Asp Asp Leu Thr Pro Gln Leu Val Leu Gln Ser Leu Asp Ser
            35                  40                  45

Arg Arg His Thr His Gly Ile Arg Pro Lys Gly Asp Gly Ile Cys Ile
        50                  55                  60

Trp Lys Val Cys Pro Pro Asp Pro Trp Arg Arg His His Leu Lys Lys
 65              70                  75                  80

Arg Asn Asn
```

<210> SEQ ID NO 54
<211> LENGTH: 33
<212> TYPE: PRT
<213> ORGANISM: Conus aurisiacus
<220> FEATURE:
<221> NAME/KEY: PEPTIDE
<222> LOCATION: (1)..(33)
<223> OTHER INFORMATION: Xaa at residues 7, 19, 20 and 22 may be Pro or
      hydroxy-Pro; Xaa at residues 1 and 24 may be Trp (D or L) or
      bromo-Trp (D or L)

<400> SEQUENCE: 54

```
His Thr His Gly Ile Arg Xaa Lys Gly Asp Gly Ile Cys Ile Xaa Lys
 1               5                  10                  15

Val Cys Xaa Xaa Asp Xaa Xaa Arg Arg His His Leu Lys Lys Arg Asn
            20                  25                  30

Asn
```

<210> SEQ ID NO 55
<211> LENGTH: 439
<212> TYPE: DNA
<213> ORGANISM: Conus aurisiacus
<220> FEATURE:
<221> NAME/KEY: CDS
<222> LOCATION: (1)..(249)

<400> SEQUENCE: 55

```
atg cag acg gcc tac tgg gtg atg gtg atg atg gtg tgg att aca       48
Met Gln Thr Ala Tyr Trp Val Met Val Met Met Val Trp Ile Thr
 1               5                  10                  15 gcc cct ctg tct gaa ggt ggt aaa ttg aac gac gta att tgg ggt ttg   96
Ala Pro Leu Ser Glu Gly Gly Lys Leu Asn Asp Val Ile Trp Gly Leu
                20                  25                  30
```

-continued

```
gtg cca cac atc tta acc cca cag cat atc ttg caa agc ctg act tcc    144
Val Pro His Ile Leu Thr Pro Gln His Ile Leu Gln Ser Leu Thr Ser
         35                  40                  45 cgt ctt cat tct gac agc agt gat cag aaa gga ggc atg aac gca tgg    192
Arg Leu His Ser Asp Ser Ser Asp Gln Lys Gly Gly Met Asn Ala Trp
 50                  55                  60 aca gga gca gga gca caa ata tgc atc tgg aag gta tgt cca cca ccc    240
Thr Gly Ala Gly Ala Gln Ile Cys Ile Trp Lys Val Cys Pro Pro Pro
 65                  70                  75                  80 cca tgg aga tgaacacaag gaaaaagatg aatgacgtca gacaaccgcc             289
Pro Trp Arg acaactgtag tacgacatcg ttgatacgac ttcagcaaat attttaacat cactgtggtt   349
gtgaagaaat cagttgcttt aaaagattgg attttccctt gtttaagagt tgtactgata   409
tcagctctgc cctgtgaagt aaagctgatg                                     439
```

<210> SEQ ID NO 56
<211> LENGTH: 83
<212> TYPE: PRT
<213> ORGANISM: Conus aurisiacus

<400> SEQUENCE: 56

```
Met Gln Thr Ala Tyr Trp Val Met Val Met Met Val Trp Ile Thr
 1               5                  10                  15

Ala Pro Leu Ser Glu Gly Gly Lys Leu Asn Asp Val Ile Trp Gly Leu
                 20                  25                  30

Val Pro His Ile Leu Thr Pro Gln His Ile Leu Gln Ser Leu Thr Ser
         35                  40                  45

Arg Leu His Ser Asp Ser Ser Asp Gln Lys Gly Gly Met Asn Ala Trp
 50                  55                  60

Thr Gly Ala Gly Ala Gln Ile Cys Ile Trp Lys Val Cys Pro Pro Pro
 65                  70                  75                  80

Pro Trp Arg
```

<210> SEQ ID NO 57
<211> LENGTH: 34
<212> TYPE: PRT
<213> ORGANISM: Conus aurisiacus
<220> FEATURE:
<221> NAME/KEY: PEPTIDE
<222> LOCATION: (1)..(34)
<223> OTHER INFORMATION: Xaa at residues 15, 25 and 33 may be Trp (D or
      L) or bromo-Trp (D or L); Xaa at residues 29, 30, 31 and 32 may be
      Pro or hydroxy-Pro

<400> SEQUENCE: 57

```
Leu His Ser Asp Ser Ser Asp Gln Lys Gly Gly Met Asn Ala Xaa Thr
 1               5                  10                  15

Gly Ala Gly Ala Gln Ile Cys Ile Xaa Lys Val Cys Xaa Xaa Xaa Xaa
                 20                  25                  30

Xaa Arg
```

<210> SEQ ID NO 58
<211> LENGTH: 412
<212> TYPE: DNA
<213> ORGANISM: Conus aurisiacus
<220> FEATURE:
<221> NAME/KEY: CDS
<222> LOCATION: (1)..(222)

<400> SEQUENCE: 58

```
atg cag acg gcc tac tgg gtg atg gtg atg atg atg gtg tgg att aca      48
Met Gln Thr Ala Tyr Trp Val Met Val Met Met Met Val Trp Ile Thr
1               5                  10                  15 gcc cct ctg tct gaa ggt ggt aaa ttg aac gac gta att tgg ggt ttg      96
Ala Pro Leu Ser Glu Gly Gly Lys Leu Asn Asp Val Ile Trp Gly Leu
                20                  25                  30 gtg cca cac atc tta acc cca cag cat atc ttg caa agc ctg act tcc     144
Val Pro His Ile Leu Thr Pro Gln His Ile Leu Gln Ser Leu Thr Ser
            35                  40                  45 cgt ctt cat tct gac agc agt gat cag aaa gga gca caa ata tgc atc     192
Arg Leu His Ser Asp Ser Ser Asp Gln Lys Gly Ala Gln Ile Cys Ile
        50                  55                  60 tgg aag gta tgt cca cca ccc cca tgg aga tgaacacaag gaaaaagatg       242
Trp Lys Val Cys Pro Pro Pro Pro Trp Arg
65                  70 aatgacgtca gacaaccgcc acaactgtag tacgacatcg ttgatacgac ttcagcaaat   302
attttaacat cactgtggtt gtgaagaaat cagttgcttt aaaagattgg attttccctt   362
gtttaggagt tgtattgata tcagctctgc cctgtgaaat aaagctgatg              412

<210> SEQ ID NO 59
<211> LENGTH: 74
<212> TYPE: PRT
<213> ORGANISM: Conus aurisiacus

<400> SEQUENCE: 59

Met Gln Thr Ala Tyr Trp Val Met Val Met Met Met Val Trp Ile Thr
1               5                  10                  15

Ala Pro Leu Ser Glu Gly Gly Lys Leu Asn Asp Val Ile Trp Gly Leu
                20                  25                  30

Val Pro His Ile Leu Thr Pro Gln His Ile Leu Gln Ser Leu Thr Ser
            35                  40                  45

Arg Leu His Ser Asp Ser Ser Asp Gln Lys Gly Ala Gln Ile Cys Ile
        50                  55                  60

Trp Lys Val Cys Pro Pro Pro Pro Trp Arg
65                  70

<210> SEQ ID NO 60
<211> LENGTH: 25
<212> TYPE: PRT
<213> ORGANISM: Conus aurisiacus
<220> FEATURE:
<221> NAME/KEY: PEPTIDE
<222> LOCATION: (1)..(25)
<223> OTHER INFORMATION: Xaa at residues 16 and 24 may be Trp (D or L)
      or bromo-Trp (D or L); Xaa at residues 20, 21, 22 and 23 may be
      Pro or hydroxy-Pro

<400> SEQUENCE: 60

Leu His Ser Asp Ser Ser Asp Gln Lys Gly Ala Gln Ile Cys Ile Xaa
1               5                  10                  15

Lys Val Cys Xaa Xaa Xaa Xaa Xaa Arg
                20                  25

<210> SEQ ID NO 61
<211> LENGTH: 439
<212> TYPE: DNA
<213> ORGANISM: Conus aurisiacus
<220> FEATURE:
<221> NAME/KEY: CDS
<222> LOCATION: (1)..(267)

<400> SEQUENCE: 61
```

```
atg cag acg gcc tac tgg gtg atg gtg atg atg atg gtg tgg att aca      48
Met Gln Thr Ala Tyr Trp Val Met Val Met Met Met Val Trp Ile Thr
1               5                   10                  15 gcc cct ctg ttt gaa ggt ggt aaa ttg aac gac gta att cgg ggt ttg      96
Ala Pro Leu Phe Glu Gly Gly Lys Leu Asn Asp Val Ile Arg Gly Leu
            20                  25                  30 gtg cca cac atc tta acc cca cag cat atc ttg caa agc ctg act tcc     144
Val Pro His Ile Leu Thr Pro Gln His Ile Leu Gln Ser Leu Thr Ser
        35                  40                  45 cgt ctt cgt tct gac agc agt gat cag aaa gga ggc atg aac gca tcg     192
Arg Leu Arg Ser Asp Ser Ser Asp Gln Lys Gly Gly Met Asn Ala Ser
    50                  55                  60 aca gga gca gga gca caa ata tgc atc tgg aag gta tgt cca cca tcc     240
Thr Gly Ala Gly Ala Gln Ile Cys Ile Trp Lys Val Cys Pro Pro Ser
65                  70                  75                  80 cca tgg aga cga aca caa gga aaa aga tgaatgacgt cagacaaccg           287
Pro Trp Arg Arg Thr Gln Gly Lys Arg
                85 ccacaactgt agtacgacat cgttgatacg acttcagcaa atattttaac atcactgtgg   347 ttgtgaagaa atcagttgct ttaaaagatt ggattttttcc ttgtttaaga gttgtactga  407 tatcagctct gcactgtgaa ataaagctga tg                                 439
```

<210> SEQ ID NO 62
<211> LENGTH: 89
<212> TYPE: PRT
<213> ORGANISM: Conus aurisiacus

<400> SEQUENCE: 62

Met Gln Thr Ala Tyr Trp Val Met Val Met Met Met Val Trp Ile Thr
1               5                   10                  15

Ala Pro Leu Phe Glu Gly Gly Lys Leu Asn Asp Val Ile Arg Gly Leu
            20                  25                  30

Val Pro His Ile Leu Thr Pro Gln His Ile Leu Gln Ser Leu Thr Ser
        35                  40                  45

Arg Leu Arg Ser Asp Ser Ser Asp Gln Lys Gly Gly Met Asn Ala Ser
    50                  55                  60

Thr Gly Ala Gly Ala Gln Ile Cys Ile Trp Lys Val Cys Pro Pro Ser
65                  70                  75                  80

Pro Trp Arg Arg Thr Gln Gly Lys Arg
                85

<210> SEQ ID NO 63
<211> LENGTH: 37
<212> TYPE: PRT
<213> ORGANISM: Conus aurisiacus
<220> FEATURE:
<221> NAME/KEY: PEPTIDE
<222> LOCATION: (1)..(37)
<223> OTHER INFORMATION: Xaa at residues 25 and 33 may be Trp (D or L)
      or bromo-Trp (D or L); Xaa at residues 29, 30 and 32 may be Pro or
      hydroxy-Pro

<400> SEQUENCE: 63

Leu Arg Ser Asp Ser Ser Asp Gln Lys Gly Gly Met Asn Ala Ser Thr
1               5                   10                  15

Gly Ala Gly Ala Gln Ile Cys Ile Xaa Lys Val Cys Xaa Xaa Ser Xaa
            20                  25                  30

Xaa Arg Arg Thr Gln
        35

<210> SEQ ID NO 64
<211> LENGTH: 412
<212> TYPE: DNA
<213> ORGANISM: Conus achatinus
<220> FEATURE:
<221> NAME/KEY: CDS
<222> LOCATION: (1)..(240)

<400> SEQUENCE: 64

```
atg cag acg gcc tac tgg gtg atg gtg atg atg atg gtg tgg att aca       48
Met Gln Thr Ala Tyr Trp Val Met Val Met Met Met Val Trp Ile Thr
1               5                   10                  15 gcc cct ctg tct gaa ggt ggt aaa ttg aac gac gta att cgg ggt ttg       96
Ala Pro Leu Ser Glu Gly Gly Lys Leu Asn Asp Val Ile Arg Gly Leu
                20                  25                  30 gtg cca cac atc tta acc cca cag cat atc ttg caa agt ctg act tcc      144
Val Pro His Ile Leu Thr Pro Gln His Ile Leu Gln Ser Leu Thr Ser
            35                  40                  45 cgt ctt cgt tct gac aac ggt ggt tcg agt gga gca caa ata tgc atc      192
Arg Leu Arg Ser Asp Asn Gly Gly Ser Ser Gly Ala Gln Ile Cys Ile
        50                  55                  60 tgg aag gtg tgt cca cca tcc cca tgg aga cga cca caa gga aaa aga      240
Trp Lys Val Cys Pro Pro Ser Pro Trp Arg Arg Pro Gln Gly Lys Arg
65                  70                  75                  80 tgaacggcgt cagacaaccg ccacaactgt agtgggacat cgttgatacg acttcagcaa    300
atattttaac atcactgtgg ttgtgaagaa atcagttgct ttaaaagatt ggattttttcc   360 ttgtttaaga gttgtactga tatcagctct gccctatgaa ataaagctga tg            412
```

<210> SEQ ID NO 65
<211> LENGTH: 80
<212> TYPE: PRT
<213> ORGANISM: Conus achatinus

<400> SEQUENCE: 65

Met Gln Thr Ala Tyr Trp Val Met Val Met Met Met Val Trp Ile Thr
1               5                   10                  15

Ala Pro Leu Ser Glu Gly Gly Lys Leu Asn Asp Val Ile Arg Gly Leu
                20                  25                  30

Val Pro His Ile Leu Thr Pro Gln His Ile Leu Gln Ser Leu Thr Ser
            35                  40                  45

Arg Leu Arg Ser Asp Asn Gly Gly Ser Ser Gly Ala Gln Ile Cys Ile
        50                  55                  60

Trp Lys Val Cys Pro Pro Ser Pro Trp Arg Arg Pro Gln Gly Lys Arg
65                  70                  75                  80

<210> SEQ ID NO 66
<211> LENGTH: 28
<212> TYPE: PRT
<213> ORGANISM: Conus achatinus
<220> FEATURE:
<221> NAME/KEY: PEPTIDE
<222> LOCATION: (1)..(28)
<223> OTHER INFORMATION: Xaa at residues 16 and 24 may be Trp (D or L)
      or bromo-Trp (D or L); Xaa at residues 20, 21, 23 and 27 may be
      Pro or hydroxy-Pro

<400> SEQUENCE: 66

Leu Arg Ser Asp Asn Gly Gly Ser Ser Gly Ala Gln Ile Cys Ile Xaa
1               5                   10                  15

Lys Val Cys Xaa Xaa Ser Xaa Xaa Arg Arg Xaa Gln

<210> SEQ ID NO 67
<211> LENGTH: 399
<212> TYPE: DNA
<213> ORGANISM: Conus purpurascens
<220> FEATURE:
<221> NAME/KEY: CDS
<222> LOCATION: (1)..(213)

<400> SEQUENCE: 67

| | | | | | | | | | | | | | | | | |
|---|---|---|---|---|---|---|---|---|---|---|---|---|---|---|---|---|
| atg | cag | acg | gcc | tac | tgg | gtg | atg | gtg | atg | acg | atg | gtg | tgg | att | aca | 48 |
| Met | Gln | Thr | Ala | Tyr | Trp | Val | Met | Val | Met | Thr | Met | Val | Trp | Ile | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcc | cct | ctg | tct | gaa | ggt | gga | aaa | ctg | aac | gat | gta | att | cgg | ggt | ttg | 96 |
| Ala | Pro | Leu | Ser | Glu | Gly | Gly | Lys | Leu | Asn | Asp | Val | Ile | Arg | Gly | Leu | |
| | | | 20 | | | | | 25 | | | | | 30 | | | |

| | | | | | | | | | | | | | | | | |
|---|---|---|---|---|---|---|---|---|---|---|---|---|---|---|---|---|
| gtg | cca | gac | gac | tta | gcc | cta | cag | ctt | atc | ttg | caa | agt | ccg | gtt | ttc | 144 |
| Val | Pro | Asp | Asp | Leu | Ala | Leu | Gln | Leu | Ile | Leu | Gln | Ser | Pro | Val | Phe | |
| | | | 35 | | | | | 40 | | | | | 45 | | | |

| | | | | | | | | | | | | | | | | |
|---|---|---|---|---|---|---|---|---|---|---|---|---|---|---|---|---|
| cgt | cgt | caa | tct | gaa | gag | gaa | aaa | ata | tgc | ctc | tgg | aag | ata | tgt | cca | 192 |
| Arg | Arg | Gln | Ser | Glu | Glu | Glu | Lys | Ile | Cys | Leu | Trp | Lys | Ile | Cys | Pro | |
| | 50 | | | | | 55 | | | | | 60 | | | | | |

| | | | | | | | |
|---|---|---|---|---|---|---|---|
| cca | ccc | cca | tgg | aga | cga | tca | taaggaaaaa aaaatgaatg acgtcagaca | 243 |
| Pro | Pro | Pro | Trp | Arg | Arg | Ser | |
| 65 | | | | 70 | | | | accaccacaa ctgtaatacg acatcgttaa tacgacttca gcaaacattt taacatcact 303 gtggttgtga agaaatcagt tgctttagaa gcttggattt ttccttgttt aagagttgta 363 ctgatatcag ctctgcccta tgaaataaag ctgatg 399

<210> SEQ ID NO 68
<211> LENGTH: 71
<212> TYPE: PRT
<213> ORGANISM: Conus purpurascens

<400> SEQUENCE: 68

Met Gln Thr Ala Tyr Trp Val Met Val Met Thr Met Val Trp Ile Thr
1               5                   10                  15

Ala Pro Leu Ser Glu Gly Gly Lys Leu Asn Asp Val Ile Arg Gly Leu
            20                  25                  30

Val Pro Asp Asp Leu Ala Leu Gln Leu Ile Leu Gln Ser Pro Val Phe
        35                  40                  45

Arg Arg Gln Ser Glu Glu Glu Lys Ile Cys Leu Trp Lys Ile Cys Pro
    50                  55                  60

Pro Pro Pro Trp Arg Arg Ser
65                  70

<210> SEQ ID NO 69
<211> LENGTH: 21
<212> TYPE: PRT
<213> ORGANISM: Conus purpurascens
<220> FEATURE:
<221> NAME/KEY: PEPTIDE
<222> LOCATION: (1)..(21)
<223> OTHER INFORMATION: Xaa at residue 1 is Gln or pyro-Glu; Xaa at
      residues 3,4 and 5 may be Glu or Gla; Xaa at residues 10 and 18
      may be Trp (D or L) or bromo-Trp (D or L); Xaa at residues 14, 15,
      16 and 17 may be Pro or hydroxy-Pro

<400> SEQUENCE: 69

Xaa Ser Xaa Xaa Xaa Lys Ile Cys Leu Xaa Lys Ile Cys Xaa Xaa Xaa
1               5                   10                  15

-continued

```
Xaa Xaa Arg Arg Ser
         20

<210> SEQ ID NO 70
<211> LENGTH: 398
<212> TYPE: DNA
<213> ORGANISM: Conus purpurascens
<220> FEATURE:
<221> NAME/KEY: CDS
<222> LOCATION: (1)..(213)

<400> SEQUENCE: 70 atg cag acg gcc tac tgg gtg atg gtg atg atg atg gtg tgg att aca      48
Met Gln Thr Ala Tyr Trp Val Met Val Met Met Met Val Trp Ile Thr
1               5                   10                  15 gcc cct ctg tct gag ggt aga aaa ccg aac gat gta att cgg ggt ttg      96
Ala Pro Leu Ser Glu Gly Arg Lys Pro Asn Asp Val Ile Arg Gly Leu
                20                  25                  30 gtg cca gat gac tta gcc cta cag ctt atc ttg caa agt cag gtt tcc     144
Val Pro Asp Asp Leu Ala Leu Gln Leu Ile Leu Gln Ser Gln Val Ser
            35                  40                  45 cgt cgt gaa tct aat ggg gtg gaa ata tgc atg tgg aag gta tgt cca     192
Arg Arg Glu Ser Asn Gly Val Glu Ile Cys Met Trp Lys Val Cys Pro
    50                  55                  60 cca tcc cca tgg aga cga tca taaggaaaaa aaatgaatga cgtcagacaa        243
Pro Ser Pro Trp Arg Arg Ser
65                  70 ccaccacaac tgtaatacga catcgttaat acgacttcag caaacatttt aacatcactg   303
tggttgtgaa gaaatcagtt gctttaaaag attggatttt tccttgttta agagttgtac   363
tgatatcagc tctgccctat gaaataaagc tgatg                              398

<210> SEQ ID NO 71
<211> LENGTH: 71
<212> TYPE: PRT
<213> ORGANISM: Conus purpurascens

<400> SEQUENCE: 71

Met Gln Thr Ala Tyr Trp Val Met Val Met Met Met Val Trp Ile Thr
1               5                   10                  15

Ala Pro Leu Ser Glu Gly Arg Lys Pro Asn Asp Val Ile Arg Gly Leu
                20                  25                  30

Val Pro Asp Asp Leu Ala Leu Gln Leu Ile Leu Gln Ser Gln Val Ser
            35                  40                  45

Arg Arg Glu Ser Asn Gly Val Glu Ile Cys Met Trp Lys Val Cys Pro
    50                  55                  60

Pro Ser Pro Trp Arg Arg Ser
65                  70

<210> SEQ ID NO 72
<211> LENGTH: 21
<212> TYPE: PRT
<213> ORGANISM: Conus purpurascens
<220> FEATURE:
<221> NAME/KEY: PEPTIDE
<222> LOCATION: (1)..(21)
<223> OTHER INFORMATION: Xaa at residue 1 is Gln or pyro-Glu; Xaa at
      residue 6 may be Glu or Gla; Xaa at residues 10 and 18 may be Trp
      (D or L) or bromo-Trp (D or L); Xaa at residues 14, 15 and 17 may
      be Pro or hydroxy-Pro

<400> SEQUENCE: 72
```

```
Xaa Ser Asn Gly Val Xaa Ile Cys Met Xaa Lys Val Cys Xaa Xaa Ser
1               5                   10                  15

Xaa Xaa Arg Arg Ser
            20
```

<210> SEQ ID NO 73
<211> LENGTH: 409
<212> TYPE: DNA
<213> ORGANISM: Conus stercusmuscarum
<220> FEATURE:
<221> NAME/KEY: CDS
<222> LOCATION: (1)..(213)

<400> SEQUENCE: 73

```
atg cag acg gcc tac tgg gtg atg gtg atg atg atg gtg tgg att aca    48
Met Gln Thr Ala Tyr Trp Val Met Val Met Met Met Val Trp Ile Thr
1               5                   10                  15 gcc cct ctg tct gaa ggt ggt aaa ttg acc gac gta att cgg ggt ttg    96
Ala Pro Leu Ser Glu Gly Gly Lys Leu Thr Asp Val Ile Arg Gly Leu
                20                  25                  30 gtg cca cac atc tta acc cca cag cat atc ttg caa agt atg act tcc   144
Val Pro His Ile Leu Thr Pro Gln His Ile Leu Gln Ser Met Thr Ser
            35                  40                  45 cgt ctt ggt att ggc agc agt gat caa aat gca caa ata tgc atc tgg   192
Arg Leu Gly Ile Gly Ser Ser Asp Gln Asn Ala Gln Ile Cys Ile Trp
        50                  55                  60 aag gta tgt cca cca tcc cca tagagacgac cataaggaaa aagatgaatg      243
Lys Val Cys Pro Pro Ser Pro
65                  70 acgtcagaca accgccacaa ctgtagtacg acatcgttga tacgacttca gcaaatattt  303
taacatcact gtggttgtga agaaatcagt tgctttaaaa gattggattt ttccttgttt  363
aagagttgta ctgatatcag ctctgccctg tgaaataaag ctgatg                409
```

<210> SEQ ID NO 74
<211> LENGTH: 71
<212> TYPE: PRT
<213> ORGANISM: Conus stercusmuscarum

<400> SEQUENCE: 74

```
Met Gln Thr Ala Tyr Trp Val Met Val Met Met Met Val Trp Ile Thr
1               5                   10                  15

Ala Pro Leu Ser Glu Gly Gly Lys Leu Thr Asp Val Ile Arg Gly Leu
                20                  25                  30

Val Pro His Ile Leu Thr Pro Gln His Ile Leu Gln Ser Met Thr Ser
            35                  40                  45

Arg Leu Gly Ile Gly Ser Ser Asp Gln Asn Ala Gln Ile Cys Ile Trp
        50                  55                  60

Lys Val Cys Pro Pro Ser Pro
65                  70
```

<210> SEQ ID NO 75
<211> LENGTH: 22
<212> TYPE: PRT
<213> ORGANISM: Conus stercusmuscarum
<220> FEATURE:
<221> NAME/KEY: PEPTIDE
<222> LOCATION: (1)..(22)
<223> OTHER INFORMATION: Xaa at residue 15 may be Trp or bromo-Trp; Xaa
      at residue 19, 20 and 22 may be Pro or hydroxy-Pro

<400> SEQUENCE: 75

-continued

```
Leu Gly Ile Gly Ser Ser Asp Gln Asn Ala Gln Ile Cys Ile Xaa Lys
1               5                   10                  15

Val Cys Xaa Xaa Ser Xaa
            20
```

<210> SEQ ID NO 76
<211> LENGTH: 433
<212> TYPE: DNA
<213> ORGANISM: Conus baileyi
<220> FEATURE:
<221> NAME/KEY: CDS
<222> LOCATION: (1)..(216)

<400> SEQUENCE: 76

```
atg cag acg gcc tac tgg gtg atg gtg atg ata atg gtg tgg att aca       48
Met Gln Thr Ala Tyr Trp Val Met Val Met Ile Met Val Trp Ile Thr
1               5                   10                  15 gtc cct ctg tct gaa ggt ggt aaa ttg aac gac ata att cgg ggt ttg       96
Val Pro Leu Ser Glu Gly Gly Lys Leu Asn Asp Ile Ile Arg Gly Leu
            20                  25                  30 ttg cca gac aac ttc ccc cca cag ctt acc ttg cat cgt ctg gtt tcc      144
Leu Pro Asp Asn Phe Pro Pro Gln Leu Thr Leu His Arg Leu Val Ser
        35                  40                  45 cgt cgt cat tct gac agc att att ctg agg ggc tta tgt atc tgg aag      192
Arg Arg His Ser Asp Ser Ile Ile Leu Arg Gly Leu Cys Ile Trp Lys
    50                  55                  60 gtg tgt gaa cct ccg cca caa aga tgatctggtc caaagccaaa aaacgaatga     246
Val Cys Glu Pro Pro Pro Gln Arg
65              70 tgtcagacaa ccgccacagc tttagtacga catggttaat acgacttcag caaatatttc    306
aacatcactg tggttgtgaa gaaatcagtt actttaaaag attggaatga tgtcagctgt    366
gcactatcaa ataaagttga tgtgacaaaa aaaaaaaaaa aaaagtact ctgcgttgtt    426 actcgag                                                              433
```

<210> SEQ ID NO 77
<211> LENGTH: 72
<212> TYPE: PRT
<213> ORGANISM: Conus baileyi

<400> SEQUENCE: 77

```
Met Gln Thr Ala Tyr Trp Val Met Val Met Ile Met Val Trp Ile Thr
1               5                   10                  15

Val Pro Leu Ser Glu Gly Gly Lys Leu Asn Asp Ile Ile Arg Gly Leu
            20                  25                  30

Leu Pro Asp Asn Phe Pro Pro Gln Leu Thr Leu His Arg Leu Val Ser
        35                  40                  45

Arg Arg His Ser Asp Ser Ile Ile Leu Arg Gly Leu Cys Ile Trp Lys
    50                  55                  60

Val Cys Glu Pro Pro Pro Gln Arg
65              70
```

<210> SEQ ID NO 78
<211> LENGTH: 22
<212> TYPE: PRT
<213> ORGANISM: Conus baileyi
<220> FEATURE:
<221> NAME/KEY: PEPTIDE
<222> LOCATION: (1)..(22)
<223> OTHER INFORMATION: Xaa at residue 13 may be Trp (D or L) or bromo-
      Trp (D or L); Xaa at residue 17 may be Glu or Gla; Xaa at residues
      18, 19 and 20 may be Pro or hydroxy-Pro

```
<400> SEQUENCE: 78

His Ser Asp Ser Ile Ile Leu Arg Gly Leu Cys Ile Xaa Lys Val Cys
1               5                   10                  15

Xaa Xaa Xaa Xaa Gln Arg
            20

<210> SEQ ID NO 79
<211> LENGTH: 413
<212> TYPE: DNA
<213> ORGANISM: Conus bocki
<220> FEATURE:
<221> NAME/KEY: CDS
<222> LOCATION: (1)..(270)

<400> SEQUENCE: 79 atg cag acg gcc tac tgg gtg atg gtg atg atg atg gtg tgg att aca      48
Met Gln Thr Ala Tyr Trp Val Met Val Met Met Met Val Trp Ile Thr
1               5                   10                  15 gcc cct ctg tct gaa agt gat aaa ctg aac gac gta att cgg ggt ttg      96
Ala Pro Leu Ser Glu Ser Asp Lys Leu Asn Asp Val Ile Arg Gly Leu
                20                  25                  30 gtg cca gac aac tta acc cca cag ctt atc ttg cga agt ctg att tcc     144
Val Pro Asp Asn Leu Thr Pro Gln Leu Ile Leu Arg Ser Leu Ile Ser
            35                  40                  45 cgt cgt cgt tct gac aag gat gat ccg gga gga caa gaa tgt tac tgg     192
Arg Arg Arg Ser Asp Lys Asp Asp Pro Gly Gly Gln Glu Cys Tyr Trp
        50                  55                  60 aac gta tgt gca cca aac cag gga gac cac atg atc tta aga aaa aag     240
Asn Val Cys Ala Pro Asn Gln Gly Asp His Met Ile Leu Arg Lys Lys
65                  70                  75                  80 atg aat gac gac aga caa ccg cca caa ctg taatacgaca tcgttaatac       290
Met Asn Asp Asp Arg Gln Pro Pro Gln Leu
                85                  90 gacttcagca aatattttaa catcactgtg gttgtgaaga atcagttgc tttaaaagat    350 tggattttc cgtgtttaag agctgtactg atatctgctc tgccctgtga aataaagctg    410
atg                                                                 413

<210> SEQ ID NO 80
<211> LENGTH: 90
<212> TYPE: PRT
<213> ORGANISM: Conus bocki

<400> SEQUENCE: 80

Met Gln Thr Ala Tyr Trp Val Met Val Met Met Met Val Trp Ile Thr
1               5                   10                  15

Ala Pro Leu Ser Glu Ser Asp Lys Leu Asn Asp Val Ile Arg Gly Leu
                20                  25                  30

Val Pro Asp Asn Leu Thr Pro Gln Leu Ile Leu Arg Ser Leu Ile Ser
            35                  40                  45

Arg Arg Arg Ser Asp Lys Asp Asp Pro Gly Gly Gln Glu Cys Tyr Trp
        50                  55                  60

Asn Val Cys Ala Pro Asn Gln Gly Asp His Met Ile Leu Arg Lys Lys
65                  70                  75                  80

Met Asn Asp Asp Arg Gln Pro Pro Gln Leu
                85                  90

<210> SEQ ID NO 81
<211> LENGTH: 40
```

```
<212> TYPE: PRT
<213> ORGANISM: Conus bocki
<220> FEATURE:
<221> NAME/KEY: PEPTIDE
<222> LOCATION: (1)..(40)
<223> OTHER INFORMATION: Xaa at residues 7, 19, 37, 38 may be Pro or
      hydroxy-Pro; Xaa at residue 11 may be Glu or Gla; Xaa at residue
      14 may be Trp (D or L) or bromo-Trp (D or L); Xaa at residue 13
      may be Tyr, 125I-Tyr, mono-iodo-Tyr, di-iodo-Tyr, O-sulpho-Tyr or
      O-phospho-Tyr

<400> SEQUENCE: 81

Arg Ser Asp Lys Asp Asp Xaa Gly Gly Gln Xaa Cys Xaa Xaa Asn Val
1               5                   10                  15

Cys Ala Xaa Asn Gln Gly Asp His Met Ile Leu Arg Lys Lys Met Asn
            20                  25                  30

Asp Asp Arg Gln Xaa Xaa Gln Leu
            35                  40

<210> SEQ ID NO 82
<211> LENGTH: 496
<212> TYPE: DNA
<213> ORGANISM: Conus chaldaeus
<220> FEATURE:
<221> NAME/KEY: CDS
<222> LOCATION: (21)..(260)

<400> SEQUENCE: 82
gaattcgccc ttatggatcc atg cag acg gcc tac tgg gtg atg atg ggg atg      53
                     Met Gln Thr Ala Tyr Trp Val Met Met Gly Met
                      1               5                  10 atg atg gtg tgg att aca gcc cct ctg tct gga ggt ggt aaa ctg aac       101
Met Met Val Trp Ile Thr Ala Pro Leu Ser Gly Gly Gly Lys Leu Asn
            15                  20                  25 gac gta att cgg ggt ttg gtg cca gac gac tta acc cta cag cgt atg       149
Asp Val Ile Arg Gly Leu Val Pro Asp Asp Leu Thr Leu Gln Arg Met
        30                  35                  40 ttc gaa act ccg gtt tcc cat cgt ctt tct gag ggc aga aat tcg acg       197
Phe Glu Thr Pro Val Ser His Arg Leu Ser Glu Gly Arg Asn Ser Thr
    45                  50                  55 gta cac ata tgt acg tgg aag gta tgt cca cct ccc cca tgg aga cga       245
Val His Ile Cys Thr Trp Lys Val Cys Pro Pro Pro Pro Trp Arg Arg
60                  65                  70                  75 cca cat gga caa aga tgaatgacgt cagacaacct ccacaactgt agtacgacat       300
Pro His Gly Gln Arg
                80 cgttaacacg acgtcagcta atcttttaac atcactgtgg ctgtgaagaa ctcggttgct      360 ttaaaagatt ggattttttcc ttgtttaaga gttgtgctga tatgaactct gcactacgaa    420 ataaagctga tgtgacaaac aaaaaaaaga aaaaaaaag tactctgcgt tgttactcga      480 gcttaagggc gaattc                                                      496

<210> SEQ ID NO 83
<211> LENGTH: 80
<212> TYPE: PRT
<213> ORGANISM: Conus chaldaeus

<400> SEQUENCE: 83

Met Gln Thr Ala Tyr Trp Val Met Met Gly Met Met Met Val Trp Ile
1               5                   10                  15

Thr Ala Pro Leu Ser Gly Gly Gly Lys Leu Asn Asp Val Ile Arg Gly
            20                  25                  30
```

```
Leu Val Pro Asp Asp Leu Thr Leu Gln Arg Met Phe Glu Thr Pro Val
        35                  40                  45
Ser His Arg Leu Ser Glu Gly Arg Asn Ser Thr Val His Ile Cys Thr
    50                  55                  60
Trp Lys Val Cys Pro Pro Pro Trp Arg Arg Pro His Gly Gln Arg
65                  70                  75                  80

<210> SEQ ID NO 84
<211> LENGTH: 29
<212> TYPE: PRT
<213> ORGANISM: Conus chaldaeus
<220> FEATURE:
<221> NAME/KEY: PEPTIDE
<222> LOCATION: (1)..(29)
<223> OTHER INFORMATION: Xaa at residue 3 may be Glu or Gla; Xaa at
      residues 14 and 22 may be Trp (D or L) or bromo-Trp (D or L); Xaa
      at residues 18, 19, 20, 21 and 25 may be Pro or hydroxy-Pro

<400> SEQUENCE: 84

Leu Ser Xaa Gly Arg Asn Ser Thr Val His Ile Cys Thr Xaa Lys Val
1               5                   10                  15
Cys Xaa Xaa Xaa Xaa Xaa Arg Arg Xaa His Gly Gln Arg
            20                  25

<210> SEQ ID NO 85
<211> LENGTH: 499
<212> TYPE: DNA
<213> ORGANISM: Conus chaldaeus
<220> FEATURE:
<221> NAME/KEY: CDS
<222> LOCATION: (21)..(260)

<400> SEQUENCE: 85
```

| | | |
|---|---|---|
| gaattcgccc ttatggatcc atg cag acg gcc tac tgg gtg atg atg ggg atg | 53 | |
|                                   Met Gln Thr Ala Tyr Trp Val Met Met Gly Met | | |
|                                  1              5                  10 | | |

```
atg atg gtg tgg att aca gcc cct ctg tct gga ggt ggt aaa ctg aac        101
Met Met Val Trp Ile Thr Ala Pro Leu Ser Gly Gly Gly Lys Leu Asn
            15                  20                  25 gac gta att cgg ggt ttg gtg cca gac gac tta acc cta cag cgt atg        149
Asp Val Ile Arg Gly Leu Val Pro Asp Asp Leu Thr Leu Gln Arg Met
        30                  35                  40 ttc gaa act ccg gtt tcc cat cgt ctt tct gag ggc aga aat tcg acg        197
Phe Glu Thr Pro Val Ser His Arg Leu Ser Glu Gly Arg Asn Ser Thr
    45                  50                  55 gta cac ata tgt atg tgg aag gta tgt cca cct ccc cca tgg aga cga        245
Val His Ile Cys Met Trp Lys Val Cys Pro Pro Pro Pro Trp Arg Arg
60                  65                  70                  75 cca cat gga caa aga tgaatgacgt cagacaacct ccacaactgt agtacgacat        300
Pro His Gly Gln Arg
                80 cgttaacacg acgtcagcta atcttttaac atcactgtgg ttgtgaagaa atcggttgct      360 ttaaaagatt ggattttttcc ttgtttaaga gttgtgctga tatgaactct gcactacgaa     420 ataaagctga tgtgacaaac ggaaaaaaaa aaaaaaaaaa aagtactctg cgttgttact      480 cgagcttaag ggcgaattc                                                   499

<210> SEQ ID NO 86
<211> LENGTH: 80
<212> TYPE: PRT
<213> ORGANISM: Conus chaldaeus

<400> SEQUENCE: 86
```

```
Met Gln Thr Ala Tyr Trp Val Met Met Gly Met Met Val Trp Ile
1               5                   10                  15

Thr Ala Pro Leu Ser Gly Gly Gly Lys Leu Asn Asp Val Ile Arg Gly
            20                  25                  30

Leu Val Pro Asp Asp Leu Thr Leu Gln Arg Met Phe Glu Thr Pro Val
        35                  40                  45

Ser His Arg Leu Ser Glu Gly Arg Asn Ser Thr Val His Ile Cys Met
    50                  55                  60

Trp Lys Val Cys Pro Pro Pro Trp Arg Arg Pro His Gly Gln Arg
65              70                  75                  80
```

<210> SEQ ID NO 87
<211> LENGTH: 29
<212> TYPE: PRT
<213> ORGANISM: Conus chaldaeus
<220> FEATURE:
<221> NAME/KEY: PEPTIDE
<222> LOCATION: (1)..(29)
<223> OTHER INFORMATION: Xaa at residue 3 may be Glu or Gla; Xaa at
      residues 14 and 22 may be Trp (D or L) or bromo-Trp (D or L); Xaa
      at residues 18, 19, 20, 21 and 25 may be Pro or hydroxy-Pro

<400> SEQUENCE: 87

```
Leu Ser Xaa Gly Arg Asn Ser Thr Val His Ile Cys Met Xaa Lys Val
1               5                   10                  15

Cys Xaa Xaa Xaa Xaa Xaa Arg Arg Xaa His Gly Gln Arg
            20                  25
```

<210> SEQ ID NO 88
<211> LENGTH: 490
<212> TYPE: DNA
<213> ORGANISM: Conus cinereus
<220> FEATURE:
<221> NAME/KEY: CDS
<222> LOCATION: (21)..(305)

<400> SEQUENCE: 88

```
gaattcgccc ttatggatcc atg cag acg gcc tac tgg gtg atg gtg atg atg        53
                     Met Gln Thr Ala Tyr Trp Val Met Val Met Met
                     1               5                   10 ttg gtg tgg att aca gcc cct ctg cct gag ggt ggt aaa ccg aag cac         101
Leu Val Trp Ile Thr Ala Pro Leu Pro Glu Gly Gly Lys Pro Lys His
             15                  20                  25 gta att cgg ggt ttg gta cca gac gac tta acc cca cag cat atc ttg         149
Val Ile Arg Gly Leu Val Pro Asp Asp Leu Thr Pro Gln His Ile Leu
         30                  35                  40 cga agt ttg att tcc cgt cgt tca tct ggc tgc agt gtt tcg ttg ggc         197
Arg Ser Leu Ile Ser Arg Arg Ser Ser Gly Cys Ser Val Ser Leu Gly
     45                  50                  55 ttc aaa tgc ttc tgg aag agc tgt aca gta atc cca gtg aga cca ttt         245
Phe Lys Cys Phe Trp Lys Ser Cys Thr Val Ile Pro Val Arg Pro Phe
60                  65                  70                  75 gta tct ctg gaa gaa gaa aat gaa tgc cag aaa gtc caa ata agt gca         293
Val Ser Leu Glu Glu Glu Asn Glu Cys Gln Lys Val Gln Ile Ser Ala
                80                  85                  90 gta tgg ggt cct tgatacgact tcagcaagga tcactgtggt tgtgaagaaa             345
Val Trp Gly Pro
            95 tcagttgctt taaagatttt gattttcct tgtttaagag ttgtactgat atcagctctg        405 tactatgaaa taaagctgat gtgacaaaca aaaaaaaaa aaaaaaagt actctgcgtt         465
```

```
gttactcgag cttaagggcg aattc                                         490
```

<210> SEQ ID NO 89
<211> LENGTH: 95
<212> TYPE: PRT
<213> ORGANISM: Conus cinereus

<400> SEQUENCE: 89

```
Met Gln Thr Ala Tyr Trp Val Met Val Met Met Leu Val Trp Ile Thr
1               5                   10                  15

Ala Pro Leu Pro Glu Gly Gly Lys Pro Lys His Val Ile Arg Gly Leu
            20                  25                  30

Val Pro Asp Asp Leu Thr Pro Gln His Ile Leu Arg Ser Leu Ile Ser
        35                  40                  45

Arg Arg Ser Ser Gly Cys Ser Val Ser Leu Gly Phe Lys Cys Phe Trp
50                  55                  60

Lys Ser Cys Thr Val Ile Pro Val Arg Pro Phe Val Ser Leu Glu Glu
65                  70                  75                  80

Glu Asn Glu Cys Gln Lys Val Gln Ile Ser Ala Val Trp Gly Pro
            85                  90                  95
```

<210> SEQ ID NO 90
<211> LENGTH: 45
<212> TYPE: PRT
<213> ORGANISM: Conus cinereus
<220> FEATURE:
<221> NAME/KEY: PEPTIDE
<222> LOCATION: (1)..(45)
<223> OTHER INFORMATION: Xaa at residues 14 and 43 may be Trp (D or L)
      or bromo-Trp (D or L); Xaa at residues 21, 24 and 45 may be Pro or
      hydroxy-Pro; Xaa at residues 29, 30, 31 adn 33 may be Glu or Gla

<400> SEQUENCE: 90

```
Ser Ser Gly Cys Ser Val Ser Leu Gly Phe Lys Cys Phe Xaa Lys Ser
1               5                   10                  15

Cys Thr Val Ile Xaa Val Arg Xaa Phe Val Ser Leu Xaa Xaa Xaa Asn
            20                  25                  30

Xaa Cys Gln Lys Val Gln Ile Ser Ala Val Xaa Gly Xaa
        35                  40                  45
```

<210> SEQ ID NO 91
<211> LENGTH: 497
<212> TYPE: DNA
<213> ORGANISM: Conus cinereus
<220> FEATURE:
<221> NAME/KEY: CDS
<222> LOCATION: (21)..(263)

<400> SEQUENCE: 91

```
gaattcgccc ttatggatcc atg cag acg gcc tac tgg gtg atg gtg atg atg     53
                     Met Gln Thr Ala Tyr Trp Val Met Val Met Met
                     1               5                   10 gtg gtg gtg tgg att aca gcc cct ctg cct gaa ggt ggt aaa ccg gag       101
Val Val Val Trp Ile Thr Ala Pro Leu Pro Glu Gly Gly Lys Pro Glu
                15                  20                  25 cac gta att cgg ggt ttg gtg cca gac gac tta acc cca cag ctt atc       149
His Val Ile Arg Gly Leu Val Pro Asp Asp Leu Thr Pro Gln Leu Ile
        30                  35                  40 ttg cga agt ctg att tcc cgt cgt agt tct gac ggc aag gca aaa aga       197
Leu Arg Ser Leu Ile Ser Arg Arg Ser Ser Asp Gly Lys Ala Lys Arg
    45                  50                  55 aat tgt ttc tgg aag gca tgt gta cca gaa caa tgg aga caa cgt gat       245
```

```
Asn Cys Phe Trp Lys Ala Cys Val Pro Glu Gln Trp Arg Gln Arg Asp
 60                 65                  70                  75 ctt aag gaa aaa gat gaa tgatgtcaga caaccgccat cactgtagta              293
Leu Lys Glu Lys Asp Glu
                80 tgacatcgtt aatacgactt aagcaaatat tttaacatca ctgtggatct gaagaaatca     353 gttgctttaa aagattggat ttttcctcgt ttaagagttg tactgatgtc agctctgcac     413 tgtgaaataa agctgatgtg acaaacgaaa aaaaaaaaaa aaaaaagta ctctgcgttg      473 ttactcgagc ttaagggcga attc                                            497
```

<210> SEQ ID NO 92
<211> LENGTH: 81
<212> TYPE: PRT
<213> ORGANISM: Conus cinereus

<400> SEQUENCE: 92

```
Met Gln Thr Ala Tyr Trp Val Met Val Met Met Val Val Val Trp Ile
 1               5                  10                  15

Thr Ala Pro Leu Pro Glu Gly Gly Lys Pro Glu His Val Ile Arg Gly
            20                  25                  30

Leu Val Pro Asp Asp Leu Thr Pro Gln Leu Ile Leu Arg Ser Leu Ile
        35                  40                  45

Ser Arg Arg Ser Ser Asp Gly Lys Ala Lys Arg Asn Cys Phe Trp Lys
    50                  55                  60

Ala Cys Val Pro Glu Gln Trp Arg Gln Arg Asp Leu Lys Glu Lys Asp
65                  70                  75                  80

Glu
```

<210> SEQ ID NO 93
<211> LENGTH: 30
<212> TYPE: PRT
<213> ORGANISM: Conus cinereus
<220> FEATURE:
<221> NAME/KEY: PEPTIDE
<222> LOCATION: (1)..(30)
<223> OTHER INFORMATION: Xaa at residues 12 and 20 may be Trp (D or L)
      or bromo-Trp (D or L); Xaa at residue 17 may be Pro or hydroxy-
      Pro; Xaa at residues 18, 27 and 30 may be Glu or Gla

<400> SEQUENCE: 93

```
Ser Ser Asp Gly Lys Ala Lys Arg Asn Cys Phe Xaa Lys Ala Cys Val
 1               5                  10                  15

Xaa Xaa Gln Xaa Arg Gln Arg Asp Leu Lys Xaa Lys Asp Xaa
            20                  25                  30
```

<210> SEQ ID NO 94
<211> LENGTH: 496
<212> TYPE: DNA
<213> ORGANISM: Conus cinereus
<220> FEATURE:
<221> NAME/KEY: CDS
<222> LOCATION: (21)..(263)

<400> SEQUENCE: 94

```
gaattcgccc ttatggatcc atg cag acg gcc tac tgg gtg atg gtg atg atg    53
                     Met Gln Thr Ala Tyr Trp Val Met Val Met Met
                      1               5                  10 atg gtg gtg tgg att aca gcc cct ctg cct gaa ggt ggt aaa ccg aag      101
Met Val Val Trp Ile Thr Ala Pro Leu Pro Glu Gly Gly Lys Pro Lys
            15                  20                  25
```

```
cac gta att cgg ggt ttg gtg cca gac gac tta acc cca cag ctt atc    149
His Val Ile Arg Gly Leu Val Pro Asp Asp Leu Thr Pro Gln Leu Ile
         30                  35                  40 ttg cga agt ctg att tcc cgt cgt agt tct gac ggc aag gca aaa aga    197
Leu Arg Ser Leu Ile Ser Arg Arg Ser Ser Asp Gly Lys Ala Lys Arg
 45                  50                  55 aat tgt ttc tgg aag gca tgt gta cca gaa caa tgg aga caa cgt gat    245
Asn Cys Phe Trp Lys Ala Cys Val Pro Glu Gln Trp Arg Gln Arg Asp
 60                  65                  70                  75 cct aag gaa aaa gat gaa tgatgtcaga caaccgccat cactgtagta           293
Pro Lys Glu Lys Asp Glu
                 80 tgacatcgtt aatacgactt aagcaaatat tttaacatca ctgtggatct gaagaaatca  353 gttgctttaa aagattggat ttttcctcgt ttaagagttg tactgatgtc agctctgcac  413 tgtgaaataa agctgacgtg acaagcaaaa aaaaaaaaaa aaaaagtac tctgcgttgt   473 tactcgagct taagggcgaa ttc                                          496

<210> SEQ ID NO 95
<211> LENGTH: 81
<212> TYPE: PRT
<213> ORGANISM: Conus cinereus

<400> SEQUENCE: 95

Met Gln Thr Ala Tyr Trp Val Met Val Met Met Val Val Trp Ile
1               5                   10                  15

Thr Ala Pro Leu Pro Glu Gly Gly Lys Pro Lys His Val Ile Arg Gly
            20                  25                  30

Leu Val Pro Asp Asp Leu Thr Pro Gln Leu Ile Leu Arg Ser Leu Ile
        35                  40                  45

Ser Arg Arg Ser Ser Asp Gly Lys Ala Lys Arg Asn Cys Phe Trp Lys
    50                  55                  60

Ala Cys Val Pro Glu Gln Trp Arg Gln Arg Asp Pro Lys Glu Lys Asp
65                  70                  75                  80

Glu

<210> SEQ ID NO 96
<211> LENGTH: 30
<212> TYPE: PRT
<213> ORGANISM: Conus cinereus
<220> FEATURE:
<221> NAME/KEY: PEPTIDE
<222> LOCATION: (1)..(30)
<223> OTHER INFORMATION: Xaa at residues 12 and 20 may be Trp (D or L)
      or bromo-Trp (D or L); Xaa at residues 17 and 25 may be Pro or
      hydroxy-Pro; Xaa at residues 18, 27 and 30 may be Glu or Gla

<400> SEQUENCE: 96

Ser Ser Asp Gly Lys Ala Lys Arg Asn Cys Phe Xaa Lys Ala Cys Val
1               5                   10                  15

Xaa Xaa Gln Xaa Arg Gln Arg Asp Xaa Lys Xaa Lys Asp Xaa
            20                  25                  30

<210> SEQ ID NO 97
<211> LENGTH: 493
<212> TYPE: DNA
<213> ORGANISM: Conus cinereus
<220> FEATURE:
<221> NAME/KEY: CDS
<222> LOCATION: (21)..(260)

<400> SEQUENCE: 97
```

```
gaattcgccc ttatggatcc atg cag acg gcc tac tgg gtg atg gtg ata atg         53
                     Met Gln Thr Ala Tyr Trp Val Met Val Ile Met
                     1               5                   10 atg gtg tgg att aca gcc cct ctg tct gaa ggt ggt aaa ccg aag cac           101
Met Val Trp Ile Thr Ala Pro Leu Ser Glu Gly Gly Lys Pro Lys His
            15                  20                  25 gta att cgg ggt ttg gtg cca gtc gac tta acc cca cag ctt atc ttg           149
Val Ile Arg Gly Leu Val Pro Val Asp Leu Thr Pro Gln Leu Ile Leu
        30                  35                  40 cga agt ctg att tcc cgt cgt agt tct gac ggc aag gca aaa aaa caa           197
Arg Ser Leu Ile Ser Arg Arg Ser Ser Asp Gly Lys Ala Lys Lys Gln
    45                  50                  55 tgt gcc tgg aag aca tgt gta cca acc caa tgg aga cga cgt gat ctt           245
Cys Ala Trp Lys Thr Cys Val Pro Thr Gln Trp Arg Arg Arg Asp Leu
60                  65                  70                  75 aag gaa aaa gat gaa tgatgtcaga caaccgccat cactgtagta tgacatcgtt          300
Lys Glu Lys Asp Glu
                80 aatacgactt aagcaaatat tttaacatca ctgtggttct gaagaaatca gttgctttaa        360 aagattggat ttttccttgt ttaagagttg tactgatatc agctctgcac tgtgaaataa        420 agctgatgtg acaaacaaaa aaaaaaaaaa aaaaaagtac tctgcgttgt tactcgagct        480 taagggcgaa ttc                                                           493

<210> SEQ ID NO 98
<211> LENGTH: 80
<212> TYPE: PRT
<213> ORGANISM: Conus cinereus

<400> SEQUENCE: 98

Met Gln Thr Ala Tyr Trp Val Met Val Ile Met Met Val Trp Ile Thr
1               5                   10                  15

Ala Pro Leu Ser Glu Gly Gly Lys Pro Lys His Val Ile Arg Gly Leu
            20                  25                  30

Val Pro Val Asp Leu Thr Pro Gln Leu Ile Leu Arg Ser Leu Ile Ser
        35                  40                  45

Arg Arg Ser Ser Asp Gly Lys Ala Lys Lys Gln Cys Ala Trp Lys Thr
    50                  55                  60

Cys Val Pro Thr Gln Trp Arg Arg Arg Asp Leu Lys Glu Lys Asp Glu
65                  70                  75                  80

<210> SEQ ID NO 99
<211> LENGTH: 30
<212> TYPE: PRT
<213> ORGANISM: Conus cinereus
<220> FEATURE:
<221> NAME/KEY: PEPTIDE
<222> LOCATION: (1)..(30)
<223> OTHER INFORMATION: Xaa at residues 12 and 20 may be Trp (D or L)
      or bromo-Trp (D or L); Xaa at residue 17 may be Pro or hydroxy-
      Pro; Xaa at residues 27 and 30 may be Glu or Gla

<400> SEQUENCE: 99

Ser Ser Asp Gly Lys Ala Lys Lys Gln Cys Ala Xaa Lys Thr Cys Val
1               5                   10                  15

Xaa Thr Gln Xaa Arg Arg Arg Asp Leu Lys Xaa Lys Asp Xaa
            20                  25                  30

<210> SEQ ID NO 100
<211> LENGTH: 496
```

```
<212> TYPE: DNA
<213> ORGANISM: Conus circumcisus
<220> FEATURE:
<221> NAME/KEY: CDS
<222> LOCATION: (21)..(263)

<400> SEQUENCE: 100
gaattcgccc ttatggatcc atg cag acg gcc tac tgg gtg atg gtg atg atg      53
                      Met Gln Thr Ala Tyr Trp Val Met Val Met Met
                       1               5                  10 atg gtg tgg att aca gcc cct ctg tct gaa ggt ggt aaa ttg aac gac        101
Met Val Trp Ile Thr Ala Pro Leu Ser Glu Gly Gly Lys Leu Asn Asp
            15                  20                  25 gta att cgg ggt ttg gtg cca cac atc tta acc cca cag cat atc ttg        149
Val Ile Arg Gly Leu Val Pro His Ile Leu Thr Pro Gln His Ile Leu
         30                  35                  40 caa ggt ctg act tcc cgt ctt cgt tct gac agc agt ggt cag aaa gga        197
Gln Gly Leu Thr Ser Arg Leu Arg Ser Asp Ser Ser Gly Gln Lys Gly
     45                  50                  55 gca caa ata tgc atc tgg aag gta tgt cca cta tcc cca tgg aga cga        245
Ala Gln Ile Cys Ile Trp Lys Val Cys Pro Leu Ser Pro Trp Arg Arg
 60                  65                  70                  75 cca caa gga aaa gat gaa tgacgtcaga caaccgctac aactgtagta               293
Pro Gln Gly Lys Asp Glu
                80 cgacatcgtt gatacgactt cagcaaatat tttaacatca ctgtggttgt gaagaaatca      353 gctgctttaa aagattggat ttttccttgt ttaagagttg tactgatatc agctctgcac      413 tatgaaataa agctgatgtg acaaacaaaa aaaaaaaaa aaaaaagtac tctgcgttgt       473 tactcgagct taagggcgaa ttc                                              496

<210> SEQ ID NO 101
<211> LENGTH: 81
<212> TYPE: PRT
<213> ORGANISM: Conus circumcisus

<400> SEQUENCE: 101

Met Gln Thr Ala Tyr Trp Val Met Val Met Met Val Trp Ile Thr
 1               5                  10                  15

Ala Pro Leu Ser Glu Gly Gly Lys Leu Asn Asp Val Ile Arg Gly Leu
                 20                  25                  30

Val Pro His Ile Leu Thr Pro Gln His Ile Leu Gln Gly Leu Thr Ser
             35                  40                  45

Arg Leu Arg Ser Asp Ser Ser Gly Gln Lys Gly Ala Gln Ile Cys Ile
         50                  55                  60

Trp Lys Val Cys Pro Leu Ser Pro Trp Arg Arg Pro Gln Gly Lys Asp
 65                  70                  75                  80

Glu

<210> SEQ ID NO 102
<211> LENGTH: 32
<212> TYPE: PRT
<213> ORGANISM: Conus circumcisus
<220> FEATURE:
<221> NAME/KEY: PEPTIDE
<222> LOCATION: (1)..(32)
<223> OTHER INFORMATION: Xaa at residues 16 and 24 may be Trp (D or L)
      or bromo-Trp (D or L); Xaa at residues 20, 23 and 27 may be Pro or
      hydroxy-Pro; Xaa at residue 32 may be Glu or Gla

<400> SEQUENCE: 102
```

```
Leu Arg Ser Asp Ser Ser Gly Gln Lys Gly Ala Gln Ile Cys Ile Xaa
1               5                   10                  15

Lys Val Cys Xaa Leu Ser Xaa Xaa Arg Arg Xaa Gln Gly Lys Asp Xaa
            20                  25                  30
```

```
<210> SEQ ID NO 103
<211> LENGTH: 496
<212> TYPE: DNA
<213> ORGANISM: Conus consors
<220> FEATURE:
<221> NAME/KEY: CDS
<222> LOCATION: (21)..(242)

<400> SEQUENCE: 103
gaattcgccc ttatggatcc atg cag acg gcc tac tgg gtg atg gtg atg atg      53
                     Met Gln Thr Ala Tyr Trp Val Met Val Met Met
                      1               5                   10 atg gtg tgg att aca gcc cct ctg tct gaa ggt ggt aaa ttg aac gac       101
Met Val Trp Ile Thr Ala Pro Leu Ser Glu Gly Gly Lys Leu Asn Asp
            15                  20                  25 gta att cgg ggt ttg gtg cca cac ttc tta acc cca cag cat atc ttg       149
Val Ile Arg Gly Leu Val Pro His Phe Leu Thr Pro Gln His Ile Leu
        30                  35                  40 caa agt ctg act tcc cgt aat ggt tct ggc agc agt aat cag aaa gaa       197
Gln Ser Leu Thr Ser Arg Asn Gly Ser Gly Ser Ser Asn Gln Lys Glu
    45                  50                  55 gca caa cta tgc atc tgg aag gta tgt cca cca acc cca tgg aga           242
Ala Gln Leu Cys Ile Trp Lys Val Cys Pro Pro Thr Pro Trp Arg
60                  65                  70 tgaccacaag gaaaagatg aacggcgtca gacaaccgcc acaactgtag tgggacatcg      302
ttgatacgac ttcagcaaat attttaacat cactgtggtt gtgaagaaat cagttgtttt    362
aaaagattgg attttccctt gtttaagagt tgtactgata tcagctctgc actatgaaat    422
aaagctgatg tgacaagcaa aaaaaaaaaa aaaaaagta ctctgcgttg ttactcgagc     482
ttaagggcga attc                                                       496
```

```
<210> SEQ ID NO 104
<211> LENGTH: 74
<212> TYPE: PRT
<213> ORGANISM: Conus consors

<400> SEQUENCE: 104

Met Gln Thr Ala Tyr Trp Val Met Val Met Met Val Trp Ile Thr
1               5                   10                  15

Ala Pro Leu Ser Glu Gly Gly Lys Leu Asn Asp Val Ile Arg Gly Leu
            20                  25                  30

Val Pro His Phe Leu Thr Pro Gln His Ile Leu Gln Ser Leu Thr Ser
        35                  40                  45

Arg Asn Gly Ser Gly Ser Ser Asn Gln Lys Glu Ala Gln Leu Cys Ile
    50                  55                  60

Trp Lys Val Cys Pro Pro Thr Pro Trp Arg
65                  70
```

```
<210> SEQ ID NO 105
<211> LENGTH: 25
<212> TYPE: PRT
<213> ORGANISM: Conus consors
<220> FEATURE:
<221> NAME/KEY: PEPTIDE
<222> LOCATION: (1)..(25)
<223> OTHER INFORMATION: Xaa at residue 10 may be Glu or Gla; Xaa at
```

-continued residues 16 and 24 may be Trp (D or L) or bromo-Trp (D or L); Xaa
at residues 20, 21 and 23 may be Pro or hydroxy-Pro

<400> SEQUENCE: 105

```
Asn Gly Ser Gly Ser Ser Asn Gln Lys Xaa Ala Gln Leu Cys Ile Xaa
1               5                   10                  15
Lys Val Cys Xaa Xaa Thr Xaa Xaa Arg
            20                  25
```

<210> SEQ ID NO 106
<211> LENGTH: 496
<212> TYPE: DNA
<213> ORGANISM: Conus consors
<220> FEATURE:
<221> NAME/KEY: CDS
<222> LOCATION: (21)..(242)

<400> SEQUENCE: 106

```
gaattcgccc ttatggatcc atg cag acg gcc tac tgg gtg atg gtg atg atg      53
                      Met Gln Thr Ala Tyr Trp Val Met Val Met Met
                      1               5                   10 atg gtg tgg att aca gcc cct ctg tct gaa ggt ggt aaa ctg aac ggc       101
Met Val Trp Ile Thr Ala Pro Leu Ser Glu Gly Gly Lys Leu Asn Gly
            15                  20                  25 gta att cgg ggt ttg gtg tca cac atc tta atc cca cag cat acc ttg       149
Val Ile Arg Gly Leu Val Ser His Ile Leu Ile Pro Gln His Thr Leu
        30                  35                  40 cga agt ctg act tcc cgt gat cgt tct gac aac ggt ggt tcg agt gga       197
Arg Ser Leu Thr Ser Arg Asp Arg Ser Asp Asn Gly Gly Ser Ser Gly
    45                  50                  55 gca caa ata tgc atc tgg aag gta tgt cca cca tcc cca tgg aaa           242
Ala Gln Ile Cys Ile Trp Lys Val Cys Pro Pro Ser Pro Trp Lys
60                  65                  70 tgaccacaag gaaaaagatg aacggcgtca gacaaccacc acaactgtag tgggacatcg     302
ttgatacgac ttcagcaaat attttaacat cactgtggtc gtgaagaaat cagttgcttt     362
aaaagattgg atttttcctt gtttaagagt tgtactgata tcagctctgc actatgaaat     422
aaagctgatg tgacaaacaa aaaaaaaaaa aaaaaagta ctctgcgttg ttactcgagc      482
ttaagggcga attc                                                        496
```

<210> SEQ ID NO 107
<211> LENGTH: 74
<212> TYPE: PRT
<213> ORGANISM: Conus consors

<400> SEQUENCE: 107

```
Met Gln Thr Ala Tyr Trp Val Met Val Met Met Val Trp Ile Thr
1               5                   10                  15
Ala Pro Leu Ser Glu Gly Gly Lys Leu Asn Gly Val Ile Arg Gly Leu
            20                  25                  30
Val Ser His Ile Leu Ile Pro Gln His Thr Leu Arg Ser Leu Thr Ser
        35                  40                  45
Arg Asp Arg Ser Asp Asn Gly Gly Ser Ser Gly Ala Gln Ile Cys Ile
    50                  55                  60
Trp Lys Val Cys Pro Pro Ser Pro Trp Lys
65                  70
```

<210> SEQ ID NO 108
<211> LENGTH: 25
<212> TYPE: PRT

```
<213> ORGANISM: Conus consors
<220> FEATURE:
<221> NAME/KEY: PEPTIDE
<222> LOCATION: (1)..(25)
<223> OTHER INFORMATION: Xaa at residues 16 and 24 may be Trp (D or L)
      or bromo-Trp (D or L); Xaa at residues 20, 21 and 23 may be Pro or
      hydroxy-Pro

<400> SEQUENCE: 108

Asp Arg Ser Asp Asn Gly Gly Ser Ser Gly Ala Gln Ile Cys Ile Xaa
1               5                   10                  15

Lys Val Cys Xaa Xaa Ser Xaa Xaa Lys
            20                  25

<210> SEQ ID NO 109
<211> LENGTH: 459
<212> TYPE: DNA
<213> ORGANISM: Conus coronatus
<220> FEATURE:
<221> NAME/KEY: CDS
<222> LOCATION: (1)..(240)

<400> SEQUENCE: 109 atg cag acg gcc tac tgg gtg atg atg atg atg atg gtg tgg att       48
Met Gln Thr Ala Tyr Trp Val Met Met Met Met Met Val Trp Ile
1               5                   10                  15 aca gcc cct ctg tct gaa ggt ggt aaa ctg aac gac gta att cgg ggt   96
Thr Ala Pro Leu Ser Glu Gly Gly Lys Leu Asn Asp Val Ile Arg Gly
            20                  25                  30 ttg gtg cca gac gac tta acc cta cag cgt atg ttc aaa gct ctg gtt  144
Leu Val Pro Asp Asp Leu Thr Leu Gln Arg Met Phe Lys Ala Leu Val
        35                  40                  45 tcc cat cgt ctt tct gac ggc aga gat tgg acg gga tac ata tgt atc  192
Ser His Arg Leu Ser Asp Gly Arg Asp Trp Thr Gly Tyr Ile Cys Ile
    50                  55                  60 tgg aag gca tgt cca cgt ccc cca tgg atc cca cca aag gga aaa aga  240
Trp Lys Ala Cys Pro Arg Pro Pro Trp Ile Pro Pro Lys Gly Lys Arg
65                  70                  75                  80 tgaatgacgt cagacaaccg ccacaactgt agtacgacat cgttaacaca acttcagcta  300
atattttaac atcactgtgg ttgtgaagaa atcggttgct ttaaaagatt gaatttttcg  360
tttaagagtt gtgctgatac gagctctgca ctatgaaata agctgatgt gacaaacaaa   420 aaaaaaaaaa aaaaaaagta ctctgcgttg ttactcgag                         459

<210> SEQ ID NO 110
<211> LENGTH: 80
<212> TYPE: PRT
<213> ORGANISM: Conus coronatus

<400> SEQUENCE: 110

Met Gln Thr Ala Tyr Trp Val Met Met Met Met Met Val Trp Ile
1               5                   10                  15

Thr Ala Pro Leu Ser Glu Gly Gly Lys Leu Asn Asp Val Ile Arg Gly
            20                  25                  30

Leu Val Pro Asp Asp Leu Thr Leu Gln Arg Met Phe Lys Ala Leu Val
        35                  40                  45

Ser His Arg Leu Ser Asp Gly Arg Asp Trp Thr Gly Tyr Ile Cys Ile
    50                  55                  60

Trp Lys Ala Cys Pro Arg Pro Pro Trp Ile Pro Pro Lys Gly Lys Arg
65                  70                  75                  80
```

-continued

```
<210> SEQ ID NO 111
<211> LENGTH: 26
<212> TYPE: PRT
<213> ORGANISM: Conus coronatus
<220> FEATURE:
<221> NAME/KEY: PEPTIDE
<222> LOCATION: (1)..(26)
<223> OTHER INFORMATION: Xaa at residues 7, 14 and 22 may be Trp or
      bromo-Trp; Xaa at residue 10 may be Tyr, 125I-Tyr, mono-iodo-Tyr,
      di-iodo-Tyr, O-sulpho-Tyr or O-phospho-Tyr; Xaa at residues 18,
      29, 21, 24 and 25 may be Pro or hydroxy-Pro

<400> SEQUENCE: 111

Leu Ser Asp Gly Arg Asp Xaa Thr Gly Xaa Ile Cys Ile Xaa Lys Ala
1               5                   10                  15

Cys Xaa Arg Xaa Xaa Xaa Ile Xaa Xaa Lys
            20                  25

<210> SEQ ID NO 112
<211> LENGTH: 495
<212> TYPE: DNA
<213> ORGANISM: Conus ebraeus
<220> FEATURE:
<221> NAME/KEY: CDS
<222> LOCATION: (21)..(236)

<400> SEQUENCE: 112
gaattcgccc ttatggatcc atg cag acg gcc tac tgg gtg atg atg atg      53
                     Met Gln Thr Ala Tyr Trp Val Met Met Met
                      1               5                  10 atg atg gtg tgg att aca gcc cct ctg tct gaa ggc ggt aaa ctg aac   101
Met Met Val Trp Ile Thr Ala Pro Leu Ser Glu Gly Gly Lys Leu Asn
             15                  20                  25 gac gta att cgg ggt ttg gtg cca gac gac tta acc cta cag cgt atg   149
Asp Val Ile Arg Gly Leu Val Pro Asp Asp Leu Thr Leu Gln Arg Met
         30                  35                  40 ttc aaa agt ctg ttt tcc cat cgt ctt tct ggc ggc aca tat tcg agg   197
Phe Lys Ser Leu Phe Ser His Arg Leu Ser Gly Gly Thr Tyr Ser Arg
     45                  50                  55 gta gac aca tgc atc tgg aag gta tgt cca caa tct cca tagggacgat    246
Val Asp Thr Cys Ile Trp Lys Val Cys Pro Gln Ser Pro
 60                  65                  70 catatggaaa aagatgagtg acatcagaca actgccacaa ctgtagtacg acatcgttaa   306
cacgacttca gctaatattt taacatcact gtggttgtga agaaatcggt tgctttaaaa   366
gattggattt ttccttgttt aagagttgtg ctgatatgag ctctgcacta tgaaataaag   426
ctgatgtgac aaacaaaaaa aaaaaaaaaa aagtactctg cgttgttact cgagcttaag   486
ggcgaattc                                                          495

<210> SEQ ID NO 113
<211> LENGTH: 72
<212> TYPE: PRT
<213> ORGANISM: Conus ebraeus

<400> SEQUENCE: 113

Met Gln Thr Ala Tyr Trp Val Met Met Met Met Met Val Trp Ile
1               5                  10                  15

Thr Ala Pro Leu Ser Glu Gly Gly Lys Leu Asn Asp Val Ile Arg Gly
             20                  25                  30

Leu Val Pro Asp Asp Leu Thr Leu Gln Arg Met Phe Lys Ser Leu Phe
         35                  40                  45

Ser His Arg Leu Ser Gly Gly Thr Tyr Ser Arg Val Asp Thr Cys Ile
```

```
                50              55              60
Trp Lys Val Cys Pro Gln Ser Pro
 65                  70

<210> SEQ ID NO 114
<211> LENGTH: 21
<212> TYPE: PRT
<213> ORGANISM: Conus ebraeus
<220> FEATURE:
<221> NAME/KEY: PEPTIDE
<222> LOCATION: (1)..(21)
<223> OTHER INFORMATION: Xaa at residue 6 may be Tyr, 125I-Tyr, mono-
      iodo-Tyr, di-iodo-Tyr, O-sulpho-Tyr or O-phospho-Tyr; Xaa at
      residue 14 may be Trp (D or L) or bromo-Trp (D or L); Xaa at
      residues 18 and 21 may be Pro or hydroxy-Pro

<400> SEQUENCE: 114

Leu Ser Gly Gly Thr Xaa Ser Arg Val Asp Thr Cys Ile Xaa Lys Val
 1               5                  10                  15

Cys Xaa Gln Ser Xaa
            20

<210> SEQ ID NO 115
<211> LENGTH: 537
<212> TYPE: DNA
<213> ORGANISM: Conus geographus
<220> FEATURE:
<221> NAME/KEY: CDS
<222> LOCATION: (21)..(299)

<400> SEQUENCE: 115
```

| | | |
|---|---|---|
| gaattcgccc ttatggatcc atg cag acg gcc tac tgg gtg atg ctg atg atg | | 53 |
|                      Met Gln Thr Ala Tyr Trp Val Met Leu Met Met | | |
|                       1               5                  10       | | |
| atg gtg tgc atc aca gcc cct ctg cct gaa ggt ggt aaa ccg aac agc | | 101 |
| Met Val Cys Ile Thr Ala Pro Leu Pro Glu Gly Gly Lys Pro Asn Ser | | |
|             15                  20                  25           | | |
| gga att cgg ggt ttg gtg cca aac gac tta act cca cag cat acc ttg | | 149 |
| Gly Ile Arg Gly Leu Val Pro Asn Asp Leu Thr Pro Gln His Thr Leu | | |
|         30                  35                  40               | | |
| cga agt ctg att tcc cgt cgt caa act gac gtt ctg ctg gag gct acc | | 197 |
| Arg Ser Leu Ile Ser Arg Arg Gln Thr Asp Val Leu Leu Glu Ala Thr | | |
|     45                  50                  55                   | | |
| ctt ttg aca aca cca gcc ccc gag cag aga ttg ttc tgc ttc tgg aag | | 245 |
| Leu Leu Thr Thr Pro Ala Pro Glu Gln Arg Leu Phe Cys Phe Trp Lys | | |
|  60                  65                  70                  75  | | |
| tca tgt acg tgg agg ccc tac cct tgg aga cga cgt gat ctt aat gga | | 293 |
| Ser Cys Thr Trp Arg Pro Tyr Pro Trp Arg Arg Arg Asp Leu Asn Gly | | |
|                  80                  85                  90      | | |
| aaa cga tgaatgacgc cagacaaccg ccacaactgt agtacgacat cgttaatacg | | 349 |
| Lys Arg                                                          | | |
| acttcagcaa acattttaac ataactgtgg ttgtgaagaa atcagttgct ttaaaagatt | | 409 |
| ggattttttcc ttgtttcaga gttgtactga tatgagctct gcaccatgaa ataaagctga | | 469 |
| agtgacgaac aaaaaaaaaa aaaaaaaaaa agtactctgc gttgttactc gagcttaagg | | 529 |
| gcgaattc | | 537 |

```
<210> SEQ ID NO 116
<211> LENGTH: 93
<212> TYPE: PRT
<213> ORGANISM: Conus geographus

<400> SEQUENCE: 116
```

-continued

```
Met Gln Thr Ala Tyr Trp Val Met Leu Met Met Val Cys Ile Thr
1               5                   10                  15

Ala Pro Leu Pro Glu Gly Gly Lys Pro Asn Ser Gly Ile Arg Gly Leu
                20                  25                  30

Val Pro Asn Asp Leu Thr Pro Gln His Thr Leu Arg Ser Leu Ile Ser
            35                  40                  45

Arg Arg Gln Thr Asp Val Leu Leu Glu Ala Thr Leu Leu Thr Thr Pro
50                  55                  60

Ala Pro Glu Gln Arg Leu Phe Cys Phe Trp Lys Ser Cys Thr Trp Arg
65                  70                  75                  80

Pro Tyr Pro Trp Arg Arg Asp Leu Asn Gly Lys Arg
                85                  90
```

<210> SEQ ID NO 117
<211> LENGTH: 40
<212> TYPE: PRT
<213> ORGANISM: Conus geographus
<220> FEATURE:
<221> NAME/KEY: PEPTIDE
<222> LOCATION: (1)..(40)
<223> OTHER INFORMATION: Xaa at residue 1 is Gln or pyro-Glu; Xaa at
      residues 7 and 17 may be Glu or Gla; Xaa at residues 14, 16, 31
      and 33 may be Pro or hydroxy-Pro; Xaa at residues 24, 29 and 34
      may be Trp (D or L) or bromo-Trp (D or L)
<220> FEATURE:
<221> NAME/KEY: PEPTIDE
<222> LOCATION: (1)..(40)
<223> OTHER INFORMATION: Xaa at residue 32 may be Tyr, 125I-Tyr, mono-
      iodo-Tyr, di-iodo-Tyr, O-sulpho-Tyr or O-phospho-Tyr

<400> SEQUENCE: 117

```
Xaa Thr Asp Val Leu Leu Xaa Ala Thr Leu Leu Thr Thr Xaa Ala Xaa
1               5                   10                  15

Xaa Gln Arg Leu Phe Cys Phe Xaa Lys Ser Cys Thr Xaa Arg Xaa Xaa
                20                  25                  30

Xaa Xaa Arg Arg Arg Asp Leu Asn
            35                  40
```

<210> SEQ ID NO 118
<211> LENGTH: 457
<212> TYPE: DNA
<213> ORGANISM: Conus gladiator
<220> FEATURE:
<221> NAME/KEY: CDS
<222> LOCATION: (1)..(246)

<400> SEQUENCE: 118

```
atg cag acg gcc tac tgg gtg atg gtg atg atg atg gtg tgg gtt aca      48
Met Gln Thr Ala Tyr Trp Val Met Val Met Met Met Val Trp Val Thr
1               5                   10                  15 gtc cct cga tct gaa ggt ggc acg tgg aac tac tta att cgg ggt ttg      96
Val Pro Arg Ser Glu Gly Gly Thr Trp Asn Tyr Leu Ile Arg Gly Leu
                20                  25                  30 gtg cca gac gac cta acc cca cag ctt acc ttg cat cgt ctg gtt acc    144
Val Pro Asp Asp Leu Thr Pro Gln Leu Thr Leu His Arg Leu Val Thr
            35                  40                  45 cgt cgt cat cct gcc aac gtt aga cag cag ggg aaa ata tgt gta tgg    192
Arg Arg His Pro Ala Asn Val Arg Gln Gln Gly Lys Ile Cys Val Trp
50                  55                  60 aag gtg tgt cca cca tgg cca gta aga tca cct ggt cca cag cca aaa    240
Lys Val Cys Pro Pro Trp Pro Val Arg Ser Pro Gly Pro Gln Pro Lys
65                  70                  75                  80
```

-continued

```
aac aaa tgacgtcaga caaccgccac aactttagta cgacatcgtt gatacaactt      296
Asn Lys cagcaagtat tttaacatca ctgtggctct gaagaaatca gttgctttaa aagattggat   356
ttttccttgt tttagagttt tactgatatc agctctgcac tatgaaataa agatgtgacg   416
aaaaaaaaaa aaaaaaaaag tactctgcgt tgttactcga g                      457
```

<210> SEQ ID NO 119
<211> LENGTH: 82
<212> TYPE: PRT
<213> ORGANISM: Conus gladiator

<400> SEQUENCE: 119

```
Met Gln Thr Ala Tyr Trp Val Met Val Met Met Val Trp Val Thr
1               5                   10                  15

Val Pro Arg Ser Glu Gly Gly Thr Trp Asn Tyr Leu Ile Arg Gly Leu
                20                  25                  30

Val Pro Asp Asp Leu Thr Pro Gln Leu Thr Leu His Arg Leu Val Thr
            35                  40                  45

Arg Arg His Pro Ala Asn Val Arg Gln Gln Gly Lys Ile Cys Val Trp
        50                  55                  60

Lys Val Cys Pro Pro Trp Pro Val Arg Ser Pro Gly Pro Gln Pro Lys
65                  70                  75                  80

Asn Lys
```

<210> SEQ ID NO 120
<211> LENGTH: 32
<212> TYPE: PRT
<213> ORGANISM: Conus gladiator
<220> FEATURE:
<221> NAME/KEY: PEPTIDE
<222> LOCATION: (1)..(32)
<223> OTHER INFORMATION: Xaa at residues 3, 18, 19, 21, 25, 27 and 29
      may be Pro or hydroxy-Pro; Xaa at residues 14 and 20 may be Trp (D
      or L) or bromo-Trp (D or L)

<400> SEQUENCE: 120

```
His Xaa Ala Asn Val Arg Gln Gln Gly Lys Ile Cys Val Xaa Lys Val
1               5                   10                  15

Cys Xaa Xaa Xaa Xaa Val Arg Ser Xaa Gly Xaa Gln Xaa Lys Asn Lys
            20                  25                  30
```

<210> SEQ ID NO 121
<211> LENGTH: 459
<212> TYPE: DNA
<213> ORGANISM: Conus gladiator
<220> FEATURE:
<221> NAME/KEY: CDS
<222> LOCATION: (1)..(246)

<400> SEQUENCE: 121

```
atg cag acg gcc tac tgg gtg atg gtg atg atg atg gtg tgg gtt aca    48
Met Gln Thr Ala Tyr Trp Val Met Val Met Met Met Val Trp Val Thr
1               5                   10                  15 gtc cct cga tct gaa ggt ggc acg tgg aac tac tta att cgg ggt ttg    96
Val Pro Arg Ser Glu Gly Gly Thr Trp Asn Tyr Leu Ile Arg Gly Leu
                20                  25                  30 gtg cca gac gac cta acc cca cag ctt acc ttg cat cgt ctg gtt acc   144
Val Pro Asp Asp Leu Thr Pro Gln Leu Thr Leu His Arg Leu Val Thr
            35                  40                  45 cgt cgt cat cct gcc aac gtt aga cag cag ggg aaa ata tgt gta tgg   192
Arg Arg His Pro Ala Asn Val Arg Gln Gln Gly Lys Ile Cys Val Trp
```

-continued

```
              50                  55                  60
aag gtg tgt cca cca tcg cca gta aga tca cct ggt cca ctg cca aaa      240
Lys Val Cys Pro Pro Ser Pro Val Arg Ser Pro Gly Pro Leu Pro Lys
 65                  70                  75                  80 aac aaa tgacgtcaga caaccgccac aactttagta cgacatcgtt gatacaactt       296
Asn Lys cagcaagtat tttaacatca ctgtggctct gaagaaatca gttgcttaa aagattggat    356 ttttccttgt tttagagttt tactgatatc agctctgcac tatgaaataa agatgtgacg   416
gacaaaaaaa aaaaaaaaaa agtactctgc gttgttactc gag                     459
```

<210> SEQ ID NO 122
<211> LENGTH: 82
<212> TYPE: PRT
<213> ORGANISM: Conus gladiator

<400> SEQUENCE: 122

```
Met Gln Thr Ala Tyr Trp Val Met Val Met Met Val Trp Val Thr
  1               5                  10                  15

Val Pro Arg Ser Glu Gly Gly Thr Trp Asn Tyr Leu Ile Arg Gly Leu
                 20                  25                  30

Val Pro Asp Asp Leu Thr Pro Gln Leu Thr Leu His Arg Leu Val Thr
             35                  40                  45

Arg Arg His Pro Ala Asn Val Arg Gln Gln Gly Lys Ile Cys Val Trp
         50                  55                  60

Lys Val Cys Pro Pro Ser Pro Val Arg Ser Pro Gly Pro Leu Pro Lys
 65                  70                  75                  80

Asn Lys
```

<210> SEQ ID NO 123
<211> LENGTH: 32
<212> TYPE: PRT
<213> ORGANISM: Conus gladiator
<220> FEATURE:
<221> NAME/KEY: PEPTIDE
<222> LOCATION: (1)..(32)
<223> OTHER INFORMATION: Xaa at residues 2, 18, 19, 21, 25, 27 and 29
      may be Pro or hydroxy-Pro; Xaa at residue 14 may be Trp (D or L)
      or bromo-Trp (D or L)

<400> SEQUENCE: 123

```
His Xaa Ala Asn Val Arg Gln Gln Gly Lys Ile Cys Val Xaa Lys Val
  1               5                  10                  15

Cys Xaa Xaa Ser Xaa Val Arg Ser Xaa Gly Xaa Leu Xaa Lys Asn Lys
                 20                  25                  30
```

<210> SEQ ID NO 124
<211> LENGTH: 499
<212> TYPE: DNA
<213> ORGANISM: Conus litoglyphus
<220> FEATURE:
<221> NAME/KEY: CDS
<222> LOCATION: (21)..(254)

<400> SEQUENCE: 124

```
gaattcgccc ttatggatcc atg cag acg gcc tac tgg gtg atg gtg atg atg   53
                      Met Gln Thr Ala Tyr Trp Val Met Val Met Met
                        1               5                  10 atg gtg tgg att aca gcc cct ctg tct gaa ggt gat aaa ttg aac gac     101
Met Val Trp Ile Thr Ala Pro Leu Ser Glu Gly Asp Lys Leu Asn Asp
             15                  20                  25
```

```
gta att cgg ggt ttg gtg cca gat aac tta gcc cca cag ctt gtt ttg      149
Val Ile Arg Gly Leu Val Pro Asp Asn Leu Ala Pro Gln Leu Val Leu
        30                  35                  40 caa agt ctg gat tcc cgt cgt cat cct cac ggc att cgt cag gat gga      197
Gln Ser Leu Asp Ser Arg Arg His Pro His Gly Ile Arg Gln Asp Gly
 45                  50                  55 gcc caa ata tgt atc tgg aag ata tgt cca cca tcc cca tgg aga cga      245
Ala Gln Ile Cys Ile Trp Lys Ile Cys Pro Pro Ser Pro Trp Arg Arg
 60                  65                  70                  75 ctt gga tct taagaaaga aacaattgac gtcagacaac cgccacatct              294
Leu Gly Ser tgagtacgac atcgttaata cgacttcagc aaatatgaaa ttttcagcat cactgtggtt    354
gtgaagaaat cagttgcttt aaaagattgg atttgtcctt gtttaagagt tgtactgatg    414
tcatctctgc actatgaaat aaagctgatg tgaaaaaaaa aaaaaaagt actctgcgtt     474 gttactcgag cttaagggcg aattc                                          499
```

<210> SEQ ID NO 125
<211> LENGTH: 78
<212> TYPE: PRT
<213> ORGANISM: Conus litoglyphus

<400> SEQUENCE: 125

```
Met Gln Thr Ala Tyr Trp Val Met Val Met Met Val Trp Ile Thr
 1               5                  10                  15

Ala Pro Leu Ser Glu Gly Asp Lys Leu Asn Asp Val Ile Arg Gly Leu
                20                  25                  30

Val Pro Asp Asn Leu Ala Pro Gln Leu Val Leu Gln Ser Leu Asp Ser
            35                  40                  45

Arg Arg His Pro His Gly Ile Arg Gln Asp Gly Ala Gln Ile Cys Ile
         50                  55                  60

Trp Lys Ile Cys Pro Pro Ser Pro Trp Arg Arg Leu Gly Ser
65                  70                  75
```

<210> SEQ ID NO 126
<211> LENGTH: 28
<212> TYPE: PRT
<213> ORGANISM: Conus litoglyphus
<220> FEATURE:
<221> NAME/KEY: PEPTIDE
<222> LOCATION: (1)..(28)
<223> OTHER INFORMATION: Xaa at residues 2, 19, 20 and 22 may be Pro or
      hydroxy-Pro; Xaa at residues 15 and 23 may be Trp (D or L) or
      bromo-Trp (D or L)

<400> SEQUENCE: 126

```
His Xaa His Gly Ile Arg Gln Asp Gly Ala Gln Ile Cys Ile Xaa Lys
 1               5                  10                  15

Ile Cys Xaa Xaa Ser Xaa Xaa Arg Arg Leu Gly Ser
                20                  25
```

<210> SEQ ID NO 127
<211> LENGTH: 507
<212> TYPE: DNA
<213> ORGANISM: Conus litoglyphus
<220> FEATURE:
<221> NAME/KEY: CDS
<222> LOCATION: (21)..(254)

<400> SEQUENCE: 127

```
gaattcgccc ttatggatcc atg cag acg gcc tac tgg gtg atg gtg atg atg    53
                       Met Gln Thr Ala Tyr Trp Val Met Val Met Met
```

```
                1               5                       10
atg gtg tgg att aca gcc cct ctg tct gaa ggt gat aaa ttg aac gac        101
Met Val Trp Ile Thr Ala Pro Leu Ser Glu Gly Asp Lys Leu Asn Asp
            15                      20                      25 gta att cgg ggt ttg gtg cca gat aac tta gcc cca cag ctt gtt ttg        149
Val Ile Arg Gly Leu Val Pro Asp Asn Leu Ala Pro Gln Leu Val Leu
        30                      35                      40 caa agt ctg gat tcc cgt cgt cat cct cac ggc att cgt cag gat gga        197
Gln Ser Leu Asp Ser Arg Arg His Pro His Gly Ile Arg Gln Asp Gly
    45                      50                      55 gcc caa ata tgt atc tgg aag ata tgt cca cca tcc cca tgg aaa cga        245
Ala Gln Ile Cys Ile Trp Lys Ile Cys Pro Pro Ser Pro Trp Lys Arg
60                      65                      70                      75 ctt gga tct taagaaaaga acaattgac gtcagacaac cgccacaact                 294
Leu Gly Ser tgagtacgac atcgttaata caacttcagc aaatatgaaa ttttcagcat cactgtggtt      354
gtgaagaaat cagttgcttt aaaggattgg atttgtcctt gtttaagagt tgtactgatg      414
tcatctctgc actatgaaat aaagctgatg tgacaagcaa aaaaaaaaaa aaaaaagtac      474
tctgcgttgt tactcgagct taagggcgaa ttc                                   507
```

<210> SEQ ID NO 128
<211> LENGTH: 78
<212> TYPE: PRT
<213> ORGANISM: Conus litoglyphus

<400> SEQUENCE: 128

```
Met Gln Thr Ala Tyr Trp Val Met Val Met Met Val Trp Ile Thr
1               5                   10                  15

Ala Pro Leu Ser Glu Gly Asp Lys Leu Asn Asp Val Ile Arg Gly Leu
            20                  25                  30

Val Pro Asp Asn Leu Ala Pro Gln Leu Val Leu Gln Ser Leu Asp Ser
        35                  40                  45

Arg Arg His Pro His Gly Ile Arg Gln Asp Gly Ala Gln Ile Cys Ile
    50                  55                  60

Trp Lys Ile Cys Pro Pro Ser Pro Trp Lys Arg Leu Gly Ser
65                  70                  75
```

<210> SEQ ID NO 129
<211> LENGTH: 28
<212> TYPE: PRT
<213> ORGANISM: Conus litoglyphus
<220> FEATURE:
<221> NAME/KEY: PEPTIDE
<222> LOCATION: (1)..(28)
<223> OTHER INFORMATION: Xaa at residues 2, 19, 20 and 22 may be Pro or
      hydroxy-Pro; Xaa at residues 15 and 23 may be Trp (D or L) or
      bromo-Trp (D or L)

<400> SEQUENCE: 129

```
His Xaa His Gly Ile Arg Gln Asp Gly Ala Gln Ile Cys Ile Xaa Lys
1               5                   10                  15

Ile Cys Xaa Xaa Ser Xaa Xaa Lys Arg Leu Gly Ser
            20                  25
```

<210> SEQ ID NO 130
<211> LENGTH: 507
<212> TYPE: DNA
<213> ORGANISM: Conus litteratus
<220> FEATURE:
<221> NAME/KEY: CDS

```
<222> LOCATION: (21)..(299)

<400> SEQUENCE: 130
gaattcgccc ttatggatcc atg cag acg gcc tac tgg gtg atg gtg atg atg        53
                     Met Gln Thr Ala Tyr Trp Val Met Val Met Met
                      1               5                  10 atg gtg ggg att aca gcc cct ctg tct gaa ggt cgt aaa ttg aac gac         101
Met Val Gly Ile Thr Ala Pro Leu Ser Glu Gly Arg Lys Leu Asn Asp
             15                  20                  25 gca att cgg ggt ttg gtg cca gat gac tta acc cca cag ctt ttg cga         149
Ala Ile Arg Gly Leu Val Pro Asp Asp Leu Thr Pro Gln Leu Leu Arg
         30                  35                  40 agt ccg gtt tcg act cct tat cct gag ttt cat ctt gat gaa cct tat         197
Ser Pro Val Ser Thr Pro Tyr Pro Glu Phe His Leu Asp Glu Pro Tyr
     45                  50                  55 ctg aag ata ccc gta tgt atc tgg aag ata tgt cca cca aac cta ttg         245
Leu Lys Ile Pro Val Cys Ile Trp Lys Ile Cys Pro Pro Asn Leu Leu
 60                  65                  70                  75 aga cga cgt gat ctt aag aaa aga aac aaa gta cgt cag aca acc gcc         293
Arg Arg Arg Asp Leu Lys Lys Arg Asn Lys Val Arg Gln Thr Thr Ala
                 80                  85                  90 aca act tgagtacgac atcgttcata caacttgagc aaatatttca gcatcactat          349
Thr Thr ggttgtgaag aaatcagttg ctttaaaaga ttggatcttt ccttgtttaa gagttgtatt       409
gatgtcagct ctgcactctg aaataaagct gatgtgacaa acaaaaaaaa aaaaaaaaa        469 agtactctgc gttgttactc gagcttaagg gcgaattc                               507

<210> SEQ ID NO 131
<211> LENGTH: 93
<212> TYPE: PRT
<213> ORGANISM: Conus litteratus

<400> SEQUENCE: 131

Met Gln Thr Ala Tyr Trp Val Met Val Met Met Val Gly Ile Thr
 1               5                  10                  15

Ala Pro Leu Ser Glu Gly Arg Lys Leu Asn Asp Ala Ile Arg Gly Leu
                 20                  25                  30

Val Pro Asp Asp Leu Thr Pro Gln Leu Leu Arg Ser Pro Val Ser Thr
             35                  40                  45

Pro Tyr Pro Glu Phe His Leu Asp Glu Pro Tyr Leu Lys Ile Pro Val
         50                  55                  60

Cys Ile Trp Lys Ile Cys Pro Pro Asn Leu Leu Arg Arg Arg Asp Leu
 65                  70                  75                  80

Lys Lys Arg Asn Lys Val Arg Gln Thr Thr Ala Thr Thr
                 85                  90

<210> SEQ ID NO 132
<211> LENGTH: 50
<212> TYPE: PRT
<213> ORGANISM: Conus litteratus
<220> FEATURE:
<221> NAME/KEY: PEPTIDE
<222> LOCATION: (1)..(50)
<223> OTHER INFORMATION: Xaa at residues 2, 6, 8, 15, 20, 28 and 29 may
      be Pro or hydroxy-Pro; Xaa at residues 7 and 16 may be Tyr, 125I-
      Tyr, mono-iodo-Tyr, di-iodo-Tyr, O-sulpho-Tyr or O-phospho-Tyr;
      Xaa at residues 9 and 14 may be Glu or Gla
<220> FEATURE:
<221> NAME/KEY: PEPTIDE
<222> LOCATION: (1)..(50)
<223> OTHER INFORMATION: Xaa at residue 24 may be Trp (D or L) or bromo-
```

-continued

Trp (D or L)

<400> SEQUENCE: 132

Ser Xaa Val Ser Thr Xaa Xaa Xaa Xaa Phe His Leu Asp Xaa Xaa Xaa
1               5                   10                  15

Leu Lys Ile Xaa Val Cys Ile Xaa Lys Ile Cys Xaa Xaa Asn Leu Leu
            20                  25                  30

Arg Arg Arg Asp Leu Lys Lys Arg Asn Lys Val Arg Gln Thr Thr Ala
        35                  40                  45

Thr Thr
    50

<210> SEQ ID NO 133
<211> LENGTH: 508
<212> TYPE: DNA
<213> ORGANISM: Conus litteratus
<220> FEATURE:
<221> NAME/KEY: CDS
<222> LOCATION: (21)..(275)

<400> SEQUENCE: 133
gaattcgccc ttatggatcc atg cag acg gcc tac tgg gtg atg gtg atg atg        53
                     Met Gln Thr Ala Tyr Trp Val Met Val Met Met
                       1               5                  10 atg gtg ggg att aca gcc cct ctg tct gaa ggt cgt aaa ttg aac gac         101
Met Val Gly Ile Thr Ala Pro Leu Ser Glu Gly Arg Lys Leu Asn Asp
            15                  20                  25 gca att cgg ggt ttg gtg cca aat gac tta acc cca cag ctt ttg caa        149
Ala Ile Arg Gly Leu Val Pro Asn Asp Leu Thr Pro Gln Leu Leu Gln
        30                  35                  40 agt ctg gtt tcc cgt cgt cat cgt gtg ttt cat ctt gac aac act tat        197
Ser Leu Val Ser Arg Arg His Arg Val Phe His Leu Asp Asn Thr Tyr
    45                  50                  55 ctc aag ata ccc ata tgt gcc tgg aag gta tgt cca cca acc cca tgg        245
Leu Lys Ile Pro Ile Cys Ala Trp Lys Val Cys Pro Pro Thr Pro Trp
60                  65                  70                  75 aga cga cgt gat ctt aag aaa aga aac aaa tgacgtcaga caaccgccac           295
Arg Arg Arg Asp Leu Lys Lys Arg Asn Lys
                80                  85 aacttgagta cgacattgtt aatgcgactt gagcaaattt ttcagcatca ctatggttgt       355
aaagaaatca gctgctttaa acgattggat ctttccttat ttaagagttg tattgatgtc       415
agctctgcac tctgaaataa agctgatgtg acaaacaaaa aaaaaaaaaa aaaaaagtac       475
tctgcgttgt tactcgagct taagggcgaa ttc                                    508

<210> SEQ ID NO 134
<211> LENGTH: 85
<212> TYPE: PRT
<213> ORGANISM: Conus litteratus

<400> SEQUENCE: 134

Met Gln Thr Ala Tyr Trp Val Met Val Met Met Val Gly Ile Thr
1               5                   10                  15

Ala Pro Leu Ser Glu Gly Arg Lys Leu Asn Asp Ala Ile Arg Gly Leu
            20                  25                  30

Val Pro Asn Asp Leu Thr Pro Gln Leu Leu Gln Ser Leu Val Ser Arg
        35                  40                  45

Arg His Arg Val Phe His Leu Asp Asn Thr Tyr Leu Lys Ile Pro Ile
    50                  55                  60

```
Cys Ala Trp Lys Val Cys Pro Pro Thr Pro Trp Arg Arg Arg Asp Leu
 65                  70                  75                  80

Lys Lys Arg Asn Lys
                 85
```

<210> SEQ ID NO 135
<211> LENGTH: 36
<212> TYPE: PRT
<213> ORGANISM: Conus litteratus
<220> FEATURE:
<221> NAME/KEY: PEPTIDE
<222> LOCATION: (1)..(36)
<223> OTHER INFORMATION: Xaa at residue 10 may be Tyr, 125I-Tyr, mono-
     iodo-Tyr, di-iodo-Tyr, O-sulpho-Tyr or O-phospho-Tyr; Xaa at
     residues 14, 22, 23 and 25 may be Pro or hydroxy-Pro; Xaa at
     residues 18 and 26 may be Trp (D or L) or bromo-Trp (D or L)

<400> SEQUENCE: 135

```
His Arg Val Phe His Leu Asp Asn Thr Xaa Leu Lys Ile Xaa Ile Cys
 1               5                  10                  15

Ala Xaa Lys Val Cys Xaa Xaa Thr Xaa Xaa Arg Arg Arg Asp Leu Lys
                 20                  25                  30

Lys Arg Asn Lys
             35
```

<210> SEQ ID NO 136
<211> LENGTH: 498
<212> TYPE: DNA
<213> ORGANISM: Conus loroisii
<220> FEATURE:
<221> NAME/KEY: CDS
<222> LOCATION: (21)..(236)
<220> FEATURE:
<221> NAME/KEY: misc_feature
<222> LOCATION: (1)..(498)
<223> OTHER INFORMATION: n may be any base

<400> SEQUENCE: 136

```
gaattcgccc ttatggatcc atg cag acg gcc tac tgg gtg atg gtg atg atg         53
                     Met Gln Thr Ala Tyr Trp Val Met Val Met Met
                       1               5                  10 atg gtg tgg att aaa ggc cct gtg tct gaa ggt ggt aaa ttg aac gac          101
Met Val Trp Ile Lys Gly Pro Val Ser Glu Gly Gly Lys Leu Asn Asp
             15                  20                  25 gta att cgg ggt ttg gtg cca gac gac tta acc cca cag ctt atc ttg          149
Val Ile Arg Gly Leu Val Pro Asp Asp Leu Thr Pro Gln Leu Ile Leu
         30                  35                  40 caa agt ctg atg tcc cgt cgt cgt tct gac agc gat gtt cgg gag gtg          197
Gln Ser Leu Met Ser Arg Arg Arg Ser Asp Ser Asp Val Arg Glu Val
     45                  50                  55 tac ata tta tgc atc tgg aag ata tgt cca cca ttg cca tgaagacgac           246
Tyr Ile Leu Cys Ile Trp Lys Ile Cys Pro Pro Leu Pro
 60                  65                  70 atgatcttaa ggaaaaggat aaacgacgtc agacaaccgc tacaactgta gtacgacatc        306
gttaatacga cttcagcaaa tatttgaaca tcactgtggt tgtgaagaaa tcagttgctt        366
taaacgattg gatttttcct taagagttgc actgatatca gctctgcact atgaaataaa        426
gctgatgtga ctaccaaaaa aaaaaaaaaa aaaaagtact ntgcgttgtt actcgagctt        486
aagggcgaat tc                                                            498
```

<210> SEQ ID NO 137
<211> LENGTH: 72
<212> TYPE: PRT

<213> ORGANISM: Conus loroisii
<220> FEATURE:
<221> NAME/KEY: misc_feature
<222> LOCATION: (1)..(498)
<223> OTHER INFORMATION: n may be any base

<400> SEQUENCE: 137

```
Met Gln Thr Ala Tyr Trp Val Met Val Met Met Val Trp Ile Lys
1               5                   10                  15

Gly Pro Val Ser Glu Gly Gly Lys Leu Asn Asp Val Ile Arg Gly Leu
                20                  25                  30

Val Pro Asp Leu Thr Pro Gln Leu Ile Leu Gln Ser Leu Met Ser
            35                  40                  45

Arg Arg Arg Ser Asp Ser Asp Val Arg Glu Val Tyr Ile Leu Cys Ile
    50                  55                  60

Trp Lys Ile Cys Pro Pro Leu Pro
65                  70
```

<210> SEQ ID NO 138
<211> LENGTH: 22
<212> TYPE: PRT
<213> ORGANISM: Conus loroisii
<220> FEATURE:
<221> NAME/KEY: PEPTIDE
<222> LOCATION: (1)..(22)
<223> OTHER INFORMATION: Xaa at residue 8 may be Glu or Gla; Xaa at
      residue 10 may be Tyr, 125I-Tyr, mono-iodo-Tyr, di-iodo-Tyr, O-
      sulpho-Tyr or O-phospho-Tyr; Xaa at residue 15 may be Trp (D or L)
      or bromo-Trp (D or L); Xaa at residues 19, 20 and 22 may be Pro or
      hydroxy-Pro

<400> SEQUENCE: 138

```
Arg Ser Asp Ser Asp Val Arg Xaa Val Xaa Ile Leu Cys Ile Xaa Lys
1               5                   10                  15

Ile Cys Xaa Xaa Leu Xaa
            20
```

<210> SEQ ID NO 139
<211> LENGTH: 495
<212> TYPE: DNA
<213> ORGANISM: Conus magus
<220> FEATURE:
<221> NAME/KEY: CDS
<222> LOCATION: (21)..(242)

<400> SEQUENCE: 139

```
gaattcgccc ttatggatcc atg cag acg gcc tac tgg gtg atg gtg atg atg       53
                     Met Gln Thr Ala Tyr Trp Val Met Val Met Met
                      1               5                  10 atg gtg tgg att aca gcc cct ctg tct gaa ggt ggt aaa ttg aac gac         101
Met Val Trp Ile Thr Ala Pro Leu Ser Glu Gly Gly Lys Leu Asn Asp
            15                  20                  25 gta att cgg ggt ttg gtg cca cac tcc tta acc cca cag cat atc ttg         149
Val Ile Arg Gly Leu Val Pro His Ser Leu Thr Pro Gln His Ile Leu
            30                  35                  40 caa agt ctg act tcc cgt aat ggt tct ggc agc agc aat cag aaa gaa         197
Gln Ser Leu Thr Ser Arg Asn Gly Ser Gly Ser Ser Asn Gln Lys Glu
    45                  50                  55 gca caa cta tgc atc tgg aag gta tgt cca cca tcc cca tgg aga             242
Ala Gln Leu Cys Ile Trp Lys Val Cys Pro Pro Ser Pro Trp Arg
60                  65                  70 tgaccacaag gaaaaagatg aacggcgtca gacaaccgcc acaactgtag tgggacatcg       302
ttgatacgac ttcaacaaat attttaacat cactgtggtt gtaaagaaat cagttgcttt       362
```

-continued

```
aaaagattgg atttttcctt gtttaagagt tgtactgata tcagctctgc actatgaaat      422
aaagctgatg tgacaaacaa aaaaaaaaaa aaaaaagtac tctgcgttgt tactcgagct      482
taagggcgaa ttc                                                         495
```

<210> SEQ ID NO 140
<211> LENGTH: 74
<212> TYPE: PRT
<213> ORGANISM: Conus magus

<400> SEQUENCE: 140

```
Met Gln Thr Ala Tyr Trp Val Met Val Met Met Val Trp Ile Thr
1               5                   10                  15

Ala Pro Leu Ser Glu Gly Gly Lys Leu Asn Asp Val Ile Arg Gly Leu
            20                  25                  30

Val Pro His Ser Leu Thr Pro Gln His Ile Leu Gln Ser Leu Thr Ser
        35                  40                  45

Arg Asn Gly Ser Gly Ser Ser Asn Gln Lys Glu Ala Gln Leu Cys Ile
    50                  55                  60

Trp Lys Val Cys Pro Pro Ser Pro Trp Arg
65                  70
```

<210> SEQ ID NO 141
<211> LENGTH: 25
<212> TYPE: PRT
<213> ORGANISM: Conus magus
<220> FEATURE:
<221> NAME/KEY: PEPTIDE
<222> LOCATION: (1)..(25)
<223> OTHER INFORMATION: Xaa at residue 10 may be Glu or Gla; Xaa at
      residues 16 and 24 may be Trp (D or L) or bromo-Trp (D or L); Xaa
      at residues 20, 21 and 23 may be Pro or hydroxy-Pro

<400> SEQUENCE: 141

```
Asn Gly Ser Gly Ser Ser Asn Gln Lys Xaa Ala Gln Leu Cys Ile Xaa
1               5                   10                  15

Lys Val Cys Xaa Xaa Ser Xaa Xaa Arg
            20                  25
```

<210> SEQ ID NO 142
<211> LENGTH: 587
<212> TYPE: DNA
<213> ORGANISM: Conus miles
<220> FEATURE:
<221> NAME/KEY: CDS
<222> LOCATION: (21)..(347)
<220> FEATURE:
<221> NAME/KEY: misc_feature
<222> LOCATION: (1)..(587)
<223> OTHER INFORMATION: n may be any nucleotide

<400> SEQUENCE: 142

```
gaattcgccc ttatggatcc atg cag acg gcc tac tgg gtg atg atg atg gtg    53
                     Met Gln Thr Ala Tyr Trp Val Met Met Met Val
                      1               5                  10 gtg atg atg gtg ggg gtt act gtc gct ggc tcc ctg cct gtg ttt gat      101
Val Met Met Val Gly Val Thr Val Ala Gly Ser Leu Pro Val Phe Asp
            15                  20                  25 gac gac aac gac tct gac ccc gct gtc aag cgc gct atc acg tgg tcc      149
Asp Asp Asn Asp Ser Asp Pro Ala Val Lys Arg Ala Ile Thr Trp Ser
        30                  35                  40 cgc atc ctg ggc gtg tct cca gcc ttc ctg gca cag cag cga gcg ctg      197
Arg Ile Leu Gly Val Ser Pro Ala Phe Leu Ala Gln Gln Arg Ala Leu
```

```
                45                  50                  55
gtt ccc ttc gcc aac cga ttc atc agt gag cag aaa cgt ttc cga ccc        245
Val Pro Phe Ala Asn Arg Phe Ile Ser Glu Gln Lys Arg Phe Arg Pro
 60                  65                  70                  75 gcc atg cag agc cga tca gga gga atg tcg ctg tgc cta tgg aaa gtg        293
Ala Met Gln Ser Arg Ser Gly Gly Met Ser Leu Cys Leu Trp Lys Val
                 80                  85                  90 tgt cct gca gcc ccc tgg ctg gtc gcc aaa cgt aaa cag gaa acc agc        341
Cys Pro Ala Ala Pro Trp Leu Val Ala Lys Arg Lys Gln Glu Thr Ser
             95                 100                 105 gac tac tgacgtcata cctctaaaga cccactcatg acgtcaacgc tgaactgacg         397
Asp Tyr tcaccgacag ctccaacgtc acagcaggag cgagagagag gctggagcat ttctctttct       457
tttggttttt cgagttgaag tgtgatcagc tgggctggtg aaaaaattgt tgagtaaagt       517
tgaatgaaaa tcaaaaaaaa aaaaaaaaaa agtactctgc gttggtactc gaggcttaaa       577 ggcgnaattc                                                              587

<210> SEQ ID NO 143
<211> LENGTH: 109
<212> TYPE: PRT
<213> ORGANISM: Conus miles
<220> FEATURE:
<221> NAME/KEY: misc_feature
<222> LOCATION: (1)..(587)
<223> OTHER INFORMATION: n may be any nucleotide

<400> SEQUENCE: 143

Met Gln Thr Ala Tyr Trp Val Met Met Val Val Met Met Val Gly
 1               5                  10                  15

Val Thr Val Ala Gly Ser Leu Pro Val Phe Asp Asp Asp Asn Asp Ser
                 20                  25                  30

Asp Pro Ala Val Lys Arg Ala Ile Thr Trp Ser Arg Ile Leu Gly Val
             35                  40                  45

Ser Pro Ala Phe Leu Ala Gln Gln Arg Ala Leu Val Pro Phe Ala Asn
         50                  55                  60

Arg Phe Ile Ser Glu Gln Lys Arg Phe Arg Pro Ala Met Gln Ser Arg
 65                  70                  75                  80

Ser Gly Gly Met Ser Leu Cys Leu Trp Lys Val Cys Pro Ala Ala Pro
                 85                  90                  95

Trp Leu Val Ala Lys Arg Lys Gln Glu Thr Ser Asp Tyr
            100                 105

<210> SEQ ID NO 144
<211> LENGTH: 37
<212> TYPE: PRT
<213> ORGANISM: Conus miles
<220> FEATURE:
<221> NAME/KEY: PEPTIDE
<222> LOCATION: (1)..(37)
<223> OTHER INFORMATION: Xaa at residues 3, 21 and 24 may be Pro or
      hydroxy-Pro; Xaa at residues 17 and 25 may be Trp (D or L) or
      bromo-Trp (D or L); Xaa at residue 33 may be Glu or Gla;
<220> FEATURE:
<221> NAME/KEY: PEPTIDE
<222> LOCATION: (1)..(37)
<223> OTHER INFORMATION: Xaa at residue 37 may be Tyr, 125I-Tyr, mono-
      iodo-Tyr, di-iodo-Tyr, O-sulpho-Tyr or O-phospho-Tyr

<400> SEQUENCE: 144

Phe Arg Xaa Ala Met Gln Ser Arg Ser Gly Gly Met Ser Leu Cys Leu
 1               5                  10                  15
```

Xaa Lys Val Cys Xaa Ala Ala Xaa Xaa Leu Val Ala Lys Arg Lys Gln
           20                  25                  30

Xaa Thr Ser Asp Xaa
        35

<210> SEQ ID NO 145
<211> LENGTH: 499
<212> TYPE: DNA
<213> ORGANISM: Conus miles
<220> FEATURE:
<221> NAME/KEY: CDS
<222> LOCATION: (21)..(401)

<400> SEQUENCE: 145

| | | |
|---|---|---|
| gaattcgccc ttatggatcc atg cag acg gcc tac tgg gtg atg gtg atg atg<br>                                       Met Gln Thr Ala Tyr Trp Val Met Val Met Met<br>                                         1              5                     10 | 53 |

```
atg gtg gtg ggt tca ccg tcg gga gtc acg tcc atc ggt ctc aca gtc      101
Met Val Val Gly Ser Pro Ser Gly Val Thr Ser Ile Gly Leu Thr Val
            15                  20                  25 cta cgt cgc gca acc atg gtg atg act cca ttc atg aca aga cga ttc      149
Leu Arg Arg Ala Thr Met Val Met Thr Pro Phe Met Thr Arg Arg Phe
        30                  35                  40 atc aac atc tgt ttg ccc gtc ttc ctc tgg aga aca acg acc atc          197
Ile Asn Ile Cys Leu Pro Val Phe Leu Trp Arg Thr Thr Thr Ile
    45                  50                  55 gtt ctg tgg atc ttc ctg cag tgt atg cgc cgg gcc agg cac gtg tgc      245
Val Leu Trp Ile Phe Leu Gln Cys Met Arg Arg Ala Arg His Val Cys
60                  65                  70                  75 gtt cta ctt ttg ttc ttg acc tca ttg cag ata ggg gtt ggt gca gac      293
Val Leu Leu Leu Phe Leu Thr Ser Leu Gln Ile Gly Val Gly Ala Asp
                80                  85                  90 gac atg aaa cta cag cgc caa aga cgt caa ggt ttc tgt tgc gtc gtt      341
Asp Met Lys Leu Gln Arg Gln Arg Arg Gln Gly Phe Cys Cys Val Val
            95                 100                 105 atc ccg att ctt tgg ttc tgt tgt ggg ggt tac cgc aca aat ggc act      389
Ile Pro Ile Leu Trp Phe Cys Cys Gly Gly Tyr Arg Thr Asn Gly Thr
        110                 115                 120 gca ctg gcc gat tgaaagaact gcaataaacg gaatggcaag aaggaataaa          441
Ala Leu Ala Asp
    125 aaaaaaaaaa aaaaaaaaaa agtactctgc gttgttactc gagcttaagg gcgaattc      499
```

<210> SEQ ID NO 146
<211> LENGTH: 127
<212> TYPE: PRT
<213> ORGANISM: Conus miles

<400> SEQUENCE: 146

Met Gln Thr Ala Tyr Trp Val Met Val Met Met Val Val Gly Ser
1               5                   10                  15

Pro Ser Gly Val Thr Ser Ile Gly Leu Thr Val Leu Arg Arg Ala Thr
            20                  25                  30

Met Val Met Thr Pro Phe Met Thr Arg Arg Phe Ile Asn Ile Cys Leu
        35                  40                  45

Pro Val Phe Leu Trp Arg Thr Thr Thr Ile Val Leu Trp Ile Phe
    50                  55                  60

Leu Gln Cys Met Arg Arg Ala Arg His Val Cys Val Leu Leu Leu Phe
65                  70                  75                  80

```
Leu Thr Ser Leu Gln Ile Gly Val Gly Ala Asp Asp Met Lys Leu Gln
                85                  90                  95

Arg Gln Arg Arg Gln Gly Phe Cys Cys Val Val Ile Pro Ile Leu Trp
            100                 105                 110

Phe Cys Cys Gly Gly Tyr Arg Thr Asn Gly Thr Ala Leu Ala Asp
        115                 120                 125

<210> SEQ ID NO 147
<211> LENGTH: 27
<212> TYPE: PRT
<213> ORGANISM: Conus miles
<220> FEATURE:
<221> NAME/KEY: PEPTIDE
<222> LOCATION: (1)..(27)
<223> OTHER INFORMATION: Xaa at residue 1 is Gln or pyro-Glu; Xaa at
      residue 9 may be Pro or hydroxy-Pro; Xaa at residue 12 may be Trp
      (D or L) or bromo-Trp (D or L); Xaa at residue 18 may be Tyr,
      125I-Tyr, mono-iodo-Tyr, di-iodo-Tyr, O-sulpho-Tyr or O-phospho-
      Tyr

<400> SEQUENCE: 147

Xaa Gly Phe Cys Cys Val Val Ile Xaa Ile Leu Xaa Phe Cys Cys Gly
1               5                   10                  15

Gly Xaa Arg Thr Asn Gly Thr Ala Leu Ala Asp
            20                  25

<210> SEQ ID NO 148
<211> LENGTH: 450
<212> TYPE: DNA
<213> ORGANISM: Conus muriculatus
<220> FEATURE:
<221> NAME/KEY: CDS
<222> LOCATION: (1)..(237)

<400> SEQUENCE: 148 atg cag acg gcc tac tgg gtg atg gtg atg atg gtg tgg att aca         48
Met Gln Thr Ala Tyr Trp Val Met Val Met Met Val Trp Ile Thr
1               5                   10                  15 gcc cct ttg tct gaa ggt ggt aaa ctg aac gat gta att cgg ggt ttc     96
Ala Pro Leu Ser Glu Gly Gly Lys Leu Asn Asp Val Ile Arg Gly Phe
            20                  25                  30 gcg cta gat gac tta gcc caa agc cgt att atg caa agt ctg gtt ttc    144
Ala Leu Asp Asp Leu Ala Gln Ser Arg Ile Met Gln Ser Leu Val Phe
        35                  40                  45 agt cat cag cct ctt cca acg gca tcc ata tgt atc tgg aag ata tgt    192
Ser His Gln Pro Leu Pro Thr Ala Ser Ile Cys Ile Trp Lys Ile Cys
    50                  55                  60 cca cca gac cca tgg aga cga cat gat ctt cag aaa agt aac aaa        237
Pro Pro Asp Pro Trp Arg Arg His Asp Leu Gln Lys Ser Asn Lys
65                  70                  75 tgacgtcaga caaccgccac aacttgaata caacatcatt aatacgactt cagcaaatat  297
tttaacatca ctgtgattgt tcggaagtca gttgctttaa aggattggat ttgtccctgt  357
tgtattgatg tcaactctgc actatgaaat aaagctgatg tgacaaacaa gaaaaaaaaa  417
aaaaaaaaaa agtactctgc gttgttactc gag                               450

<210> SEQ ID NO 149
<211> LENGTH: 79
<212> TYPE: PRT
<213> ORGANISM: Conus muriculatus

<400> SEQUENCE: 149

Met Gln Thr Ala Tyr Trp Val Met Val Met Met Val Trp Ile Thr
```

```
  1               5                  10                 15
Ala Pro Leu Ser Glu Gly Gly Lys Leu Asn Asp Val Ile Arg Gly Phe
         20                  25                 30

Ala Leu Asp Asp Leu Ala Gln Ser Arg Ile Met Gln Ser Leu Val Phe
         35                  40                 45

Ser His Gln Pro Leu Pro Thr Ala Ser Ile Cys Ile Trp Lys Ile Cys
         50                  55                 60

Pro Pro Asp Pro Trp Arg Arg His Asp Leu Gln Lys Ser Asn Lys
65                  70                  75
```

<210> SEQ ID NO 150
<211> LENGTH: 38
<212> TYPE: PRT
<213> ORGANISM: Conus muriculatus
<220> FEATURE:
<221> NAME/KEY: PEPTIDE
<222> LOCATION: (1)..(38)
<223> OTHER INFORMATION: Xaa at residues 11, 13, 24, 25 and 27 may be
    Pro or hydroxy-Pro; Xaa at residue 20 and 28 may be Trp or bromo-
    Trp

<400> SEQUENCE: 150

```
Ile Met Gln Ser Leu Val Phe Ser His Gln Xaa Leu Xaa Thr Ala Ser
1               5                  10                 15

Ile Cys Ile Xaa Lys Ile Cys Xaa Xaa Asp Xaa Xaa Arg Arg His Asp
         20                  25                 30

Leu Gln Lys Ser Asn Lys
         35
```

<210> SEQ ID NO 151
<211> LENGTH: 437
<212> TYPE: DNA
<213> ORGANISM: Conus musicus
<220> FEATURE:
<221> NAME/KEY: CDS
<222> LOCATION: (1)..(240)

<400> SEQUENCE: 151

```
atg cag acg gcc tac tgg gtg atg atg atg acg atg atg gtg tgg atg     48
Met Gln Thr Ala Tyr Trp Val Met Met Met Thr Met Met Val Trp Met
1               5                  10                 15 aca gcc cct ctg tct gaa ggt cgt cca ctg agc gac gaa gtt cgg ggt     96
Thr Ala Pro Leu Ser Glu Gly Arg Pro Leu Ser Asp Glu Val Arg Gly
         20                  25                 30 atg gtg cca ggc gac ttg gtc cta cag tat ctg ttc cca agt ctg gct    144
Met Val Pro Gly Asp Leu Val Leu Gln Tyr Leu Phe Pro Ser Leu Ala
         35                  40                 45 ttc agt cct ccg gac ata tgt acg tgg aag gta tgt cca cca ccc cca    192
Phe Ser Pro Pro Asp Ile Cys Thr Trp Lys Val Cys Pro Pro Pro Pro
         50                  55                 60 tgg aga cga cca aaa aaa ata aca gac gtc aga cag ccg cca caa ctg    240
Trp Arg Arg Pro Lys Lys Ile Thr Asp Val Arg Gln Pro Pro Gln Leu
65                  70                  75                 80 tagtacgaca tcgttgatac ggcttcagca aatattttca acatcactgc ggttgtgaag    300
aaatcagttg ctttaaaatg ttggattttt ccttgtttaa aagagctgta ctgatgtcag    360
ccctgcatta cgaaataaag ctgatgtgac aaacaaaaaa aaaaaaaaaa aaaaagtact    420
ctgcgttgtt actcgag                                                   437
```

<210> SEQ ID NO 152
<211> LENGTH: 80

```
<212> TYPE: PRT
<213> ORGANISM: Conus musicus

<400> SEQUENCE: 152

Met Gln Thr Ala Tyr Trp Val Met Met Met Thr Met Met Val Trp Met
1               5                   10                  15

Thr Ala Pro Leu Ser Glu Gly Arg Pro Leu Ser Asp Glu Val Arg Gly
            20                  25                  30

Met Val Pro Gly Asp Leu Val Leu Gln Tyr Leu Phe Pro Ser Leu Ala
        35                  40                  45

Phe Ser Pro Pro Asp Ile Cys Thr Trp Lys Val Cys Pro Pro Pro
50                  55                  60

Trp Arg Arg Pro Lys Lys Ile Thr Asp Val Arg Gln Pro Pro Gln Leu
65              70                  75                  80

<210> SEQ ID NO 153
<211> LENGTH: 49
<212> TYPE: PRT
<213> ORGANISM: Conus musicus
<220> FEATURE:
<221> NAME/KEY: PEPTIDE
<222> LOCATION: (1)..(49)
<223> OTHER INFORMATION: Xaa at residues 4, 14, 20, 21, 30, 31, 32, 33,
      37, 46 and 47 may be Pro or hydroxy-Pro; Xaa at residue 11 may be
      Tyr, 125I-Tyr, mono-iodo-Tyr, di-iodo-Tyr, O-sulpho-Tyr or O-
      phospho-Tyr; Xaa at residues 26 and 34 may be Trp (D or L) or
      bromo-Trp (D or L)

<400> SEQUENCE: 153

Gly Met Val Xaa Gly Asp Leu Val Leu Gln Xaa Leu Phe Xaa Ser Leu
1               5                   10                  15

Ala Phe Ser Xaa Xaa Asp Ile Cys Thr Xaa Lys Val Cys Xaa Xaa Xaa
            20                  25                  30

Xaa Xaa Arg Arg Xaa Lys Lys Ile Thr Asp Val Arg Gln Xaa Xaa Gln
        35                  40                  45

Leu

<210> SEQ ID NO 154
<211> LENGTH: 436
<212> TYPE: DNA
<213> ORGANISM: Conus musicus
<220> FEATURE:
<221> NAME/KEY: CDS
<222> LOCATION: (1)..(216)

<400> SEQUENCE: 154 atg cag acg gcc tac tgg gtg atg atg atg atg atg gtg tgg atg         48
Met Gln Thr Ala Tyr Trp Val Met Met Met Met Met Val Trp Met
1               5                   10                  15 aca gcc cct ctg tct gaa ggt cgt aaa ctg atc gac aaa gtt cgg ggt     96
Thr Ala Pro Leu Ser Glu Gly Arg Lys Leu Ile Asp Lys Val Arg Gly
            20                  25                  30 atg ggg cca ggc gac tta tcc cta cag aaa atg ttc cca agt ctg gct    144
Met Gly Pro Gly Asp Leu Ser Leu Gln Lys Met Phe Pro Ser Leu Ala
        35                  40                  45 tta ggt cct ggg gga gac gta ata tgt agg tgg aag gta tgt cca cca    192
Leu Gly Pro Gly Gly Asp Val Ile Cys Arg Trp Lys Val Cys Pro Pro
50                  55                  60 acc cca tgg aaa cga cta ata aaa taactgacgt cagacagccg ccacaactgt   246
Thr Pro Trp Lys Arg Leu Ile Lys
65              70 agtacgacat cgttgatacg acttcagcaa atatttcaac atcactgcgg ttgtgaagaa   306
```

-continued

```
atcagttgct ttaaaagatt ggattttttcc ttgtttaaag agttgtactg atatcagctc    366
tgcattacga aataaagctg atgtgacaaa caaaaaaaaa aaaaaaaagt actctgcgtt    426
gttactcgag                                                           436
```

<210> SEQ ID NO 155
<211> LENGTH: 72
<212> TYPE: PRT
<213> ORGANISM: Conus musicus

<400> SEQUENCE: 155

```
Met Gln Thr Ala Tyr Trp Val Met Met Met Met Met Val Trp Met
1               5                   10                  15

Thr Ala Pro Leu Ser Glu Gly Arg Lys Leu Ile Asp Lys Val Arg Gly
            20                  25                  30

Met Gly Pro Gly Asp Leu Ser Leu Gln Lys Met Phe Pro Ser Leu Ala
        35                  40                  45

Leu Gly Pro Gly Gly Asp Val Ile Cys Arg Trp Lys Val Cys Pro Pro
    50                  55                  60

Thr Pro Trp Lys Arg Leu Ile Lys
65                  70
```

<210> SEQ ID NO 156
<211> LENGTH: 41
<212> TYPE: PRT
<213> ORGANISM: Conus musicus
<220> FEATURE:
<221> NAME/KEY: PEPTIDE
<222> LOCATION: (1)..(41)
<223> OTHER INFORMATION: Xaa at residues 4, 14, 20, 32, 33 and 35 may be
      Pro or hydroxy-Pro; Xaa at residues 28 and 36 may be Trp (D or L)
      or bromo-Trp (D or L)

<400> SEQUENCE: 156

```
Gly Met Gly Xaa Gly Asp Leu Ser Leu Gln Lys Met Phe Xaa Ser Leu
1               5                   10                  15

Ala Leu Gly Xaa Gly Gly Asp Val Ile Cys Arg Xaa Lys Val Cys Xaa
            20                  25                  30

Xaa Thr Xaa Xaa Lys Arg Leu Ile Lys
        35                  40
```

<210> SEQ ID NO 157
<211> LENGTH: 449
<212> TYPE: DNA
<213> ORGANISM: Conus musicus
<220> FEATURE:
<221> NAME/KEY: CDS
<222> LOCATION: (1)..(243)

<400> SEQUENCE: 157

```
atg cag acg gcc tac tgg gtg atg atg atg acg atg atg gtg tgg         48
Met Gln Thr Ala Tyr Trp Val Met Met Met Thr Met Met Val Trp
1               5                   10                  15 atg aca gcc cct ctg tct gaa ggt cgt cca ctg agc gac aaa gtt cgg     96
Met Thr Ala Pro Leu Ser Glu Gly Arg Pro Leu Ser Asp Lys Val Arg
            20                  25                  30 ggt atg gtg cca ggc gac tta gcc ctg cag tat ctg ttc cca agt ctg    144
Gly Met Val Pro Gly Asp Leu Ala Leu Gln Tyr Leu Phe Pro Ser Leu
        35                  40                  45 gct ttc aat ccc ccg gac ata tgt acg tgg aag gta tgt cca cca ccc    192
Ala Phe Asn Pro Pro Asp Ile Cys Thr Trp Lys Val Cys Pro Pro Pro
    50                  55                  60
```

```
cca tgg aga cga cca aaa aaa ata act gac gtc gga cag ccg cca caa      240
Pro Trp Arg Arg Pro Lys Lys Ile Thr Asp Val Gly Gln Pro Pro Gln
 65                  70                  75                  80 ctg tagtacgaca tcgttgatac gacttcagca aatattttca acatcactgc           293
Leu ggttgtgaag aaatcagttg ttttaaaagg ttggattttt ccttgtttaa aagagctgta    353
ctgatgtcag ctctgcatta cgaaataaag ctgatgtgac aaacgaaaaa aaaaaaaaaa    413
aaaaaaaaaa aaaagtactc tgcgttgtta ctcgag                              449

<210> SEQ ID NO 158
<211> LENGTH: 81
<212> TYPE: PRT
<213> ORGANISM: Conus musicus

<400> SEQUENCE: 158

Met Gln Thr Ala Tyr Trp Val Met Met Met Thr Met Met Val Trp
 1               5                  10                  15

Met Thr Ala Pro Leu Ser Glu Gly Arg Pro Leu Ser Asp Lys Val Arg
                20                  25                  30

Gly Met Val Pro Gly Asp Leu Ala Leu Gln Tyr Leu Phe Pro Ser Leu
            35                  40                  45

Ala Phe Asn Pro Pro Asp Ile Cys Thr Trp Lys Val Cys Pro Pro Pro
        50                  55                  60

Pro Trp Arg Arg Pro Lys Lys Ile Thr Asp Val Gly Gln Pro Pro Gln
 65                  70                  75                  80

Leu

<210> SEQ ID NO 159
<211> LENGTH: 49
<212> TYPE: PRT
<213> ORGANISM: Conus musicus
<220> FEATURE:
<221> NAME/KEY: PEPTIDE
<222> LOCATION: (1)..(49)
<223> OTHER INFORMATION: Xaa at residues 4, 14, 20, 21, 30, 31, 32, 33,
      37, 46 and 47 may be Pro or hydroxy-Pro; Xaa at residue 11 may be
      Tyr, 125I-Tyr, mono-iodo-Tyr, di-iodo-Tyr, O-sulpho-Tyr or O-
      phospho-Tyr; Xaa at residues 26 and 34 may be Trp (D or L) or
      bromo-Trp (D or L)

<400> SEQUENCE: 159

Gly Met Val Xaa Gly Asp Leu Ala Leu Gln Xaa Leu Phe Xaa Ser Leu
 1               5                  10                  15

Ala Phe Asn Xaa Xaa Asp Ile Cys Thr Xaa Lys Val Cys Xaa Xaa Xaa
                20                  25                  30

Xaa Xaa Arg Arg Xaa Lys Lys Ile Thr Asp Val Gly Gln Xaa Xaa Gln
            35                  40                  45

Leu

<210> SEQ ID NO 160
<211> LENGTH: 436
<212> TYPE: DNA
<213> ORGANISM: Conus musicus
<220> FEATURE:
<221> NAME/KEY: CDS
<222> LOCATION: (1)..(240)

<400> SEQUENCE: 160 atg cag acg gcc tac tgg gtg atg atg atg acg atg atg gtg tgg atg     48
Met Gln Thr Ala Tyr Trp Val Met Met Met Thr Met Met Val Trp Met
```

```
                    1               5                   10                  15
aca gcc cct ctg tct gaa ggt cgt cca ctg agc gac aaa gtt cgg ggt    96
Thr Ala Pro Leu Ser Glu Gly Arg Pro Leu Ser Asp Lys Val Arg Gly
                    20                  25                  30 atg gtg cca ggc gac tta gtc ctg cag tat ctg ttc cca agt ctg gct   144
Met Val Pro Gly Asp Leu Val Leu Gln Tyr Leu Phe Pro Ser Leu Ala
            35                  40                  45 ttc aat cct ccg gac ata tgt acg tgg aag gta tgt cca cca ccc cca   192
Phe Asn Pro Pro Asp Ile Cys Thr Trp Lys Val Cys Pro Pro Pro Pro
        50                  55                  60 tgg aga cga cca aaa aaa ata act gac gtc aga cag ccg cca caa ctg   240
Trp Arg Arg Pro Lys Lys Ile Thr Asp Val Arg Gln Pro Pro Gln Leu
65                  70                  75                  80 tagtacgaca tcgttgatac gacttcagca aatattttca acatcactgc ggttgtgaag    300
aaatcagttg ttttaaaagg ttggattttt ccttgtttaa aagagctgta ctgatgtcag    360
ctctgcatta cgaaataaag ctgatgtgac aagcaaaaaa aaaaaaaaaa aaaagtactc    420
tgcgttgtta ctcgag                                                    436
```

<210> SEQ ID NO 161
<211> LENGTH: 80
<212> TYPE: PRT
<213> ORGANISM: Conus musicus

<400> SEQUENCE: 161

```
Met Gln Thr Ala Tyr Trp Val Met Met Thr Met Met Val Trp Met
1               5                   10                  15

Thr Ala Pro Leu Ser Glu Gly Arg Pro Leu Ser Asp Lys Val Arg Gly
                    20                  25                  30

Met Val Pro Gly Asp Leu Val Leu Gln Tyr Leu Phe Pro Ser Leu Ala
            35                  40                  45

Phe Asn Pro Pro Asp Ile Cys Thr Trp Lys Val Cys Pro Pro Pro Pro
        50                  55                  60

Trp Arg Arg Pro Lys Lys Ile Thr Asp Val Arg Gln Pro Pro Gln Leu
65                  70                  75                  80
```

<210> SEQ ID NO 162
<211> LENGTH: 49
<212> TYPE: PRT
<213> ORGANISM: Conus musicus
<220> FEATURE:
<221> NAME/KEY: PEPTIDE
<222> LOCATION: (1)..(49)
<223> OTHER INFORMATION: Xaa at residues 4, 14, 20, 21, 30, 31, 32, 33,
      37, 46 and 47 may be Pro or hydroxy-Pro; Xaa at residue 11 may be
      Tyr, 125I-Tyr, mono-iodo-Tyr, di-iodo-Tyr, O-sulpho-Tyr or O-
      phospho-Tyr; Xaa at residues 26 and 34 may be Trp (D or L) or
      bromo-Trp (D or L)

<400> SEQUENCE: 162

```
Gly Met Val Xaa Gly Asp Leu Val Leu Gln Xaa Leu Phe Xaa Ser Leu
1               5                   10                  15

Ala Phe Asn Xaa Xaa Asp Ile Cys Thr Xaa Lys Val Cys Xaa Xaa Xaa
            20                  25                  30

Xaa Xaa Arg Arg Xaa Lys Lys Ile Thr Asp Val Arg Gln Xaa Xaa Gln
        35                  40                  45

Leu
```

<210> SEQ ID NO 163
<211> LENGTH: 462

```
<212> TYPE: DNA
<213> ORGANISM: Conus mustelinus
<220> FEATURE:
<221> NAME/KEY: CDS
<222> LOCATION: (1)..(225)

<400> SEQUENCE: 163 atg cag acg gcc tac tgg gtg atg gtg atg atg atg gcg tgg tat aca      48
Met Gln Thr Ala Tyr Trp Val Met Val Met Met Met Ala Trp Tyr Thr
1               5                   10                  15 acc cct gtg tct gaa tgt ggg aaa ttg aac aac gta att cgg ggt ttt      96
Thr Pro Val Ser Glu Cys Gly Lys Leu Asn Asn Val Ile Arg Gly Phe
                20                  25                  30 gtg cca aag gac tgg acc cca atg ctt ccc tgg cgt cgt cta gtt tcc    144
Val Pro Lys Asp Trp Thr Pro Met Leu Pro Trp Arg Arg Leu Val Ser
            35                  40                  45 cat acc agc agc aag tat cca ggt gtg act ttt tgt cca tgg aag gtg    192
His Thr Ser Ser Lys Tyr Pro Gly Val Thr Phe Cys Pro Trp Lys Val
        50                  55                  60 tgt ccg cca gcg cca tgg aga ata ctt ggg gtc taacgcaaaa aaatacatga   245
Cys Pro Pro Ala Pro Trp Arg Ile Leu Gly Val
65                  70                  75 cgtcagacaa ccgccaccgc tttagtacga catcgttcat acgtctccag caagtatttt   305
aacatcactg tggttgtgaa gaagtcagta gctttaaaag attggatttt ttccttgttt   365
aagagttgta ctgacatgag ttctgcacta tgaaataaag ttgatgtgac gaacgaaaaa   425
aaaaaaaaaa aaaagtact ctgcgttgtt actcgag                              462

<210> SEQ ID NO 164
<211> LENGTH: 75
<212> TYPE: PRT
<213> ORGANISM: Conus mustelinus

<400> SEQUENCE: 164

Met Gln Thr Ala Tyr Trp Val Met Val Met Met Met Ala Trp Tyr Thr
1               5                   10                  15

Thr Pro Val Ser Glu Cys Gly Lys Leu Asn Asn Val Ile Arg Gly Phe
                20                  25                  30

Val Pro Lys Asp Trp Thr Pro Met Leu Pro Trp Arg Arg Leu Val Ser
            35                  40                  45

His Thr Ser Ser Lys Tyr Pro Gly Val Thr Phe Cys Pro Trp Lys Val
        50                  55                  60

Cys Pro Pro Ala Pro Trp Arg Ile Leu Gly Val
65                  70                  75

<210> SEQ ID NO 165
<211> LENGTH: 30
<212> TYPE: PRT
<213> ORGANISM: Conus mustelinus
<220> FEATURE:
<221> NAME/KEY: PEPTIDE
<222> LOCATION: (1)..(30)
<223> OTHER INFORMATION: Xaa at residue 9 may be Tyr, 125I-Tyr, mono-
      iodo-Tyr, di-iodo-Tyr, O-sulpho-Tyr or O-phospho-Tyr; Xaa at
      residues 10, 16, 21, 22 and 24 may be Pro or hydroxy-Pro; Xaa at
      residues 17 and 25 may be Trp (D or L) or bromo-Trp (D or L)

<400> SEQUENCE: 165

Leu Val Ser His Thr Ser Ser Lys Xaa Xaa Gly Val Thr Phe Cys Xaa
1               5                   10                  15

Xaa Lys Val Cys Xaa Xaa Ala Xaa Xaa Arg Ile Leu Gly Val
                20                  25                  30
```

<210> SEQ ID NO 166
<211> LENGTH: 619
<212> TYPE: DNA
<213> ORGANISM: Conus nobilis
<220> FEATURE:
<221> NAME/KEY: CDS
<222> LOCATION: (21)..(350)

<400> SEQUENCE: 166

| | | | | | | | | | | | | | |
|---|---|---|---|---|---|---|---|---|---|---|---|---|---|
| gaattcgccc | ttatggatcc | atg | cag | acg | gcc | tac | tgg | gtg | atg | atg | atg | gtg | 53 |
| | | Met | Gln | Thr | Ala | Tyr | Trp | Val | Met | Met | Met | Val | |
| | | 1 | | 5 | | | | | 10 | | | | |

| | | | | | | | | | | | | |
|---|---|---|---|---|---|---|---|---|---|---|---|---|
| gtg gtg atg atg gtg ggg gtt act gtc gct ggc tca ctg tct gtg ttt | 101 |
| Val Val Met Met Val Gly Val Thr Val Ala Gly Ser Leu Ser Val Phe | |
| 15  20  25 | |

| gat gat gac aac gac tct gac cca gct gtc aag cgc gcc atc acg tgg | 149 |
|---|
| Asp Asp Asp Asn Asp Ser Asp Pro Ala Val Lys Arg Ala Ile Thr Trp |
| 30  35  40 |

| tct cga ttc ctg ggc gcg tct cca gcc ttc ctg gca cag cag cga gcg | 197 |
|---|
| Ser Arg Phe Leu Gly Ala Ser Pro Ala Phe Leu Ala Gln Gln Arg Ala |
| 45  50  55 |

| ctg gct ccc ttc gcc aac cga ccc atc aat gag cag aaa cgt ttc cga | 245 |
|---|
| Leu Ala Pro Phe Ala Asn Arg Pro Ile Asn Glu Gln Lys Arg Phe Arg |
| 60  65  70  75 |

| cct gcc gtg aag agc cga tca cga cga gcg ccg ccg tgc gtg tgg aag | 293 |
|---|
| Pro Ala Val Lys Ser Arg Ser Arg Arg Ala Pro Pro Cys Val Trp Lys |
| 80  85  90 |

| gtg tgt ccc gct ccc ccc tgg ctg gtc acc aaa cgt aaa cag gaa acc | 341 |
|---|
| Val Cys Pro Ala Pro Pro Trp Leu Val Thr Lys Arg Lys Gln Glu Thr |
| 95  100  105 |

| agc gac tac tgacgtcata cctcaataga ccgactcatg acttcaacgc | 390 |
|---|
| Ser Asp Tyr |
| 110 | tgaattgacg tcaccgagag ctccaacgtc acagcaggag cgagagagag agagagagag   450 agagaaagag agagaaaag gctggagtat ttctctttct tttggttttt cgtgttgaag   510 tgtgatcagc tgggctggtt caaaattgtt gaataaagtt gaatgaaaat caaaaaaaaa   570 aaaaaaaaaa aagtactctg cgttgttact cgagcttaag ggcgaattc   619

<210> SEQ ID NO 167
<211> LENGTH: 110
<212> TYPE: PRT
<213> ORGANISM: Conus nobilis

<400> SEQUENCE: 167

Met Gln Thr Ala Tyr Trp Val Met Met Val Val Met Met Val
1               5                   10                  15

Gly Val Thr Val Ala Gly Ser Leu Ser Val Phe Asp Asp Asn Asp
            20                  25                  30

Ser Asp Pro Ala Val Lys Arg Ala Ile Thr Trp Ser Arg Phe Leu Gly
        35                  40                  45

Ala Ser Pro Ala Phe Leu Ala Gln Gln Arg Ala Leu Ala Pro Phe Ala
    50                  55                  60

Asn Arg Pro Ile Asn Glu Gln Lys Arg Phe Arg Pro Ala Val Lys Ser
65                  70                  75                  80

Arg Ser Arg Arg Ala Pro Pro Cys Val Trp Lys Val Cys Pro Ala Pro
                85                  90                  95

Pro Trp Leu Val Thr Lys Arg Lys Gln Glu Thr Ser Asp Tyr

```
<210> SEQ ID NO 168
<211> LENGTH: 37
<212> TYPE: PRT
<213> ORGANISM: Conus nobilis
<220> FEATURE:
<221> NAME/KEY: PEPTIDE
<222> LOCATION: (1)..(37)
<223> OTHER INFORMATION: Xaa at residues 3, 13, 14, 21, 23 and 24 may be
      Pro or hydroxy-Pro; Xaa at residues 17 and 25 may be Trp (D or L)
      or bromo-Trp (D or L); Xaa at residue 33 may be Glu or Gla;
<220> FEATURE:
<221> NAME/KEY: PEPTIDE
<222> LOCATION: (1)..(37)
<223> OTHER INFORMATION: Xaa at residue 37 may be Tyr, 125I-Tyr, mono-
      iodo-Tyr, di-iodo-Tyr, O-sulpho-Tyr or O-phospho-Tyr

<400> SEQUENCE: 168

Phe Arg Xaa Ala Val Lys Ser Arg Ser Arg Arg Ala Xaa Xaa Cys Val
1               5                   10                  15

Xaa Lys Val Cys Xaa Ala Xaa Xaa Xaa Leu Val Thr Lys Arg Lys Gln
            20                  25                  30

Xaa Thr Ser Asp Xaa
        35

<210> SEQ ID NO 169
<211> LENGTH: 494
<212> TYPE: DNA
<213> ORGANISM: Conus nobilis
<220> FEATURE:
<221> NAME/KEY: CDS
<222> LOCATION: (21)..(242)

<400> SEQUENCE: 169
gaattcgccc ttatggatcc atg cag acg gcc tac tgg gtg atg gtg atg atg      53
                     Met Gln Thr Ala Tyr Trp Val Met Val Met Met
                      1               5                  10 atg gtg tgg att aca gcc cct ctg tct gaa ggt ggt aaa ttg aac gac       101
Met Val Trp Ile Thr Ala Pro Leu Ser Glu Gly Gly Lys Leu Asn Asp
         15                  20                  25 gta att cgg ggt ttg gtg cca cac ttc tta acc cca cag cat atc ttg       149
Val Ile Arg Gly Leu Val Pro His Phe Leu Thr Pro Gln His Ile Leu
     30                  35                  40 caa agt ctg act tcc cgt aat ggt tct ggc agc agt aat cag aaa gaa       197
Gln Ser Leu Thr Ser Arg Asn Gly Ser Gly Ser Ser Asn Gln Lys Glu
 45                  50                  55 gcg caa cta tgc atc tgg aag gta tgt cca cca acc cca tgg aga           242
Ala Gln Leu Cys Ile Trp Lys Val Cys Pro Pro Thr Pro Trp Arg
60                  65                  70 tgatcacaag gaaaagatg aacggcgtca gacaaccgcc acaactgtag tgggacatcg      302
ttgatacgac ttcagcaaat attttaacat cactgtggtt gtgaagaaat cagttgtttt    362
aaaagattgg attttccctt gtttaagagt tgtactgata tcagctctgc actatgaaat    422
aaagctgatg tgacaagcaa aaaaaaaaaa aaaagtact ctgcgttgtt actcgagctt     482
aagggcgaat tc                                                         494

<210> SEQ ID NO 170
<211> LENGTH: 74
<212> TYPE: PRT
<213> ORGANISM: Conus nobilis

<400> SEQUENCE: 170
```

```
Met Gln Thr Ala Tyr Trp Val Met Val Met Met Val Trp Ile Thr
1               5                  10                  15

Ala Pro Leu Ser Glu Gly Gly Lys Leu Asn Asp Val Ile Arg Gly Leu
                20                  25                  30

Val Pro His Phe Leu Thr Pro Gln His Ile Leu Gln Ser Leu Thr Ser
            35                  40                  45

Arg Asn Gly Ser Gly Ser Ser Asn Gln Lys Glu Ala Gln Leu Cys Ile
        50                  55                  60

Trp Lys Val Cys Pro Pro Thr Pro Trp Arg
65                  70
```

<210> SEQ ID NO 171
<211> LENGTH: 25
<212> TYPE: PRT
<213> ORGANISM: Conus nobilis
<220> FEATURE:
<221> NAME/KEY: PEPTIDE
<222> LOCATION: (1)..(25)
<223> OTHER INFORMATION: Xaa at residue 10 may be Glu or Gla; Xaa at
      residues 16 and 24 may be Trp or bromo-Trp; Xaa at residues 20, 21
      and 23 may be Pro or hydroxy-Pro

<400> SEQUENCE: 171

```
Asn Gly Ser Gly Ser Ser Asn Gln Lys Xaa Ala Gln Leu Cys Ile Xaa
1               5                  10                  15

Lys Val Cys Xaa Xaa Thr Xaa Xaa Arg
            20                  25
```

<210> SEQ ID NO 172
<211> LENGTH: 604
<212> TYPE: DNA
<213> ORGANISM: Conus nobilis
<220> FEATURE:
<221> NAME/KEY: CDS
<222> LOCATION: (21)..(350)

<400> SEQUENCE: 172

```
gaattcgccc ttatggatcc atg cag acg gcc tac tgg gtg atg atg atg gtg      53
                     Met Gln Thr Ala Tyr Trp Val Met Met Met Val
                     1               5                  10 gtg gtg atg atg gtg ggg gtt act gtc gct ggc tca ctg tct gtg ttt       101
Val Val Met Met Val Gly Val Thr Val Ala Gly Ser Leu Ser Val Phe
            15                  20                  25 gat gac gac aat gac tct gac cca gct gtc aag cgc gcc atc acg tgg       149
Asp Asp Asp Asn Asp Ser Asp Pro Ala Val Lys Arg Ala Ile Thr Trp
            30                  35                  40 tct cga ttc ctg ggc gcg tct cca gcc ttc ctg gca cag cag cga gcg       197
Ser Arg Phe Leu Gly Ala Ser Pro Ala Phe Leu Ala Gln Gln Arg Ala
    45                  50                  55 ctg gct ccc ttc gcc aac cga ccc atc aat gag cag aaa cgt ttc cga       245
Leu Ala Pro Phe Ala Asn Arg Pro Ile Asn Glu Gln Lys Arg Phe Arg
60                  65                  70                  75 cct gcc gtg aag agc cga tca cga cga gcg ccg ccg tgc gta tgg aag       293
Pro Ala Val Lys Ser Arg Ser Arg Arg Ala Pro Pro Cys Val Trp Lys
                80                  85                  90 gtg tgt ccc gct ccc ccc tgg ctg gtc acc aaa cgt aaa cag gaa acc       341
Val Cys Pro Ala Pro Pro Trp Leu Val Thr Lys Arg Lys Gln Glu Thr
            95                  100                 105 agc gac tac tgacgtcata cctcaataga ccgactcatg acttcaacgc              390
Ser Asp Tyr
        110 tgaattgacc tcaccgagag ctccaacgtc acagcaggag cgagagagag agagagagag    450
```

-continued

```
agagagagag aaaggctgga gtatttctct ttctttcggt ttttcgtgtt gaagtgtgat      510
cagctgggct ggttcaaaat tgttgaataa agttgaataa aaaaaaaaaa aaaaaaagta      570
ctctgcgttg ttactcgagc ttaagggcga attc                                  604
```

<210> SEQ ID NO 173
<211> LENGTH: 110
<212> TYPE: PRT
<213> ORGANISM: Conus nobilis

<400> SEQUENCE: 173

```
Met Gln Thr Ala Tyr Trp Val Met Met Met Val Val Val Met Met Val
1               5                   10                  15

Gly Val Thr Val Ala Gly Ser Leu Ser Val Phe Asp Asp Asn Asp
            20                  25                  30

Ser Asp Pro Ala Val Lys Arg Ala Ile Thr Trp Ser Arg Phe Leu Gly
        35                  40                  45

Ala Ser Pro Ala Phe Leu Ala Gln Gln Arg Ala Leu Ala Pro Phe Ala
    50                  55                  60

Asn Arg Pro Ile Asn Glu Gln Lys Arg Phe Arg Pro Ala Val Lys Ser
65                  70                  75                  80

Arg Ser Arg Arg Ala Pro Pro Cys Val Trp Lys Val Cys Pro Ala Pro
                85                  90                  95

Pro Trp Leu Val Thr Lys Arg Lys Gln Glu Thr Ser Asp Tyr
            100                 105                 110
```

<210> SEQ ID NO 174
<211> LENGTH: 37
<212> TYPE: PRT
<213> ORGANISM: Conus nobilis
<220> FEATURE:
<221> NAME/KEY: PEPTIDE
<222> LOCATION: (1)..(37)
<223> OTHER INFORMATION: Xaa at residues 3, 13, 14, 21, 23 and 24 may be
      Pro or hydroxy-Pro; Xaa at residues 17 and 25 may be Trp (D or L)
      or bromo-Trp (D or L); Xaa at residue 33 may be Glu or Gla;
<220> FEATURE:
<221> NAME/KEY: PEPTIDE
<222> LOCATION: (1)..(37)
<223> OTHER INFORMATION: Xaa at residue 37 may be Tyr, 125I-Tyr, mono-
      iodo-Tyr, di-iodo-Tyr, O-sulpho-Tyr or O-phospho-Tyr

<400> SEQUENCE: 174

```
Phe Arg Xaa Ala Val Lys Ser Arg Ser Arg Arg Ala Xaa Xaa Cys Val
1               5                   10                  15

Xaa Lys Val Cys Xaa Ala Xaa Xaa Xaa Leu Val Thr Lys Arg Lys Gln
            20                  25                  30

Xaa Thr Ser Asp Xaa
        35
```

<210> SEQ ID NO 175
<211> LENGTH: 391
<212> TYPE: DNA
<213> ORGANISM: Conus parius
<220> FEATURE:
<221> NAME/KEY: CDS
<222> LOCATION: (21)..(275)

<400> SEQUENCE: 175

```
gaattcgccc ttatggatcc atg cag acg gcc tac tgg gtg atg gtg atg atg      53
                      Met Gln Thr Ala Tyr Trp Val Met Val Met Met
                       1               5                  10
```

```
atg gtg gtg tgg att aca gcc cct ttg tct gaa ggt ggt aaa ccg aag       101
Met Val Val Trp Ile Thr Ala Pro Leu Ser Glu Gly Gly Lys Pro Lys
         15                  20                  25 cac gca att cgg ggt ttg gtg cca gac gac tta acc cca cag ctt atc       149
His Ala Ile Arg Gly Leu Val Pro Asp Asp Leu Thr Pro Gln Leu Ile
             30                  35                  40 ttg cga agt ctg att tcc cgt cgt agt tct ttc ggc aag gat gcg aaa       197
Leu Arg Ser Leu Ile Ser Arg Arg Ser Ser Phe Gly Lys Asp Ala Lys
 45                  50                  55 ccc ccc ttt agt tgt tca ggc ctc cga ggg ggt tgc gtc cta cct ccc       245
Pro Pro Phe Ser Cys Ser Gly Leu Arg Gly Gly Cys Val Leu Pro Pro
 60              65                  70                  75 aat ctc agg cca aag ttc aac aaa ggt gga taacaaaccc aagcgttcct        295
Asn Leu Arg Pro Lys Phe Asn Lys Gly Gly
                 80                  85 agttatacga atgccagcaa ataaaagcag tttgattgtg aaaaaaaaaa aaaaaaaag     355 tactctgcgt tgttactcga gcttaagggc gaattc                              391
```

<210> SEQ ID NO 176
<211> LENGTH: 85
<212> TYPE: PRT
<213> ORGANISM: Conus parius

<400> SEQUENCE: 176

Met Gln Thr Ala Tyr Trp Val Met Val Met Met Val Val Trp Ile
1               5                   10                  15

Thr Ala Pro Leu Ser Glu Gly Gly Lys Pro Lys His Ala Ile Arg Gly
            20                  25                  30

Leu Val Pro Asp Asp Leu Thr Pro Gln Leu Ile Leu Arg Ser Leu Ile
        35                  40                  45

Ser Arg Arg Ser Ser Phe Gly Lys Asp Ala Lys Pro Pro Phe Ser Cys
    50                  55                  60

Ser Gly Leu Arg Gly Gly Cys Val Leu Pro Pro Asn Leu Arg Pro Lys
65                  70                  75                  80

Phe Asn Lys Gly Gly
                85

<210> SEQ ID NO 177
<211> LENGTH: 25
<212> TYPE: PRT
<213> ORGANISM: Conus parius
<220> FEATURE:
<221> NAME/KEY: PEPTIDE
<222> LOCATION: (1)..(25)
<223> OTHER INFORMATION: Xaa at residues 1, 3, 15, 16 and 20 may be Pro
      or hydroxy-Pro

<400> SEQUENCE: 177

Xaa Xaa Phe Ser Cys Ser Gly Leu Arg Gly Gly Cys Val Leu Xaa Xaa
1               5                   10                  15

Asn Leu Arg Xaa Lys Phe Asn Lys Gly
            20                  25

<210> SEQ ID NO 178
<211> LENGTH: 390
<212> TYPE: DNA
<213> ORGANISM: Conus parius
<220> FEATURE:
<221> NAME/KEY: CDS
<222> LOCATION: (19)..(273)

<400> SEQUENCE: 178

```
gaattcgccc ttggatcc atg cag acg gcc tac tgg gtg atg gtg atg atg        51
                    Met Gln Thr Ala Tyr Trp Val Met Val Met Met
                     1               5                  10 atg gtg atg tgg att aca gcc cct ctg tct gaa ggt ggt aaa ccg aag         99
Met Val Met Trp Ile Thr Ala Pro Leu Ser Glu Gly Gly Lys Pro Lys
         15                  20                  25 ctc ata att cgg ggt ttg gtg cca aac gac tta acc cca cag cgt atc        147
Leu Ile Ile Arg Gly Leu Val Pro Asn Asp Leu Thr Pro Gln Arg Ile
         30                  35                  40 ttg cga agt ctg att tcc ggg cgt act tat ggc atc tat gat gcg aaa        195
Leu Arg Ser Leu Ile Ser Gly Arg Thr Tyr Gly Ile Tyr Asp Ala Lys
    45                  50                  55 ccc ccc ttt agt tgt gca ggc ctc cga ggg ggt tgc gtc cta cct ccc        243
Pro Pro Phe Ser Cys Ala Gly Leu Arg Gly Gly Cys Val Leu Pro Pro
60                  65                  70                  75 aat ctc agg cca aag ttc aag gaa ggt cga taaaaaccc aagcgttcct           293
Asn Leu Arg Pro Lys Phe Lys Glu Gly Arg
                80                  85 agttatacga atgccagcaa ataaaagcag tttgattgcg aaaaaaaaaa aaaaaaaaa       353 gtactctgcg ttgttactcg agcttaaggg cgaattc                               390

<210> SEQ ID NO 179
<211> LENGTH: 85
<212> TYPE: PRT
<213> ORGANISM: Conus parius

<400> SEQUENCE: 179

Met Gln Thr Ala Tyr Trp Val Met Val Met Met Val Met Trp Ile
1               5                   10                  15

Thr Ala Pro Leu Ser Glu Gly Gly Lys Pro Lys Leu Ile Ile Arg Gly
                20                  25                  30

Leu Val Pro Asn Asp Leu Thr Pro Gln Arg Ile Leu Arg Ser Leu Ile
            35                  40                  45

Ser Gly Arg Thr Tyr Gly Ile Tyr Asp Ala Lys Pro Pro Phe Ser Cys
    50                  55                  60

Ala Gly Leu Arg Gly Gly Cys Val Leu Pro Pro Asn Leu Arg Pro Lys
65                  70                  75                  80

Phe Lys Glu Gly Arg
                85

<210> SEQ ID NO 180
<211> LENGTH: 24
<212> TYPE: PRT
<213> ORGANISM: Conus parius
<220> FEATURE:
<221> NAME/KEY: PEPTIDE
<222> LOCATION: (1)..(24)
<223> OTHER INFORMATION: Xaa at residues 1, 2, 15, 16 and 20 may be Pro
      or hydroxy-Pro; Xaa at residue 24 may be Glu or Gla

<400> SEQUENCE: 180

Xaa Xaa Phe Ser Cys Ala Gly Leu Arg Gly Gly Cys Val Leu Xaa Xaa
1               5                   10                  15

Asn Leu Arg Xaa Lys Phe Lys Xaa
                20

<210> SEQ ID NO 181
<211> LENGTH: 489
<212> TYPE: DNA
<213> ORGANISM: Conus planorbis
```

```
<220> FEATURE:
<221> NAME/KEY: CDS
<222> LOCATION: (21)..(251)

<400> SEQUENCE: 181
gaattcgccc ttatggatcc atg cag acg gcc tac tgg gtg atg atg atg        53
                     Met Gln Thr Ala Tyr Trp Val Met Met Met
                       1               5                  10 atg gtg tgg att aca ggc cat ctg tct gaa ggt ggc aaa ttg aag gat     101
Met Val Trp Ile Thr Gly His Leu Ser Glu Gly Gly Lys Leu Lys Asp
         15                  20                  25 gca att agg ggt ttg gtg cca gac gac ttg acc tca atg ttt gcg ttg     149
Ala Ile Arg Gly Leu Val Pro Asp Asp Leu Thr Ser Met Phe Ala Leu
     30                  35                  40 cat ctt ccg gtt tcc cat tct cgg tct agc agc aat ggt ctg aag aga     197
His Leu Pro Val Ser His Ser Arg Ser Ser Ser Asn Gly Leu Lys Arg
 45                  50                  55 gct gac cta tgt atc cac aag att tgt cca cca cgg tat cac caa agc     245
Ala Asp Leu Cys Ile His Lys Ile Cys Pro Pro Arg Tyr His Gln Ser
 60                  65                  70                  75 caa caa taaagacgt cagacaacca ccacaacttt agtatgacat cgttaatagg       301
Gln Gln acttcagcaa gtattttaac atcactgtgg ttgtgatgaa atcagtcgcc ttaaagatt    361 ggcttttttcc ttgtttaaga gttgtacttg tatcagcttt gcacttcgaa ataaagttga  421
tgtgatgaac caaaaaaaaa aaaaaaaaaa agtactctgc gttgttactc gagcttaagg   481
gcgaattc                                                            489

<210> SEQ ID NO 182
<211> LENGTH: 77
<212> TYPE: PRT
<213> ORGANISM: Conus planorbis

<400> SEQUENCE: 182

Met Gln Thr Ala Tyr Trp Val Met Met Met Met Val Trp Ile Thr
  1               5                  10                  15

Gly His Leu Ser Glu Gly Gly Lys Leu Lys Asp Ala Ile Arg Gly Leu
                 20                  25                  30

Val Pro Asp Asp Leu Thr Ser Met Phe Ala Leu His Leu Pro Val Ser
             35                  40                  45

His Ser Arg Ser Ser Ser Asn Gly Leu Lys Arg Ala Asp Leu Cys Ile
         50                  55                  60

His Lys Ile Cys Pro Pro Arg Tyr His Gln Ser Gln Gln
 65                  70                  75

<210> SEQ ID NO 183
<211> LENGTH: 26
<212> TYPE: PRT
<213> ORGANISM: Conus planorbis
<220> FEATURE:
<221> NAME/KEY: PEPTIDE
<222> LOCATION: (1)..(26)
<223> OTHER INFORMATION: Xaa at residues 18 and 19 may be Pro or
      hydroxy-Pro; Xaa at residue 21 may be Tyr, 125I-Tyr, mono-iodo-
      Tyr, di-iodo-Tyr, O-sulpho-Tyr or O-phospho-Ty

<400> SEQUENCE: 183

Ser Ser Ser Asn Gly Leu Lys Arg Ala Asp Leu Cys Ile His Lys Ile
  1               5                  10                  15

Cys Xaa Xaa Arg Xaa His Gln Ser Gln Gln
                 20                  25
```

<210> SEQ ID NO 184
<211> LENGTH: 834
<212> TYPE: DNA
<213> ORGANISM: Conus pulicarius
<220> FEATURE:
<221> NAME/KEY: CDS
<222> LOCATION: (1)..(246)
<220> FEATURE:
<221> NAME/KEY: misc_feature
<222> LOCATION: (1)..(834)
<223> OTHER INFORMATION: n may be any nucleotide

<400> SEQUENCE: 184

| | | | | | | | | | | | | | | | | |
|---|---|---|---|---|---|---|---|---|---|---|---|---|---|---|---|---|
| atg | cag | acg | gcc | tac | tgg | gtg | atg | gtg | atg | atg | atg | gtg | tgg | gtt | | 48 |
| Met | Gln | Thr | Ala | Tyr | Trp | Val | Met | Val | Met | Met | Met | Val | Trp | Val | | |
| 1 | | | | 5 | | | | | 10 | | | | | 15 | | |

| aca | gcg | cct | gtg | tct | gaa | ggt | ggt | aaa | ttg | agc | gac | gta | att | cgg | ggt | 96 |
|---|---|---|---|---|---|---|---|---|---|---|---|---|---|---|---|---|
| Thr | Ala | Pro | Val | Ser | Glu | Gly | Gly | Lys | Leu | Ser | Asp | Val | Ile | Arg | Gly | |
| | | | 20 | | | | | 25 | | | | | 30 | | | |

| ttg | gtg | cca | gac | gac | ata | acc | cca | cag | att | att | ttg | caa | agt | ctg | aat | 144 |
|---|---|---|---|---|---|---|---|---|---|---|---|---|---|---|---|---|
| Leu | Val | Pro | Asp | Asp | Ile | Thr | Pro | Gln | Ile | Ile | Leu | Gln | Ser | Leu | Asn | |
| | | 35 | | | | | 40 | | | | | 45 | | | | |

| gcc | agt | cgt | cat | gct | tac | aga | cgt | gtt | cgt | ctg | aga | gga | cag | ata | tgt | 192 |
|---|---|---|---|---|---|---|---|---|---|---|---|---|---|---|---|---|
| Ala | Ser | Arg | His | Ala | Tyr | Arg | Arg | Val | Arg | Leu | Arg | Gly | Gln | Ile | Cys | |
| 50 | | | | | 55 | | | | | 60 | | | | | | |

| atc | tgg | aag | gta | tgt | cca | cca | cta | cta | caa | tgg | ata | cat | cca | tta | gta | 240 |
|---|---|---|---|---|---|---|---|---|---|---|---|---|---|---|---|---|
| Ile | Trp | Lys | Val | Cys | Pro | Pro | Leu | Leu | Gln | Trp | Ile | His | Pro | Leu | Val | |
| 65 | | | | 70 | | | | | 75 | | | | | 80 | | |

| aaa | aga | tgaatgacat | cagacaaccg | ccacaactgt | agtacgacat | cgttaacacg | 296 |
|---|---|---|---|---|---|---|---|
| Lys | Arg | | | | | | |

| acttcagcaa | atattctaac | atcacagtgg | gttgtgaaga | natcggttg | gctttaaaaa | 356 |
|---|---|---|---|---|---|---|
| aaanaatggg | ggnttttccc | cntgggttta | aaaaaanntn | ggnccgggn | aannnccnn | 416 |
| nntnnnccccc | ccccnntngg | gagaaaaaaa | aaanncnnt | nnnggggggn | nnncnaaaaa | 476 |
| aaaaaaaaaa | aaaaaaaaaa | aaaaancccc | nggggggntg | ntttnccc | cncccccngg | 536 |
| gggggggggn | gntttnnccc | cccccccgng | gggggggggg | ntttnnttt | nngggggngc | 596 |
| cccccccccc | cccnnncnnn | nnaanaannn | nngggggggg | ggaanaaaaa | nannnnnnnn | 656 |
| nnnnnnnnnn | ttttntcnnt | cnnccgngnn | gnnaaaaaaa | aaanttnatt | tntnnannnc | 716 |
| nncnnnccnn | cnncnnaccc | nnccccnncc | ncnncanncn | nagannanga | ggggggggng | 776 |
| nnnnggngna | nnnnnannnn | nnngaannng | aggngngnnn | cncgncnncg | cncnngnc | 834 |

<210> SEQ ID NO 185
<211> LENGTH: 82
<212> TYPE: PRT
<213> ORGANISM: Conus pulicarius
<220> FEATURE:
<221> NAME/KEY: misc_feature
<222> LOCATION: (1)..(834)
<223> OTHER INFORMATION: n may be any nucleotide

<400> SEQUENCE: 185

Met Gln Thr Ala Tyr Trp Val Met Val Met Met Met Val Trp Val
1               5                   10                  15

Thr Ala Pro Val Ser Glu Gly Gly Lys Leu Ser Asp Val Ile Arg Gly
            20                  25                  30

Leu Val Pro Asp Asp Ile Thr Pro Gln Ile Ile Leu Gln Ser Leu Asn
        35                  40                  45

Ala Ser Arg His Ala Tyr Arg Arg Val Arg Leu Arg Gly Gln Ile Cys

```
                    50                  55                  60
Ile Trp Lys Val Cys Pro Pro Leu Leu Gln Trp Ile His Pro Leu Val
 65                  70                  75                  80

Lys Arg

<210> SEQ ID NO 186
<211> LENGTH: 26
<212> TYPE: PRT
<213> ORGANISM: Conus pulicarius
<220> FEATURE:
<221> NAME/KEY: PEPTIDE
<222> LOCATION: (1)..(26)
<223> OTHER INFORMATION: Xaa at residues 10 and 19 may be Trp (D or L)
      or bromo-Trp (D or L); Xaa at residues 14, 15 and 22 may be Pro or
      hydroxy-Pro

<400> SEQUENCE: 186

Val Arg Leu Arg Gly Gln Ile Cys Ile Xaa Lys Val Cys Xaa Xaa Leu
 1               5                  10                  15

Leu Gln Xaa Ile His Xaa Leu Val Lys Arg
            20                  25

<210> SEQ ID NO 187
<211> LENGTH: 471
<212> TYPE: DNA
<213> ORGANISM: Conus pulicarius
<220> FEATURE:
<221> NAME/KEY: CDS
<222> LOCATION: (1)..(246)

<400> SEQUENCE: 187
```

| | | |
|---|---|---|
| atg cag acg gcc tac tgg gtg atg gtg atg atg atg gtg tgg gtt | 48 | |
| Met Gln Thr Ala Tyr Trp Val Met Val Met Met Met Val Trp Val | | |
|  1               5                  10                  15 | | |
| aca gcg cct gtg tct gaa ggt ggt aaa ttg agc gac gta att cgg ggt | 96 | |
| Thr Ala Pro Val Ser Glu Gly Gly Lys Leu Ser Asp Val Ile Arg Gly | | |
|                 20                  25                  30 | | |
| ttg gtg cca gac gac tta acc cca cag att atc ttg caa agt ctg aat | 144 | |
| Leu Val Pro Asp Asp Leu Thr Pro Gln Ile Ile Leu Gln Ser Leu Asn | | |
|            35                  40                  45 | | |
| gcc agt cgt cat gct tac aga cgt gtt cgt ccg aga gga cag ata tgt | 192 | |
| Ala Ser Arg His Ala Tyr Arg Arg Val Arg Pro Arg Gly Gln Ile Cys | | |
|  50                  55                  60 | | |
| atc tgg aag gta tgt cca cca cta cta caa tgg ata cat cca tta gta | 240 | |
| Ile Trp Lys Val Cys Pro Pro Leu Leu Gln Trp Ile His Pro Leu Val | | |
|  65                  70                  75                  80 | | |
| aaa aga tgaatgacat cagacaaccg ccacaactgt agtacggcat cgttaacacg | 296 | |
| Lys Arg | | |
| acttcagcaa atattttaac atcacagtgg ttgtgaagaa atcggttgct ttaaaaaaag | 356 | |
| attgggtttt tccttgttta agagttgtac tgatatcagt tctgcactat gaaataaagc | 416 | |
| tgatgtgacg aacaaaaaaa aaaaaaaaaa aaagtactct gcgttgttac tcgag | 471 | |

```
<210> SEQ ID NO 188
<211> LENGTH: 82
<212> TYPE: PRT
<213> ORGANISM: Conus pulicarius

<400> SEQUENCE: 188

Met Gln Thr Ala Tyr Trp Val Met Val Met Met Met Val Trp Val
 1               5                  10                  15

Thr Ala Pro Val Ser Glu Gly Gly Lys Leu Ser Asp Val Ile Arg Gly
```

```
                      20                  25                  30
Leu Val Pro Asp Asp Leu Thr Pro Gln Ile Ile Leu Gln Ser Leu Asn
                  35                  40                  45

Ala Ser Arg His Ala Tyr Arg Arg Val Arg Pro Arg Gly Gln Ile Cys
             50                  55                  60

Ile Trp Lys Val Cys Pro Pro Leu Leu Gln Trp Ile His Pro Leu Val
 65                  70                  75                  80

Lys Arg

<210> SEQ ID NO 189
<211> LENGTH: 26
<212> TYPE: PRT
<213> ORGANISM: Conus pulicarius
<220> FEATURE:
<221> NAME/KEY: PEPTIDE
<222> LOCATION: (1)..(26)
<223> OTHER INFORMATION: Xaa at residues 3, 14, 15 and 22 may be Pro or
      hydroxy-Pro; Xaa at residues 10 and 19 may be Trp (D or L) or
      bromo-Trp (D or L)

<400> SEQUENCE: 189

Val Arg Xaa Arg Gly Gln Ile Cys Ile Xaa Lys Val Cys Xaa Xaa Leu
 1               5                  10                  15

Leu Gln Xaa Ile His Xaa Leu Val Lys Arg
             20                  25

<210> SEQ ID NO 190
<211> LENGTH: 471
<212> TYPE: DNA
<213> ORGANISM: Conus pulicarius
<220> FEATURE:
<221> NAME/KEY: CDS
<222> LOCATION: (1)..(246)

<400> SEQUENCE: 190 atg cag acg gcc tac tgg gtg atg gtg atg atg atg gtg tgg gtt          48
Met Gln Thr Ala Tyr Trp Val Met Val Met Met Met Val Trp Val
 1               5                  10                  15 aca gcg cct gtg tct gaa ggt ggt aaa ttg agc gac gta att cgg ggt      96
Thr Ala Pro Val Ser Glu Gly Gly Lys Leu Ser Asp Val Ile Arg Gly
                 20                  25                  30 ttg gtg cca gac gac ata acc cca cag att atc ttg caa agt ctg aat    144
Leu Val Pro Asp Asp Ile Thr Pro Gln Ile Ile Leu Gln Ser Leu Asn
             35                  40                  45 gcc agt cgt cat gct tac aga cct gtt cgt ctg aga gga cag ata tgt    192
Ala Ser Arg His Ala Tyr Arg Pro Val Arg Leu Arg Gly Gln Ile Cys
         50                  55                  60 atc tgg aag gta tgt cca cca cta cta caa tgg ata cat cca tta gta    240
Ile Trp Lys Val Cys Pro Pro Leu Leu Gln Trp Ile His Pro Leu Val
 65                  70                  75                  80 aaa aga tgaatgacat cagacaaccg ccacaactgt agtacgacat cgttaacacg     296
Lys Arg acttcagcaa atattttaac atcacagtgg ttgtgaagaa atcggttgct ttaaaaaag    356 attgggtttt tccttgttta agagttgtac tgatatcagt tctgcactat gaaataaagc  416
tgatgtgacg aacaaaaaaa aaaaaaaaaa aaagtactct gcgttgttac tcgag        471

<210> SEQ ID NO 191
<211> LENGTH: 82
<212> TYPE: PRT
<213> ORGANISM: Conus pulicarius
```

```
<400> SEQUENCE: 191

Met Gln Thr Ala Tyr Trp Val Met Val Met Met Met Val Trp Val
1               5                   10                  15

Thr Ala Pro Val Ser Glu Gly Gly Lys Leu Ser Asp Val Ile Arg Gly
            20                  25                  30

Leu Val Pro Asp Asp Ile Thr Pro Gln Ile Ile Leu Gln Ser Leu Asn
                35                  40                  45

Ala Ser Arg His Ala Tyr Arg Pro Val Arg Leu Arg Gly Gln Ile Cys
        50                  55                  60

Ile Trp Lys Val Cys Pro Pro Leu Leu Gln Trp Ile His Pro Leu Val
65                  70                  75                  80

Lys Arg

<210> SEQ ID NO 192
<211> LENGTH: 27
<212> TYPE: PRT
<213> ORGANISM: Conus pulicarius
<220> FEATURE:
<221> NAME/KEY: PEPTIDE
<222> LOCATION: (1)..(27)
<223> OTHER INFORMATION: Xaa at residues 1, 15, 16 and 23 may be Pro or
      hydroxy-Pro; Xaa at residues 11 and 20 may be Trp (D or L) or
      bromo-Trp (D or L)

<400> SEQUENCE: 192

Xaa Val Arg Leu Arg Gly Gln Ile Cys Ile Xaa Lys Val Cys Xaa Xaa
1               5                   10                  15

Leu Leu Gln Xaa Ile His Xaa Leu Val Lys Arg
            20                  25

<210> SEQ ID NO 193
<211> LENGTH: 375
<212> TYPE: DNA
<213> ORGANISM: Conus rattus
<220> FEATURE:
<221> NAME/KEY: CDS
<222> LOCATION: (1)..(282)

<400> SEQUENCE: 193 atg cag acg gcc tac tgg gtg atg gtg atg atg gtg gtg gtg ggg ttc      48
Met Gln Thr Ala Tyr Trp Val Met Val Met Met Val Val Val Gly Phe
1               5                   10                  15 acc gtc ggg ggt cac gtc cat caa tct cac agt cct aca tcg cgc agc      96
Thr Val Gly Gly His Val His Gln Ser His Ser Pro Thr Ser Arg Ser
            20                  25                  30 cat ggt gat gac tcc att cat gac aag acg att cat caa cat ctg ttt     144
His Gly Asp Asp Ser Ile His Asp Lys Thr Ile His Gln His Leu Phe
        35                  40                  45 gcc cgt ctt cct ctg gag aac aac gac gac cat cgt tct gtg gat ctt     192
Ala Arg Leu Pro Leu Glu Asn Asn Asp Asp His Arg Ser Val Asp Leu
50                  55                  60 cct gca ggg acc agc gca ggc gac atg aaa cca caa cgc caa aga cgt     240
Pro Ala Gly Thr Ser Ala Gly Asp Met Lys Pro Gln Arg Gln Arg Arg
65                  70                  75                  80 ctc tgc tgc atc ttt gcc att ctt tgg ttc tgt tgt ctc ggt             282
Leu Cys Cys Ile Phe Ala Ile Leu Trp Phe Cys Cys Leu Gly
                85                  90 taacagtaca aattgcaatg cactggccga ttgaagaac tgcaataaac ggaaaaaaa     342 aaaaaaaaaa agtactctgc gttgttactc gag                                375
```

<210> SEQ ID NO 194
<211> LENGTH: 94
<212> TYPE: PRT
<213> ORGANISM: Conus rattus

<400> SEQUENCE: 194

```
Met Gln Thr Ala Tyr Trp Val Met Val Met Met Val Val Gly Phe
1               5                   10                  15

Thr Val Gly Gly His Val His Gln Ser His Ser Pro Thr Ser Arg Ser
            20                  25                  30

His Gly Asp Asp Ser Ile His Asp Lys Thr Ile His Gln His Leu Phe
        35                  40                  45

Ala Arg Leu Pro Leu Glu Asn Asn Asp Asp His Arg Ser Val Asp Leu
    50                  55                  60

Pro Ala Gly Thr Ser Ala Gly Asp Met Lys Pro Gln Arg Gln Arg Arg
65                  70                  75                  80

Leu Cys Cys Ile Phe Ala Ile Leu Trp Phe Cys Cys Leu Gly
                85                  90
```

<210> SEQ ID NO 195
<211> LENGTH: 13
<212> TYPE: PRT
<213> ORGANISM: Conus rattus
<220> FEATURE:
<221> NAME/KEY: PEPTIDE
<222> LOCATION: (1)..(13)
<223> OTHER INFORMATION: Xaa at residue 9 may be Trp (D or L) or bromo-
      Trp (D or L

<400> SEQUENCE: 195

```
Leu Cys Cys Ile Phe Ala Ile Leu Xaa Phe Cys Cys Leu
1               5                   10
```

<210> SEQ ID NO 196
<211> LENGTH: 494
<212> TYPE: DNA
<213> ORGANISM: Conus striatus
<220> FEATURE:
<221> NAME/KEY: CDS
<222> LOCATION: (21)..(287)

<400> SEQUENCE: 196

```
gaattcgccc ttatggatcc atg cag acg gcc tac tgg gtg atg gtg atg atg        53
                      Met Gln Thr Ala Tyr Trp Val Met Val Met Met
                      1               5                   10 atg gtg tgg att aca gcc cct ctg tct gaa ggt ggt aaa ttg aac gac         101
Met Val Trp Ile Thr Ala Pro Leu Ser Glu Gly Gly Lys Leu Asn Asp
            15                  20                  25 gta att cgg ggt ttg gtg cca cac atc tta acc cca cag cat atc ttg         149
Val Ile Arg Gly Leu Val Pro His Ile Leu Thr Pro Gln His Ile Leu
        30                  35                  40 caa agt ctg att tcc cct ctt cgt tct aac aac ggt cgt tcg agt gga         197
Gln Ser Leu Ile Ser Pro Leu Arg Ser Asn Asn Gly Arg Ser Ser Gly
    45                  50                  55 gca caa ata tgc atc tgg aag gta tgt cca cca tcc cca tgg aga caa         245
Ala Gln Ile Cys Ile Trp Lys Val Cys Pro Pro Ser Pro Trp Arg Gln
60                  65                  70                  75 cca caa gaa atg atg aat gac atc aga caa ccg cca caa ctg                 287
Pro Gln Glu Met Met Asn Asp Ile Arg Gln Pro Pro Gln Leu
                80                  85 tagtacgaca tcgttgatac gactttagca aatattttaa catcactgtg gttgtgaaga       347
aatcagttgc tttaaaagat tggattttc cttgtttaag agttgtactg atatcagctc        407
```

```
tgcactatga aataaagctg atgtgacaaa caaaaaaaaa aaaaaaaaaa gtactctgcg      467
ttgttactcg agcttaaggg cgaattc                                          494
```

```
<210> SEQ ID NO 197
<211> LENGTH: 89
<212> TYPE: PRT
<213> ORGANISM: Conus striatus

<400> SEQUENCE: 197
```

Met Gln Thr Ala Tyr Trp Val Met Val Met Met Val Trp Ile Thr
1               5                   10                  15

Ala Pro Leu Ser Glu Gly Gly Lys Leu Asn Asp Val Ile Arg Gly Leu
                20                  25                  30

Val Pro His Ile Leu Thr Pro Gln His Ile Leu Gln Ser Leu Ile Ser
            35                  40                  45

Pro Leu Arg Ser Asn Asn Gly Arg Ser Ser Gly Ala Gln Ile Cys Ile
        50                  55                  60

Trp Lys Val Cys Pro Pro Ser Pro Trp Arg Gln Pro Gln Glu Met Met
65                  70                  75                  80

Asn Asp Ile Arg Gln Pro Pro Gln Leu
                85

```
<210> SEQ ID NO 198
<211> LENGTH: 38
<212> TYPE: PRT
<213> ORGANISM: Conus striatus
<220> FEATURE:
<221> NAME/KEY: PEPTIDE
<222> LOCATION: (1)..(38)
<223> OTHER INFORMATION: Xaa at residues 14 and 22 may be Trp (D or L)
      or bromo-Trp (D or L); Xaa at residues 18, 19, 21, 25, 35 and 36
      may be Pro or hydroxy-Pro; Xaa at residue 27 may be Glu or Gla

<400> SEQUENCE: 198
```

Ser Asn Asn Gly Arg Ser Ser Gly Ala Gln Ile Cys Ile Xaa Lys Val
1               5                   10                  15

Cys Xaa Xaa Ser Xaa Xaa Arg Gln Xaa Gln Xaa Met Met Asn Asp Ile
            20                  25                  30

Arg Gln Xaa Xaa Gln Leu
        35

```
<210> SEQ ID NO 199
<211> LENGTH: 412
<212> TYPE: DNA
<213> ORGANISM: Conus striolatus
<220> FEATURE:
<221> NAME/KEY: CDS
<222> LOCATION: (1)..(240)

<400> SEQUENCE: 199
``` atg cag acg gcc tac tgg gtg atg gtg atg atg atg gtg tgg att aca      48
Met Gln Thr Ala Tyr Trp Val Met Val Met Met Met Val Trp Ile Thr
1               5                   10                  15 gac cct ctg tct gaa ggt ggt aaa ttg aac gac gta att cgg ggt ttg      96
Asp Pro Leu Ser Glu Gly Gly Lys Leu Asn Asp Val Ile Arg Gly Leu
                20                  25                  30 gtg cca cgc atc tta acc cca cag cat acc ttg cga agt ccg act tcc     144
Val Pro Arg Ile Leu Thr Pro Gln His Thr Leu Arg Ser Pro Thr Ser
            35                  40                  45 ctt ctt cgt tct aac acc ggt ggt tcg agt gga gca caa ata tgc atc     192
Leu Leu Arg Ser Asn Thr Gly Gly Ser Ser Gly Ala Gln Ile Cys Ile -continued

```
              50                  55                  60
tgg aag gta tgt cca cca tcc cca tgg aga cga tca caa gga aaa aga      240
Trp Lys Val Cys Pro Pro Ser Pro Trp Arg Arg Ser Gln Gly Lys Arg
65                  70                  75                  80 tgaatgacgt cagacaagcg ccacaactgt agtacgacat cgttgatacg acttcagcaa    300
gtattttaac atcactgtgg ttgtgaagaa atcagttgct ttaaaagatt ggattttttcc   360 ttgtttaaga gttgtactga tatcagctct gccctgtgaa ataaagctga tg            412
```

<210> SEQ ID NO 200
<211> LENGTH: 80
<212> TYPE: PRT
<213> ORGANISM: Conus striolatus

<400> SEQUENCE: 200

```
Met Gln Thr Ala Tyr Trp Val Met Val Met Met Val Trp Ile Thr
1               5                   10                  15

Asp Pro Leu Ser Glu Gly Gly Lys Leu Asn Asp Val Ile Arg Gly Leu
                20                  25                  30

Val Pro Arg Ile Leu Thr Pro Gln His Thr Leu Arg Ser Pro Thr Ser
            35                  40                  45

Leu Leu Arg Ser Asn Thr Gly Gly Ser Ser Gly Ala Gln Ile Cys Ile
        50                  55                  60

Trp Lys Val Cys Pro Pro Ser Pro Trp Arg Arg Ser Gln Gly Lys Arg
65                  70                  75                  80
```

<210> SEQ ID NO 201
<211> LENGTH: 26
<212> TYPE: PRT
<213> ORGANISM: Conus striolatus
<220> FEATURE:
<221> NAME/KEY: PEPTIDE
<222> LOCATION: (1)..(26)
<223> OTHER INFORMATION: Xaa at residues 14 and 22 may be Trp (D or L)
      or bromo-Trp (D or L); Xaa at residues 18, 19 and 21 may be Pro or
      hydroxy-Pro

<400> SEQUENCE: 201

```
Ser Asn Thr Gly Gly Ser Ser Gly Ala Gln Ile Cys Ile Xaa Lys Val
1               5                   10                  15

Cys Xaa Xaa Ser Xaa Xaa Arg Arg Ser Gln
            20                  25
```

<210> SEQ ID NO 202
<211> LENGTH: 412
<212> TYPE: DNA
<213> ORGANISM: Conus striolatus
<220> FEATURE:
<221> NAME/KEY: CDS
<222> LOCATION: (1)..(240)

<400> SEQUENCE: 202

```
atg cag acg gcc tac tgg gtg atg gtg atg atg gtg tgg att aca          48
Met Gln Thr Ala Tyr Trp Val Met Val Met Met Val Trp Ile Thr
1               5                   10                  15 gcc cct ctg tct gaa ggt ggt aaa ttg aac gac gta att cgg ggt ttg      96
Ala Pro Leu Ser Glu Gly Gly Lys Leu Asn Asp Val Ile Arg Gly Leu
                20                  25                  30 gtg cca cac atc tta acc cca cag cat atc ttg caa agt ctg att tcc     144
Val Pro His Ile Leu Thr Pro Gln His Ile Leu Gln Ser Leu Ile Ser
            35                  40                  45 cct ctt cgt tct aac aac ggt cgt tcg agt gga gca caa ata tgc atc     192
```

-continued

```
Pro Leu Arg Ser Asn Asn Gly Arg Ser Ser Gly Ala Gln Ile Cys Ile
     50                  55                  60 tgg aag gta tgt cca cca tcc cca tgg aga cga tca caa gga aaa aga    240
Trp Lys Val Cys Pro Pro Ser Pro Trp Arg Arg Ser Gln Gly Lys Arg
 65              70                  75                  80 tgaatgacgt cagacaagcg ccacaactgt agtacgacat cgttgatacg acttcagcaa    300
gtattttaac atcactgtgg ttgtgaagaa atcagttgct ttaaaagatt ggattttttcc    360 ttgtttaaga gttgtactga tatcagctct gcactgtgaa ataaagctga tg            412
```

<210> SEQ ID NO 203
<211> LENGTH: 80
<212> TYPE: PRT
<213> ORGANISM: Conus striolatus

<400> SEQUENCE: 203

```
Met Gln Thr Ala Tyr Trp Val Met Val Met Met Val Trp Ile Thr
 1               5                  10                  15

Ala Pro Leu Ser Glu Gly Gly Lys Leu Asn Asp Val Ile Arg Gly Leu
             20                  25                  30

Val Pro His Ile Leu Thr Pro Gln His Ile Leu Gln Ser Leu Ile Ser
         35                  40                  45

Pro Leu Arg Ser Asn Asn Gly Arg Ser Ser Gly Ala Gln Ile Cys Ile
     50                  55                  60

Trp Lys Val Cys Pro Pro Ser Pro Trp Arg Arg Ser Gln Gly Lys Arg
 65              70                  75                  80
```

<210> SEQ ID NO 204
<211> LENGTH: 26
<212> TYPE: PRT
<213> ORGANISM: Conus striolatus
<220> FEATURE:
<221> NAME/KEY: PEPTIDE
<222> LOCATION: (1)..(26)
<223> OTHER INFORMATION: Xaa at residues 14 and 22 may be Trp (D or L)
      or bromo-Trp (D or L); Xaa at residues 18, 19 and 21 may be Pro or
      hydroxy-Pro

<400> SEQUENCE: 204

```
Ser Asn Asn Gly Arg Ser Ser Gly Ala Gln Ile Cys Ile Xaa Lys Val
 1               5                  10                  15

Cys Xaa Xaa Ser Xaa Xaa Arg Arg Ser Gln
             20                  25
```

<210> SEQ ID NO 205
<211> LENGTH: 497
<212> TYPE: DNA
<213> ORGANISM: Conus striolatus
<220> FEATURE:
<221> NAME/KEY: CDS
<222> LOCATION: (21)..(257)

<400> SEQUENCE: 205

```
gaattcgccc ttatggatcc atg cag acg gcc tac tgg gtg atg gtg atg atg    53
                     Met Gln Thr Ala Tyr Trp Val Met Val Met Met
                      1               5                  10 atg gtg tgg att aaa gac cct ctg tct gaa ggt ggt aaa ttg aac gac    101
Met Val Trp Ile Lys Asp Pro Leu Ser Glu Gly Gly Lys Leu Asn Asp
             15                  20                  25 gta att cgg ggt ttg gtg cca cac atc tta acc cca cag cat atc ttg    149
Val Ile Arg Gly Leu Val Pro His Ile Leu Thr Pro Gln His Ile Leu
         30                  35                  40
```

-continued

```
caa agt ctg att tcc cct ctt cgt tct aac aac ggt cgt tcg agt gga    197
Gln Ser Leu Ile Ser Pro Leu Arg Ser Asn Asn Gly Arg Ser Ser Gly
     45                  50                  55 gca caa ata tgc aac tgg aag gta tgt cca cca tcc cca tgg aga cga    245
Ala Gln Ile Cys Asn Trp Lys Val Cys Pro Pro Ser Pro Trp Arg Arg
 60                  65                  70                  75 cca cga gga aaa tgatgaatga catcagacaa ccgccacaac tgtagtacga        297
Pro Arg Gly Lys cttcgttgat acgactttag caaatatttt aacatcactg tggttgtgaa gaaatcagtt  357
gctttaaaag attggatttt tccttgttta agagttgtac tgatatcagc tctgcactat  417
gaaataaagc tgatgtgaca acaaaaaaaa aaaaaaaaaa aaagtactct gcgttgttac  477
tcgagcttaa gggcgaattc                                              497
```

<210> SEQ ID NO 206
<211> LENGTH: 79
<212> TYPE: PRT
<213> ORGANISM: Conus striolatus

<400> SEQUENCE: 206

```
Met Gln Thr Ala Tyr Trp Val Met Val Met Met Val Trp Ile Lys
  1               5                  10                  15

Asp Pro Leu Ser Glu Gly Gly Lys Leu Asn Asp Val Ile Arg Gly Leu
             20                  25                  30

Val Pro His Ile Leu Thr Pro Gln His Ile Leu Gln Ser Leu Ile Ser
         35                  40                  45

Pro Leu Arg Ser Asn Asn Gly Arg Ser Ser Gly Ala Gln Ile Cys Asn
     50                  55                  60

Trp Lys Val Cys Pro Pro Ser Pro Trp Arg Arg Pro Arg Gly Lys
 65                  70                  75
```

<210> SEQ ID NO 207
<211> LENGTH: 26
<212> TYPE: PRT
<213> ORGANISM: Conus striolatus
<220> FEATURE:
<221> NAME/KEY: PEPTIDE
<222> LOCATION: (1)..(26)
<223> OTHER INFORMATION: Xaa at residues 14 and 22 may be Trp (D or L)
      or bromo-Trp (D or L); Xaa at residues 18, 19, 21 and 25 may be
      Pro or hydroxy-Pro

<400> SEQUENCE: 207

```
Ser Asn Asn Gly Arg Ser Ser Gly Ala Gln Ile Cys Asn Xaa Lys Val
  1               5                  10                  15

Cys Xaa Xaa Ser Xaa Xaa Arg Arg Xaa Arg
             20                  25
```

<210> SEQ ID NO 208
<211> LENGTH: 496
<212> TYPE: DNA
<213> ORGANISM: Conus striolatus
<220> FEATURE:
<221> NAME/KEY: CDS
<222> LOCATION: (21)..(287)

<400> SEQUENCE: 208

```
gaattcgccc ttatggatcc atg cag acg gcc tac tgg gtg atg gtg atg atg    53
                     Met Gln Thr Ala Tyr Trp Val Met Val Met Met
                       1               5                  10 atg gtg tgg att aca gcc cct ctg tct gaa ggt ggt aaa ttg aac gac    101
Met Val Trp Ile Thr Ala Pro Leu Ser Glu Gly Gly Lys Leu Asn Asp
```

```
                15                   20                   25
gta att cgg ggt ttg gtg cca cac atc tta acc cca cag cat atc ttg        149
Val Ile Arg Gly Leu Val Pro His Ile Leu Thr Pro Gln His Ile Leu
         30                  35                  40 caa agt ctg att tcc cct ctt cgt tct aac aac ggt cgt tcg agt gga        197
Gln Ser Leu Ile Ser Pro Leu Arg Ser Asn Asn Gly Arg Ser Ser Gly
     45                  50                  55 gca caa ata tgc atc tgg aag gta tgt cca cca tcc cca tgg aga caa        245
Ala Gln Ile Cys Ile Trp Lys Val Cys Pro Pro Ser Pro Trp Arg Gln
 60                  65                  70                  75 cca caa gaa atg atg aat gac atc aga caa ccg cca caa ctg                287
Pro Gln Glu Met Met Asn Asp Ile Arg Gln Pro Pro Gln Leu
                     80                  85 tagtacgaca tcgttgatac gactttagca aatattttaa catcactgtg gttgtgaaga      347
aatcagttgc tttaaaagat tggatttttc cttgtttaag agttgtactg atatcagctc      407
tgcactatga aataaagctg atgtgacaaa cgaaaaaaaa aaaaaaaaaa aagtactctg      467
cgttgttact cgagcttaag ggcgaattc                                        496
```

<210> SEQ ID NO 209
<211> LENGTH: 89
<212> TYPE: PRT
<213> ORGANISM: Conus striolatus

<400> SEQUENCE: 209

```
Met Gln Thr Ala Tyr Trp Val Met Val Met Met Val Trp Ile Thr
 1               5                  10                  15

Ala Pro Leu Ser Glu Gly Gly Lys Leu Asn Asp Val Ile Arg Gly Leu
             20                  25                  30

Val Pro His Ile Leu Thr Pro Gln His Ile Leu Gln Ser Leu Ile Ser
         35                  40                  45

Pro Leu Arg Ser Asn Asn Gly Arg Ser Ser Gly Ala Gln Ile Cys Ile
     50                  55                  60

Trp Lys Val Cys Pro Pro Ser Pro Trp Arg Gln Pro Gln Glu Met Met
 65                  70                  75                  80

Asn Asp Ile Arg Gln Pro Pro Gln Leu
                     85
```

<210> SEQ ID NO 210
<211> LENGTH: 38
<212> TYPE: PRT
<213> ORGANISM: Conus striolatus
<220> FEATURE:
<221> NAME/KEY: PEPTIDE
<222> LOCATION: (1)..(38)
<223> OTHER INFORMATION: Xaa at residues 14 and 22 may be Trp (D or L)
      or bromo-Trp (D or L); Xaa at residues 18, 19, 21, 25, 35 and 36
      may be Pro or hydroxy-Pro; Xaa at residue 27 may be Glu or Gla

<400> SEQUENCE: 210

```
Ser Asn Asn Gly Arg Ser Ser Gly Ala Gln Ile Cys Ile Xaa Lys Val
 1               5                  10                  15

Cys Xaa Xaa Ser Xaa Xaa Arg Gln Xaa Gln Xaa Met Met Asn Asp Ile
             20                  25                  30

Arg Gln Xaa Xaa Gln Leu
         35
```

<210> SEQ ID NO 211
<211> LENGTH: 413
<212> TYPE: DNA

<213> ORGANISM: Conus sulcatus
<220> FEATURE:
<221> NAME/KEY: CDS
<222> LOCATION: (1)..(234)

<400> SEQUENCE: 211

| | | | | | | | | | | | | | | | | |
|---|---|---|---|---|---|---|---|---|---|---|---|---|---|---|---|---|
| atg | cag | acg | gcc | tac | tgg | gtg | atg | gtg | atg | atg | gtg | tgg | att | aca | | 48 |
| Met | Gln | Thr | Ala | Tyr | Trp | Val | Met | Val | Met | Met | Val | Trp | Ile | Thr | | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcc | tct | ctg | tct | gaa | ggt | ggt | aaa | ccg | aac | gac | gtc | att | cgg | ggt | ttt | 96 |
| Ala | Ser | Leu | Ser | Glu | Gly | Gly | Lys | Pro | Asn | Asp | Val | Ile | Arg | Gly | Phe | |
| | | | 20 | | | | | 25 | | | | | 30 | | | |

| | | | | | | | | | | | | | | | | |
|---|---|---|---|---|---|---|---|---|---|---|---|---|---|---|---|---|
| gtg | cca | gac | gac | tta | acc | cca | cag | ctt | atc | ttg | cga | agt | ctg | att | tcc | 144 |
| Val | Pro | Asp | Asp | Leu | Thr | Pro | Gln | Leu | Ile | Leu | Arg | Ser | Leu | Ile | Ser | |
| | | | 35 | | | | | 40 | | | | | 45 | | | |

| | | | | | | | | | | | | | | | | |
|---|---|---|---|---|---|---|---|---|---|---|---|---|---|---|---|---|
| cgt | cgt | cgt | tct | gac | aag | gat | gtt | ggg | aag | aga | atg | gaa | tgt | tac | tgg | 192 |
| Arg | Arg | Arg | Ser | Asp | Lys | Asp | Val | Gly | Lys | Arg | Met | Glu | Cys | Tyr | Trp | |
| | | 50 | | | | | 55 | | | | | 60 | | | | |

| | | | | | | | | | | | | |
|---|---|---|---|---|---|---|---|---|---|---|---|---|
| aag | gca | tgt | aga | ccc | acg | cta | tcg | aga | cga | cat | gat | ctt | ggg | 234 |
| Lys | Ala | Cys | Arg | Pro | Thr | Leu | Ser | Arg | Arg | His | Asp | Leu | Gly | |
| 65 | | | | 70 | | | | | 75 | | | | | | taaaagatga atgacgtcag acaacagcca caactatagt atgacatcgt taatacgact    294 tcagcaaata ttttaacatc actgtggttg tgaagaaatc agttgcttta aaagattgga    354 tttttccgtg tttaagagtt gtactgatat cagctctgcc ctgtgaaata aagctgatg    413

<210> SEQ ID NO 212
<211> LENGTH: 78
<212> TYPE: PRT
<213> ORGANISM: Conus sulcatus

<400> SEQUENCE: 212

Met Gln Thr Ala Tyr Trp Val Met Val Met Met Val Trp Ile Thr
1               5                   10                  15

Ala Ser Leu Ser Glu Gly Gly Lys Pro Asn Asp Val Ile Arg Gly Phe
            20                  25                  30

Val Pro Asp Asp Leu Thr Pro Gln Leu Ile Leu Arg Ser Leu Ile Ser
        35                  40                  45

Arg Arg Arg Ser Asp Lys Asp Val Gly Lys Arg Met Glu Cys Tyr Trp
    50                  55                  60

Lys Ala Cys Arg Pro Thr Leu Ser Arg Arg His Asp Leu Gly
65                  70                  75

<210> SEQ ID NO 213
<211> LENGTH: 27
<212> TYPE: PRT
<213> ORGANISM: Conus sulcatus
<220> FEATURE:
<221> NAME/KEY: PEPTIDE
<222> LOCATION: (1)..(27)
<223> OTHER INFORMATION: Xaa at residue 11 may be Glu or Gla; Xaa at
      residue 13 may be Tyr, 125I-Tyr, mono-iodo-Tyr, di-iodo-Tyr, O-
      sulpho-Tyr or O-phospho-Tyr; Xaa at residue 14 may be Trp (D or L)
      or bromo-Trp (D or L); Xaa at residue 19 may be Pro or hydroxy-Pro

<400> SEQUENCE: 213

Arg Ser Asp Lys Asp Val Gly Lys Arg Met Xaa Cys Xaa Xaa Lys Ala
1               5                   10                  15

Cys Arg Xaa Thr Leu Ser Arg Arg His Asp Leu
            20                  25

<210> SEQ ID NO 214

```
<211> LENGTH: 472
<212> TYPE: DNA
<213> ORGANISM: Conus terebra
<220> FEATURE:
<221> NAME/KEY: CDS
<222> LOCATION: (1)..(234)

<400> SEQUENCE: 214 atg cag acg gcc tac tgg gtg atg gtg atg atg gtg tgg att aca         48
Met Gln Thr Ala Tyr Trp Val Met Val Met Met Val Trp Ile Thr
1               5                   10                  15 gcc cct ctg tct gaa ggt gat aaa ttg aac gac gta att cgg ggt ttg     96
Ala Pro Leu Ser Glu Gly Asp Lys Leu Asn Asp Val Ile Arg Gly Leu
                20                  25                  30 gtg cca gat aac tta gcc cca cag ctt gtt ttg caa agt ctg gat tcc    144
Val Pro Asp Asn Leu Ala Pro Gln Leu Val Leu Gln Ser Leu Asp Ser
            35                  40                  45 cgt cgt cat cct cac ggc att cgt cag gat gga gcc caa ata tgt atc    192
Arg Arg His Pro His Gly Ile Arg Gln Asp Gly Ala Gln Ile Cys Ile
        50                  55                  60 tgg aag ata tgt cca cca tcc cca tgg aaa cga ctt gga tct            234
Trp Lys Ile Cys Pro Pro Ser Pro Trp Lys Arg Leu Gly Ser
65                  70                  75 taagaaaaga aacaattgac gtcagacaac cgccacaact tgagtacgac atcgttaata   294
caacttcagc aaatatgaaa ttttcagcat cactgtggtt gtgaagaaat cagttgcttt   354
aaaagattgg atttgtcctt gtttaagagt tgtactgatg tcatctctgc actgtgaaat   414
aaagctgatg tgacaaacaa aaaaaaaaaa aaaaagtac tctgcgttgt tactcgag     472

<210> SEQ ID NO 215
<211> LENGTH: 78
<212> TYPE: PRT
<213> ORGANISM: Conus terebra

<400> SEQUENCE: 215

Met Gln Thr Ala Tyr Trp Val Met Val Met Met Val Trp Ile Thr
1               5                   10                  15

Ala Pro Leu Ser Glu Gly Asp Lys Leu Asn Asp Val Ile Arg Gly Leu
                20                  25                  30

Val Pro Asp Asn Leu Ala Pro Gln Leu Val Leu Gln Ser Leu Asp Ser
            35                  40                  45

Arg Arg His Pro His Gly Ile Arg Gln Asp Gly Ala Gln Ile Cys Ile
        50                  55                  60

Trp Lys Ile Cys Pro Pro Ser Pro Trp Lys Arg Leu Gly Ser
65                  70                  75

<210> SEQ ID NO 216
<211> LENGTH: 28
<212> TYPE: PRT
<213> ORGANISM: Conus terebra
<220> FEATURE:
<221> NAME/KEY: PEPTIDE
<222> LOCATION: (1)..(28)
<223> OTHER INFORMATION: Xaa at residues 2, 19, 20 and 22 may be Pro or
      hydroxy-Pro; Xaa at residues 15 and 23 may be Trp (D or L) or
      bromo-Trp (D or L)

<400> SEQUENCE: 216

His Xaa His Gly Ile Arg Gln Asp Gly Ala Gln Ile Cys Ile Xaa Lys
1               5                   10                  15

Ile Cys Xaa Xaa Ser Xaa Xaa Lys Arg Leu Gly Ser
                20                  25
```

<210> SEQ ID NO 217
<211> LENGTH: 474
<212> TYPE: DNA
<213> ORGANISM: Conus terebra
<220> FEATURE:
<221> NAME/KEY: CDS
<222> LOCATION: (1)..(234)

<400> SEQUENCE: 217

| | | | | | | | | | | | | | | | | |
|---|---|---|---|---|---|---|---|---|---|---|---|---|---|---|---|---|
| atg | cag | acg | gcc | tac | tgg | gtg | atg | gtg | atg | atg | atg | gtg | tgg | att | aca | 48 |
| Met | Gln | Thr | Ala | Tyr | Trp | Val | Met | Val | Met | Met | Met | Val | Trp | Ile | Thr | |
| 1 | | | | 5 | | | | | 10 | | | | | 15 | | |
| gcc | cct | ctg | tct | gaa | ggt | gat | aaa | ttg | aac | gac | gta | att | cgg | ggt | ttg | 96 |
| Ala | Pro | Leu | Ser | Glu | Gly | Asp | Lys | Leu | Asn | Asp | Val | Ile | Arg | Gly | Leu | |
| | | | | 20 | | | | | 25 | | | | | 30 | | |
| gtg | cca | gat | aac | tta | gcc | cca | cag | ctt | gtt | ttg | cat | agt | ctg | gat | tcc | 144 |
| Val | Pro | Asp | Asn | Leu | Ala | Pro | Gln | Leu | Val | Leu | His | Ser | Leu | Asp | Ser | |
| | | 35 | | | | | 40 | | | | | 45 | | | | |
| cgt | cgt | cat | cct | cac | ggc | att | cgt | cag | gat | gga | gcc | caa | ata | tgt | atc | 192 |
| Arg | Arg | His | Pro | His | Gly | Ile | Arg | Gln | Asp | Gly | Ala | Gln | Ile | Cys | Ile | |
| | 50 | | | | | 55 | | | | | 60 | | | | | |
| tgg | aag | ata | tgt | cca | cca | tcc | cca | tgg | aga | cga | ctt | gga | tct | | | 234 |
| Trp | Lys | Ile | Cys | Pro | Pro | Ser | Pro | Trp | Arg | Arg | Leu | Gly | Ser | | | |
| 65 | | | | 70 | | | | | 75 | | | | | | | |

| | | |
|---|---|---|
| taagaaaaga aacaattgac gtcagacaac cgccacatct tgagtacgac atcgttaata | | 294 |
| cgacttcagc aaatatgaaa ttttcagcat cactgtggtt gtgaagaaat cagttgcctt | | 354 |
| aaaagattgg atttgtcctt gtttaagagt tgtactgatg tcatctctgc actatgaaat | | 414 |
| aaagctgatg tgacaaacaa aaaaaaaaaa aaaaaaagt actctgcgtt gttactcgag | | 474 |

<210> SEQ ID NO 218
<211> LENGTH: 78
<212> TYPE: PRT
<213> ORGANISM: Conus terebra

<400> SEQUENCE: 218

Met Gln Thr Ala Tyr Trp Val Met Val Met Met Met Val Trp Ile Thr
1               5                   10                  15

Ala Pro Leu Ser Glu Gly Asp Lys Leu Asn Asp Val Ile Arg Gly Leu
                20                  25                  30

Val Pro Asp Asn Leu Ala Pro Gln Leu Val Leu His Ser Leu Asp Ser
            35                  40                  45

Arg Arg His Pro His Gly Ile Arg Gln Asp Gly Ala Gln Ile Cys Ile
        50                  55                  60

Trp Lys Ile Cys Pro Pro Ser Pro Trp Arg Arg Leu Gly Ser
65                  70                  75

<210> SEQ ID NO 219
<211> LENGTH: 28
<212> TYPE: PRT
<213> ORGANISM: Conus terebra
<220> FEATURE:
<221> NAME/KEY: PEPTIDE
<222> LOCATION: (1)..(28)
<223> OTHER INFORMATION: Xaa at residues 2, 19, 20 and 22 may be Pro or
      hydroxy-Pro; Xaa at residues 15 and 23 may be Trp (D or L) or
      bromo-Trp (D or L)

<400> SEQUENCE: 219

His Xaa His Gly Ile Arg Gln Asp Gly Ala Gln Ile Cys Ile Xaa Lys
1               5                   10                  15

```
Ile Cys Xaa Xaa Ser Xaa Xaa Arg Arg Leu Gly Ser
            20                  25
```

```
<210> SEQ ID NO 220
<211> LENGTH: 485
<212> TYPE: DNA
<213> ORGANISM: Conus vexillum
<220> FEATURE:
<221> NAME/KEY: CDS
<222> LOCATION: (21)..(236)

<400> SEQUENCE: 220
gaattcgccc ttatggatcc atg cag atg gcc tac tgg gtg atg gtg atg atg         53
                      Met Gln Met Ala Tyr Trp Val Met Val Met Met
                       1               5                  10 atg gtg tgg att aaa ggc cct gtg tcc gaa ggt ggt aaa ttg aac gac         101
Met Val Trp Ile Lys Gly Pro Val Ser Glu Gly Gly Lys Leu Asn Asp
         15                  20                  25 gta att cgg ggt ttg gtg cca gac gac ttg acc cca gtg tct gcc ttg         149
Val Ile Arg Gly Leu Val Pro Asp Asp Leu Thr Pro Val Ser Ala Leu
     30                  35                  40 cat cat ccg gtt tcc cat cgt cgg tct cac agc agt agt ttg tgg tgt         197
His His Pro Val Ser His Arg Arg Ser His Ser Ser Ser Leu Trp Cys
 45                  50                  55 gta tgt cca ttc agg gtg tgt cca cca tgc cat gga aga tgacctggtc         246
Val Cys Pro Phe Arg Val Cys Pro Pro Cys His Gly Arg
60                  65                  70 ccaaaccaac aaaataacgt cagacaaccg ccacaacttt agtacgacat cccttaatac       306
gacttcagca gtattttaa catcactatg gtgtgatgaa atcagttgct ttaaaagatt         366 ggattttttcc ttgtttaaga gttgcactga taacagccca gcagtatgaa ataaagttga      426
tgtggcaaaa aaaaaaaaaa aagtactctg cgttgttact cgagcttaag ggcgaattc        485

<210> SEQ ID NO 221
<211> LENGTH: 72
<212> TYPE: PRT
<213> ORGANISM: Conus vexillum

<400> SEQUENCE: 221

Met Gln Met Ala Tyr Trp Val Met Val Met Met Val Trp Ile Lys
 1               5                  10                  15

Gly Pro Val Ser Glu Gly Gly Lys Leu Asn Asp Val Ile Arg Gly Leu
            20                  25                  30

Val Pro Asp Asp Leu Thr Pro Val Ser Ala Leu His His Pro Val Ser
        35                  40                  45

His Arg Arg Ser His Ser Ser Ser Leu Trp Cys Val Cys Pro Phe Arg
     50                  55                  60

Val Cys Pro Pro Cys His Gly Arg
65                  70

<210> SEQ ID NO 222
<211> LENGTH: 19
<212> TYPE: PRT
<213> ORGANISM: Conus vexillum
<220> FEATURE:
<221> NAME/KEY: PEPTIDE
<222> LOCATION: (1)..(19)
<223> OTHER INFORMATION: Xaa at residue 7 may be Trp (D or L) or bromo-
      Trp (D or L); Xaa at residues 11, 16 and 17 may be Pro or hydroxy-
      Pro

<400> SEQUENCE: 222
```

Ser His Ser Ser Ser Leu Xaa Cys Val Cys Xaa Phe Arg Val Cys Xaa
1               5                   10                  15

Xaa Cys His

<210> SEQ ID NO 223
<211> LENGTH: 481
<212> TYPE: DNA
<213> ORGANISM: Conus vexillum
<220> FEATURE:
<221> NAME/KEY: CDS
<222> LOCATION: (21)..(257)

<400> SEQUENCE: 223

```
gaattcgccc ttatggatcc atg cag acg gcc tac tgg gtg atg gtg atg atg    53
                     Met Gln Thr Ala Tyr Trp Val Met Val Met Met
                       1               5                  10 atg gtg tgg att aca gcc cct ttg tct gaa ggt ggt aaa ctg aac gat     101
Met Val Trp Ile Thr Ala Pro Leu Ser Glu Gly Gly Lys Leu Asn Asp
         15                  20                  25 gta att cgg ggt ttc gcg cta gat gac tta gcc caa agc cgt att atg     149
Val Ile Arg Gly Phe Ala Leu Asp Asp Leu Ala Gln Ser Arg Ile Met
     30                  35                  40 caa agt ctg gtt ttc agt cat cag cct ctt cca acg gca tcc ata tgt     197
Gln Ser Leu Val Phe Ser His Gln Pro Leu Pro Thr Ala Ser Ile Cys
 45                  50                  55 atc tgg aag ata tgt cca cca gac cca tgg aga cga cat gat ctt cag     245
Ile Trp Lys Ile Cys Pro Pro Asp Pro Trp Arg Arg His Asp Leu Gln
60                  65                  70                  75 aaa agt aac aaa tgacgtcaga caaccgccac aacttgaata caacatcatt         297
Lys Ser Asn Lys aatacgactt cagcaaatat tttagcatca ctgtgattgt tcggaagtca gttgctttaa   357
aagattggat ttgtccctgt tgtattgatg tcaactctgc actatgaaat aaagctgatg   417
tgacaagcaa aaaaaaaaaa aaaaaagta ctctgcgttg ttactcgagc ttaagggcga    477
attc                                                               481
```

<210> SEQ ID NO 224
<211> LENGTH: 79
<212> TYPE: PRT
<213> ORGANISM: Conus vexillum

<400> SEQUENCE: 224

Met Gln Thr Ala Tyr Trp Val Met Val Met Met Val Trp Ile Thr
1               5                   10                  15

Ala Pro Leu Ser Glu Gly Gly Lys Leu Asn Asp Val Ile Arg Gly Phe
                20                  25                  30

Ala Leu Asp Asp Leu Ala Gln Ser Arg Ile Met Gln Ser Leu Val Phe
            35                  40                  45

Ser His Gln Pro Leu Pro Thr Ala Ser Ile Cys Ile Trp Lys Ile Cys
        50                  55                  60

Pro Pro Asp Pro Trp Arg Arg His Asp Leu Gln Lys Ser Asn Lys
65                  70                  75

<210> SEQ ID NO 225
<211> LENGTH: 38
<212> TYPE: PRT
<213> ORGANISM: Conus vexillum
<220> FEATURE:
<221> NAME/KEY: PEPTIDE
<222> LOCATION: (1)..(38)

<223> OTHER INFORMATION: Xaa at residues 11, 14, 24, 25 and 27 may be
     Pro or hydroxy-Pro; Xaa at residues 20 and 28 may be Trp (D or L)
     or bromo-Trp (D or L)

<400> SEQUENCE: 225

Ile Met Gln Ser Leu Val Phe Ser His Gln Xaa Leu Xaa Thr Ala Ser
1               5                   10                  15

Ile Cys Ile Xaa Lys Ile Cys Xaa Xaa Asp Xaa Xaa Arg Arg His Asp
            20                  25                  30

Leu Gln Lys Ser Asn Lys
        35

<210> SEQ ID NO 226
<211> LENGTH: 384
<212> TYPE: DNA
<213> ORGANISM: Conus vexillum
<220> FEATURE:
<221> NAME/KEY: CDS
<222> LOCATION: (1)..(285)

<400> SEQUENCE: 226 atg cag acg gcc tac tgg gtg atg gtg atg atg atg gtg gtg ggg ttc     48
Met Gln Thr Ala Tyr Trp Val Met Val Met Met Met Val Val Gly Phe
1               5                   10                  15 acc gtc gag agt cac gtc cat cag tct cac agt cct aca tcg cgc agc     96
Thr Val Glu Ser His Val His Gln Ser His Ser Pro Thr Ser Arg Ser
            20                  25                  30 cat ggt gat gac tcc att cat gac aag acg att cat caa cat ctg ttt    144
His Gly Asp Asp Ser Ile His Asp Lys Thr Ile His Gln His Leu Phe
        35                  40                  45 gcc cgt ctt cct ctg gag aac aac gac gac cat cgt tct gtg gat ctt    192
Ala Arg Leu Pro Leu Glu Asn Asn Asp Asp His Arg Ser Val Asp Leu
    50                  55                  60 cct gca ggg act agc gca ggc gac atg aaa cca caa cgc cag aaa cgt    240
Pro Ala Gly Thr Ser Ala Gly Asp Met Lys Pro Gln Arg Gln Lys Arg
65                  70                  75                  80 ttc tgc tgc atc ttt gcc ccg att ctt ttg ttc tgt tgt ttc ggt        285
Phe Cys Cys Ile Phe Ala Pro Ile Leu Leu Phe Cys Cys Phe Gly
                85                  90                  95 taacagcaca aattacactg cactggccga ttgaaagaac tgcaataaac ggtaaagcaa   345
aaaaaaaaaa aaaaaagta ctctgcgttg ttactcgag                          384

<210> SEQ ID NO 227
<211> LENGTH: 95
<212> TYPE: PRT
<213> ORGANISM: Conus vexillum

<400> SEQUENCE: 227

Met Gln Thr Ala Tyr Trp Val Met Val Met Met Met Val Val Gly Phe
1               5                   10                  15

Thr Val Glu Ser His Val His Gln Ser His Ser Pro Thr Ser Arg Ser
            20                  25                  30

His Gly Asp Asp Ser Ile His Asp Lys Thr Ile His Gln His Leu Phe
        35                  40                  45

Ala Arg Leu Pro Leu Glu Asn Asn Asp Asp His Arg Ser Val Asp Leu
    50                  55                  60

Pro Ala Gly Thr Ser Ala Gly Asp Met Lys Pro Gln Arg Gln Lys Arg
65                  70                  75                  80

Phe Cys Cys Ile Phe Ala Pro Ile Leu Leu Phe Cys Cys Phe Gly
                85                  90                  95

```
<210> SEQ ID NO 228
<211> LENGTH: 14
<212> TYPE: PRT
<213> ORGANISM: Conus vexillum
<220> FEATURE:
<221> NAME/KEY: PEPTIDE
<222> LOCATION: (1)..(14)
<223> OTHER INFORMATION: Xaa at residue 7 may be Pro or hydroxy-Pro

<400> SEQUENCE: 228

Phe Cys Cys Ile Phe Ala Xaa Ile Leu Leu Phe Cys Cys Phe
1               5                   10

<210> SEQ ID NO 229
<211> LENGTH: 40
<212> TYPE: PRT
<213> ORGANISM: Conus tulipa

<400> SEQUENCE: 229

Glx Thr Asp Val Leu Leu Glu Ala Thr Leu Leu Thr Thr Pro Ala Pro
1               5                   10                  15

Glu Gln Arg Leu Phe Cys Phe Trp Lys Ser Cys Trp Pro Arg Pro Tyr
            20                  25                  30

Pro Trp Arg Arg Arg Asp Leu Asn
        35                  40

<210> SEQ ID NO 230
<211> LENGTH: 40
<212> TYPE: PRT
<213> ORGANISM: Conus magus

<400> SEQUENCE: 230

Glx Thr Asp Val Leu Leu Asp Ala Thr Leu Leu Thr Thr Pro Ala Pro
1               5                   10                  15

Glu Gln Arg Leu Phe Cys Phe Trp Lys Ser Cys Trp Pro Arg Pro Tyr
            20                  25                  30

Pro Trp Arg Arg Arg Asn Leu Asn
        35                  40

<210> SEQ ID NO 231
<211> LENGTH: 40
<212> TYPE: PRT
<213> ORGANISM: Conus geographus

<400> SEQUENCE: 231

Glx Thr Asp Val Leu Leu Glu Ala Thr Leu Leu Thr Thr Pro Ala Pro
1               5                   10                  15

Glu Gln Arg Leu Phe Cys Phe Trp Lys Ser Cys Thr Trp Arg Pro Tyr
            20                  25                  30

Pro Trp Arg Arg Arg Asp Leu Asn
        35                  40

<210> SEQ ID NO 232
<211> LENGTH: 21
<212> TYPE: PRT
<213> ORGANISM: Conus tulipa

<400> SEQUENCE: 232

Leu Phe Cys Phe Trp Lys Ser Cys Trp Pro Arg Pro Tyr Pro Trp Arg
1               5                   10                  15

Arg Arg Asp Leu Asn
```

20

<210> SEQ ID NO 233
<211> LENGTH: 21
<212> TYPE: PRT
<213> ORGANISM: Conus magus

<400> SEQUENCE: 233

Leu Phe Cys Phe Trp Lys Ser Cys Trp Pro Arg Pro Tyr Pro Trp Arg
1               5                   10                  15

Arg Arg Asn Leu Asn
            20

<210> SEQ ID NO 234
<211> LENGTH: 21
<212> TYPE: PRT
<213> ORGANISM: Conus geographus

<400> SEQUENCE: 234

Leu Phe Cys Phe Trp Lys Ser Cys Thr Trp Arg Pro Tyr Pro Trp Arg
1               5                   10                  15

Arg Arg Asp Leu Asn
            20

<210> SEQ ID NO 235
<211> LENGTH: 19
<212> TYPE: PRT
<213> ORGANISM: Conus generalis

<400> SEQUENCE: 235

Ser His Ser Ser Ser Leu Trp Cys Val Cys Pro Phe Arg Val Cys Pro
1               5                   10                  15

Pro Cys His

<210> SEQ ID NO 236
<211> LENGTH: 19
<212> TYPE: PRT
<213> ORGANISM: Conus vexillum

<400> SEQUENCE: 236

Ser His Ser Ser Ser Leu Trp Cys Val Cys Pro Phe Arg Val Cys Pro
1               5                   10                  15

Pro Cys His

<210> SEQ ID NO 237
<211> LENGTH: 33
<212> TYPE: PRT
<213> ORGANISM: Conus flavidus

<400> SEQUENCE: 237

His Asp His Gly Ile Arg Pro Lys Arg Val Asp Ile Cys Asn Trp Arg
1               5                   10                  15

Ile Cys Ala Pro Asn Pro Leu Arg Arg His Asp Leu Lys Lys Gly Asn
            20                  25                  30

Asn

<210> SEQ ID NO 238
<211> LENGTH: 33
<212> TYPE: PRT
<213> ORGANISM: Conus emaciatus

<400> SEQUENCE: 238

His Thr His Gly Ile Arg Pro Lys Gly Asp Gly Ile Cys Ile Trp Lys
1               5                   10                  15

Val Cys Pro Pro Asp Pro Trp Arg Arg His Arg Leu Lys Lys Arg Asn
            20                  25                  30

Asn

<210> SEQ ID NO 239
<211> LENGTH: 33
<212> TYPE: PRT
<213> ORGANISM: Conus aurisiacus

<400> SEQUENCE: 239

His Thr His Gly Ile Arg Pro Lys Gly Asp Gly Ile Cys Ile Trp Lys
1               5                   10                  15

Val Cys Pro Pro Asp Pro Trp Arg Arg His His Leu Lys Lys Arg Asn
            20                  25                  30

Asn

<210> SEQ ID NO 240
<211> LENGTH: 28
<212> TYPE: PRT
<213> ORGANISM: Conus terebra

<400> SEQUENCE: 240

His Pro His Gly Ile Arg Gln Asp Gly Ala Gln Ile Cys Ile Trp Lys
1               5                   10                  15

Ile Cys Pro Pro Ser Pro Trp Lys Arg Leu Gly Ser
            20                  25

<210> SEQ ID NO 241
<211> LENGTH: 28
<212> TYPE: PRT
<213> ORGANISM: Conus terebra

<400> SEQUENCE: 241

His Pro His Gly Ile Arg Gln Asp Gly Ala Gln Ile Cys Ile Trp Lys
1               5                   10                  15

Ile Cys Pro Pro Ser Pro Trp Arg Arg Leu Gly Ser
            20                  25

<210> SEQ ID NO 242
<211> LENGTH: 28
<212> TYPE: PRT
<213> ORGANISM: Conus litoglyphus

<400> SEQUENCE: 242

His Pro His Gly Ile Arg Gln Asp Gly Ala Gln Ile Cys Ile Trp Lys
1               5                   10                  15

Ile Cys Pro Pro Ser Pro Trp Arg Leu Gly Ser
            20                  25

<210> SEQ ID NO 243
<211> LENGTH: 28
<212> TYPE: PRT
<213> ORGANISM: Conus litoglyphus

<400> SEQUENCE: 243

His Pro His Gly Ile Arg Gln Asp Gly Ala Gln Ile Cys Ile Trp Lys
1               5                   10                  15

Ile Cys Pro Pro Ser Pro Trp Arg Arg Leu Gly Ser

<210> SEQ ID NO 244
<211> LENGTH: 23
<212> TYPE: PRT
<213> ORGANISM: Conus consors

<400> SEQUENCE: 244

Asp Arg Ser Asp Asn Gly Gly Ser Ser Gly Ala Gln Ile Cys Ile Trp
1               5                   10                  15

Lys Val Cys Pro Pro Ser Pro
            20

<210> SEQ ID NO 245
<211> LENGTH: 25
<212> TYPE: PRT
<213> ORGANISM: Conus consors

<400> SEQUENCE: 245

Asp Arg Ser Asp Asn Gly Gly Ser Ser Gly Ala Gln Ile Cys Ile Trp
1               5                   10                  15

Lys Val Cys Pro Pro Ser Pro Trp Lys
            20                  25

<210> SEQ ID NO 246
<211> LENGTH: 28
<212> TYPE: PRT
<213> ORGANISM: Conus consors

<400> SEQUENCE: 246

Ala Arg Ser Asp Asn Gly Gly Ser Ser Gly Ala Gln Ile Cys Ile Trp
1               5                   10                  15

Lys Val Cys Pro Pro Ser Pro Trp Arg Arg Pro Gln
            20                  25

<210> SEQ ID NO 247
<211> LENGTH: 26
<212> TYPE: PRT
<213> ORGANISM: Conus striolatus

<400> SEQUENCE: 247

Ser Asn Thr Gly Gly Ser Ser Gly Ala Gln Ile Cys Ile Trp Lys Val
1               5                   10                  15

Cys Pro Pro Ser Pro Trp Arg Arg Ser Gln
            20                  25

<210> SEQ ID NO 248
<211> LENGTH: 26
<212> TYPE: PRT
<213> ORGANISM: Conus striolatus

<400> SEQUENCE: 248

Ser Asn Asn Gly Arg Ser Ser Gly Ala Gln Ile Cys Asn Trp Lys Val
1               5                   10                  15

Cys Pro Pro Ser Pro Trp Arg Arg Pro Arg
            20                  25

<210> SEQ ID NO 249
<211> LENGTH: 26
<212> TYPE: PRT
<213> ORGANISM: Conus striolatus

<400> SEQUENCE: 249

Ser Asn Asn Gly Arg Ser Ser Gly Ala Gln Ile Cys Ile Trp Lys Val
1               5                   10                  15

Cys Pro Pro Ser Pro Trp Arg Arg Ser Gln
            20                  25

<210> SEQ ID NO 251
<211> LENGTH: 38
<212> TYPE: PRT
<213> ORGANISM: Conus striolatus

<400> SEQUENCE: 250

Ser Asn Asn Gly Arg Ser Ser Gly Ala Gln Ile Cys Ile Trp Lys Val
1               5                   10                  15

Cys Pro Pro Ser Pro Trp Arg Gln Pro Gln Glu Met Met Asn Asp Ile
            20                  25                  30

Arg Gln Pro Pro Gln Leu
        35

<210> SEQ ID NO 251
<211> LENGTH: 38
<212> TYPE: PRT
<213> ORGANISM: Conus striatus

<400> SEQUENCE: 251

Ser Asn Asn Gly Arg Ser Ser Gly Ala Gln Ile Cys Ile Trp Lys Val
1               5                   10                  15

Cys Pro Pro Ser Pro Trp Arg Gln Pro Gln Glu Met Met Asn Asp Ile
            20                  25                  30

Arg Gln Pro Pro Gln Leu
        35

<210> SEQ ID NO 252
<211> LENGTH: 25
<212> TYPE: PRT
<213> ORGANISM: Conus aurisiacus

<400> SEQUENCE: 252

Leu His Ser Asp Ser Ser Asp Gln Lys Gly Ala Gln Ile Cys Ile Trp
1               5                   10                  15

Lys Val Cys Pro Pro Pro Trp Arg
            20                  25

<210> SEQ ID NO 253
<211> LENGTH: 34
<212> TYPE: PRT
<213> ORGANISM: Conus aurisiacus

<400> SEQUENCE: 253

Leu His Ser Asp Ser Ser Asp Gln Lys Gly Gly Met Asn Ala Trp Thr
1               5                   10                  15

Gly Ala Gly Ala Gln Ile Cys Ile Trp Lys Val Cys Pro Pro Pro
            20                  25                  30

Trp Arg

<210> SEQ ID NO 254
<211> LENGTH: 37
<212> TYPE: PRT
<213> ORGANISM: Conus aurisiacus

<400> SEQUENCE: 254

```
Leu Arg Ser Asp Ser Ser Asp Gln Lys Gly Gly Met Asn Ala Ser Thr
1               5                   10                  15

Gly Ala Gly Ala Gln Ile Cys Ile Trp Lys Val Cys Pro Ser Pro
            20                  25                  30

Trp Arg Arg Thr Gln
        35
```

<210> SEQ ID NO 255
<211> LENGTH: 28
<212> TYPE: PRT
<213> ORGANISM: Conus circumcisus

<400> SEQUENCE: 255

```
Leu Arg Ser Asp Ser Ser Gly Gln Lys Gly Ala Gln Ile Cys Ile Trp
1               5                   10                  15

Lys Val Cys Pro Leu Ser Pro Trp Arg Arg Pro Gln
            20                  25
```

<210> SEQ ID NO 256
<211> LENGTH: 32
<212> TYPE: PRT
<213> ORGANISM: Conus circumcisus

<400> SEQUENCE: 256

```
Leu Arg Ser Asp Ser Ser Gly Gln Lys Gly Ala Gln Ile Cys Ile Trp
1               5                   10                  15

Lys Val Cys Pro Leu Ser Pro Trp Arg Arg Pro Gln Gly Lys Asp Glu
            20                  25                  30
```

<210> SEQ ID NO 257
<211> LENGTH: 28
<212> TYPE: PRT
<213> ORGANISM: Conus achatinus

<400> SEQUENCE: 257

```
Leu Arg Ser Asp Asn Gly Gly Ser Gly Ala Gln Ile Cys Ile Trp
1               5                   10                  15

Lys Val Cys Pro Pro Ser Pro Trp Arg Arg Pro Gln
            20                  25
```

<210> SEQ ID NO 258
<211> LENGTH: 22
<212> TYPE: PRT
<213> ORGANISM: Conus stercusmuscarum

<400> SEQUENCE: 258

```
Leu Gly Ile Gly Ser Ser Asp Gln Asn Ala Gln Ile Cys Ile Trp Lys
1               5                   10                  15

Val Cys Pro Pro Ser Pro
            20
```

<210> SEQ ID NO 259
<211> LENGTH: 25
<212> TYPE: PRT
<213> ORGANISM: Conus consors

<400> SEQUENCE: 259

```
Asn Gly Ser Gly Ser Ser Asn Gln Lys Glu Ala Gln Leu Cys Ile Trp
1               5                   10                  15

Lys Val Cys Pro Pro Ser Pro Trp Arg
            20                  25
```

```
<210> SEQ ID NO 260
<211> LENGTH: 25
<212> TYPE: PRT
<213> ORGANISM: Conus consors

<400> SEQUENCE: 260

Asn Gly Ser Gly Ser Ser Asn Gln Lys Glu Ala Gln Leu Cys Ile Trp
1               5                   10                  15

Lys Val Cys Pro Pro Thr Pro Trp Arg
            20                  25

<210> SEQ ID NO 261
<211> LENGTH: 25
<212> TYPE: PRT
<213> ORGANISM: Conus magus

<400> SEQUENCE: 261

Asn Gly Ser Gly Ser Ser Asn Gln Lys Glu Ala Gln Leu Cys Ile Trp
1               5                   10                  15

Lys Val Cys Pro Pro Ser Pro Trp Arg
            20                  25

<210> SEQ ID NO 262
<211> LENGTH: 25
<212> TYPE: PRT
<213> ORGANISM: Conus nobilis

<400> SEQUENCE: 262

Asn Gly Ser Gly Ser Ser Asn Gln Lys Glu Ala Gln Leu Cys Ile Trp
1               5                   10                  15

Lys Val Cys Pro Pro Thr Pro Trp Arg
            20                  25

<210> SEQ ID NO 263
<211> LENGTH: 27
<212> TYPE: PRT
<213> ORGANISM: Conus sulcatus

<400> SEQUENCE: 263

Arg Ser Asp Lys Asp Val Gly Lys Arg Met Glu Cys Tyr Trp Lys Ala
1               5                   10                  15

Cys Arg Pro Thr Leu Ser Arg Arg His Asp Leu
            20                  25

<210> SEQ ID NO 264
<211> LENGTH: 40
<212> TYPE: PRT
<213> ORGANISM: Conus bocki

<400> SEQUENCE: 264

Arg Ser Asp Lys Asp Asp Pro Gly Gly Gln Glu Cys Tyr Trp Asn Val
1               5                   10                  15

Cys Ala Pro Asn Gln Gly Asp His Met Ile Leu Arg Lys Lys Met Asn
            20                  25                  30

Asp Asp Arg Gln Pro Pro Gln Leu
        35                  40

<210> SEQ ID NO 265
<211> LENGTH: 19
<212> TYPE: PRT
<213> ORGANISM: Conus betulinus
```

```
<400> SEQUENCE: 265

Arg Ser Asp Ser Asp Val Arg Glu Val Pro Val Cys Ser Trp Lys Ile
1               5                   10                  15

Cys Pro Pro

<210> SEQ ID NO 266
<211> LENGTH: 22
<212> TYPE: PRT
<213> ORGANISM: Conus loroisii

<400> SEQUENCE: 266

Arg Ser Asp Ser Asp Val Arg Glu Val Tyr Ile Leu Cys Ile Trp Lys
1               5                   10                  15

Ile Cys Pro Pro Leu Pro
            20

<210> SEQ ID NO 267
<211> LENGTH: 32
<212> TYPE: PRT
<213> ORGANISM: Conus gladiator

<400> SEQUENCE: 267

His Pro Ala Asn Val Arg Gln Gln Gly Lys Ile Cys Val Trp Lys Val
1               5                   10                  15

Cys Pro Pro Trp Pro Val Arg Ser Pro Gly Pro Gln Pro Lys Asn Lys
            20                  25                  30

<210> SEQ ID NO 268
<211> LENGTH: 32
<212> TYPE: PRT
<213> ORGANISM: Conus gladiator

<400> SEQUENCE: 268

His Pro Ala Asn Val Arg Gln Gln Gly Lys Ile Cys Val Trp Lys Val
1               5                   10                  15

Cys Pro Pro Ser Pro Val Arg Ser Pro Gly Pro Leu Pro Lys Asn Lys
            20                  25                  30

<210> SEQ ID NO 269
<211> LENGTH: 41
<212> TYPE: PRT
<213> ORGANISM: Conus musicus

<400> SEQUENCE: 269

Gly Met Gly Pro Gly Asp Leu Ser Leu Gln Lys Met Phe Pro Ser Leu
1               5                   10                  15

Ala Leu Gly Pro Gly Gly Asp Val Ile Cys Arg Trp Lys Val Cys Pro
            20                  25                  30

Pro Thr Pro Trp Lys Arg Leu Ile Lys
        35                  40

<210> SEQ ID NO 270
<211> LENGTH: 49
<212> TYPE: PRT
<213> ORGANISM: Conus musicus

<400> SEQUENCE: 270

Gly Met Val Pro Gly Asp Leu Ala Leu Gln Tyr Leu Phe Pro Ser Leu
1               5                   10                  15

Ala Phe Asn Pro Pro Asp Ile Cys Thr Trp Lys Val Cys Pro Pro Pro
            20                  25                  30
```

```
Pro Trp Arg Arg Pro Lys Lys Ile Thr Asp Val Gly Gln Pro Pro Gln
        35                  40                  45

Leu

<210> SEQ ID NO 271
<211> LENGTH: 49
<212> TYPE: PRT
<213> ORGANISM: Conus musicus

<400> SEQUENCE: 271

Gly Met Val Pro Gly Asp Leu Val Leu Gln Tyr Leu Phe Pro Ser Leu
1               5                   10                  15

Ala Phe Ser Pro Pro Asp Ile Cys Thr Trp Lys Val Cys Pro Pro Pro
            20                  25                  30

Pro Trp Arg Arg Pro Lys Lys Ile Thr Asp Val Arg Gln Pro Pro Gln
        35                  40                  45

Leu

<210> SEQ ID NO 272
<211> LENGTH: 49
<212> TYPE: PRT
<213> ORGANISM: Conus musicus

<400> SEQUENCE: 272

Gly Met Val Pro Gly Asp Leu Val Leu Gln Tyr Leu Phe Pro Ser Leu
1               5                   10                  15

Ala Phe Asn Pro Pro Asp Ile Cys Thr Trp Lys Val Cys Pro Pro Pro
            20                  25                  30

Pro Trp Arg Arg Pro Lys Lys Ile Thr Asp Val Arg Gln Pro Pro Gln
        35                  40                  45

Leu

<210> SEQ ID NO 273
<211> LENGTH: 29
<212> TYPE: PRT
<213> ORGANISM: Conus miles

<400> SEQUENCE: 273

Glx Gln Asp Gln Ser Pro His His Val Cys Cys Ala Ile Gly Pro Val
1               5                   10                  15

Leu Pro Phe Cys Cys Val Ser Trp Leu His Lys Leu His
            20                  25

<210> SEQ ID NO 274
<211> LENGTH: 14
<212> TYPE: PRT
<213> ORGANISM: Conus miles

<400> SEQUENCE: 274

Leu Cys Cys Ile Phe Ala Pro Ile Leu Trp Phe Cys Cys His
1               5                   10

<210> SEQ ID NO 275
<211> LENGTH: 13
<212> TYPE: PRT
<213> ORGANISM: Conus rattus

<400> SEQUENCE: 275

Leu Cys Cys Ile Phe Ala Ile Leu Trp Phe Cys Cys Leu
1               5                   10
```

<210> SEQ ID NO 276
<211> LENGTH: 15
<212> TYPE: PRT
<213> ORGANISM: Conus capitaneus

<400> SEQUENCE: 276

Gly Phe Cys Cys Asp Phe Pro Pro Ile Phe Trp Phe Cys Cys Ile
1               5                   10                  15

<210> SEQ ID NO 277
<211> LENGTH: 25
<212> TYPE: PRT
<213> ORGANISM: Conus miles

<400> SEQUENCE: 277

Glx Gly Phe Cys Cys Val Val Ile Pro Ile Leu Trp Phe Cys Cys Gly
1               5                   10                  15

Gly Tyr Arg Thr Asn Gly Thr Ala Asp
            20                  25

<210> SEQ ID NO 278
<211> LENGTH: 14
<212> TYPE: PRT
<213> ORGANISM: Conus vexillum

<400> SEQUENCE: 278

Phe Cys Cys Ile Phe Ala Pro Ile Leu Leu Phe Cys Cys Phe
1               5                   10

<210> SEQ ID NO 279
<211> LENGTH: 45
<212> TYPE: PRT
<213> ORGANISM: Conus sulcatus

<400> SEQUENCE: 279

Glx Ser Gly Cys Arg Val Pro Phe Glu Leu Lys Cys Ile Trp Lys Phe
1               5                   10                  15

Cys Thr Ile Tyr Pro Ser Arg Pro Phe Ala Ser Leu Glu Glu Lys Asp
            20                  25                  30

Glu Cys Gln Thr Val Thr Ile Thr Val Thr Trp Asp Phe
        35                  40                  45

<210> SEQ ID NO 280
<211> LENGTH: 45
<212> TYPE: PRT
<213> ORGANISM: Conus cinereus

<400> SEQUENCE: 280

Ser Ser Gly Cys Ser Val Ser Leu Gly Phe Lys Cys Phe Trp Lys Ser
1               5                   10                  15

Cys Thr Val Ile Pro Val Arg Pro Phe Val Ser Leu Glu Glu Glu Asn
            20                  25                  30

Glu Cys Gln Lys Val Gln Ile Ser Ala Val Trp Gly Pro
        35                  40                  45

<210> SEQ ID NO 281
<211> LENGTH: 25
<212> TYPE: PRT
<213> ORGANISM: Conus parius

<400> SEQUENCE: 281

Pro Pro Phe Ser Cys Ser Gly Leu Arg Gly Gly Cys Val Leu Pro Pro
1               5                   10                  15

Asn Leu Arg Pro Lys Phe Asn Lys Gly
            20                  25

<210> SEQ ID NO 282
<211> LENGTH: 24
<212> TYPE: PRT
<213> ORGANISM: Conus parius

<400> SEQUENCE: 282

Pro Pro Phe Ser Cys Ala Gly Leu Arg Gly Gly Cys Val Leu Pro Pro
1               5                   10                  15

Asn Leu Arg Pro Lys Phe Lys Glu
            20

<210> SEQ ID NO 283
<211> LENGTH: 29
<212> TYPE: PRT
<213> ORGANISM: Conus wittigi

<400> SEQUENCE: 283

Ser Ser Asp Gly Ser Asp Pro Lys Ala Lys Lys Gln Cys Met Trp Lys
1               5                   10                  15

Arg Cys Ile Pro Asp Gln Ser Arg Leu Glu Glu Asp Glu
            20                  25

<210> SEQ ID NO 284
<211> LENGTH: 30
<212> TYPE: PRT
<213> ORGANISM: Conus cinereus

<400> SEQUENCE: 284

Ser Ser Asp Gly Lys Ala Lys Lys Gln Cys Ala Trp Lys Thr Cys Val
1               5                   10                  15

Pro Thr Gln Trp Arg Arg Arg Asp Leu Lys Glu Lys Asp Glu
            20                  25                  30

<210> SEQ ID NO 285
<211> LENGTH: 30
<212> TYPE: PRT
<213> ORGANISM: Conus cinereus

<400> SEQUENCE: 285

Ser Ser Asp Gly Lys Ala Lys Arg Asn Cys Phe Trp Lys Ala Cys Val
1               5                   10                  15

Pro Glu Gln Trp Arg Gln Arg Asp Pro Lys Glu Lys Asp Glu
            20                  25                  30

<210> SEQ ID NO 286
<211> LENGTH: 30
<212> TYPE: PRT
<213> ORGANISM: Conus cinereus

<400> SEQUENCE: 286

Ser Ser Asp Gly Lys Ala Lys Arg Asn Cys Phe Trp Lys Ala Cys Val
1               5                   10                  15

Pro Glu Gln Trp Arg Gln Arg Asp Leu Lys Glu Lys Asp Glu
            20                  25                  30

<210> SEQ ID NO 287
<211> LENGTH: 37

```
<212> TYPE: PRT
<213> ORGANISM: Conus nobilis

<400> SEQUENCE: 287

Phe Arg Pro Ala Val Lys Ser Arg Ser Arg Arg Ala Pro Pro Cys Val
1               5                   10                  15

Trp Lys Val Cys Pro Ala Pro Pro Trp Leu Val Thr Lys Arg Lys Gln
            20                  25                  30

Glu Thr Ser Asp Tyr
        35

<210> SEQ ID NO 288
<211> LENGTH: 37
<212> TYPE: PRT
<213> ORGANISM: Conus nobilis

<400> SEQUENCE: 288

Phe Arg Pro Ala Val Lys Ser Arg Ser Arg Arg Ala Pro Pro Cys Val
1               5                   10                  15

Trp Lys Val Cys Pro Ala Pro Pro Trp Leu Val Thr Lys Arg Lys Gln
            20                  25                  30

Glu Thr Ser Asp Tyr
        35

<210> SEQ ID NO 289
<211> LENGTH: 37
<212> TYPE: PRT
<213> ORGANISM: Conus miles

<400> SEQUENCE: 289

Phe Arg Pro Ala Met Gln Ser Arg Ser Gly Gly Met Ser Leu Cys Leu
1               5                   10                  15

Trp Lys Val Cys Pro Ala Ala Pro Trp Leu Val Ala Lys Arg Lys Gln
            20                  25                  30

Glu Thr Ser Asp Tyr
        35

<210> SEQ ID NO 290
<211> LENGTH: 21
<212> TYPE: PRT
<213> ORGANISM: Conus tulipa

<400> SEQUENCE: 290

His Phe Asn Ser Val Val Pro Thr Val Tyr Ile Cys Met Trp Lys Val
1               5                   10                  15

Cys Pro Pro Ser Pro
            20

<210> SEQ ID NO 291
<211> LENGTH: 21
<212> TYPE: PRT
<213> ORGANISM: Conus purpurascens

<400> SEQUENCE: 291

Glx Ser Glu Glu Glu Lys Ile Cys Leu Trp Lys Ile Cys Pro Pro Pro
1               5                   10                  15

Pro Trp Arg Arg Ser
            20

<210> SEQ ID NO 292
<211> LENGTH: 21
```

<212> TYPE: PRT
<213> ORGANISM: Conus purpurascens

<400> SEQUENCE: 292

Glu Ser Asn Gly Val Glu Ile Cys Met Trp Lys Val Cys Pro Pro Ser
1               5                   10                  15

Pro Trp Arg Arg Ser
            20

<210> SEQ ID NO 293
<211> LENGTH: 38
<212> TYPE: PRT
<213> ORGANISM: Conus vexillum

<400> SEQUENCE: 293

Ile Met Gln Ser Leu Val Phe Ser His Gln Pro Leu Pro Thr Ala Ser
1               5                   10                  15

Ile Cys Ile Trp Lys Ile Cys Pro Pro Asp Pro Trp Arg Arg His Asp
            20                  25                  30

Leu Gln Lys Ser Asn Lys
        35

<210> SEQ ID NO 294
<211> LENGTH: 38
<212> TYPE: PRT
<213> ORGANISM: Conus muriculatus

<400> SEQUENCE: 294

Ile Met Gln Ser Leu Val Phe Ser His Gln Pro Leu Pro Thr Ala Ser
1               5                   10                  15

Ile Cys Ile Trp Lys Ile Cys Pro Pro Asp Pro Trp Arg Arg His Asp
            20                  25                  30

Leu Gln Lys Ser Asn Lys
        35

<210> SEQ ID NO 295
<211> LENGTH: 26
<212> TYPE: PRT
<213> ORGANISM: Conus pulicarius

<400> SEQUENCE: 295

Val Arg Leu Arg Gly Gln Ile Cys Ile Trp Lys Val Cys Pro Pro Leu
1               5                   10                  15

Leu Gln Trp Ile His Pro Leu Val Lys Arg
            20                  25

<210> SEQ ID NO 296
<211> LENGTH: 26
<212> TYPE: PRT
<213> ORGANISM: Conus pulicarius

<400> SEQUENCE: 296

Val Arg Pro Arg Gly Gln Ile Cys Ile Trp Lys Val Cys Pro Pro Leu
1               5                   10                  15

Leu Gln Trp Ile His Pro Leu Val Lys Arg
            20                  25

<210> SEQ ID NO 297
<211> LENGTH: 27
<212> TYPE: PRT
<213> ORGANISM: Conus pulicarius -continued

```
<400> SEQUENCE: 297

Pro Val Arg Leu Arg Gly Gln Ile Cys Ile Trp Lys Val Cys Pro Pro
1               5                   10                  15

Leu Leu Gln Trp Ile His Pro Leu Val Lys Arg
            20                  25

<210> SEQ ID NO 298
<211> LENGTH: 30
<212> TYPE: PRT
<213> ORGANISM: Conus mustelinus

<400> SEQUENCE: 298

Leu Val Ser His Thr Ser Ser Lys Tyr Pro Gly Val Thr Phe Cys Pro
1               5                   10                  15

Trp Lys Val Cys Pro Pro Ala Pro Trp Arg Ile Leu Gly Val
            20                  25                  30

<210> SEQ ID NO 299
<211> LENGTH: 22
<212> TYPE: PRT
<213> ORGANISM: Conus baileyi

<400> SEQUENCE: 299

His Ser Asp Ser Ile Ile Leu Arg Gly Leu Cys Ile Trp Lys Val Cys
1               5                   10                  15

Glu Pro Pro Pro Gln Arg
            20

<210> SEQ ID NO 300
<211> LENGTH: 26
<212> TYPE: PRT
<213> ORGANISM: Conus planorbis

<400> SEQUENCE: 300

Ser Ser Ser Asn Gly Leu Lys Arg Ala Asp Leu Cys Ile His Lys Ile
1               5                   10                  15

Cys Pro Pro Arg Tyr His Gln Ser Gln Gln
            20                  25

<210> SEQ ID NO 301
<211> LENGTH: 36
<212> TYPE: PRT
<213> ORGANISM: Conus litteratus

<400> SEQUENCE: 301

His Arg Val Phe His Leu Asp Asn Thr Tyr Leu Lys Ile Pro Ile Cys
1               5                   10                  15

Ala Trp Lys Val Cys Pro Pro Thr Pro Trp Arg Arg Arg Asp Leu Lys
            20                  25                  30

Lys Arg Asn Lys
        35

<210> SEQ ID NO 302
<211> LENGTH: 50
<212> TYPE: PRT
<213> ORGANISM: Conus litteratus

<400> SEQUENCE: 302

Ser Pro Val Ser Thr Pro Tyr Pro Glu Phe His Leu Asp Glu Pro Tyr
1               5                   10                  15

Leu Lys Ile Pro Val Cys Ile Trp Lys Ile Cys Pro Pro Asn Leu Leu
```

```
                  20                  25                  30
Arg Arg Arg Asp Leu Lys Lys Arg Asn Lys Val Arg Gln Thr Thr Ala
         35                  40                  45
Thr Thr
     50

<210> SEQ ID NO 303
<211> LENGTH: 26
<212> TYPE: PRT
<213> ORGANISM: Conus coronatus

<400> SEQUENCE: 303

Leu Ser Asp Gly Arg Asp Trp Thr Gly Tyr Ile Cys Ile Trp Lys Ala
1               5                  10                  15

Cys Pro Arg Pro Pro Trp Ile Pro Pro Lys
            20                  25

<210> SEQ ID NO 304
<211> LENGTH: 29
<212> TYPE: PRT
<213> ORGANISM: Conus chaldaeus

<400> SEQUENCE: 304

Leu Ser Glu Gly Arg Asn Ser Thr Val His Ile Cys Met Trp Lys Val
1               5                  10                  15

Cys Pro Pro Pro Pro Trp Arg Arg Pro His Gly Gln Arg
            20                  25

<210> SEQ ID NO 305
<211> LENGTH: 29
<212> TYPE: PRT
<213> ORGANISM: Conus chaldaeus

<400> SEQUENCE: 305

Leu Ser Glu Gly Arg Asn Ser Thr Val His Ile Cys Thr Trp Lys Val
1               5                  10                  15

Cys Pro Pro Pro Pro Trp Arg Arg Pro His Gly Gln Arg
            20                  25

<210> SEQ ID NO 306
<211> LENGTH: 13
<212> TYPE: PRT
<213> ORGANISM: Unknown
<220> FEATURE:
<223> OTHER INFORMATION: unknown Conus species

<400> SEQUENCE: 306

Glx Cys Met Trp Lys Arg Cys Ile Pro Asp Gln Ser Arg
1               5                  10

<210> SEQ ID NO 307
<211> LENGTH: 15
<212> TYPE: PRT
<213> ORGANISM: Unknown
<220> FEATURE:
<223> OTHER INFORMATION: unknown Conus species

<400> SEQUENCE: 307

Val Asp Ile Cys Asn Trp Arg Ile Cys Ala Pro Asn Pro Leu Arg
1               5                  10                  15

<210> SEQ ID NO 308
<211> LENGTH: 13
```

<212> TYPE: PRT
<213> ORGANISM: Conus geographus
<220> FEATURE:
<221> NAME/KEY: PEPTIDE
<222> LOCATION: (1)..(13)
<223> OTHER INFORMATION: Xaa may be Trp (D or L)

<400> SEQUENCE: 308

Leu Cys Phe Xaa Lys Ser Cys Arg Pro Tyr Pro Trp Arg
1               5                   10

<210> SEQ ID NO 309
<211> LENGTH: 16
<212> TYPE: PRT
<213> ORGANISM: Conus magus
<220> FEATURE:
<221> NAME/KEY: PEPTIDE
<222> LOCATION: (1)..(16)
<223> OTHER INFORMATION: Xaa may be Trp (D or L)

<400> SEQUENCE: 309

Leu Phe Cys Phe Xaa Trp Lys Ser Cys Trp Pro Arg Pro Tyr Trp Arg
1               5                   10                  15

<210> SEQ ID NO 310
<211> LENGTH: 16
<212> TYPE: PRT
<213> ORGANISM: Conus magus
<220> FEATURE:
<221> NAME/KEY: PEPTIDE
<222> LOCATION: (1)..(16)
<223> OTHER INFORMATION: Xaa may be Trp (D or L)

<400> SEQUENCE: 310

Leu Phe Cys Phe Xaa Lys Ser Cys Trp Pro Arg Pro Tyr Pro Trp Arg
1               5                   10                  15

<210> SEQ ID NO 311
<211> LENGTH: 15
<212> TYPE: PRT
<213> ORGANISM: Conus magus
<220> FEATURE:
<221> NAME/KEY: PEPTIDE
<222> LOCATION: (1)..(15)
<223> OTHER INFORMATION: Xaa may be Phe (D or L)

<400> SEQUENCE: 311

Leu Xaa Cys Phe Trp Lys Ser Cys Trp Pro Arg Pro Tyr Trp Arg
1               5                   10                  15

<210> SEQ ID NO 312
<211> LENGTH: 15
<212> TYPE: PRT
<213> ORGANISM: Conus magus
<220> FEATURE:
<221> NAME/KEY: PEPTIDE
<222> LOCATION: (1)..(15)
<223> OTHER INFORMATION: Xaa at residue 2 may be Phe (D or L); Xaa at
      residue 5 may be Trp (D or L)

<400> SEQUENCE: 312

Leu Xaa Cys Phe Xaa Lys Ser Cys Trp Pro Arg Pro Tyr Trp Arg
1               5                   10                  15

<210> SEQ ID NO 313
<211> LENGTH: 11
<212> TYPE: PRT
<213> ORGANISM: Conus magus
<220> FEATURE:

```
<221> NAME/KEY: PEPTIDE
<222> LOCATION: (1)..(11)
<223> OTHER INFORMATION: Xaa may be Phe (D or L)

<400> SEQUENCE: 313

Leu Xaa Cys Phe Trp Lys Ser Cys Trp Pro Arg
1               5                   10

<210> SEQ ID NO 314
<211> LENGTH: 11
<212> TYPE: PRT
<213> ORGANISM: Conus magus
<220> FEATURE:
<221> NAME/KEY: PEPTIDE
<222> LOCATION: (1)..(11)
<223> OTHER INFORMATION: Xaa may be Trp (D or L)

<400> SEQUENCE: 314

Leu Phe Cys Phe Xaa Lys Ser Cys Trp Pro Arg
1               5                   10

<210> SEQ ID NO 315
<211> LENGTH: 11
<212> TYPE: PRT
<213> ORGANISM: Conus magus
<220> FEATURE:
<221> NAME/KEY: PEPTIDE
<222> LOCATION: (1)..(11)
<223> OTHER INFORMATION: Xaa at residue 2 may be Phe (D or L); Xaa at
      residue 5 may be Trp (D or L)

<400> SEQUENCE: 315

Leu Xaa Cys Phe Xaa Lys Ser Cys Trp Pro Arg
1               5                   10

<210> SEQ ID NO 316
<211> LENGTH: 9
<212> TYPE: PRT
<213> ORGANISM: Conus magus
<220> FEATURE:
<221> NAME/KEY: PEPTIDE
<222> LOCATION: (1)..(9)
<223> OTHER INFORMATION: Xaa may be Phe (D or L)

<400> SEQUENCE: 316

Leu Xaa Cys Phe Trp Lys Ser Cys Trp
1               5

<210> SEQ ID NO 317
<211> LENGTH: 9
<212> TYPE: PRT
<213> ORGANISM: Conus magus
<220> FEATURE:
<221> NAME/KEY: PEPTIDE
<222> LOCATION: (1)..(9)
<223> OTHER INFORMATION: Xaa may be Trp (D or L)

<400> SEQUENCE: 317

Leu Phe Cys Phe Xaa Lys Ser Cys Trp
1               5

<210> SEQ ID NO 318
<211> LENGTH: 9
<212> TYPE: PRT
<213> ORGANISM: Conus magus
<220> FEATURE:
<221> NAME/KEY: PEPTIDE
<222> LOCATION: (1)..(9)
<223> OTHER INFORMATION: Xaa at residue 2 may be Phe (D or L); Xaa at
``` residue 5 may be Trp (D or L)

<400> SEQUENCE: 318

Leu Xaa Cys Phe Xaa Lys Ser Cys Trp
1               5

<210> SEQ ID NO 319
<211> LENGTH: 10
<212> TYPE: PRT
<213> ORGANISM: Conus magus
<220> FEATURE:
<221> NAME/KEY: PEPTIDE
<222> LOCATION: (1)..(10)
<223> OTHER INFORMATION: Xaa may be Trp (D or L)

<400> SEQUENCE: 319

Phe Cys Phe Xaa Lys Ser Cys Trp Pro Arg
1               5                   10

<210> SEQ ID NO 320
<211> LENGTH: 10
<212> TYPE: PRT
<213> ORGANISM: Conus magus
<220> FEATURE:
<221> NAME/KEY: PEPTIDE
<222> LOCATION: (1)..(10)
<223> OTHER INFORMATION: Xaa may be Lys (D or L)

<400> SEQUENCE: 320

Phe Cys Phe Trp Xaa Ser Cys Trp Pro Arg
1               5                   10

<210> SEQ ID NO 321
<211> LENGTH: 10
<212> TYPE: PRT
<213> ORGANISM: Conus magus
<220> FEATURE:
<221> NAME/KEY: PEPTIDE
<222> LOCATION: (1)..(10)
<223> OTHER INFORMATION: Xaa may be Trp (D or L)

<400> SEQUENCE: 321

Phe Cys Phe Xaa Phe Ser Cys Trp Pro Arg
1               5                   10

<210> SEQ ID NO 322
<211> LENGTH: 10
<212> TYPE: PRT
<213> ORGANISM: Conus magus

<400> SEQUENCE: 322

Phe Cys Phe Trp Lys Ser Cys Trp Pro Arg
1               5                   10

<210> SEQ ID NO 323
<211> LENGTH: 21
<212> TYPE: PRT
<213> ORGANISM: Conus purpurascens
<220> FEATURE:
<221> NAME/KEY: PEPTIDE
<222> LOCATION: (1)..(21)
<223> OTHER INFORMATION: Xaa may be Trp (D or L)

<400> SEQUENCE: 323

Glu Ser Asn Gly Val Glu Ile Cys Met Xaa Lys Val Cys Pro Pro Ser
1               5                   10                  15

Pro Trp Arg Arg Ser

<210> SEQ ID NO 324
<211> LENGTH: 14
<212> TYPE: PRT
<213> ORGANISM: Conus striatus
<220> FEATURE:
<221> NAME/KEY: PEPTIDE
<222> LOCATION: (1)..(14)
<223> OTHER INFORMATION: Xaa may be Trp (D or L)

<400> SEQUENCE: 324

Met Glu Cys Tyr Xaa Lys Ala Cys Arg Pro Thr Leu Ser Arg
1               5                   10

<210> SEQ ID NO 325
<211> LENGTH: 16
<212> TYPE: PRT
<213> ORGANISM: Conus striatus
<220> FEATURE:
<221> NAME/KEY: PEPTIDE
<222> LOCATION: (1)..(16)
<223> OTHER INFORMATION: Xaa may be Trp (D or L)

<400> SEQUENCE: 325

Phe Glu Leu Lys Cys Ile Xaa Lys Phe Cys Thr Ile Tyr Pro Ser Arg
1               5                   10                  15

<210> SEQ ID NO 326
<211> LENGTH: 18
<212> TYPE: PRT
<213> ORGANISM: Conus striatus
<220> FEATURE:
<221> NAME/KEY: PEPTIDE
<222> LOCATION: (1)..(18)
<223> OTHER INFORMATION: Xaa may be Trp (D or L)

<400> SEQUENCE: 326

Phe Glu Leu Lys Cys Ile Xaa Lys Phe Cys Thr Ile Tyr Pro Ser Arg
1               5                   10                  15

Pro Phe

<210> SEQ ID NO 327
<211> LENGTH: 14
<212> TYPE: PRT
<213> ORGANISM: Conus tulipa
<220> FEATURE:
<221> NAME/KEY: PEPTIDE
<222> LOCATION: (1)..(14)
<223> OTHER INFORMATION: Xaa may be Trp (D or L)

<400> SEQUENCE: 327

Thr Val Tyr Ile Cys Met Xaa Lys Val Cys Pro Pro Ser Pro
1               5                   10

<210> SEQ ID NO 328
<211> LENGTH: 22
<212> TYPE: PRT
<213> ORGANISM: Conus aurisiacus
<220> FEATURE:
<221> NAME/KEY: PEPTIDE
<222> LOCATION: (1)..(22)
<223> OTHER INFORMATION: Xaa may be Trp (D or L)

<400> SEQUENCE: 328

Ser Asp Ser Ser Asp Gln Lys Ala Gln Ile Cys Ile Xaa Lys Val Cys
1               5                   10                  15

Pro Pro Pro Pro Trp Arg
            20

<210> SEQ ID NO 329
<211> LENGTH: 16
<212> TYPE: PRT
<213> ORGANISM: Conus consors
<220> FEATURE:
<221> NAME/KEY: PEPTIDE
<222> LOCATION: (1)..(16)
<223> OTHER INFORMATION: Xaa may be Trp (D or L)

<400> SEQUENCE: 329

Gly Ala Gln Ile Cys Ile Xaa Lys Val Cys Pro Pro Ser Pro Trp Arg
1               5                   10                  15

<210> SEQ ID NO 330
<211> LENGTH: 30
<212> TYPE: PRT
<213> ORGANISM: Conus musicus
<220> FEATURE:
<221> NAME/KEY: PEPTIDE
<222> LOCATION: (1)..(30)
<223> OTHER INFORMATION: Xaa may be Trp (D or L)

<400> SEQUENCE: 330

Met Phe Pro Ser Leu Ala Leu Gly Pro Gly Gly Asp Val Ile Cys Arg
1               5                   10                  15

Xaa Lys Val Cys Pro Pro Thr Pro Trp Lys Arg Leu Ile Lys
            20                  25                  30

<210> SEQ ID NO 331
<211> LENGTH: 24
<212> TYPE: PRT
<213> ORGANISM: Conus flavidus
<220> FEATURE:
<221> NAME/KEY: PEPTIDE
<222> LOCATION: (1)..(24)
<223> OTHER INFORMATION: Xaa may be Trp (D or L)

<400> SEQUENCE: 331

Val Asp Ile Cys Asn Xaa Arg Ile Cys Ala Pro Asn Pro Leu Arg Arg
1               5                   10                  15

His Asp Leu Lys Lys Gly Asn Asn
            20

<210> SEQ ID NO 332
<211> LENGTH: 15
<212> TYPE: PRT
<213> ORGANISM: Conus flavidus
<220> FEATURE:
<221> NAME/KEY: PEPTIDE
<222> LOCATION: (1)..(15)
<223> OTHER INFORMATION: Xaa may be Trp (D or L)

<400> SEQUENCE: 332

Val Asp Ile Cys Asn Xaa Arg Ile Cys Ala Pro Asn Pro Leu Arg
1               5                   10                  15

<210> SEQ ID NO 333
<211> LENGTH: 22
<212> TYPE: PRT
<213> ORGANISM: Conus geographus
<220> FEATURE:
<221> NAME/KEY: PEPTIDE
<222> LOCATION: (1)..(22)
<223> OTHER INFORMATION: Xaa may be Trp (D or L)

```
<400> SEQUENCE: 333

Arg Leu Phe Cys Phe Xaa Lys Ser Cys Thr Trp Arg Pro Tyr Pro Trp
1               5                   10                  15

Arg Arg Arg Asp Leu Asn
            20

<210> SEQ ID NO 334
<211> LENGTH: 17
<212> TYPE: PRT
<213> ORGANISM: Conus generalis
<220> FEATURE:
<221> NAME/KEY: DISULFID
<222> LOCATION: (4)..(14)

<400> SEQUENCE: 334

Ser Leu Trp Cys Val Cys Pro Phe Arg Val Cys Pro Pro Cys His Gly
1               5                   10                  15

Arg

<210> SEQ ID NO 335
<211> LENGTH: 17
<212> TYPE: PRT
<213> ORGANISM: Conus generalis
<220> FEATURE:
<221> NAME/KEY: DISULFID
<222> LOCATION: (6)..(14)

<400> SEQUENCE: 335

Ser Leu Trp Cys Val Cys Pro Phe Arg Val Cys Pro Pro Cys His Gly
1               5                   10                  15

Arg

<210> SEQ ID NO 336
<211> LENGTH: 15
<212> TYPE: PRT
<213> ORGANISM: Conus generalis
<220> FEATURE:
<221> NAME/KEY: PEPTIDE
<222> LOCATION: (1)..(15)
<223> OTHER INFORMATION: Xaa may be Phe (D or L)
<220> FEATURE:
<221> NAME/KEY: DISULFID
<222> LOCATION: (4)..(14)

<400> SEQUENCE: 336

Ser Leu Trp Cys Val Cys Pro Xaa Arg Val Cys Pro Pro Cys His
1               5                   10                  15

<210> SEQ ID NO 337
<211> LENGTH: 15
<212> TYPE: PRT
<213> ORGANISM: Conus generalis
<220> FEATURE:
<221> NAME/KEY: PEPTIDE
<222> LOCATION: (1)..(15)
<223> OTHER INFORMATION: Xaa may be Phe (D or L)
<220> FEATURE:
<221> NAME/KEY: DISULFID
<222> LOCATION: (6)..(14)

<400> SEQUENCE: 337

Ser Leu Trp Cys Val Cys Pro Xaa Arg Val Cys Pro Pro Cys His
1               5                   10                  15

<210> SEQ ID NO 338
<211> LENGTH: 6
```

```
<212> TYPE: PRT
<213> ORGANISM: Conus magus
<220> FEATURE:
<221> NAME/KEY: PEPTIDE
<222> LOCATION: (1)..(6)
<223> OTHER INFORMATION: Xaa at residues 2 and 5 may be any amino acid;
      Xaa at residue 3 may be Trp (D or L) or bromo-Trp (D or L)

<400> SEQUENCE: 338

Cys Xaa Xaa Lys Xaa Cys
1               5

<210> SEQ ID NO 339
<211> LENGTH: 6
<212> TYPE: PRT
<213> ORGANISM: Conus generalis
<220> FEATURE:
<221> NAME/KEY: PEPTIDE
<222> LOCATION: (1)..(6)
<223> OTHER INFORMATION: Xaa may be Phe (D or L)

<400> SEQUENCE: 339

Cys Pro Xaa Arg Val Cys
1               5

<210> SEQ ID NO 340
<211> LENGTH: 21
<212> TYPE: PRT
<213> ORGANISM: Conus ebraeus

<400> SEQUENCE: 340

Leu Ser Gly Gly Thr Tyr Ser Arg Val Asp Thr Cys Ile Trp Lys Val
1               5                   10                  15

Cys Pro Gln Ser Pro
            20
```

β-SUPERFAMILY CONOTOXINS

CROSS-REFERENCE TO RELATED APPLICATION

The present application is a continuation of U.S. patent application Ser. No. 10/838,226 filed on 5 May 2004 now abandoned, which in turn is a continuation of U.S. patent application Ser. No. 10/058,053 filed on 29 Jan. 2002 now abandoned. U.S. patent application Ser. No. 10/058,053 is also related to and claims priority under 35 USC §119(e) to U.S. provisional patent application Ser. No. 60/264,323 filed on 29 Jan. 2001. Each application is incorporated herein by reference.

This invention was made with Government support under Grant No. PO1 GM48677 awarded by the National Institute of General Medical Sciences, National Institutes of Health, Bethesda, Md. The United States Government has certain rights in the invention.

BACKGROUND OF THE INVENTION

The present invention is directed to β-superfamily conotoxin peptides (also referred to as β-conotoxins), derivatives or pharmaceutically acceptable salts thereof. The present invention is further directed to the use of this peptide, derivatives thereof and pharmaceutically acceptable salts thereof for the treatment of disorders associated with voltage-gated ion channels, ligand-gated ion channels and/or receptors. The invention is further directed to nucleic acid sequences encoding the conotoxin peptides and encoding propeptides, as well as the propeptides.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

*Conus* is a genus of predatory marine gastropods (snails) which envenomate their prey. Venomous cone snails use a highly developed projectile apparatus to deliver their cocktail of toxic conotoxins into their prey. In fish-eating species such as *Conus magus* the cone detects the presence of the fish using chemosensors in its siphon. When close enough it extends its proboscis and impales the fish hollow harpoon-like tooth containing venom. This immobilizes the fish and enables the cone snail to wind it into its mouth via the tooth at the end of the proboscis. For general information on *Conus* and their venom see the website address grimwade.biochem.unimelb.edu.au/cone/referenc.html. Prey capture is accomplished through a sophisticated arsenal of peptides which target specific ion channel and receptor subtypes. Each *Conus* species venom appears to contain a unique set of 50–200 peptides. The composition of the venom differs greatly between species and between individual snails within each species, each optimally evolved to paralyse it's prey. The active components of the venom are small peptides toxins, typically 10–30 amino acid residues in length and are typically highly constrained peptides due to their high density of disulphide bonds.

The venoms consist of a large number of different peptide components that when separated exhibit a range of biological activities: when injected into mice they elicit a range of physiological responses from shaking to depression. The paralytic components of the venom that have been the focus of recent investigation are the α-, ω- and μ-conotoxins. All of these conotoxins act by preventing neuronal communication, but each targets a different aspect of the process to achieve this. The α-conotoxins target nicotinic ligand gated channels, the μ-conotoxins target the voltage-gated sodium channels and the ω-conotoxins target the voltage-gated calcium channels (Olivera et al., 1985; Olivera et al., 1990). For example a linkage has been established between α-, αA- & ψ-conotoxins and the nicotinic ligand-gated ion channel; ω-conotoxins and the voltage-gated calcium channel; μ-conotoxins and the voltage-gated sodium channel; δ-conotoxins and the voltage-gated sodium channel; κ-conotoxins and the voltage-gated potassium channel; conantokins and the ligand-gated glutamate (NMDA) channel.

However, the structure and function of only a small minority of these peptides have been determined to date. For peptides where function has been determined, three classes of targets have been elucidated: voltage-gated ion channels; ligand-gated ion channels, and G-protein-linked receptors.

*Conus* peptides which target voltage-gated ion channels include those that delay the inactivation of sodium channels, as well as blockers specific for sodium channels, calcium channels and potassium channels. Peptides that target ligand-gated ion channels include antagonists of NMDA and serotonin receptors, as well as competitive and noncompetitive nicotinic receptor antagonists. Peptides which act on G-protein receptors include neurotensin and vasopressin receptor agonists. The unprecedented pharmaceutical selectivity of conotoxins is at least in part defined by a specific disulfide bond frameworks combined with hypervariable amino acids within disulfide loops (for a review see McIntosh et al., 1998).

There are drugs used in the treatment of pain, which are known in the literature and to the skilled artisan. See, for example, Merck Manual, 16th Ed. (1992). However, there is a demand for more active analgesic agents with diminished side effects and toxicity and which are non-addictive. The ideal analgesic would reduce the awareness of pain, produce analgesia over a wide range of pain types, act satisfactorily whether given orally or parenterally, produce minimal or no side effects, be free from tendency to produce tolerance and drug dependence.

Due to the high potency and exquisite selectivity of the conopeptides, several are in various stages of clinical development for treatment of human disorders. For example, two *Conus* peptides are being developed for the treatment of pain. The most advanced is ω-conotoxin MVIIA (ziconotide), an N-type calcium channel blocker (see Heading, C., 1999; U.S. Pat. No. 5,859,186). ω-Conotoxin MVIIA, isolated from *Conus magus*, is approximately 1000 times more potent than morphine, yet does not produce the tolerance or addictive properties of opiates. ω-Conotoxin MVIIA has completed Phase III (final stages) of human clinical trials and has been approved as a therapeutic agent. ω-Conotoxin MVIIA is introduced into human patients by means of an implantable, programmable pump with a catheter threaded into the intrathecal space. Preclinical testing for use in post-surgical pain is being carried out on another *Conus* peptide, contulakin-G, isolated from *Conus geographus* (Craig et al. 1999). Contulakin-G is a 16 amino acid O-linked glycopeptide whose C-terminus resembles neurotensin. It is an agonist of neurotensin receptors, but appears significantly more potent than neurotensin in inhibiting pain in in vivo assays.

In view of a large number of biologically active substances in *Conus* species it is desirable to further characterize them and to identify peptides capable of treating disorders voltage-gated ion channels, ligand-gated ion channels and/or receptors. Surprisingly, and in accordance with this invention, Applicants have discovered novel conotoxins that can be useful for the treatment of disorders involving voltage-gated ion channels, ligand-gated ion channels and/or receptors and could address a long felt need for a safe and effective treatment.

SUMMARY OF THE INVENTION

The present invention is directed to conotoxin peptides, derivatives or pharmaceutically acceptable salts thereof. The present invention is further directed to the use of this peptide, derivatives thereof and pharmaceutically acceptable salts thereof for the treatment of disorders associated with voltage-gated ion channels, ligand-gated ion channels and/or G-protein coupled receptors (GPCRs). The invention is further directed to nucleic acid sequences encoding the conotoxin peptides and encoding propeptides, as well as the propeptides.

More specifically, the present invention is directed to conotoxin peptides, having the amino acid sequences set forth in Tables 1–3 below. In the β-superfamily conotoxins containing 4-Cys residues (e.g., Gel4.1), the peptide may be bridged [1,4/2,3] or [1,3/2,4].

The present invention is also directed to derivatives or pharmaceutically acceptable salts of the conotoxin peptides or the derivatives. Examples of derivatives include peptides in which the Arg residues may be substituted by Lys, ornithine, homoarginine, nor-Lys, N-methyl-Lys, N,N-dimethyl-Lys, N,N,N-trimethyl-Lys or any synthetic basic amino acid. The Lys residues may be substituted by Arg, ornithine, homoarginine, nor-Lys, or any synthetic basic amino acid. The Tyr residues may be substituted with meta-Tyr, ortho-Tyr, nor-Tyr, $^{125}$I-Tyr, mono-halo-Tyr, di-halo-Tyr, O-sulpho-Tyr, O-phospho-Tyr, nitro-Tyr or any synthetic hydroxy containing amino acid. The Ser residues may be substituted with Thr or any synthetic hydroxylated amino acid. The Thr residues may be substituted with Ser or any synthetic hydroxylated amino acid. The Phe residues may be D or L, may be substituted at the ortho, meta, and/or para positions with a halogen or may be substituted with any synthetic aromatic amino acid. The Trp residues may be substituted with Trp (D), neo-Trp, 6-halo-Trp (D or L), preferably 6-halo, or any aromatic synthetic amino acid; and the Asn, Ser, Thr or Hyp residues may be glycosylated. The halogen may be iodo, chloro, fluoro or bromo; preferably iodo for halogen substituted-Tyr and bromo for halogen-substituted Trp. The Tyr residues may also be substituted with the 3-hydroxyl or 2-hydroxylisomers (meta-Tyr or ortho-Tyr, respectively) and corresponding O-sulpho- and O-phospho-derivatives. The acidic amino acid residues may be substituted with any synthetic acidic amino acid, e.g., tetrazolyl derivatives of Gly and Ala. The Leu may be substituted with Leu (D). The Glu residues may be substituted with Gla or Asp. The Gla residues may be substituted with Glu or Asp. The acidic amino acid residues may be substituted with any synthetic acidic amino acid, e.g. tetrazolyl derivatives of Gly and Ala. The N-terminal Gln may be substituted with pyro-glutamate (Z). The aliphatic amino acids may be substituted by synthetic derivatives bearing non-natural aliphatic branched or linear side chains $C_nH_{2n+2}$ up to and including n=8. The Met residues may be substituted with nor-leucine (Nle). The Cys residues may be in D or L configuration and may optionally be substituted with homocysteine (D or L). Basic residues in the backbone may be D or L configuration. The central Trp residue within the beta-turn is preferably epimerized to the D-form.

Examples of synthetic aromatic amino acid include, but are not limited to, nitro-Phe, 4-substituted-Phe wherein the substituent is $C_1$–$C_3$ alkyl, carboxyl, hyrdroxymethyl, sulphomethyl, halo, phenyl, —CHO, —CN, —$SO_3H$ and —NHAc. Examples of synthetic hydroxy containing amino acid, include, but are not limited to, such as 4-hydroxymethyl-Phe, 4-hydroxyphenyl-Gly, 2,6-dimethyl-Tyr and 5-amino-Tyr. Examples of synthetic basic amino acids include, but are not limited to, N-1-(2-pyrazolinyl)-Arg, 2-(4-piperinyl)-Gly, 2-(4-piperinyl)-Ala, 2-[3-(2S)pyrrolininyl)-Gly and 2-[3-(2S)pyrrolininyl)-Ala. These and other synthetic basic amino acids, synthetic hydroxy containing amino acids or synthetic aromatic amino acids are described in Building Block Index, Version 3.0 (1999 Catalog, pages 4–47 for hydroxy containing amino acids and aromatic amino acids and pages 66–87 for basic amino acids; see also web address amino-acids.com), incorporated herein by reference, by and available from RSP Amino Acid Analogues, Inc., Worcester, Mass. Examples of synthetic acid amino acids include those derivatives bearing acidic functionality, including carboxyl, phosphate, sulfonate and synthetic tetrazolyl derivatives such as described by Ornstein et al. (1993) and in U.S. Pat. No. 5,331,001, each incorporated herein by reference, and such as shown in the following schemes 1–3.

Scheme 1

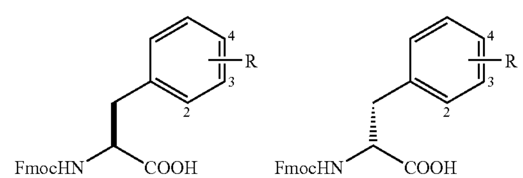

R = COOH, tetazole, $CH_2COOH$, 4-$NHSO_2CH_3$, 4-$NHSO_2$Phenyl, 4-$CH_2SO_3H$, $SO_3H$, 4-$CH_2PO_3H_2$, $CH_2CH_2COOH$, $OCH_2$Tetrazole, $CH_2S$Tetrazole HNTetrazole, $CONHSO_2R_1$ where $R_1$ is $CH_3$ or Phenyl, $SO_2$-Tetrazole, $CH_2CH_2SO_3H$, 1,2,4-tetrazole, 3-isoxazolone, amidotetrazole, $CH_2CH_2PO_3H_2$ Scheme 2

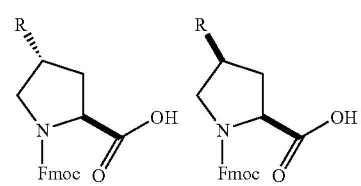

R = COOH, tetrazol, $CH_2COOH$, $CH_2$tetrazole

Scheme 3

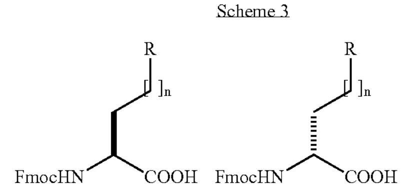

R = COOH, tetazole, $CH_2COOH$, 4-$NHSO_2CH_3$, 4-$NHSO_2$Phenyl, 4-$CH_2SO_3H$, $SO_3H$, 4-$CH_2PO_3H_2$, $CH_2CH_2COOH$, $OCH_2$Tetrazole, $CH_2S$Tetrazole, HNTetrazole, $CONHSO_2R_1$ where $R_1$ is $CH_3$ or Phenyl, $SO_2$-Tetrazole, $CH_2CH_2SO_3H$, 1,2,4-tetrazole, 3-isoxazolone, amidotetrazole, $CH_2CH_2PO_3H_2$n = 0, 1, 2, or 3

Additional derivatives are peptides in which the Asn residues may be modified to contain an N-glycan and the Ser, Thr and Hyp residues may be modified to contain an O-glycan (e.g., g-N, g-S, g-T and g-Hyp). In accordance with the present invention, a glycan shall mean any N-, S- or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The gylcan may also include similar polyhydroxy groups, such as D-penicillamine 2,5 and halogenated derivatives thereof or polypropylene glycol derivatives. The glycosidic linkage is beta and 1–4 or 1–3, preferably 1–3. The linkage between the glycan and the amino acid may be alpha or beta, preferably alpha and is 1-.

Core O-glycans have been described by Van de Steen et al. (1998), incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and connectivities) are defined for each core glycan. Suitable glycans and glycan analogs are described further in U.S. Ser. No. 09/420, 797 filed 19 Oct. 1999 (now U.S. Pat. No. 6,369,193) and in PCT Application No. PCT/US99/24380 filed 19 Oct. 1999 (PCT Published Application No. WO 00/23092), each incorporated herein by reference. A preferred glycan is Gal ($\beta1\rightarrow3$)GalNAc($\alpha1\rightarrow$).

Derivatives also include peptides in which pairs of Cys residues may be replaced pairwise with isosteric lactam or ester-thioether replacements, such as Ser/(Glu or Asp), Lys/ (Glu or Asp), Cys/(Glu or Asp) or Cys/Ala combinations. Sequential coupling by known methods (Barnay et al., 2000; Hruby et al., 1994; Bitan et al., 1997) allows replacement of native Cys bridges with lactam bridges. Thioether analogs may be readily synthesized using halo-Ala residues commercially available from RSP Amino Acid Analogues. In addition, individual Cys residues may be replaced with homoCys, seleno-Cys or penicillamine, so that disulfide bridges may be formed between Cys-homoCys or Cys-penicillamine, or homoCys-penicllamine and the like.

Derivatives and analogs also include truncations of the peptides disclosed herein. As used herein "truncations" are used to refer to peptides in which the sequence has been shortened from the mature conotoxin sequence that is predicted by the prepropeptide cleavage site with significant retention of activity of the native conotoxin. These truncations can be shortened from the N-terminus, the C-terminus, or both. As used herein significant retention of activity is used to refer to an activity of the truncated conotoxin which is less that 100-fold loss of activity and specificity.

Derivatives also include radiometal and chelated antitumor peptides. The incorporation of the radiometal eg $^{99m}Tc$, $^{111}In$, $^{90}Y$, $^{188}Re$, $^{105}RhS_4$, $^{188}Re$-tisuccin, $^{89}Sr$, $^{153}Sm$, $^{186}Re$, $^{67}Ga$, $^{211}At$, $^{212}Bi$, $^{213}Bi$, $^{177}Lu$, $^{67}Cu$, $^{64}Cu$, $^{105}Rh$, $^{47}Sc$, $^{109}Pd$] in to the conotoxin generally involves use of a chelate, specific to the particular metal, and a linker group to covalently attach the chelate to the conotoxin [the bifunctional chelate approach]. The design of useful chelates is dependent on the coordination requirements of the specific radiometal. DTPA, DOTA, $P_2S_2$—COOH BFCA requirement for kinetic TETA, NOTA are common egs. The requirement for kinetic stability of the metal complex is often achieved through the use of multidentate chelate ligands with a functionalised arm for covalent bonding to some part of the conotoxin ie the amino lysine group. Hence, the conotoxins of the present invention may be tagged to produce radiopharmaceuticals. In relation to radioligand probes of $\beta$-conotoxins for screening of small molecules, acting at unique allosteric sites, synthesis of such screening tools is not restricted to radioiodinated tyrosine derivatives. Incorporation of standard commercially available tritiated amino acid residues can also be utilized.

The present invention is further directed to a method of treating disorders associated with voltage-gated ion channels, ligand-gated ion channels and/or receptor disorders in a subject comprising administering to the subject an effective amount of the pharmaceutical composition comprising a therapeutically effective amount of a conotoxin peptide described herein or a pharmaceutically acceptable salt or solvate thereof. The present invention is also directed to a pharmaceutical composition comprising a therapeutically effective amount of a conotoxin peptide described herein or a pharmaceutically acceptable salt or solvate thereof and a pharmaceutically acceptable carrier.

More specifically, the present invention is also directed to nucleic acids which encode conotoxin peptides of the present invention or which encodes precursor peptides for these conotoxin peptides, as well as the precursor peptide. The nucleic acid sequences encoding the precursor peptides of other conotoxin peptides of the present invention are set forth in Table 1. Table 1 also sets forth the amino acid sequences of these precursor peptides.

Another embodiment of the invention contemplates a method of identifying compounds that mimic the therapeutic activity of the instant peptide, comprising the steps of: (a) conducting a biological assay on a test compound to determine the therapeutic activity; and (b) comparing the results obtained from the biological assay of the test compound to the results obtained from the biological assay of the peptide.

DETAILED DESCRIPTION OF THE PREFERRED EMBODIMENT

The present invention is directed to $\beta$-superfamily conotoxin peptides (also referred to as $\beta$-conotoxins), derivatives or pharmaceutically acceptable salts thereof. The present invention is further directed to the use of this peptide, derivatives thereof and pharmaceutically acceptable salts thereof for the treatment of disorders associated with voltage-gated ion channels, ligand-gated ion channels and/or receptors, such as G-protein coupled receptors (GPCRs). The invention is further directed to nucleic acid sequences encoding the $\beta$-superfamily conotoxin peptides and encoding propeptides, as well as the propeptides.

The present invention, in another aspect, relates to a pharmaceutical composition comprising an effective amount of a $\beta$-superfamily conotoxin peptide, a mutein thereof, an analog thereof, a derivative thereof, an active fragment thereof or pharmaceutically acceptable salts or solvates. Such a pharmaceutical composition has the capability of acting at voltage-gated ion channels, ligand-gated ion channels and/or receptors (such as G-protein coupled receptors (GPCRs)), and are thus useful for treating a disorder or disease of a living animal body, including a human, which disorder or disease is responsive to the partial or complete blockade of such channels or receptors comprising the step of administering to such a living animal body, including a human, in need thereof a therapeutically effective amount of a pharmaceutical composition of the present invention.

G-protein-coupled receptors (GPCRs) are a large, upwards of 1000, and functionally diverse protein superfamily, which form a seven transmembrane (TM) helices bundle with alternating extra-cellular and intracellular loops. GPCRs are considered to be one of the most important groups of drug targets because they are involved in a broad range of body functions and processes and are related to major diseases. Over the last decades distinct members of the G Protein-Coupled Receptor (GPCR) family emerged as prominent drug targets within pharmaceutical research, since approximately 60% of marketed prescription drugs act by selectively addressing representatives of that class of transmembrane signal transduction systems. It is noteworthy that the majority of GPCR-targeted drugs elicit their biological activity by selective agonism or antagonism of biogenic monoamine receptors, while the development status of peptide-binding GPCR-addressing compounds is still in its infancy.

The β-conotoxins may function as allosteric modulators (i.e., agonists, partial agonists, neutral antagonists, inverse agonists) of GPCRs including, but not limited to, sst ($sst_1$, $sst_2$, $sst_3$, $sst_{2a}$, $sst_{2b}$, $sst_4$, $sst_5$), cortistatin (CST), melanocortin ($MC_xR$, wherein x=1, 2, 3, 4, 5), opioid (μ, δ, κ), neurokinin ($NK_1$, $NK_2$, $NK_3$), bradykinin ($B_1$, $B_2$), galanin ($Gal_1$, $Gal_2$, $Gal_3$), $CCK_A$, $CCK_B$, endothelin, serotonin, adrenergic receptors, angiotensin ($AT_1$, $AT_2$), neuropeptide-Y, sigma1, sigma2, oxytocin, CGRP, GRPR, histamine, imidazoline, neurotensin ($NT_1$, $NT_2$, $NT_3$), VIP, vasopressin (V1a, V1b, V2), substance K, chemokine receptors ($CXCR_1$, $CXCR_2$, $CXCR_3$, $CXCR_4$, $CXCR_5$, $CCR_1$, $CCR_{2b}$, $CCR_3$, $CCR_4$, $CCR_5$, $CCR_6$, $CCR_7$, $CCR_8$, $CX_3CR_1$), $CRF_1$, $CRF_{2a}$, $CRF_{2b}$, $CRF_{2g}$, CRF-BP orexin ($Ox_1$, $Ox_2$), urotensin (UT-II), glycoprotein IIb/IIIa, thrombin receptors, orphan GPCRs (eg. $MCH_2R/SLT$, $SP1999/P_2Y_{12}$, $CRTH_2$, $NPFF_1$, $NPFF_2$, $HH_4R$, $h$-$GPR_{54}$, $CysLT_2$, neuromedin receptors, $BLTR_2$, $G_2A$, $TA_1$, $LTB_4$, ghrelin, motilin MTL-R, purinergic receptors, muscarinic receptors, ORL-1, apelin, $CB_1$, $CB_2$ and the like). For an extensive list of GPCRs see web address gpcr.org/7tm/htmls/entries.html. For additional orphan GPCR references see Shaaban (2001) and Civelli et. al. (2001). This beta turn toxin template may also be used to characterize new functional allosteric sites on known GPCRs. Radiolabelled dervatives serve as screening tools for such sites and will allow for identification of new small molecule modulators. The reverse beta turn motif serves as a template for beta turn peptidomimetic design in which the turn template contains the cone snail WK recognition "fingerprint", examples of such templates can be found in Golebiowski et al. (2001), Horwell (1996) and Beeley (2000).

Somatostatin Receptors (SSTRs): Somatostatin (SRIF), was first identified as a peptide that inhibits growth hormone release. Later it was shown to have other physiological activities, including the inhibition of the release of many endocrine secretions such as prolactin, TSH and insulin. The peptide also exhibits neuromodulatory functions and may act as a neurotransmitter. Somatostatin has two major actions; inhibition of hormone and cytokine (IFN-γ, IL-6, IL-8, IL-1) release and inhibition of cellular proliferation. SRIF can inhibit the release of hormones in the brain and almost all hormone release in the gut, together with many cytokines and growth factors eg PDGF. SRIF can be produced in cells from neuroendocrine and immune systems. It is produced in two forms SRIF-28 and SRIF-14. Additionally a novel SST-like peptide called cortistatin (CST) has been isolated from human. CST-14 shares 11 of the 14 amino acids with SRIF. One measurable difference between SRIF and CST is that SRIF increases the duration of REM sleep in rats whereas CST decreases it. It is thus possible to postulate that specific CST receptors exist.

Five sst receptors have been identified sst1, 2, 3, 4, 5. All are GPCRs and are encoded on a different chromosome. Both SRIF-14 and SRIF-28 bind to all receptors but SRIF-28 has higher affinity for $sst_5$. It must be noted that 2 isoforms of $sst_2$ exist namely, $sst_{2A}$ and $sst_{2B}$. SRIF receptors are widely expressed. Cells from the CNS, gut, pancreas, kidney, thyroid, lung and the immune system express the receptors in varying proportions.

Overproduction of growth factors from tumours can result in systemic effects, as seen in acromegaly, a chronic debilitating disease caused by excessive production of GH. SRIF analogs suppress the release of GH and thus can benefit patients. A majority of tumours originating from tissues naturally targeted by SRIF express sst receptors at high levels.

Synthetic peptides such as, lanreotide, octreotide and vapreotide bind $sst_2$ and 5 with high affinity and $sst_3$ to a lesser extent. Not only have peptide analogs of SRIF been used to reduce tumour growth directly through somatostatin receptor signalling but also medicine finds considerable use for somatostatin receptors in tumour detection and imaging and now in tumour targeting (Slooter et al., 2001).

The high level expression of somatostatin receptors (SSTR) on various tumor cells has provided the molecular basis for successful use of radiolabeled octreotide/lanreotide analogs as tumor tracers in nuclear medicine, similar chemical; modifications of conotoxins bT2, bM1, bG1 may be achieved. The vast majority of human tumors seem to overexpress the one or the other of five distinct h-SSTR sub-type receptors. Whereas neuroendocrine tumors frequently overexpress h-$SSTR_2$, intestinal adenocarcinomas seem to over-express more often h-$SSTR_3$ or h-$SSTR_4$, or both of these h-SSTR. In contrast to $^{111}$In-DTPA-DPhe1-octreotide (OCTREOSCAN) which binds to h-$SSTR_2$ and $_5$ with high affinity ($K_d$ 0.1–5 nM), to h-$SSTR_3$ with moderate affinity ($K_d$ 10–100 nM) and does not bind to h-$SSTR_1$ and h-$SSTR_4$, $^{111}$In/$^{90}$Y-DOTA-lanreotide was found to bind to h-$SSTR_{2,\,3,\,4}$, and $_5$ with high affinity, and to h-$SSTR_1$ with lower affinity ($K_d$ 200 nM). Based on its unique h-SSTR binding profile, $^{111}$In-DOTA-lanreotide was suggested to be a potential radioligand for tumor diagnosis, and $^{90}$Y-DOTA-lanreotide suitable for receptor-mediated radionuclide therapy. As opposed to $^{111}$In-DTPA-DPhe1-octreotide and $^{111}$In-DOTA-DPhe1-Tyr3-octreotide, discrepancies in the scintigraphic results were seen in about one third of (neuroendocrine) tumor patients concerning both the tumor uptake as well as detection of tumor lesions. On a molecular level, these discrepancies seem to be based on a "higher" high-affinity binding of $^{111}$In-DOTA-DPhe1-Tyr3-octreotide to h-SSTR$_2$. Other somatostatin analogs with divergent affinity to the five known h-SSTR subtype receptors have also found their way into the clinics, including $^{99m}$Tc-HYNIC-octreotide or $^{99m}$Tc-depreotide (NEOSPECT; NEOTECT).

Most of the imaging results are reported for neuroendocrine tumors (octreotide analogs) or non-small cell lung cancer ($^{99m}$Tc-depreotide), indicating high diagnostic capability of this type of receptor tracers. Consequently to their use as receptor imaging agents, h-SSTR recognizing radioligands have also been implemented for experimental receptor-targeted radionuclide therapy. The study "MAURITIUS" (MulticenterAnalysis of a Universal Receptor Imaging and Treatment Initiative, a European Study), a Phase IIa study, showed in patients with a calculated tumor dose >10 Gy/GBq $^{90}$Y-DOTA-lanreotide, the proof-of-principle for treating tumor patients with receptor imaging agents. Overall treatment results in >60 patients indicated stable tumor disease in roughly 35% of patients and regressive disease in 15% of tumor patients with different tumor entities. No acute or chronic severe hematological toxicity, change in renal or liver function parameters due to $^{90}$Y-DOTA-lanreotide, was reported. $^{90}$In-DOTA-DPhe1-Tyr3-octreotide may show a higher tumor uptake in neuroendocrine tumor lesions and may therefore provide even better treatment results in tumor patients, but there is only limited excess to long-term and survival data at present. Besides newer approaches and recent developments of $^{188}$Re-labeled radioligands no clinical results on the treatment response is available yet. In conclusion, several radioligands have been implemented on the basis of peptide receptor recognition throughout the last decade. A plentitude of preclinical data and clinical studies confirm "proof-of-principle" for their use in diagnosis as well as therapy of cancer patients. However, an optimal radiopeptide formulation does not yet exist for receptor-targeted radionuclide therapy (Virgolini, 2001).

During the last decade five different subtypes of melanocortin receptors have been identified and cloned, all of them are possible as new targets for drugs in the treatment of a number of clinical important conditions such as inflammatory diseases (MC$_1$-receptor agonists), MC$_3$/MC$_4$-receptors in the treatment of feeding disorder, agonists for treatment of obesity and antagonists for anorectic conditions. MC$_3$/MC$_4$-agonists or also assumed to be useful for treating sexual dysfunction. In the treatment of seborrheic dermatitis the MC$_5$ receptor is considered as a target. A number of peptide or peptide like ligands, agonists and/or antagonist has been discovered, however, most of them have a large similarity with the endogenous ligand α-MSH.

Melanocortins: The major source of melanocortins is the pituitary, where ACTH and β-lipotropin are the main products from the anterior pituitary, and α-MSH and β-lipotropin are major products from the intermediate lobe. All melanocortins, i.e. α-Melanocyte stimulating hormone (α-MSH), β-MSH, γ-MSH and the endogenous opioid β-endorphin, are cleaved from POMC, but β-MSH and β-endorphin emanate from the C-terminal part of POMC, i.e. the β-lipotropin. γ-MSH is cleaved from the N-terminal part of POMC. While α-MSH is a tridecapeptide proteolytically cleaved from proopiomelanocortin (POMC) comprising of the N-terminal part of ACTH and is considered as the endogenous ligand to the melanocortin receptors.

β-MSH is found in the hypothalamus, whereas γ-MSH is found in different areas of the CNS, adrenal medulla and neurons of the intestine. α-MSH has been demonstrated in the pituitary, but also in other parts of the CNS, as well as in peripheral parts of the body. Only low circulating concentrations of α-MSH have been detected in humans in normal situations, whereas the concentration is increased in several diseases.

Melanocortin Receptors MCRs: Melanocortin receptors belong to the family of G-protein coupled, 7-TM receptors, and have been identified in several tissues of the body. Today, 5 different subtypes of receptors, MC1–5, have been described. The MC$_2$ receptor binds only ACTH, and is present in the adrenal cortex and also in white adipose tissue of rodents, but not in man or primates. The MC$_1$, MC$_2$, MC$_3$, MC$_4$ and MC$_5$ receptors are distributed in different areas/organs of the body. The MC$_2$ receptor is not further discussed since it is considered as the ACTH receptor. Interestingly, the MC$_3$ receptor is expressed in low abundance during fetal life and expression increases to adult levels after birth, as demonstrated in rats. The opposite is true for the MC4 receptor, which is predominant during fetal life. However, both receptors seem to be important for different physiological functions postnatally.

The MC receptors and α-MSH are involved in several physiological functions besides affecting skin pigmentation. They have effects on learning, memory, behaviour, including sexual behaviour, regeneration in the neuromuscular system and protection from central nerve injury, cardiovascular functions, feeding and weight homeostasis, fever and immunomodulation/inflammation, exocrine functions and interact with opioids and dopamine. They are also ascribed effects such as regulation of the release of pituitary and peripheral hormone.

Examples of voltage-gated ion channels include the voltage-gated calcium channel, the voltage-gated sodium channel, the voltage-gated potassium channel and the proton-gated ion channel. Examples of ligand-gated channels include the nicotinic ligand-gated ion channel, ligand-gated glutamate (NMDA) channel and the ligand-gated 5HT$_3$ (serotonin) channel. Examples of receptors include the G-protein receptors. Activity of ψ-conotoxins is described in U.S. Pat. No. 5,969,096 and in Shon et al. (1997). Activity of bromosleeper conotoxins is described in U.S. Pat. No. 5,889,147 and in Craig et al. (1997). Activity of σ-conotoxins is described in U.S. Pat. No. 5,889,147. Activity of contryphan conotoxins is described in U.S. Pat. No. 6,077, 934 and in Jimenez et al. (1996). Activity of conopressins is described in Cruz et al. (1987) and in Kruszynski et al. (1990). Activity of γ-conotoxins is described in Fainzilber et al. (1998). Activity of αA-conotoxins is described in Jacobsen et al. (1997) and in Hopkins et al. (1995). Activity of τ-conotoxins is described in U.S. Ser. No. 09/497,491 (PCT/US00/03021, PCT published application WO 00/46371) as an antagonist for acetylcholine receptors and as analgesic agents for the treatment of pain (whether acute or chronic), including migraine, chronic pain, and neuropathic pain, without undesirable side effects. Activity of contulakins is described in U.S. Ser. No. 09/420,797 (now U.S. Pat. No. 6,369,193) (PCT/US99/24380, PCT published application WO 00/23092). Each of these references is incorporated herein by reference.

Since σ-conotoxins are antagonists of the 5HT$_3$ receptor, they are also useful in treating irritable bowel syndrome (IBS) and visceral pain. Visceral pain is a common experience in health and disease. Chronic visceral hyperalgesia in the absence of detectable organic disease has been implicated in many common functional bowel disorders (FDB), such as 113S, non-ulcer dyspepsia (NUD) and non-cardiac chest pain (NCCP).

Pain in IBS cannot be explained by normal perception of abnormal motility. In the majority of patients, sensory perception itself is abnormal. Most visceral afferent information is part of the reflex activity of digestion and does not reach concious perception. Increasing evidence suggests that long term changes in the thresholds and gain of the visceral afferent pathways are present in patients with FDBs. This has been referred to as visceral hyperalgesia (Mayer et al., 1994).

It has been proposed that FDBs are a result of increased excitability of spinal neurones. According to their model, many inputs can result in transient, short term, or life long sensitization of afferent pathways involved in visceral reflexes and sensations from the gut. The increased sensory input to interneurons and/or dorsal horn neurons in the spinal cord will result in secondary hyperalgesia, in which adjacent, undamaged viscera develop sensitivity to normal innocuous stimuli (allodynia), and central hyperexcitability as a consequence of changes in the circuitary of the dorsal horn. This central sensitization may subsequently extend to supraspinal centers also.

Altered spinal processing of visceral sensory information can explain altered sensory thresholds and altered referral patterns, the perception of visceral sensations without stimulation of visceral mechnoreceptors (sensation of incomplete evacuation), and the symptomatic involvement of multiple sites in the GI tract, including extra intestinal sites. Increased excitability of dorsal horn neurones, resulting in the recruitment of previously sub-threshold inputs, may explain cutaneous allodynia in some patients with IBS, burning sensations referred to different parts of the body, cold hypersensitivity and pain referral to upper and lower extremities.

A number of compounds have been shown to modulate visceral sensitivity in IBS patients. These include octreotide (sst$_2$; Novartis), the 5-HT$_3$ antgonists odansetron (Glaxo) and granisetron (SKB) and the peripheral kappa opioid agonist, fedotozine (Jouveinal SA). The 5-HT$_3$ antagonist alosteron (Glaxo), cuurrently in development for IBS, is active in modifying the perception of colonic distension and gut compliance in IBS patients. New drugs in development for the treatment of IBS that are targeted at pain control as well as dysmotility include 5-HT$_3$ and 5-HT$_4$ receptor antagonists. 5-HT$_3$ receptors are located throughout the central and peripheral nervous system—their role in modulating the activity of visceral afferent and enteric neurones has led to the proposal that 5-HT acts as a sensitizing agent via these receptors on visceral afferent neurones. 5-HT$_3$ receptor antagonists have been widely reported to attenuate blood pressure responses to intestinal distension. 5-HT$_3$ antagonists in development for IBS include Alosteron (phase III), which is reported to reduce abdominal pain, slow colonic transit and increase colon compliance in IBS patients. Other compounds with positive effects include the antiemetic Ramosteron (Yamanouchi), Cilansteron (Solvay) and YM-114 (Yamanouchi). An animal model for dysmotility of the GI tract has been described by Maric et al. (1989).

In addition to the above uses, the peptides of the present invention are also useful (i) for treating or diagnosis of cancer, neoplasm, solid tumor, diabetic nephropathy, fibrosis, hypophysis tumor, GI disease, IBS, restinosis, angiogenesis disorder, diabetes mellitus, endocrine tumor, diarrhea, pancreatic disease, prostate tumor, bleeding, apoptosis, inflammation, pain, diabetes, obesity, sexual dysfunction, acromegaly, glaucoma, cardiovascular, diabetic, retinopathy, depression, myocardial infarction, stroke, epilepsy, anorexia, wasting diseases, seborrheic dermatitis, schizophrenia, mood disorders, chemotherapeutic induced emesis, disorders associated with changes in blood pressure, immune disorders, nerve damage, acne, GI infections, myocardial infarction, angina, thromboembolism, cardiovascular disease, (ii) as templates for small molecule design and (iii) as screening tools.

The superfamily of seven-transmembrane-domain G-protein-coupled receptors (GPCRs) is the largest and most diverse group of transmembrane proteins involved in signal transduction. Each of the approximately 1000 family members found in vertebrates responds to stimuli as diverse as hormones, neurotransmitters, odorants and light, which selectively activate intracellular signaling events mediated by heterotrimeric G proteins. Because GPCRs are centrally positioned in the plasma membrane to initiate a cascade of cellular responses by diverse extracellular mediators, it is not surprising that modulation of GPCR function has been successful in the development of many marketed therapeutic agents. It has become clear that GPCRs for which a natural activating ligand has not yet been identified (orphan GPCRs) might provide a path to discovering new cellular substances that are important in human physiology. The process of 'de-orphanizing' these novel proteins has accelerated significantly and opened up new avenues for research in human physiology and pharmacology.

In most cases the extent of sequence homology is insufficient to assign these 'orphan' receptors to a particular receptor subfamily. Consequently, reverse molecular pharmacological and functional genomic strategies are being employed to identify the activating ligands of the cloned receptors. Briefly, the reverse molecular pharmacological methodology includes cloning and expression of orphan GPCRs in mammalian cells and screening these cells for a functional response to cognate or surrogate agonists present in biological extract preparations, peptide libraries, and complex compound collections. The functional genomics approach involves the use of "humanized" yeast cells, where the yeast GPCR transduction system is engineered to permit functional expression and coupling of human GPCRs to the endogenous signalling machinery. Both systems provide an excellent platform for identifying novel receptor ligands. Once activating ligands are identified they can be used as pharmacological tools to explore receptor function and relationship to disease.

The β-superfamily conotoxins can also be used to design a β-turn mimetic of the β-superfamily conotoxins containing a β-turn motif, e.g., the —CX1X2KX1C— (SEQ ID NO:338) motif where X1 is any amino acid and X2 is Trp in the D or L orientation (or halogenated at position 6 of the indole) or the —CPX3RVC— (SEQ ID NO:339) motif where X3 is Phe in the D or L configuration. Other β-turn motifs are also present in the β-superfamily conotoxins as evident from the peptide sequences disclosed in Tables 2 and 3. This hairpin turn would be replaced by a non-peptide turn mimetic, preferably an orally available mimetic. The unique receptor binding domains contained within the N and C-terminal regions of the β-superfamily conotoxin would then be attached to the β-turn scaffold, in such a way as to mimic the 3D spatial array within the native toxin. As an example of the β-turn motif and a β-turn mimetic, see Scheme 4.

Scheme 4

[Scheme 4 diagram: cyclic peptide structure with N-Terminal domain, C-Terminal domain, Trp, Lys, and disulfide bridge between Cys residues, leading to Generalized β-Turn structure and WK β-Turn with N-Terminal isostere and C-Terminal isostere]

The β-superfamily conotoxins of the present invention are also useful for characterizing sites on GPCRs and for identifying novel receptor ligands for GPCRS, especially orphan GCPRs. For example, the 1-beta turn toxin template may also be used to characterize new functional allosteric sites on known GPCRs. Radiolabelled derivatives serve as screening tools for such sites and will allow for identification of new small molecule modulators. The reverse beta turn motif serves as a template for beta turn peptidomimetic design in which the turn template contains the cone snail WK recognition "fingerprint", examples of such templates can be found in Golebiowski et al. (2001) and Horwell (2000). In addition, a ligand which binds to an orphan G-protein coupled receptor (orphan GPCR) can be identified by contacting a β-superfamily conotoxin with an orphan GPCR and measuring the amount of binding of the conotoxin to the orphan GPCR by methods that are well known in the art (Murphy et al., 1998). A homology search to identify other candidate ligands for testing can then be done on the basis of any peptide which binds to the orphan GPCR. The candidate ligands may be peptides or peptide mimetics.

The conotoxin peptides described herein are sufficiently small to be chemically synthesized. General chemical syntheses for preparing the foregoing conotoxin peptides are described hereinafter. Various ones of the conotoxin peptides can also be obtained by isolation and purification from specific Conus species using the technique described in U.S. Pat. No. 4,447,356 (Olivera et al., 1984); U.S. Pat. Nos. 5,514,774; 5,719,264; and 5,591,821, as well as in PCT published application WO 98/03189, the disclosures of which are incorporated herein by reference.

Although the conotoxin peptides of the present invention can be obtained by purification from cone snails, because the amounts of conotoxin peptides obtainable from individual snails are very small, the desired substantially pure conotoxin peptides are best practically obtained in commercially valuable amounts by chemical synthesis using solid-phase strategy. For example, the yield from a single cone snail may be about 10 micrograms or less of conotoxin peptides peptide. By "substantially pure" is meant that the peptide is present in the substantial absence of other biological molecules of the same type; it is preferably present in an amount of at least about 85% purity and preferably at least about 95% purity. Chemical synthesis of biologically active conotoxin peptides peptides depends of course upon correct determination of the amino acid sequence.

The conotoxin peptides can also be produced by recombinant DNA techniques well known in the art. Such techniques are described by Sambrook et al. (1989). A gene of interest (i.e., a gene that encodes a suitable conotoxin peptides) can be inserted into a cloning site of a suitable expression vector by using standard techniques. These techniques are well known to those skilled in the art. The expression vector containing the gene of interest may then be used to transfect the desired cell line. Standard transfection techniques such as calcium phosphate co-precipitation, DEAE-dextran transfection or electroporation may be utilized. A wide variety of host/expression vector combinations may be used to express a gene encoding a conotoxin peptide of interest. Such combinations are well known to a skilled artisan. The peptides produced in this manner are isolated, reduced if necessary, and oxidized to form the correct disulfide bonds.

One method of forming disulfide bonds in the conotoxin peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. No. 3,842,067 (1974) and U.S. Pat. No. 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in K. Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):$CH_2Cl_2$ (1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the -amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptido-resin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

The peptides are also synthesized using an automatic synthesizer. Amino acids are sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodiimide in N-methylpyrrolidinone (NMP) or by 2-(1H-benzotriazole-1-yl)-1,1,3,3-tetramethyluronium hexafluorophosphate (HBTU) and diethylisopropylethylamine (DIEA). The FMOC protecting group is removed by treatment with a 20% solution of piperidine in dimethylformamide (DMF). Resins are subsequently washed with DMF (twice), followed by methanol and NMP.

Muteins, analogs or active fragments, of the foregoing conotoxin peptides are also contemplated here. See, e.g., Hammerland et al. (1992). Derivative muteins, analogs or active fragments of the conotoxin peptides may be synthesized according to known techniques, including conservative amino acid substitutions, such as outlined in U.S. Pat. No. 5,545,723 (see particularly col. 2, line 50—col. 3, line 8); U.S. Pat. No. 5,534,615 (see particularly col. 19, line 45—col. 22, line 33); and U.S. Pat. No. 5,364,769 (see particularly col. 4, line 55—col. 7, line 26), each herein incorporated by reference.

Radiolabeled peptides have been used to show that perhaps only the amino acid sequence actually involved in binding to the receptor is essential for achieving tumor uptake. $^{111}$In-radiolabelled octreotide, which is used to image somatostatin positive tumors, is a prime example of this. In addition, advances in tumor biology have demonstrated metabolic pathways to deliver the nuclide within the cell cytoplasm through internalization mechanisms. Some classes of tumors have been shown to overexpress certain receptors, e.g., glutamate, AMPA, NMDA, somatostatin, melanocortin and the like, and whenever these substances can be radiolabeled and introduced to the system, they can become the lethal magic bullet by working inside the cell.

Specificity is the paramount goal in radionuclide therapy because with specificity comes safety and efficacy. The strategy in biologically targeted therapy is to chemically package the radionuclide to take advantage of metabolic pathways or tumor characteristics so that the radionuclide is localized in the target organ or tissue while the nuclear energy is discharged with minimal exposure to healthy tissue. The concentration differential of the therapeutic radio-pharmaceutical must be orders of magnitude between target and non-target tissues. Radiation doses of 4000–6000 rads are desirable in the target tissue, while only a few tens of radiation units can be functionally tolerated by some radiosensitive tissues. The short range of the emitted particles in the tissues makes them very damaging over the range in which their decay energy is deposited. The specificity of certain of the β-superfamily conotoxins for the somatostatin receptor provide the necessary specificity for the treatment and diagnosis of tumors.

Where the aim is to provide an image of the tumor, one will desire to use a diagnostic agent that is detectable upon imaging, such as a paramagnetic, radioactive or fluorogenic agent. Many diagnostic agents are known in the art to be useful for imaging purposes, as are methods for their attachment to peptides (see, e.g., U.S. Pat. Nos. 5,021,236 and 4,472,509, both incorporated herein by reference). In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III). Moreover, in the case of radioactive isotopes for therapeutic and/or diagnostic application, one might mention $^{131}$iodine, $^{123}$iodine, $^{99m}$technicium, $^{111}$indium, $^{188}$rhenium, $^{186}$rhenium, $^{67}$gallium, $^{67}$copper, $^{90}$yttrium, $^{125}$iodine, or $^{211}$astatine. Short-lived positron emission tomography (PET) isotopes, such as $^{18}$flourine, can also be used for labeling peptides for use in tumor diagnosis (Okarvi, 2001).

Where the aim is to treat the tumor, one will desire to use a radionuclide that will irradiate the tumor. Suitable radionuclides include $^{131}$iodine, $^{123}$iodine, $^{99m}$technicium, $^{111}$indium, $^{188}$rhenium, $^{186}$rhenium, $^{67}$gallium, 90yttrium, $^{105}$rhodium, $^{89}$strontium, $^{153}$samarium, $^{211}$astatine, $^{212}$bismuth, $^{213}$bismuth, $^{77}$lutetium, 67copper, $^{47}$scandium, $^{109}$palladium. Optimally, radionuclides are chosen for the specific application on the basis of physical and chemical properties such that (a) their decay mode and emitted energy are matched to the delivery site, (b) their half life and chemical properties are complementary to the biological processing and (c) production methods can yield the radionuclide at the necessary level of specific activity and radionuclide purity.

The incorporation of the radiometal into the β-superfamily conotoxins generally involves use of a chelate, specific to the particular metal, and a linker group to covalently attach the chelate to the conotoxin, i.e., a the bifunctional chelate approach. The design of useful chelates is dependent on the coordination requirements of the specific radiometal. DTPA, DOTA, $P_2S_2$—COOH BFCA requirement for kinetic TETA, NOTA are common examples. The requirement for kinetic stability of the metal complex is often achieved through the use of multidentate chelate ligands with a functionalized arm for covalent bonding to some part of the conantokin or γ-carboxyglutamate containing conopeptide, i.e., the lysine amino group. Techniques for chelating radioonuclides with proteins are well known in the art, such as demonstrated by interantional patent application publication No. WO 91/01144, incorporated herein by reference.

In some embodiments, the β-superfamily conotoxins are used in combination with one or more potentiators and/or chemotherapeutic agents for the treatment of cancer or tumors. An exemplary potentiator is triprolidine (U.S. Pat. No. 5,114,951) or its cis-isomer which are used in combination with chemotherapeutic agents. Another potentiator is procodazole, which is a non-specific immunoprotective agent active against viral and bacterial infections. Other potentiators which can be used with conantokins or γ-carboxyglutamate containing peptides and optionally another chemotherapeutic agent to treat or inhibit the growth of cancer include monensin, an anti-sense inhibitor of the RAD51 gene, bromodeoxyuridine, dipyridamole, indomethacin, a monoclonal antibody, an anti-transferrin receptor immunotoxin, metoclopramide, 7-thia-8-oxoguanosine, N-solanesyl-N,N'-bis(3,4-dimethoxybenzyl)ethylene-diamine, leucovorin, heparin, N-[4-[(4-fluorphenyl)sulfonly]phenyl]acetamide, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative, and dimethyl sulfoxide.

The chemotherapeutic agents which can be used with conantokins or γ-carboxyglutamate containing peptides and an optional potentiator are generally grouped as DNA-interactive agents, antimetabolites, tubulin-interactive agents, hormonal agents and others such as asparaginase or hydroxyurea. Each of the groups of chemotherapeutic agents can be further divided by type of activity or compound. The chemotherapeutic agents used in combination with γ-carboxy-glutamate containing peptides include members of all of these groups. For a detailed discussion of chemotherapeutic agents and their method of administration, see Dorr et al. (1994) and U.S. Pat. No. 6,290,929.

DNA-interactive agents include the alkylating agents, e.g. cisplatin, cyclophosphamide, altretamine; the DNA strand-breakage agents, such as bleomycin; the intercalating topoisomerase II inhibitors, e.g., dactinomycin and doxorubicin; the nonintercalating topoisomerase II inhibitors such as, etoposide and teniposde; and the DNA minor groove binder plicamydin. The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione.

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts.

Tubulin interactive agents act by binding to specific sites on tubulin, a protein that polymerizes to form cellular microtubules. Microtubules are critical cell structure units. When the interactive agents bind on the protein, the cell cannot form microtubules. Tubulin interactive agents include colchicine, vincristine and vinblastine, both alkaloids and paclitaxel and cytoxan.

Hormonal agents are also useful in the treatment of cancers and tumors. They are used in hormonally susceptible tumors and are usually derived from natural sources. These include: estrogens, conjugated estrogens and ethinyl estradiol and diethylstilbesterol, chlortrianisen and idenestrol; progestins such as hydroxyprogesterone caproate, medroxyprogesterone, and megestrol; and androgens such as testosterone, testosterone propionate; fluoxymesterone, methyltestosterone. Adrenal corticosteroids are derived from natural adrenal cortisol or hydrocortisone. They are used because of their anti inflammatory benefits as well as the ability of some to inhibit mitotic divisions and to halt DNA synthesis. These compounds include, prednisone, dexamethasone, methylprednisolone, and prednisolone. Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes. Antihormonal antigens include: antiestrogenic agents such as tamoxifen, antiandrogen agents such as flutamide; and antiadrenal agents such as mitotane and aminoglutethimide.

Pharmaceutical compositions containing a compound of the present invention as the active ingredient can be prepared according to conventional pharmaceutical compounding techniques. See, for example, *Remington's Pharmaceutical Sciences,* 18th Ed. (1990, Mack Publishing Co., Easton, Pa.). Typically, an antagonistic amount of active ingredient will be admixed with a pharmaceutically acceptable carrier. The carrier may take a wide variety of forms depending on the form of preparation desired for administration, e.g., intravenous, oral, parenteral or intrathecally. For examples of delivery methods see U.S. Pat. No. 5,844,077, incorporated herein by reference.

“Pharmaceutical composition” means physically discrete coherent portions suitable for medical administration. “Pharmaceutical composition in dosage unit form" means physically discrete coherent units suitable for medical administration, each containing a daily dose or a multiple (up to four times) or a sub-multiple (down to a fortieth) of a daily dose of the active compound in association with a carrier and/or enclosed within an envelope. Whether the composition contains a daily dose, or for example, a half, a third or a quarter of a daily dose, will depend on whether the pharmaceutical composition is to be administered once or, for example, twice, three times or four times a day, respectively.

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques.

Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

As used herein, the term "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyanisole (BHA), butylated hydroxytoluene (BHT), lecithin, propyl gallate, aloha-tocopherol and the like; and the metal chelating agents such as citric acid, ethylenediamine tetraacetic acid (EDTA), sorbitol, tartaric acid, phosphoric acid and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, epidural, irrigation, intramuscular, release pumps, or infusion.

For example, administration of the active agent according to this invention may be achieved using any suitable delivery means, including:
(a) pump (see, e.g., Luer & Hatton (1993), Zimm et al. (1984) and Ettinger et al. (1978));
(b), microencapsulation (see, e.g., U.S. Pat. Nos. 4,352,883; 4,353,888; and 5,084,350);
(c) continuous release polymer implants (see, e.g., U.S. Pat. No. 4,883,666);
(d) macroencapsulation (see, e.g., U.S. Pat. Nos. 5,284,761, 5,158,881, 4,976,859 and 4,968,733 and published PCT patent applications WO92/19195, WO 95/05452);
(e) naked or unencapsulated cell grafts to the CNS (see, e.g., U.S. Pat. Nos. 5,082,670 and 5,618,531);
(f) injection, either subcutaneously, intravenously, intra-arterially, intramuscularly, or to other suitable site; or
(g) oral administration, in capsule, liquid, tablet, pill, or prolonged release formulation.

In one embodiment of this invention, an active agent is delivered directly into the CNS, preferably to the brain ventricles, brain parenchyma, the intrathecal space or other suitable CNS location, most preferably intrathecally.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

The active agents, which are peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the developed sequences and the known genetic code.

Exemplary methods for administering compounds (e.g., so as to achieve sterile or aseptic conditions) will be apparent to the skilled artisan. Certain methods suitable for administering compounds useful according to the present invention are set forth in Goodman and Gilman's *The Pharmacological Basis of Therapeutics,* 7th Ed. (1985). The administration to the patient can be intermittent; or at a gradual, continuous, constant or controlled rate. Administration can be to a warm-blooded animal (e.g. a mammal, such as a mouse, rat, cat, rabbit, dog, pig, cow or monkey); but advantageously is administered to a human being. Administration occurs after general anesthesia is administered. The frequency of administration normally is determined by an anesthesiologist, and typically varies from patient to patient.

The active agent is preferably administered in an therapeutically effective amount. By a "therapeutically effective amount" or simply "effective amount" of an active compound is meant a sufficient amount of the compound to treat the desired condition at a reasonable benefit/risk ratio applicable to any medical treatment. The actual amount administered, and the rate and time-course of administration, will depend on the nature and severity of the condition being treated. Prescription of treatment, e.g. decisions on dosage, timing, etc., is within the responsibility of general practitioners or spealists, and typically takes account of the disorder to be treated, the condition of the individual patient, the site of delivery, the method of administration and other factors known to practitioners. Examples of techniques and protocols can be found in *Remington's Pharmaceutical Sciences.*

Dosage may be adjusted appropriately to achieve desired levels, locally or systemically, and depending on use as a diagnostic agent or a therapeutic agent. For therapeutic uses, the active agents of the present invention typically exhibit their effect at a dosage range from about 0.001 mg/kg to about 250 mg/kg, preferably from about 0.01 mg/kg to about 100 mg/kg of the active ingredient, more preferably from a bout 0.05 mg/kg to about 75 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved. In the event that the response in a subject is insufficient at such doses, even higher doses (or effective higher doses by a different, more localized delivery route) may be employed to the extent that patient tolerance permits. Continuous dosing over, for example 24 hours or multiple doses per day are contemplated to achieve appropriate systemic levels of compounds.

For diagnostic uses, an appropriate dosage will depend on the peptide and the detectable label. A suitable dose to be injected is in the range to enable imaging by scanning procedures known in the art. When a radiolabeled conantokin is used, it may be administered in a dose having a radioactivity of form 0.1 to 50 mCi, preferably, 0.1 to 30 mCi and more preferably, 0.1 to 20 mCi. For therpeutic uses, an appropriate dosage will depend on the peptide, the radionuculide, the size and location of the tumor and the half life of the active agent in the tumor. In general, the dose is calculated on the basis of of the radioactivity distribution to each organ and on observed target uptake. For example, the active agent may be administered at a daily dosage range having a radioactivity of from 0.1 to 3 mCi/kg, preferably 1 to 3 mCi/kg, more preferably 1 to 1.5 mCi/kg.

Advantageously, the compositions are formulated as dosage units, each unit being adapted to supply a fixed dose of active ingredients. Tablets, coated tablets, capsules, ampoules and suppositories are examples of dosage forms according to the invention.

It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian for use humans or animals.

The pharmaceutical compositions will generally contain from about 0.0001 to 99 wt. %, preferably about 0.001 to 50 wt. %, more preferably about 0.01 to 10 wt. % of the active ingredient by weight of the total composition. In addition to the active agent, the pharmaceutical compositions and medicaments can also contain other pharmaceutically active compounds. Examples of other pharmaceutically active compounds include, but are not limited to, analgesic agents, cytokines and therapeutic agents in all of the major areas of clinical medicine. When used with other pharmaceutically active compounds, the conopeptides of the present invention may be delivered in the form of drug cocktails. A cocktail is a mixture of any one of the compounds useful with this invention with another drug or agent. In this embodiment, a common administration vehicle (e.g., pill, tablet, implant, pump, injectable solution, etc.) would contain both the instant composition in combination supplementary potentiating agent. The individual drugs of the cocktail are each administered in therapeutically effective amounts. A therapeutically effective amount will be determined by the parameters described above; but, in any event, is that amount which establishes a level of the drugs in the area of body where the drugs are required for a period of time which is effective in attaining the desired effects.

The present invention also relates to rational drug design for the indentification of additional drugs which can be used for the purspeses described herein. The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. Several approaches for use in rational drug design include analysis of three-dimensional structure, alanine scans, molecular modeling and use of anti-id antibodies. These techniques are well known to those skilled in the art. Such techniques may include providing atomic coordinates defining a three-dimensional structure of a protein complex formed by said first polypeptide and said second polypeptide, and designing or selecting compounds capable of interfering with the interaction between a first polypeptide and a second polypeptide based on said atomic coordinates.

Following identification of a substance which modulates or affects polypeptide activity, the substance may be further investigated. Furthermore, it may be manufactured and/or used in preparation, i.e., manufacture or formulation, or a composition such as a medicament, pharmaceutical composition or drug. These may be administered to individuals.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This approach might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

A template molecule is then selected, onto which chemical groups that mimic the pharmacophore can be grafted. The template molecule and the chemical groups grafted thereon can be conveniently selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent it is exhibited. Further optimization or modification can then be carried out to arrive at one or more final mimetics for in vivo or clinical testing.

The present invention further relates to the use of a labeled (e.g., radiolabel, fluorophore, chromophore or the like) of the β-conotoxins described herein as a molecular tool both in vitro and in vivo, for discovery of small molecules that exert their action at or partially at the same functional site as the native toxin and capable of elucidation similar functional responses as the native toxin. In one embodiment, the displacement of a labeled β-conotoxin from its receptor or other complex by a candidate drug agent is used to identify suitable candidate drugs. In a second embodiment, a biological assay on a test compound to determine the therapeutic activity is conducted and compared to the results obtained from the biological assay of a β-conotoxin. In a third embodiment, the binding affinity of a small molecule to the receptor of a β-conotoxin is measured and compared to the binding affinity of a β-conotoxin to its receptor.

In view of the targets of the β-conotoxins, they may be used for treating the following conditions: cancer (neoplasm, solid tumor, diabetic nephropathy, fibrosis, hypophysis tumor, GI disease, IBS, restinosis, angiogenesis disorder, diabetes mellitus, endocrine tumor, diarrhea, pancreatic disease, prostate tumor, bleeding, apoptosis), inflammation, pain, diabetes, obesity, sexual dysfunction, acromegaly, glaucoma, cardiovascular, diabetic, retinopathy, depression, myocardial infarction, stroke, epilepsy, anorexia, wasting diseases, seborrheic dermatitis, schizophrenia, mood disorders, chemotherapeutic induced emesis, disorders associated with changes in blood pressure, immune disorders, nerve damage, acne, GI infections, myocardial infarction, angina, thromboembolism and cardiovascular disease.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel et al., 1992; Glover, 1985; Anand, 1992; Guthrie and Fink, 1991; Harlow and Lane, 1988; Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); Riott, *Essential Immunology*, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986).

EXAMPLES

The present invention is described by reference to the following Examples, which are offered by way of illustration and are not intended to limit the invention in any manner. Standard techniques well known in the art or the techniques specifically described below were utilized.

Example 1

Isolation of DNA Encoding β-Superfamily Conopeptides

DNA coding for β-superfamily conotoxin peptides was isolated and cloned in accordance with conventional techniques using general procedures well known in the art, such as described in Olivera et al. (1996), including using primers based on the DNA sequence of known conotoxin peptides. Alternatively, cDNA libraries was prepared from *Conus* venom duct using conventional techniques. DNA from single clones was amplified by conventional techniques using primers which correspond approximately to the M13 universal priming site and the M13 reverse universal priming site. Clones having a size of approximately 300–500 nucleotides were sequenced and screened for similarity in sequence to known conotoxins. The DNA sequences and encoded propeptide sequences are set forth in Table 1. DNA sequences coding for the mature toxin can also be prepared on the basis of the DNA sequences set forth in Table 1. An alignment of the conopeptides of the present invention is set forth in Table 2. Sequences of truncated and analog peptides are set forth in Table 3.

TABLE 1

Sequences of β-Superfamily Conotoxins

Name: Fd14.1

Species: *flavidus*

Cloned: Yes

DNA Sequence:
GGATCCATGCAGACGGCCTACTGGGTGATGGTGATGATGATGGTGTGGATTACAGC (SEQ ID NO: 1)
CCCTCTGTCTGAAGGTGGTAAATTGAACGACGTAATTCGGGGTTTGGTGCCAGATGA
CTTAACCCCACAGCTTATTTTGCAAAGTCTGGATTCCCGTCGTCATGATCACGGCAT
TCGTCCGAAGAGAGTCGACATATGTAACTGGAGGATATGTGCACCAAACCCATTGA
GACGACATGATCTTAAGAAAGGAAACAATTGACGTCAGACAACCGCCACAACTTGA
GTACGACATCGTTAATACGACTTCAGCAAATATGAAATTTTCAGCATCACTGTGGTT
GTGAAGAAATCAGTTGCTTTAAAAGGTTGGATTTGTCCTTGTTTAAGCCGTTGTACT
GATGACATCTCTGCACTATGAAATAAAGCTGATGTGACAAACTAAAAAAAAAAAAA
AAAA Translation:
MQTAYWVMVMMMVWITAPLSEGGKLNDVIRGLVPDDLTPQLILQSLDSRRHDHGIRPK (SEQ ID NO: 2)
RVDICNWRICAPNPLRRHDLKKGNN Toxin Sequence:
His-Asp-His-Gly-Ile-Arg-Xaa3-Lys-Arg-Val-Asp-Ile-Cys-Asn-Xaa4- (SEQ ID NO: 3)
Arg-Ile-Cys-Ala-Xaa3-Asn-Xaa3-Leu-Arg-Arg-His-Asp-Leu-Lys-Lys-
Gly-Asn-Asn-^

Name: Mi14.1

Species: *miles*

Cloned: Yes

DNA Sequence:
GGATCCATGCAGACGGCCTACTGGGTGATGGTGATGATGATGGTGGTGGGGCTCAC (SEQ ID NO: 4)
CGTCGGGAGTCACGTCCATCGGTCTCACAGTCCTACATCGCGCAGCCATGGTGATGA
CTCCATTCATGACAAGACGATTCATCAACATCTGTTTGCCCGTCTTCCTCTGGAGAA
CAACGACGACCATCGTTCTGTGGATCTTCCTGCAGGGAATGGTGCAGGCAACACCA
AGCAACAAGACCAAAGTCCTCATCATGTGTGTTGTGCTATTGGTCCGGTTCTTCCAT
TCTGTTGTGTCAGTTGGCTGCACAAACTCCATTGAACTGGCCAATGAAAATAACTCA
GGAATAGACAGAAAGGCAAAAAAAAAAAAAAAAAA Translation:
MQTAYWVMVMMMVVGLTVGSHVHRSHSPTSRSHGDDSIHDKTIHQHLFARLPLENND (SEQ ID NO: 5)
DHRSVDLPAGNGAGNTKQQDQSPHHVCCAIGPVLPFCCVSWLHKLH Toxin Sequence:
Xaa2-Gln-Asp-Gln-Ser-Xaa3-His-His-Val-Cys-Cys-Ala-Ile-Gly- (SEQ ID NO: 6)
Xaa3-Val-Leu-Xaa3-Phe-Cys-Cys-Val-Ser-Xaa4-Leu-His-Lys-Leu-
His-^

Name: Mi14.2

Species: *miles*

Iso-    No
lated:

Cloned: Yes

DNA Sequence:
GGATCCATGCAGACGGCCTACTGGGTGATGGTGATGATGATGGTGGTGGGGTTCAC (SEQ ID NO: 7)
CGTCGGGGGTCACGTCCATCGGTCTCACAGTCCTACATCGCGCAGCCATGGTGATGA
CTCCATTCATGACAAGACGATTCATCAACATCTGTTTGCCCGTCTTCCTCAGGAGAA
CAACGACGACCATCGTTCTGTGGATCTTCCTGCAGGGACTAGCGCAGGCGACATGA
AACCACAACGCCAAAGACGTCTCTGCTGCATCTTTGCCCCGATTCTTTGGTTCTGTT
GTCACGGTTAACAGCTCAAATTACACTGCACTGGCCGATTGAAAGAACTGCAATAA
ACGGAAAAAAAAAAAAAAAAAA Translation:
MQTAYWVMVMMMVVGFTVGGHVHRSHSPTSRSHGDDSIHDKTIHQHLFARLPQENN (SEQ ID NO: 8)
DDHRSVDLPAGTSAGDMKPQRQRRLCCIFAPILWFCCHG Toxin Sequence:
Leu-Cys-Cys-Ile-Phe-Ala-Xaa3-Ile-Leu-Xaa4-Phe-Cys-Cys-His-# (SEQ ID NO: 9)

Name: Cp14.1

TABLE 1-continued

Sequences of β-Superfamily Conotoxins

Species: *capitaneus*

Cloned: Yes

DNA Sequence:
GGATCCATGCAGACGGCCTACTGGGTGATGGTGATGATGATGGTGGTGGGGTTCAC (SEQ ID NO: 10)
CGTCGGGGGTCACGTCCATCGGTCTCACAGTCCTACATCGCGCAGCCATGGTGATGA
CTCCATTCATGACGAGACGATTCATCAACATCTGTTTGCCCGTCTTCCTCAGGAGAA
CAACGACGACCATCGTTCTGTGGATCTTCCTGCAGGGACTAGCGCAGGCGACATGA
AACCACAACGCCAAAGAGGTTTCTGCTGCGACTTTCCCCCGATTTTTTGGTTCTGTT
GTATCGGTTAACAGCACAAATTACACTGCACTGGCCGATTGAAAGAACTGCAATAA
ACGGAAAAAAAA Translation:
MQTAYWVMVMMMVVGFTVGGHVHRSHSPTSRSHGDDSIHDETIHQHLFARLPQENND (SEQ ID NO: 11)
DHRSVDLPAGTSAGDMKPQRQRGFCCDFPPIFWFCCIG Toxin Sequence:
Gly-Phe-Cys-Cys-Asp-Phe-Xaa3-Xaa3-Ile-Phe-Xaa4-Phe-Cys-Cys- (SEQ ID NO: 12)
Ile-#

Name: Ge14.1

Species: *generalis*

Cloned: Yes

DNA Sequence:
GGATCCATGCAGACGGCCTACTGGGTAATGGTGATGATGATGGTGTGGATTAAAGG (SEQ ID NO: 13)
CCCTGTGTCTGAAGGTGGTAAATTGAACGACGTAATTCGGGGTTTGGTGCCAGACG
ACTTGACCCCAGTGTTTGCCTTGCATCATCCGGTTTCCCATCGTCGGTCTCACAGCA
GTAGTTTGTGGTGTGTATGTCCATTCAGGGTGTGTCCACCATGCCATGGAAGATGAC
CTGGTCCCAAACCAACAAAATAACGTCAGACAACCGCCACAACTTTAGTACGACAT
CCCTTAATACGACTTCAGCAAGTATTTTAACATCACTATGGTGTGATGAAATCAGTT
GCTTTAAAA Translation:
MQTAYWVMVMMMVWIKGPVSEGGKLNDVIRGLVPDDLTPVFALHHPVSHRRSHSSSL (SEQ ID NO: 14)
WCVCPFRVCPPCHGR Toxin Sequence:
Ser-His-Ser-Ser-Ser-Leu-Xaa4-Cys-Val-Cys-Xaa3-Phe-Arg-Val-Cys- (SEQ ID NO: 15)
Xaa3-Xaa3-Cys-His-#

Name: Wi14.1

Species: *wittigi*

Cloned: Yes

DNA Sequence:
ATGATGTTGGTGTGGATTACAGCCCCTCTGCCTGAAGGTGGTAAACTGAAGCACGT (SEQ ID NO: 16)
AATTCGGGGTTTGGTGCCAGACGACTTAACCCCACAGCTTATCTTGCGAAGTCTGAT
TTCCCGTCGTAGTTCTGACGGCAGTGATCCGAAGGCAAAAAAACAGTGTATGTGGA
AGAGATGTATACCAGACCAATCGAGACTAGAAGAAGATGAATGATGTCAGACAAC
CGCCATCACTGTAGTATGACATCGTTAATACGACTTAAGCAAATATTTTAACATCAC
TGTGGTTCTGAAGACATCAGTTGCTTTAAAAGATTGGATTCTTCCTTGTTTAAGAGTT
GTACTGANATCATTCCTGCCCTGTGAAATAAAGCTGATGTTGACANNCAAACAAAA
AAAAAAAAAA Translation:
MMLVWITAPLPEGGKLKHVIRGLVPDDLTPQLILRSLISRRSSDGSDPKAKKQCMWKRCI (SEQ ID NO: 17)
PDQSRLEEDE Toxin Sequence:
Ser-Ser-Asp-Gly-Ser-Asp-Xaa3-Lys-Ala-Lys-Lys-Gln-Cys-Met-Xaa4- (SEQ ID NO: 18)
Lys-Arg-Cys-Ile-Xaa3-Asp-Gln-Ser-Arg-Leu-Xaa1-Xaa1-Asp-Xaa1-^

Name: Cn14.1

Species: *consors*

Cloned: Yes

DNA Sequence:
GGATCCATGCAGACGGCCTACTGGGTGATGGTGATGATGATGGTGTGGATTACAGC (SEQ ID NO: 19)
CCCTCTGTCTGAAGGTGGTAAATTGAACGACGTAATTCGGGGTTTGGTGTCACACAT

TABLE 1-continued

Sequences of β-Superfamily Conotoxins

DNA Sequence:
CTTAATCCCACAGCATACCTTGCGAAGTCTGACTTCCCGTGATCGTTCTGACAACGG
TGGTTCGAGTGGAGCACAAATATGCATCTGGAAGGTATGTCCACCATCCCCATAGA
GACGACCACGAGGAAAAAGATGAACGGCGTCAGACAACCGCCACAACTGTAGTAC
GACATCGTTGATACGACTTCAGCAACTATTTTAACATCACTGTGGTTGTGAAGAAAT
CAGTCGCTTTAAAAGATTGGATTTTTCCTTGTTTAAGAGTTGTACTGATATCAGCTCT
GCACTATGAAATAAAGCTGATGTGACATAAAAAAAAAAAAAAAAAAAGTACTCTGCGT
TGTTACTCGAG Translation:
MQTAYWVMVMMMVWITAPLSEGGKLNDVIRGLVSHILIPQHTLRSLTSRDRSDNGGSS    (SEQ ID NO: 20)
GAQICIWKVCPPSP Toxin Sequence:
Asp-Arg-Ser-Asp-Asn-Gly-Gly-Ser-Ser-Gly-Ala-Gln-Ile-Cys-Ile-    (SEQ ID NO: 21)
Xaa4-Lys-Val-Cys-Xaa3-Xaa3-Ser-Xaa3-^

Name: Cn14.2

Species: *consors*

Cloned: Yes

DNA Sequence:
GGATCCATGCAGACGGCCTACTGGGTGATGGTGATGATGATGGTGTGGATTACAGC    (SEQ ID NO: 22)
CCCTCTGTCTGAAGGTGGTAAATTGAACGACGCAATTCGGGGTTTGGTGTCACACAT
CTTAATCCCACAGCATACCTTGCGAAGTCTGACTTCCCGTGCTCGTTCTGACAACGG
TGGTTCGAGTGGAGCACAAATATGCATCTGGAAGGTATGTCCACCATCCCCATGGA
GACGACCACAAGGAAAAAGATGAATGACGTCAGACAACCGCCACAACTGTAGTAC
GACATCGTTGATACGACTTCAGCAAATATTTTAACATCACTGTGGTTGTGAAGAAAT
CAGTTGCTTTAAAAGATTGGATTTTTCCTTGTTTAAGAGTTGTACTGATATCAGCTCT
GCACTATGAAATAAAGCTGATGTGACAAACAATAAAAAAGAAAAAAAAAAAAGTA
CTCTGCGTTGTTACTCGAG Translation:
MQTAYWVMVMMMVWITAPLSEGGKLNDAIRGLVSHILIPQHTLRSLTSRARSDNGGSS    (SEQ ID NO: 23)
GAQICIWKVCPPSPWRRPQGKR Toxin Sequence:
Ala-Arg-Ser-Asp-Asn-Gly-Gly-Ser-Ser-Gly-Ala-Gln-Ile-Cys-Ile-    (SEQ ID NO: 24)
Xaa4-Lys-Val-Cys-Xaa3-Xaa3-Ser-Xaa3-Xaa4-Arg-Arg-Xaa3-Gln-#

Name: Cn14.3

Species: *consors*

Cloned: Yes

DNA Sequence:
GGATCCATGCAGACGGCCTACTGGGTGATGGTGATGATGATGGTGTGGATTACAGC    (SEQ ID NO: 25)
CCCTCTGTCTGAAGGTGGTAAATTGAACGACGTAATTCGGGGTTTGGTGCCACACTT
CTTAACCCCACAGCATATCTTGCAAAGTCTGACTTCCCGTAATGGTTCTGGCAGCAG
TAATCAGAAAGAAGCACAACTATGCATCTGGAAGGTATGTCCACCATCCCCATGGA
GATGACCACAAGGAAAAAGATGAACGGCGTCAGACAACCGCCACAACTGTAGTGG
GACATCGTTGATACGACTTCAGCAAATATTTTAACATCACTGTGGTTGTGAAGAAAT
CAGTTGCTTTAAAAGATTGGATTTTTCCTTGTTTAAGAATTGTACTGATATCAGCTCT
GCACTATGAAATAAAGCTGATGTGACAACCCAAAAAAAAAAAAAAAAAAAGTAC
TCTGCGTTGTTACTCGAG Translation:
MQTAYWVMVMMMVWITAPLSEGGKLNDVIRGLVPHFLTPQHILQSLTSRNGSGSSNQK    (SEQ ID NO: 26)
EAQLCIWKVCPPSPWR Toxin Sequence:
Asn-Gly-Ser-Gly-Ser-Ser-Asn-Gln-Lys-Xaa1-Ala-Gln-Leu-Cys-Ile-    (SEQ ID NO: 27)
Xaa4-Lys-Val-Cys-Xaa3-Xaa3-Ser-Xaa3-Xaa4-Arg-^

Name: T14.1

Species: *tulipa*

Cloned: Yes

DNA Sequence:
GGATCCATGCAGACGGCCTACTGGGTGATGCTGATGATGATGGTGTGGATTACAGC    (SEQ ID NO: 28)
CCCTCTGTCTGAAGGTGGTAAACTGAACGACGTAATTCGGGGTTTGGTGCCACACGT
CTTAACCCCACAGCATATCTTGCAAAGTCTGGTTTCCCGTCGTCATTTTAACAGCGTT
GTTCCGACGGTATACATATGCATGTGGAAGGTATGTCCACCATCGCCATAGAGACG TABLE 1-continued Sequences of β-Superfamily Conotoxins

```
ACCATAAGGAAAAAGATGAATGACGTCAGACAACCGCCACAACTGTAGTACGACAT
CGTTAATACGACTTCAGCAAATATTTTAACATCACTGTGGTTGTGAAGAAATCAGTT
GCTTTAAAAGATTGGATTTTTCCTTGTTTCAGAGTTGTACTGATATCAGCTCTGCACT
ATCAAATAAAGCTGAAGTGACAAACCNNAAAAAAAAAAAAAAAAAAAAAAAAAGTA
CTCTGCGTTGTTACTCGAG
```

Translation:
MQTAYWVMLMMMVWITAPLSEGGKLNDVIRGLVPHVLTPQHILQSLVSRRHFNSVVPT (SEQ ID NO: 29)
VYICMWKVCPPSP Toxin Sequence:
His-Phe-Asn-Ser-Val-Val-Xaa3-Thr-Val-Xaa5-Ile-Cys-Met-Xaa4- (SEQ ID NO: 30)
Lys-Val-Cys-Xaa3-Xaa3-Ser-Xaa3-^

Name: T14.2

Species: *tulipa*

Iso- No
lated:

Cloned: Yes

DNA Sequence:
```
ATGCAGACGGCCTACTGGGTGATGCTGTTGATGATGGTGGGCATTACAGCCCCTCTG         (SEQ ID NO: 31)
CCTGAAGGTGGTAAACCGAACAGCGTAATTCGGGGTTTGGTGCCAAACGACTTAAC
TCCACAGCATACCTTGCGAAGTCTGATTTCCCGTCGTCAAACTGACGTTCTTCTGGA
GGCTACCCTTTTGACAACACCAGCCCCCGAGCAGAGATTGTTCTGCTTCTGGAAGTC
ATGTTGGCCAAGGCCCTACCCTTGGAGACGACGTGATCTTAATGGAAAACGATGAA
TGACGTCAGACAACCGCCACAACTGTAGTACGACATCATTAATACGACTTCAGCAA
ATATTTTAACATTACTGTGGTTGTGAAGAAATCACTTGCTTTAAAAGATTGGTTTTTT
CCTTGTTTCAGAGTTGTACTGATATCAGCTCTGCCCTATGAAATAAAGCTGATG
```

Translation:
MQTAYWVMLLMMVGITAPLPEGGKPNSVIRGLVPNDLTPQHTLRSLISRRQTDVLLEAT (SEQ ID NO: 32)
LLTTPALPEQRLFCFWKSCWPRPYPWRRRDLNGKR Toxin Sequence:
Xaa2-Thr-Asp-Val-Leu-Leu-Xaa1-Ala-Thr-Leu-Leu-Thr-Thr-Xaa3- (SEQ ID NO: 33)
Ala-Xaa3-Xaa1-Gln-Arg-Leu-Phe-Cys-Phe-Xaa4-Lys-Ser-Cys-Xaa4-
Xaa3-Arg-Xaa3-Xaa5-Xaa3-Xaa4-Arg-Arg-Arg-Asp-Leu-Asn-#

Name: Sl14.2

Species: *sulcatus*

Cloned: Yes

DNA Sequence:
```
ATGCAGACGGCCTACTGGGTGATGGTGATGATGATGGTGTGGATTACAGCCCCTCT         (SEQ ID NO: 34)
GTCTGAAGGTGGTAAACCGAACGACGTAATTCGGGGTTTGGTGCCAGACGACTTAA
CCCCACAGCGTGTCTTGCGAAGTCTGATTTCCCGTCGTCAATCTGGCTGCAGAGTCC
CGTTTGAATTGAAATGCATCTGGAAGTTCTGTACAATATACCCATCGAGACCATTTG
CTTCTCTGGAAGAAAAAGACGAATGTCAGACAGTCACCATAACTGTAACATGGGAT
TTTTAATACGTCTCCAGCAAGTATTTTAACATCACTGTGGTTGTGAAGAAATCAGTT
GCTTTAAAAGATTGGATTTTTCCTTGTTTAAGAGTTGTACTGATATCAGCTCTGCCCT
GTGAAATAAAGCTGATG
```

Translation:
MQTAYWVMVMMMVWITAPLSEGGKPNDVIRGLVPDDLTPQRVLRSLISRRQSGCRVTPF (SEQ ID NO: 35)
ELKCIWKFCTIYPSRPFASLEEKDECQTVTITVTWDF Toxin Sequence:
Xaa2-Ser-Gly-Cys-Arg-Val-Xaa3-Phe-Xaa1-Leu-Lys-Cys-Ile-Xaa4- (SEQ ID NO: 36)
Lys-Phe-Cys-Thr-Ile-Xaa5-Xaa3-Ser-Arg-Xaa3-Phe-Ala-Ser-Leu-
Xaa1-Xaa1-Lys-Asp-Xaa3-Cys-Gln-Thr-Val-Thr-Ile-Thr-Val-Thr-
Xaa4-Asp-Phe-^

Name: Sl14.1

Species: *sulcatus*

Cloned: Yes

DNA Sequence:
ATGCAGACGGCCTACTGGGTGATGGTGATGATGATGGTGTGGATTACAGCCTCTCTG (SEQ ID NO: 37)
TCTGAAGGTGGTAAACCGAACGACGTCATTCGGGGTTTTGTGCCAGACGACTTAAC

TABLE 1-continued

Sequences of β-Superfamily Conotoxins

```
CCCACAGCTTATCTTGCGAAGTCTGATTTCCCGTCGTCGTTCTGACAAGGATGTTGG
GAAGAGAATGGAATGTTACTGGAAGGCATGTAGACCCACGCTATCGAGACGACATG
ATCTTGGGTAAAAGATGAATGACGTCAGACAACAGCCACAACTATAGTATGACATC
GTTAATACGACTTCAGCAAATATTTTAACATCACTGTGGTTGTGAAGAAATCAGTTG
CTTTAAAAGATTGGATTTTTCCGTGTTTAAGAGTTGTACTGATATCAGCTCTGCCCTG
TGAAATAAAGCTGATG
```

Translation:
MQTAYWVMVMMMVWITASLSEGGKPNDVIRGFVPDDLTPQLILRSLISRRRSDKDVGK         (SEQ ID NO: 38)
RMECYWKACRPTLSRRLHDLG Toxin Sequence:
Arg-Ser-Asp-Lys-Asp-Val-Gly-Lys-Arg-Met-Xaa1-Cys-Xaa5-Xaa4-        (SEQ ID NO: 39)
Lys-Ala-Cys-Arg-Xaa3-Thr-Leu-Ser-Arg-Arg-His-Asp-Leu-#

Name: M14.1

Species: *magus*

Cloned: Yes

DNA Sequence:
```
ATGCAGACGGCCTACTGGGTGATGCTGATGATGATGGTGTGCATCACAGCCCCTCTG           (SEQ ID NO: 40)
CCTGAAGGTGGTAAACCGAACAGCGGAATTCGGGGTTTGGTGCCAAACGACTTAAC
TCCACAGCATACCTTGCGAAGTCTGATTTCCCGTCGTCAAACTGACGTTCTTCTGGA
TGCTACCCTTTTGACAACACCAGCCCCCGAGCAGAGATTGTTCTGCTTCTGGAAGTC
ATGTTGGCCAAGGCCCTACCCTTGGAGCGACGTAATCTTAATGGAAAACGATGAA
TGACGTCAGACAACCGCCACAACTGTAGTACGACATCGTTAATACGACTTCAGCAA
ATATTTTAACATAACTGTGGTTGTGAAGAAATCGGTTGCTTTAAAAGATTGGATTTT
TCCTTGTTTCAGAGTTGTACTGATATGAGCTCTGCCCTGTGAAATAAAGCTGATG
```

Translation:
MQTAYWVMLMMMVCITAPLPEGGKPNSGIRGLVPNDLTPQHTLRSLISRRQTDVLLDA           (SEQ ID NO: 41)
TLLTTPAPEQRLFCFWKSCWPRPYPWRRRNLNGKR Toxin Sequence:
Xaa2-Thr-Asp-Val-Leu-Leu-Asp-Ala-Thr-Leu-Leu-Thr-Thr-Xaa3-Ala-      (SEQ ID NO: 42)
Xaa1-Xaa3-Gln-Arg-Leu-Phe-Cys-Phe-Xaa4-Lys-Ser-Cys-Xaa4-Xaa3-
Arg-Xaa3-Xaa5-Xaa3-Xaa4-Arg-Arg-Arg-Asn-Leu-Asn-#

Name: Em14.1

Species: *emaciatus*

Cloned: Yes

DNA Sequence:
```
ATGCAGACGGCCTACTGGGTGATGGCGATGATGATGGTGTGGATTACAGCCCCTCT           (SEQ ID NO: 43)
GTCTGAAGGTGGTAAATTGAACGACGTAATTCGGGGTTTGGTGCCAGATGACTTAA
CCCCACAGCTTGTTTTGCAAAGTCTGGATTCCCGTCGTCATACTCACGGCATTCGTC
CGAAGGGAGACGGCATATGTATCTGGAAGGTATGTCCACCAGACCCATGGAGACGA
CATCGTCTTAAGAAAAGAAACAATTGACGTCAGACAACCGCCACAACTTGAGTACG
ACATCGTTAATACGACTTCAGCAAATATGAAATTTTCAGCATCACTGTGGTTGTCAA
GAAATCAGTTGCTTTAAAAGATTGGATTTGTCCTTGTTTAAGAGTTGTACTGATGTC
AGCTCTGCCCTGTGAAATAAAGCTGATG
```

Translation:
MQTAYWVMAMMMVWITAPLSEGGKLNDVIRGLVPDDLTPQLVLQSLDSRRHTHGIRP           (SEQ ID NO: 44)
KGDGICIWKVCPPDPWRRHRLKKRNN Toxin Sequence:
His-Thr-His-Gly-Ile-Arg-Xaa3-Lys-Gly-Asp-Gly-Ile-Cys-Ile-Xaa4-      (SEQ ID NO: 45)
Lys-Val-Cys-Xaa3-Xaa3-Asp-Xaa3-Xaa4-Arg-Arg-His-Arg-Leu-Lys-
Lys-Arg-Asn-Asn-^

Name: Cr14.1

Species: *circumcisus*

Cloned: Yes

DNA Sequence:
```
ATGCAGACGGCCTACTGGGTGATGGTGATGATGGTGGTGTGGATTACAGCCCCTCT           (SEQ ID NO: 46)
GTCTGAAGGTGGTAAATCGAACGACGTAATTCGGGGTTTGGTGCCACACATCTTAA
CCCCACAGCATATCTTGCAAAGTCTGACTTCCCGTCTTCGTTCTGACAGCAGTGGTC
AGAAAGGAGCACAAATATGCATCTGGAAGGTATGTCCACTATCCCCATGGAGACGA
CCACAAGGAAAAAGATGAATGACGTCAGACAACCGCTACAACTGTAGTACGACATC
```

TABLE 1-continued

Sequences of β-Superfamily Conotoxins

DNA Sequence:
GTTGATACGACTTCAGCAAATATTTTAACATCACTGTGGTTGTGAAGAAATCAGTTG
CTTTAAAAGATTGGATTTTTCCTTGTTTAAGAGTTGTACTGATATCAGCTCTGCCCTG
TGAAATAAAGCTGATG Translation:
MQTAYWVMVMMVVWITAPLSEGGKSNDVIRGLVPHILTPQHILQSLTSRLRSDSSGQK   (SEQ ID NO: 47)
GAQICIWKVCPLSPWRRPQGKR Toxin Sequence:
Leu-Arg-Ser-Asp-Ser-Ser-Gly-Gln-Lys-Gly-Ala-Gln-Ile-Cys-Ile-   (SEQ ID NO: 48)
Xaa4-Lys-Val-Cys-Xaa3-Leu-Ser-Xaa3-Xaa4-Arg-Arg-Xaa3-Gln-#

Name: Bt14.1

Species: *betulinus*

Cloned: Yes

DNA Sequence:
ATGCAGACGGCCTACTGGGTGATGGTGATGATGATGGTGTGGATTACAGCCCCTCT   (SEQ ID NO: 49)
GTCCGAAGGTGGTAAACTGAACGATGTAATTCGGGCTTTGGCGCCAGACGACGTAA
CCCCACAGTTTATCTTGCGAAGTCTGATTTCCCGTCGTCGTTCTGACAGCGATGTTCG
GGAGGTACCCGTATGTTCCTGGAAGATATGTCCACCATAGCCATAGAGACGACATG
ATCTTAAGGAAAAAGAGAAATGACGTCAGACAACCGCCACAACTGTAGTACGGCAT
CGTTAATACGACTTCAGCAAATGTTTTAACATCACTGTGGTTGTGAAGAAATCAGCT
GCTTTAAAAGATTGGATTTTTCCTTAAGAGTTGCACTGATGTCAGTTCTGCCCTGTG
AAATAAAGCTGATG Translation:
MQTAYWVMVMMMVWITAPLSEGGKLNPVIRALAPDDVTPQFILRSLISRRRSDSDVRE   (SEQ ID NO: 50)
VPVCSWKICPP Toxin Sequence:
Arg-Ser-Asp-Ser-Asp-Val-Arg-Xaa1-Val-Xaa3-Val-Cys-Ser-Xaa4-   (SEQ ID NO: 51)
Lys-Ile-Cys-Xaa3-Xaa3-^

Name: A14.1

Species: *aurisiacus*

Cloned: Yes

DNA Sequence:
ATGCAGACGGCCTACTGGGTGATGGCGATGATGATGGTGTGGATTACAGCCCCTCT   (SEQ ID NO: 52)
GTCTGAAGGTGGTAAATTGAACGACGTAATTCGGGGTTTGGTGCCAGATGACTTAA
CCCCACAGCTTGTTTTGCAAAGTCTGGATTCCCGTCGTCATACTCACGGCATTCGTC
CGAAGGGAGACGGCATATGTATCTGGAAGGTATGTCCACCAGACCCATGGAGACGA
CATCATCTTAAGAAAAGAAACAATTGACGTCAGACAACCGCCACAACTTGAGTACG
ACATCGTTAATACGACTTCAGCAAATATGAAATTTTCAGCATCACTGTGGTTGTCAA
GAAATCAGTTGCTTTAAAAGATTGGATTTGTCCTTGTTTAAGAGTTGTACTGATGTC
AGCTCTGCCCTATGAAATAAAGCTGATG Translation:
MQTAYWVMAMMMVWITAPLSEGGKLNDVIRGLVPDDLTPQLVLQSLDSRRHTHGIRP   (SEQ ID NO: 53)
KGDGICIWKVCPPDPWRRHHLKKRNN Toxin Sequence:
His-Thr-His-Gly-Ile-Arg-Xaa3-Lys-Gly-Asp-Gly-Ile-Cys-Ile-Xaa4-   (SEQ ID NO: 54)
Lys-Val-Cys-Xaa3-Xaa3-Asp-Xaa3-Xaa4-Arg-Arg-His-His-Leu-Lys-
Lys-Arg-Asn-Asn-^

Name: A14.2

Species: *aurisiacus*

Cloned: Yes

DNA Sequence:
ATGCAGACGGCCTACTGGGTGATGGTGATGATGATGGTGTGGATTACAGCCCCTCT   (SEQ ID NO: 55)
GTCTGAAGGTGGTAAATTGAACGACGTAATTTGGGGTTTGGTGCCACACATCTTAAC
CCCACAGCATATCTTGCAAAGCCTGACTTCCCGTCTTCATTCTGACAGCAGTGATCA
GAAAGGAGGCATGAACGCATGGACAGGAGCAGGAGCACAAATATGCATCTGGAAG
GTATGTCCACCACCCCATGGAGATGAACACAAGGAAAAAGATGAATGACGTCAGA
CAACCGCCACAACTGTAGTACGACATCGTTGATACGACTTCAGCAAATATTTTAACA
TCACTGTGGTTGTGAAGAAATCAGTTGCTTTAAAAGATTGGATTTTTCCTTGTTTAAG
AGTTGTACTGATATCAGCTCTGCCCTGTGAAGTAAAGCTGATG TABLE 1-continued Sequences of β-Superfamily Conotoxins Translation:
MQTAYWVMVMMMVWITAPLSEGGKLNDVIWGLVPHILTPQHILQSLTSRLHSDSSDQK  (SEQ ID NO: 56)
GGMNAWTGAGAQICIWKVCPPPPWR Toxin Sequence:
Leu-His-Ser-Asp-Ser-Ser-Asp-Gln-Lys-Gly-Gly-Met-Asn-Ala-Xaa4-  (SEQ ID NO: 57)
Thr-Gly-Ala-Gly-Ala-Gln-Ile-Cys-Ile-Xaa3-Xaa3-Xaa3-Xaa3-Xaa4-
Arg-^

Name:   A14.3

Species: *aurisiacus*

Cloned: Yes

DNA Sequence:
ATGCAGACGGCCTACTGGGTGATGGTGATGATGATGGTGTGGATTACAGCCCCTCT  (SEQ ID NO: 58)
GTCTGAAGGTGGTAAATTGAACGACGTAATTTGGGGTTTGGTGCCACACATCTTAAC
CCCACAGCATATCTTGCAAAGCCTGACTTCCCGTCTTCATTCTGACAGCAGTGATCA
GAAAGGAGCACAAATATGCATCTGGAAGGTATGTCCACCACCCCCATGGAGATGAA
CACAAGGAAAAAGATGAATGACGTCAGACAACCGCCACAACTGTAGTACGACATC
GTTGATACGACTTCAGCAAATATTTTAACATCACTGTGGTTGTGAAGAAATCAGTTG
CTTTAAAAGATTGGATTTTTCCTTGTTTAGGAGTTGTATTGATATCAGCTCTGCCCTG
TGAAATAAAGCTGATG Translation:
MQTAYWVMVMMMVWITAPLSEGGKLNDVIWGLVPHILTPQHILQSLTSRLHSDSSDQK  (SEQ ID NO: 59)
GAQICIWKVCPPPPWR Toxin Sequence:
Leu-His-Ser-Asp-Ser-Ser-Asp-Gln-Lys-Gly-Ala-Gln-Ile-Cys-Ile-  (SEQ ID NO: 60)
Xaa4-Lys-Val-Cys-Xaa3-Xaa3-Xaa3-Xaa3-Xaa4-Arg- Name:   A14.4

Species: *aurisiacus*

Cloned: Yes

DNA Sequence:
ATGCAGACGGCCTACTGGGTGATGGTGATGATGATGGTGTGGATTACAGCCCCTCT  (SEQ ID NO: 61)
GTTTGAAGGTGGTAAATTGAACGACGTAATTCGGGGTTTGGTGCCACACATCTTAAC
CCCACAGCATATCTTGCAAAGCCTGACTTCCCGTCTTCGTTCTGACAGCAGTGATCA
GAAAGGAGGCATGAACGCATCGACAGGAGCAGGAGCACAAATATGCATCTGGAAG
GTATGTCCACCATCCCCATGGAGACGAACACAAGGAAAAAGATGAATGACGTCAGA
CAACCGCCACAACTGTAGTACGACATCGTTGATACGACTTCAGCAAATATTTTAACA
TCACTGTGGTTGTGAAGAAATCAGTTGCTTTAAAAGATTGGATTTTTCCTTGTTTAAG
AGTTGTACTGATATCAGCTCTGCACTGTGAAATAAAGCTGATG Translation:
MQTAYWVMVMMMVWITAPLFEGGKLNDVIRGLVPHILTPQHILQSLTSRLRSDSSDQK  (SEQ ID NO: 62)
GGMNASTGAGAQICIWKVCPPSPWRRTQGKR Toxin Sequence:
Leu-Arg-Ser-Asp-Ser-Ser-Asp-Gln-Lys-Gly-Gly-Met-Asn-Ala-Ser-  (SEQ ID NO: 63)
Thr-Gly-Ala-Gly-Ala-Gln-Ile-Cys-Ile-Xaa4-Lys-Val-Cys-Xaa3-
Xaa3-Ser-Xaa3-Xaa4-Arg-Arg-Thr-Gln-#

Name:   Ac14.1

Species: *achatinus*

Cloned: Yes

DNA Sequence:
ATGCAGACGGCCTACTGGGTGATGGTGATGATGATGGTGTGGATTACAGCCCCTCT  (SEQ ID NO: 64)
GTCTGAAGGTGGTAAATTGAACGACGTAATTCGGGGTTTGGTGCCACACATCTTAAC
CCCACAGCATATCTTGCAAAGTCTGACTTCCCGTCTTCGTTCTGACAACGGTGGTTC
GAGTGGAGCACAAATATGCATCTGGAAGGTGTGTCCACCATCCCCATGGAGACGAC
CACAAGGAAAAAGATGAACGGCGTCAGACAACCGCCACAACTGTAGTGGGACATC
GTTGATACGACTTCAGCAAATATTTTAACATCACTGTGGTTGTGAAGAAATCAGTTG
CTTTAAAAGATTGGATTTTTCCTTGTTTAAGAGTTGTACTGATATCAGCTCTGCCCTA
TGAAATAAAGCTGATG Translation:
MQTAYWVMVMMMVWITAPLSEGGKLNDVIRGLVPHILTPQHILQSLTSRLRSDNGGSS  (SEQ ID NO: 65)
GAQICIWKVCPPSPWRRPQGKR

TABLE 1-continued

Sequences of β-Superfamily Conotoxins

Toxin Sequence:
Leu-Arg-Ser-Asp-Asn-Gly-Gly-Ser-Ser-Gly-Ala-Gln-Ile-Cys-Ile- (SEQ ID NO: 66)
Xaa4-Lys-Val-Cys-Xaa3-Xaa3-Ser-Xaa3-Xaa4-Arg-Arg-Xaa3-Gln-#

Name: P14.2

Species: *purpurascens*

Cloned: Yes

DNA Sequence:
ATGCAGACGGCCTACTGGGTGATGGTGATGACGATGGTGTGGATTACAGCCCCTCT (SEQ ID NO: 67)
GTCTGAAGGTGGAAAACTGAACGATGTAATTCGGGGTTTGGTGCCAGACGACTTAG
CCCTACAGCTTATCTTGCAAAGTCCGGTTTTCCGTCGTCAATCTGAAGAGGAAAAAA
TATGCCTCTGGAAGATATGTCCACCACCCCCATGGAGACGATCATAAGGAAAAAAA
AATGAATGACGTCAGACAACCACCACAACTGTAATACGACATCGTTAATACGACTT
CAGCAAACATTTTAACATCACTGTGGTTGTGAAGAAATCAGTTGCTTTAGAAGCTTG
GATTTTTCCTTGTTTAAGAGTTGTACTGATATCAGCTCTGCCCTATGAAATAAAGCT
GATG Translation:
MQTAYWVMVMTMVWITAPLSEGGKLNDVIRGLVPDDLALQLILQSPVFRRQSEEEKIC (SEQ ID NO: 68)
LWKICPPPPWRRS Toxin Sequence:
Xaa2-Ser-Xaa1-Xaa1-Xaa1-Lys-Ile-Cys-Leu-Xaa4-Lys-Ile-Cys-Xaa3- (SEQ ID NO: 69)
Xaa3-Xaa3-Xaa3-Xaa4-Arg-Arg-Ser- Name: P14.1

Species: *purpurascens*

Cloned: Yes

DNA Sequence:
ATGCAGACGGCCTACTGGGTGATGGTGATGATGATGGTGTGGATTACAGCCCCTCT (SEQ ID NO: 70)
GTCTGAGGGTAGAAAACCGAACGATGTAATTCGGGGTTTGGTGCCAGATGACTTAG
CCCTACAGCTTATCTTGCAAAGTCAGGTTTCCCGTCGTGAATCTAATGGGGTGGAAA
TATGCATGTGGAAGGTATGTCCACCATCCCCATGGAGACGATCATAAGGAAAAAAA
ATGAATGACGTCAGACAACCACCACAACTGTAATACGACATCGTTAATACGACTTC
AGCAAACATTTTAACATCACTGTGGTTGTGAAGAAATCAGTTGCTTTAAAAGATTGG
ATTTTTCCTTGTTTAAGAGTTGTACTGATATCAGCTCTGCCCTATGAAATAAAGCTG
ATG Translation:
MQTAYWVMVMMMVWITAPLSEGRKPNDVIRGLVPDDLALQLILQSQVSRRESNGVEIC (SEQ ID NO: 71)
MWKVCPPSPWRRS Toxin Sequence:
Xaa1-Ser-Asn-Gly-Val-Xaa1-Ile-Cys-Met-Xaa4-Lys-Val-Cys-Xaa3- (SEQ ID NO: 72)
Xaa3-Ser-Xaa3-Xaa4-Arg-Arg-Ser- Name: Sm14.1

Species: *stercusmuscarum*

Cloned: Yes

DNA Sequence:
ATGCAGACGGCCTACTGGGTGATGGTGATGATGATGGTGTGGATTACAGCCCCTCT (SEQ ID NO: 73)
GTCTGAAGGTGGTAAATTGACCGACGTAATTCGGGGTTTGGTGCCACACATCTTAAC
CCCACAGCATATCTTGCAAAGTATGACTTCCCGTCTTGGTATTGGCAGCAGTGATCA
AAATGCACAAATATGCATCTGGAAGGTATGTCCACCATCCCCATAGAGACGACCAT
AAGGAAAAAGATGAATGACGTCAGACAACCGCCACAACTGTAGTACGACATCGTTG
ATACGACTTCAGCAAATATTTTAACATCACTGTGGTTGTGAAGAAATCAGTTGCTTT
AAAAGATTGGATTTTTCCTTGTTTAAGAGTTGTACTGATATCAGCTCTGCCCTGTGA
AATAAAGCTGATG Translation:
MQTAYWVMVMMMVWITAPLSEGGKLTDVIRGLVPHILTPQHILQSMTSRLGIGSSDQN (SEQ ID NO: 74)
AQICIWKVCPPSP Toxin Sequence:
Leu-Gly-Ile-Gly-Ser-Ser-Asp-Gln-Asn-Ala-Gln-Ile-Cys-Ile-Xaa4- (SEQ ID NO: 75)
Lys-Val-Cys-Xaa3-Xaa3-Ser-Xaa3-

TABLE 1-continued

Sequences of β-Superfamily Conotoxins

Name: Ba14.1

Species: *baileyi*

Cloned: Yes

DNA Sequence:
ATGCAGACGGCCTACTGGGTGATGGTGATGATAATGGTGTGGATTACAGTCCCTCTG  (SEQ ID NO: 76)
TCTGAAGGTGGTAAATTGAACGACATAATTCGGGGTTTGTTGCCAGACAACTTCCCC
CCACAGCTTACCTTGCATCGTCTGGTTTCCCGTCGTCATTCTGACAGCATTATTCTGA
GGGGCTTATGTATCTGGAAGGTGTGTGAACCTCCGCCACAAAGATGATCTGGTCCA
AAGCCAAAAAACGAATGATGTCAGACAACCGCCACAGCTTTAGTACGACATGGTTA
ATACGACTTCAGCAAATATTTCAACATCACTGTGGTTGTGAAGAAATCAGTTACTTT
AAAAGATTGGAATGATGTCAGCTGTGCACTATCAAATAAAGTTGATGTGACAAAAA
AAAAAAAAAAAAAAAGTACTCTGCGTTGTTACTCGAG Translation:
MQTAYWVMVMIMVWITVPLSEGGKLNDIIRGLLPDNFPPQLTLHRLVSRRHSDSIILRGL  (SEQ ID NO: 77)
CIWKVCEPPPQR Toxin Sequence:
His-Ser-Asp-Ser-Ile-Ile-Leu-Arg-Gly-Leu-Cys-Ile-Xaa4-Lys-Val-  (SEQ ID NO: 78)
Cys-Xaa1-Xaa3-Xaa3-Xaa3-Gln-Arg- Name: Bk14.1

Species: *bocki*

Cloned:
Yes

DNA Sequence:
ATGCAGACGGCCTACTGGGTGATGGTGATGATGATGGTGTGGATTACAGCCCCTCT  (SEQ ID NO: 79)
GTCTGAAAGTGATAAACTGAACGACGTAATTCGGGGTTTGGTGCCAGACAACTTAA
CCCCACAGCTTATCTTGCGAAGTCTGATTTCCCGTCGTCGTTCTGACAAGGATGATC
CGGGAGGACAAGAATGTTACTGGAACGTATGTGCACCAAACCAGGGAGACCACAT
GATCTTAAGAAAAAAGATGAATGACGACAGACAACCGCCACAACTGTAATACGAC
ATCGTTAATACGACTTCAGCAAATATTTTAACATCACTGTGGTTGTGAAGAAATCAG
TTGCTTTAAAAGATTGGATTTTTCCGTGTTTAAGAGCTGTACTGATATCTGCTCTGCC
CTGTGAAATAAAGCTGATG Translation:
MQTAYWVMVMMMVWITAPLSESDKLNPVIRGLVPDNLTPQLILRSLISRRRSDKDDPG  (SEQ ID NO: 80)
GQECYWNVCAPNQGDHMILRKKMNDDRQPPQL Toxin Sequence:
Arg-Ser-Asp-Lys-Asp-Asp-Xaa3-Gly-Gly-Gln-Xaa1-Cys-Xaa5-Xaa4-  (SEQ ID NO: 81)
Asn-Val-Cys-Ala-Xaa3-Asn-Gln-Gly-Asp-His-Met-Ile-Leu-Arg-Lys-
Lys-Met-Asn-Asp-Asp-Arg-Gln-Xaa3-Xaa3-Gln-Leu- Name: Cd14.1

Species: *chaldaeus*

Cloned: Yes

DNA Sequence:
GAATTCGCCCTTATGGATCCATGCAGACGGCCTACTGGGTGATGATGGGGATGATG  (SEQ ID NO: 82)
ATGGTGTGGATTACAGCCCCTCTGTCTGGAGGTGGTAAACTGAACGACGTAATTCG
GGGTTTGGTGCCAGACGACTTAACCCTACAGCGTATGTTCGAAACTCCGGTTTCCCA
TCGTCTTTCTGAGGGCAGAAATTCGACGGTACACATATGTACGTGGAAGGTATGTCC
ACCTCCCCCATGGAGACGACCACATGGACAAAGATGAATGACGTCAGACAACCTCC
ACAACTGTAGTACGACATCGTTAACACGACGTCAGCTAATCTTTTAACATCACTGTG
GCTGTGAAGAACTCGGTTGCTTTAAAAGATTGGATTTTTCCTTGTTTAAGAGTTGTG
CTGATATGAACTCTGCACTACGAAATAAAGCTGATGTGACAAACAAAAAAAAGAAA
AAAAAAAGTACTCTGCGTTGTTACTCGAGCTTAAGGGCGAATTC Translation:
MQTAYWVMMGMMMVWITAPLSGGGKLNDVIRGLVPDDLTLQRMFETPVSHRLSEGR  (SEQ ID NO: 83)
NSTVHICTWKVCPPPPWRRPHGQR Toxin Sequence:
Leu-Ser-Xaa1-Gly-Arg-Asn-Ser-Thr-Val-His-Ile-Cys-Thr-Xaa4-Lys-  (SEQ ID NO: 84)
Val-Cys-Xaa3-Xaa3-Xaa3-Xaa3-Xaa4-Arg-Arg-Xaa3-His-Gly-Gln-
Arg- Name: Cd14.2

TABLE 1-continued

Sequences of β-Superfamily Conotoxins

Species: *chaldaeus*

Cloned: Yes

DNA Sequence:
GAATTCGCCCTTATGGATCCATGCAGACGGCCTACTGGGTGATGATGGGGATGATG (SEQ ID NO: 85)
ATGGTGTGGATTACAGCCCCTCTGTCTGGAGGTGGTAAACTGAACGACGTAATTCG
GGGTTTGGTGCCAGACGACTTAACCCTACAGCGTATGTTCGAAACTCCGGTTTCCCA
TCGTCTTTCTGAGGGCAGAAATTCGACGGTACACATATGTATGTGGAAGGTATGTCC
ACCTCCCCCATGGAGACGACCACATGGACAAAGATGAATGACGTCAGACAACCTCC
ACAACTGTAGTACGACATCGTTAACACGACGTCAGCTAATCTTTTAACATCACTGTG
GTTGTGAAGAAATCGGTTGCTTTAAAAGATTGGATTTTTCCTTGTTTAAGAGTTGTG
CTGATATGAACTCTGCACTACGAAATAAAGCTGATGTGACAAACGAAAAAAAAAA
AAAAAAAAAAGTACTCTGCGTTGTTACTCGAGCTTAAGGGCGAATTC Translation:
MQTAYWVMMGMMMVWITAPLSGGGKPLNDVIRGLVPDDLTLQRMFETPVSHRLSEGR (SEQ ID NO: 86)
NSTVHICMWKVCPPPPWRRPHGQR Toxin Sequence:
Leu-Ser-Xaa1-Gly-Arg-Asn-Ser-Thr-Val-His-Ile-Cys-Met-Xaa4-Lys- (SEQ ID NO: 87)
Val-Cys-Xaa3-Xaa3-Xaa3-Xaa3-Xaa4-Arg-Arg-Xaa3-His-Gly-Gln-
Arg- Name: Ci14.1

Species: *cinereus*

Cloned: Yes

DNA Sequence:
GAATTCGCCCTTATGGATCCATGCAGACGGCCTACTGGGTGATGGTGATGATGTTGG (SEQ ID NO: 88)
TGTGGATTACAGCCCCTCTGCCTGAGGGTGGTAAACCGAAGCACGTAATTCGGGGT
TTGGTACCAGACGACTTAACCCCACAGCATATCTTGCGAAGTTTGATTTCCCGTCGT
TCATCTGGCTGCAGTGTTTCGTTGGGCTTCAAATGCTTCTGGAAGAGCTGTACAGTA
ATCCCAGTGAGACCATTTGTATCTCTGGAAGAAGAAATGAATGCCAGAAAGTCCA
AATAAGTGCAGTATGGGGTCCTTGATACGACTTCAGCAAGGATCACTGTGGTTGTG
AAGAAATCAGTTGCTTTAAAAGATTTGATTTTTCCTTGTTTAAGAGTTGTACTGATAT
CAGCTCTGTACTATGAAATAAAGCTGATGTGACAAACAAAAAAAAAAAAAAAAA
AGTACTCTGCGTTGTTACTCGAGCTTAAGGGCGAATTC Translation:
MQTAYWVMVMMLVWITAPLPEGGKPKHVIRGLVPDDLTPQHILRSLISRRSSGCSVSLG (SEQ ID NO: 89)
FKCFWKSCTVIPVRPFVSLEEENECQKVQISAVWGP Toxin Sequence:
Ser-Ser-Gly-Cys-Ser-Val-Ser-Leu-Gly-Phe-Lys-Cys-Phe-Xaa4-Lys- (SEQ ID NO: 90)
Ser-Cys-Thr-Val-Ile-Xaa3-Val-Arg-Xaa3-Phe-Val-Ser-Leu-Xaa1-
Xaa1-Xaa1-Asn-Xaa1-Cys-Gln-Lys-Val-Gln-Ile-Ser-Ala-Val-Xaa4-
Gly-Xaa3-

Name: Ci14.2

Species: *cinereus*

Cloned: Yes

DNA Sequence:
GAATTCGCCCTTATGGATCCATGCAGACGGCCTACTGGGTGATGGTGATGATGGTG (SEQ ID NO: 91)
GTGGTGTGGATTACAGCCCCTCTGCCTGAAGGTGGTAAACCGGAGCACGTAATTCG
GGGTTTGGTGCCAGACGACTTAACCCCACAGCTTATCTTGCGAAGTCTGATTTCCCG
TCGTAGTTCTGACGGCAAGGCAAAAGAAATTGTTTCTGGAAGGCATGTGTACCAG
AACAATGGAGACAACGTGATCTTAAGGAAAAAGATGAATGATGTCAGACAACCGC
CATCACTGTAGTATGACATCGTTAATACGACTTAAGCAAATATTTTAACATCACTGT
GGATCTGAAGAAATCAGTTGCTTTAAAAGATTGGATTTTTCCTCGTTTAAGAGTTGT
ACTGATGTCAGCTCTGCACTGTGAAATAAAGCTGATGTGACAAACGAAAAAAAAAA
AAAAAAAAAAGTACTCTGCGTTGTTACTCGAGCTTAAGGGCGAATTC Translation:
MQTAYWVMVMMVVVWITAPLPEGGKPEHVIRGLVPDDLTPQLILRSLISRRSSDGKAK (SEQ ID NO: 92)
RNCFWKACVPEQWRQRDLKEKDE Toxin Sequence:
Ser-Ser-Asp-Gly-Lys-Ala-Lys-Arg-Asn-Cys-Phe-Xaa4-Lys-Ala-Cys- (SEQ ID NO: 93)
Val-Xaa3-Xaa1-Gln-Xaa4-Arg-Gln-Arg-Asp-Leu-Lys-Xaa1-Lys-Asp-
Xaa1-

TABLE 1-continued

Sequences of β-Superfamily Conotoxins

Name: Ci14.3

Species: *cinereus*

Cloned: Yes

DNA Sequence:
GAATTCGCCCTTATGGATCCATGCAGACGGCCTACTGGGTGATGGTGATGATGATG (SEQ ID NO: 94)
GTGGTGTGGATTACAGCCCCTCTGCCTGAAGGTGGTAAACCGAAGCACGTAATTCG
GGGTTTGGTGCCAGACGACTTAACCCCACAGCTTATCTTGCGAAGTCTGATTTCCCG
TCGTAGTTCTGACGGCAAGGCAAAAAGAAATTGTTTCTGGAAGGCATGTGTACCAG
AACAATGGAGACAACGTGATCCTAAGGAAAAAGATGAATGATGTCAGACAACCGC
CATCACTGTAGTATGACATCGTTAATACGACTTAAGCAAATATTTTAACATCACTGT
GGATCTGAAGAAATCAGTTGCTTTAAAAGATTGGATTTTTCCTCGTTTAAGAGTTGT
ACTGATGTCAGCTCTGCACTGTGAAATAAAGCTGACGTGACAAGCAAAAAAAAAAA
AAAAAAAAAGTACTCTGCGTTGTTACTCGAGCTTAAGGGCGAATTC Translation:
MQTAYWVMVMMMVVWITAPLPEGGKPKHVIRGLVPDDLTPQLILRSLISRRSSDGKAK (SEQ ID NO: 95)
RNCFWKACVPEQWRQRDPKEKDE Toxin Sequence:
Ser-Ser-Asp-Gly-Lys-Ala-Lys-Arg-Asn-Cys-Phe-Xaa4-Lys-Ala-Cys- (SEQ ID NO: 96)
Val-Xaa3-Xaa1-Gln-Xaa4-Arg-Gln-Arg-Asp-Xaa3-Lys-Xaa1-Lys-Asp-
Xaa1-^

Name: Ci14.4

Species: *cinereus*

Cloned: Yes

DNA Sequence:
GAATTCGCCCTTATGGATCCATGCAGACGGCCTACTGGGTGATGGTGATAATGATG (SEQ ID NO: 97)
GTGTGGATTACAGCCCCTCTGTCTGAAGGTGGTAAACCGAAGCACGTAATTCGGGG
TTTGGTGCCAGTCGACTTAACCCCACAGCTTATCTTGCGAAGTCTGATTTCCCGTCGT
AGTTCTGACGGCAAGGCAAAAAAACAATGTGCCTGGAAGACATGTGTACCAACCCA
ATGGAGACGACGTGATCTTAAGGAAAAAGATGAATGATGTCAGACAACCGCCATCA
CTGTAGTATGACATCGTTAATACGACTTAAGCAAATATTTTAACATCACTGTGGTTC
TGAAGAAATCAGTTGCTTTAAAAGATTGGATTTTTCCTTGTTTAAGAGTTGTACTGA
TATCAGCTCTGCACTGTGAAATAAAGCTGATGTGACAAACAAAAAAAAAAAAAAAA
AAAAGTACTCTGCGTTGTTACTCGAGCTTAAGGGCGAATTC Translation:
MQTAYWVMVIMMMVWITAPLSEGGKPKHVIRGLVPVDLTPQLILRSLISRRSSDGKAKKQ (SEQ ID NO: 98)
CAWKTCVPTQWRRRDLKEKDE Toxin Sequence:
Ser-Ser-Asp-Gly-Lys-Ala-Lys-Lys-Gln-Cys-Ala-Xaa4-Lys-Thr-Cys- (SEQ ID NO: 99)
Val-Xaa3-Thr-Gln-Xaa4-Arg-Arg-Arg-Asp-Leu-Lys-Xaa1-Lys-Asp-
Xaa1-^

Name: Cr14.2

Species: *circumcisus*

Cloned: Yes

DNA Sequence:
GAATTCGCCCTTATGGATCCATGCAGACGGCCTACTGGGTGATGGTGATGATGATG (SEQ ID NO: 100)
GTGTGGATTACAGCCCCTCTGTCTGAAGGTGGTAAATTGAACGACGTAATTCGGGGT
TTGGTGCCACACATCTTAACCCCACAGCATATCTTGCAAGGTCTGACTTCCCGTCTT
CGTTCTGACAGCAGTGGTCAGAAAGGAGCACAAATATGCATCTGGAAGGTATGTCC
ACTATCCCCATGGAGACGACCACAAGGAAAAGATGAATGACGTCAGACAACCGCTA
CAACTGTAGTACGACATCGTTGATACGACTTCAGCAAATATTTTAACATCACTGTGG
TTGTGAAGAAATCAGCTGCTTTAAAAGATTGGATTTTTCCTTGTTTAAGAGTTGTACT
GATATCAGCTCTGCACTATGAAATAAAGCTGATGTGACAAACAAAAAAAAAAAAAA
AAAAAGTACTCTGCGTTGTTACTCGAGCTTAAGGGCGAATTC Translation:
MQTAYWVMVMMMVWITAPLSEGGKLNDVIRGLVPHILTPQHILQGLTSRLRSDSSGQK (SEQ ID NO: 101)
GAQICIWKVCPLSPWRRPQGKDE Toxin Sequence:
Leu-Arg-Ser-Asp-Ser-Ser-Gly-Gln-Lys-Gly-Ala-Gln-Ile-Cys-Ile- (SEQ ID NO: 102)
Xaa4-Lys-Val-Cys-Xaa3-Leu-Ser-Xaa3-Xaa4-Arg-Arg-Xaa3-Gln-Gly-

TABLE 1-continued

Sequences of β-Superfamily Conotoxins

Lys-Asp-Xaa1-^

Name: Cn14.4

Species: *consors*

Cloned: Yes

DNA Sequence:
GAATTCGCCCTTATGGATCCATGCAGACGGCCTACTGGGTGATGGTGATGATGATG (SEQ ID NO: 103)
GTGTGGATTACAGCCCCTCTGTCTGAAGGTGGTAAATTGAACGACGTAATTCGGGGT
TTGGTGCCACACTTCTTAACCCCACAGCATATCTTGCAAAGTCTGACTTCCCGTAAT
GGTTCTGGCAGCAGTAATCAGAAAGAAGCACAACTATGCATCTGGAAGGTATGTCC
ACCAACCCCATGGAGATGACCACAAGGAAAAAGATGAACGGCGTCAGACAACCGC
CACAACTGTAGTGGGACATCGTTGATACGACTTCAGCAAATATTTTAACATCACTGT
GGTTGTGAAGAAATCAGTTGTTTTAAAAGATTGGATTTTTCCTTGTTTAAGAGTTGT
ACTGATATCAGCTCTGCACTATGAAATAAAGCTGATGTGACAAGCAAAAAAAAAAA
AAAAAAAAGTACTCTGCGTTGTTACTCGAGCTTAAGGGCGAATTC Translation:
MQTAYWVMVMMMVWITAPLSEGGKLNDVIRGLVPHFLTPQHILQSLTSRNGSGSSNQK (SEQ ID NO: 104)
EAQLCIWKVCPPTPWR Toxin Sequence:
Asn-Gly-Ser-Gly-Ser-Ser-Asn-Gln-Lys-Xaa1-Ala-Gln-Leu-Cys-Ile- (SEQ ID NO: 105)
Xaa4-Lys-Val-Cys-Xaa3-Xaa3-Thr-Xaa3-Xaa4-Arg-^

Name: Cn14.5

Species: *consors*

Cloned: Yes

DNA Sequence:
GAATTCGCCCTTATGGATCCATGCAGACGGCCTACTGGGTGATGGTGATGATGATG (SEQ ID NO: 106)
GTGTGGATTACAGCCCCTCTGTCTGAAGGTGGTAAACTGAACGGCGTAATTCGGGG
TTTGGTGTCACACATCTTAATCCCACAGCATACCTTGCAAGTCTGACTTCCCGTGA
TCGTTCTGACAACGGTGGTTCGAGTGGAGCACAAATATGCATCTGGAAGGTATGTC
CACCATCCCCATGGAAATGACCACAAGGAAAAAGATGAACGGCGTCAGACAACCA
CCACAACTGTAGTGGGACATCGTTGATACGACTTCAGCAAATATTTTAACATCACTG
TGGTCGTGAAGAAATCAGTTGCTTTAAAAGATTGGATTTTTCCTTGTTTAAGAGTTG
TACTGATATCAGCTCTGCACTATGAAATAAAGCTGATGTGACAAACAAAAAAAAAA
AAAAAAAAAGTACTCTGCGTTGTTACTCGAGCTTAAGGGCGAATTC Translation:
MQTAYWVMVMMMVWITAPLSEGGKLNGVIRGLVSHILIPQHTLRSLTSRDRSDNGGSS (SEQ ID NO: 107)
GAQICIWKVCPPSPWK Toxin Sequence:
Asp-Arg-Ser-Asp-Asn-Gly-Gly-Ser-Ser-Gly-Ala-Gln-Ile-Cys-Ile- (SEQ ID NO: 108)
Xaa4-Lys-Val-Cys-Xaa3-Xaa3-Ser-Xaa3-Xaa4-Lys-^

Name: Ct14.1

Species: *coronatus*

Cloned: Yes

DNA Sequence:
ATGCAGACGGCCTACTGGGTGATGATGATGATGATGATGGTGTGGATTACAGCCCC (SEQ ID NO: 109)
TCTGTCTGAAGGTGGTAAACTGAACGACGTAATTCGGGGTTTGGTGCCAGACGACTT
AACCCTACAGCGTATGTTCAAAGCTCTGGTTTCCCATCGTCTTTCTGACGGCAGAGA
TTGGACGGGATACATATGTATCTGGAAGGCATGTCCACGTCCCCATGGATCCCACC
AAAGGGAAAAAGATGAATGACGTCAGACAACCGCCACAACTGTAGTAGGACATCG
TTAACACAACTTCAGCTAATATTTTAACATCACTGTGGTTGTGAAGAAATCGGTTGC
TTTAAAAGATTGAATTTTTCGTTTAAGAGTTGTGCTGATACGAGCTCTGCACTATGA
AATAAAGCTGATGTGACAAACAAAAAAAAAAAAAAAAAAAGTACTCTGCGTTGTT
ACTCGAG Translation:
MQTAYWVMMMMMVWITAPLSEGGKLNDVIRGLVPDDLTLQRMFKALVSHRLSDGR (SEQ ID NO: 110)
DWTGYICIWKACPRPPWIPPKGKR Toxin Sequence:
Leu-Ser-Asp-Gly-Arg-Asp-Xaa4-Thr-Gly-Xaa5-Ile-Cys-Ile-Xaa4- (SEQ ID NO: 111)
Lys-Ala-Cys-Xaa3-Arg-Xaa3-Xaa3-Xaa4-Ile-Xaa3-Xaa3-Lys-#

TABLE 1-continued

Sequences of β-Superfamily Conotoxins

Name: Eb14.1

Species: *ebraeus*

Cloned: Yes

DNA Sequence:
GAATTCGCCCTTATGGATCCATGCAGACGGCCTACTGGGTGATGATGATGATGATG (SEQ ID NO: 112)
ATGGTGTGGATTACAGCCCCTCTGTCTGAAGGCGGTAAACTGAACGACGTAATTCG
GGGTTTGGTGCCAGACGACTTAACCCTACAGCGTATGTTCAAAAGTCTGTTTTCCCA
TCGTCTTTCTGGCGGCACATATTCGAGGGTAGACACATGCATCTGGAAGGTATGTCC
ACAATCTCCATAGGGACGATCATATGGAAAAAGATGAGTGACATCAGACAACTGCC
ACAACTGTAGTACGACATCGTTAACACGACTTCAGCTAATATTTTAACATCACTGTG
GTTGTGAAGAAATCGGTTGCTTTAAAAGATTGGATTTTTCCTTGTTTAAGAGTTGTG
CTGATATGAGCTCTGCACTATGAAATAAAGCTGATGTGACAAACAAAAAAAAAAAA
AAAAAAGTACTCTGCGTTGTTACTCGAGCTTAAGGGCGAATTC Translation:
MQTAYWVMMMMMVWITAPLSEGGKLNDVIRGLVPDDLTLQRMFKSLFSHRLSGGT (SEQ ID NO: 113)
YSRVDTCIWKVCPQSP Toxin Sequence:
Leu-Ser-Gly-Gly-Thr-Xaa5-Ser-Arg-Val-Asp-Thr-Cys-Ile-Xaa4-Lys- (SEQ ID NO: 114)
Val-Cys-Xaa3-Gln-Ser-Xaa3-^

Name: G14.2

Species: *geographus*

Cloned: Yes

DNA Sequence:
GAATTCGCCCTTATGGATCCATGCAGACGGCCTACTGGGTGATGCTGATGATGATGG (SEQ ID NO: 115)
TGTGCATCACAGCCCCTCTGCCTGAAGGTGGTAAACCGAACAGCGGAATTCGGGGT
TTGGTGCCAAACGACTTAACTCCACAGCATACCTTGCGAAGTCTGATTTCCCGTCGT
CAAACTGACGTTCTTCTGGAGGCTACCCTTTTGACAACACCAGCCCCCGAGCAGAG
ATTGTTCTGCTTCTGGAAGTCATGTACGTGGAGGCCCTACCCTTGGAGACGACGTGA
TCTTAATGGAAAACGATGAATGACGCCAGACAACCGCCACAACTGTAGTACGACAT
CGTTAATACGACTTCAGCAAACATTTTAACATAACTGTGGTTGTGAAGAAATCAGTT
GCTTTAAAAGATTGGATTTTTCCTTGTTTCAGAGTTGTACTGATATGAGCTCTGCACC
ATGAAATAAAGCTGAAGTGACGAACAAAAAAAAAAAAAAAAAAAAAAGTACTCTGC
GTTGTTACTCGAGCTTAAGGGCGAATTC Translation:
MQTAYWVMLMMMVCITAPLPEGGKPNSGIRGLVPNDLTPQHTLRSLISRRQTDVLLEA (SEQ ID NO: 116)
TLLTTPAPEQRLFCFWKSCTWRPYPWRRRDLNGKR Toxin Sequence:
Xaa2-Thr-Asp-Val-Leu-Leu-Xaa1-Ala-Thr-Leu-Leu-Thr-Thr-Xaa3- (SEQ ID NO: 117)
Ala-Xaa3-Xaa1-Gln-Arg-Leu-Phe-Cys-Phe-Xaa4-Lys-Ser-Cys-Thr-
Xaa4-Arg-Xaa3-Xaa5-Xaa3-Xaa4-Arg-Arg-Arg-Asp-Leu-Asn-#

Name: Gd14.1

Species: *gladiator*

Cloned: Yes

DNA Sequence:
ATGCAGACGGCCTACTGGGTGATGGTGATGATGATGGTGTGGGTTACAGTCCCTCG (SEQ ID NO: 118)
ATCTGAAGGTGGCACGTGGAACTACTTAATTCGGGGTTTGGTGCCAGACGACCTAA
CCCCACAGCTTACCTTGCATCGTCTGGTTACCCGTCGTCATCCTGCCAACGTTAGAC
AGCAGGGGAAAATATGTGTATGGAAGGTGTGTCCACCATGGCCAGTAAGATCACCT
GGTCCACAGCCAAAAAACAAATGACGTCAGACAACCGCCACAACTTTAGTACGACA
TCGTTGATACAACTTCAGCAAGTATTTTAACATCACTGTGGCTCTGAAGAAATCAGT
TGCTTTAAAAGATTGGATTTTTCCTTGTTTTAGAGTTTTACTGATATCAGCTCTGCAC
TATGAAATAAAGATGTGACGAAAAAAAAAAAAAAAAAAAAGTACTCTGCGTTGTTAC
TCGAG Translation:
MQTAYWVMVMMMVWVTVPRSEGGTWNYLIRGLVPDDLTPQLTLHRLVTRRHPANVR (SEQ ID NO: 119)
QQGKICVWKVCPPWPVRSPGPQPKNK Toxin Sequence:
His-Xaa3-Ala-Asn-Val-Arg-Gln-Gln-Gly-Lys-Ile-Cys-Val-Xaa4-Lys- (SEQ ID NO: 120)
Val-Cys-Xaa3-Xaa3-Xaa4-Xaa3-Val-Arg-Ser-Xaa3-Gly-Xaa3-Gln-
Xaa3-Lys-Asn-Lys-^

TABLE 1-continued

Sequences of β-Superfamily Conotoxins

Name: Gd14.2

Species: *gladiator*

Cloned: Yes

DNA Sequence:
ATGCAGACGGCCTACTGGGTGATGGTGATGATGATGGTGTGGGTTACAGTCCCTCG (SEQ ID NO: 121)
ATCTGAAGGTGGCACGTGGAACTACTTAATTCGGGGTTTGGTGCCAGACGACCTAA
CCCCACAGCTTACCTTGCATCGTCTGGTTACCCGTCGTCATCCTGCCAACGTTAGAC
AGCAGGGGAAAATATGTGTATGGAAGGTGTGTCCACCATCGCCAGTAAGATCACCT
GGTCCACTGCCAAAAAACAAATGACGTCAGACAACCGCCACAACTTTAGTACGACA
TCGTTGATACAACTTCAGCAAGTATTTTAACATCACTGTGGCTCTGAAGAAATCAGT
TGCTTTAAAAGATTGGATTTTTCCTTGTTTTAGAGTTTTACTGATATCAGCTCTGCAC
TATGAAATAAAGATGTGACGGACAAAAAAAAAAAAAAAAAAGTACTCTGCGTTGTT
ACTCGAG Translation:
MQTAYWVMVMMMVWVTVPRSEGGTWNYLIRGLVPDDLTPQLTLHRLVTRRHPANVR (SEQ ID NO: 122)
QQGKICVWKVCPPSPVRSPGPLPKNK Toxin Sequence:
His-Xaa3-Ala-Asn-Val-Arg-Gln-Gln-Gly-Lys-Ile-Cys-Val-Xaa4-Lys- (SEQ ID NO: 123)
Val-Cys-Xaa3-Xaa3-Ser-Xaa3-Val-Arg-Ser-Xaa3-Gly-Xaa3-Leu-Xaa3-
Lys-Asn-Lys-^

Name: Ly14.1

Species: *litoglyphus*

Cloned: Yes

DNA Sequence:
GAATTCGCCCTTATGGATCCATGCAGACGGCCTACTGGGTGATGGTGATGATGATG (SEQ ID NO: 124)
GTGTGGATTACAGCCCCTCTGTCTGAAGGTGATAAATTGAACGACGTAATTCGGGGT
TTGGTGCCAGATAACTTAGCCCCACAGCTTGTTTTGCAAAGTCTGGATTCCCGTCGT
CATCCTCACGGCATTCGTCAGGATGGAGCCCAAATATGTATCTGGAAGATATGTCCA
CCATCCCCATGGAGACGACTTGGATCTTAAGAAAAGAAACAATTGACGTCAGACAA
CCGCCACATCTTGAGTACGACATCGTTAATACGACTTCAGCAAATATGAAATTTTCA
GCATCACTGTGGTTGTGAAGAAATCAGTTGCTTTAAAAGATTGGATTTGTCCTTGTT
TAAGAGTTGTACTGATGTCATCTCTGCACTATGAAATAAAGCTGATGTGAAAAAAA
AAAAAAAAAGTACTCTGCGTTGTTACTCGAGCTTAAGGGCGAATTC Translation:
MQTAYWVMVMMMVWITAPLSEGDKLNDVIRGLVPDNLAPQLVLQSLDSRRHPHGIRQ (SEQ ID NO: 125)
DGAQICIWKICPPSPWRRLGS Toxin Sequence:
His-Xaa3-His-Gly-Ile-Arg-Gln-Asp-Gly-Ala-Gln-Ile-Cys-Ile-Xaa4- (SEQ ID NO: 126)
Lys-Ile-Cys-Xaa3-Xaa3-Ser-Xaa3-Xaa4-Arg-Arg-Leu-Gly-Ser-^

Name: Ly14.2

Species: *litoglyphus*

Cloned: Yes

DNA Sequence:
GAATTCGCCCTTATGGATCCATGCAGACGGCCTACTGGGTGATGGTGATGATGATG (SEQ ID NO: 127)
GTGTGGATTACAGCCCCTCTGTCTGAAGGTGATAAATTGAACGACGTAATTCGGGGT
TTGGTGCCAGATAACTTAGCCCCACAGCTTGTTTTGCAAAGTCTGGATTCCCGTCGT
CATCCTCACGGCATTCGTCAGGATGGAGCCCAAATATGTATCTGGAAGATATGTCCA
CCATCCCCATGGAAACGACTTGGATCTTAAGAAAAGAAACAATTGACGTCAGACAA
CCGCCACAACTTGAGTACGACATCGTTAATACAACTTCAGCAAATATGAAATTTTCA
GCATCACTGTGGTTGTGAAGAAATCAGTTGCTTTAAAGGATTGGATTTGTCCTTGTT
TAAGAGTTGTACTGATGTCATCTCTGCACTATGAAATAAAGCTGATGTGACAAGCA
AAAAAAAAAAAAAAAGTACTCTGCGTTGTTACTCGAGCTTAAGGGCGAATTC Translation:
MQTAYWVMVMMMVWITAPLSEGDKLNDVIRGLVPDNLAPQLVLQSLDSRRHIPHGIRQ (SEQ ID NO: 128)
DGAQICIWKICPPSPWKRLGS Toxin Sequence:
His-Xaa3-His-Gly-Ile-Arg-Gln-Asp-Gly-Ala-Gln-Ile-Cys-Ile-Xaa4- (SEQ ID NO: 129)
Lys-Ile-Cys-Xaa3-Xaa3-Ser-Xaa3-Xaa4-Lys-Arg-Leu-Gly-Ser-^

TABLE 1-continued

Sequences of β-Superfamily Conotoxins

Name: Lt14.1

Species: *litteratus*

Cloned: Yes

DNA Sequence:
GAATTCGCCCTTATGGATCCATGCAGACGGCCTACTGGGTGATGGTGATGATGATG (SEQ ID NO: 130)
GTGGGGATTACAGCCCCTCTGTCTGAAGGTCGTAAATTGAACGACGCAATTCGGGG
TTTGGTGCCAGATGACTTAACCCCACAGCTTTTGCGAAGTCCGGTTTCGACTCCTTA
TCCTGAGTTTCATCTTGATGAACCTTATCTGAAGATACCCGTATGTATCTGGAAGAT
ATGTCCACCAAACCTATTGAGACGACGTGATCTTAAGAAAAGAAACAAAGTACGTC
AGACAACCGCCACAACTTGAGTACGACATCGTTCATACAACTTGAGCAAATATTTC
AGCATCACTATGGTTGTGAAGAAATCAGTTGCTTTAAAAGATTGGATCTTTCCTTGT
TTAAGAGTTGTATTGATGTCAGCTCTGCACTCTGAAATAAAGCTGATGTGACAAACA
AAAAAAAAAAAAAAAAAAAGTACTCTGCGTTGTTACTCGAGCTTAAGGGCGAATTC Translation:
MQTAYWVMVMMMVGITAPLSEGRKLNDAIRGLVPDDLTPQLLRSPVSTPYPEFHLDEP (SEQ ID NO: 131)
YLKIPVCIWKICPPNLLRRRDLKKRNKVRQTTATT Toxin Sequence:
Ser-Xaa3-Val-Ser-Thr-Xaa3-Xaa5-Xaa3-Xaa1-Phe-His-Leu-Asp-Xaa1- (SEQ ID NO: 132)
Xaa3-Xaa5-Leu-Lys-Ile-Xaa3-Val-Cys-Ile-Xaa4-Lys-Ile-Cys-Xaa3-
Xaa3-Asn-Leu-Leu-Arg-Arg-Arg-Asp-Leu-Lys-Lys-Arg-Asn-Lys-Val-
Arg-Gln-Thr-Thr-Ala-Thr-Thr- Name: Lt14.2

Species: *litteratus*

Cloned: Yes

DNA Sequence:
GAATTCGCCCTTATGGATCCATGCAGACGGCCTACTGGGTGATGGTGATGATGATG (SEQ ID NO: 133)
GTGGGGATTACAGCCCCTCTGTCTGAAGGTCGTAAATTGAACGACGCAATTCGGGG
TTTGGTGCCAAATGACTTAACCCCACAGCTTTTGCAAAGTCTGGTTTCCCGTCGTCA
TCGTGTGTTTCATCTTGACAACACTTATCTCAAGATACCCATATGTGCCTGGAAGGT
ATGTCCACCAACCCATGGAGACGACGTGATCTTAAGAAAAGAAACAAATGACGTC
AGACAACCGCCACAACTTGAGTACGACATTGTTAATGCGACTTGAGCAAATTTTTCA
GCATCACTATGGTTGTAAAGAAATCAGCTGCTTTAAACGATTGGATCTTTCCTTATT
TAAGAGTTGTATTGATGTCAGCTCTGCACTCTGAAATAAAGCTGATGTGACAAACA
AAAAAAAAAAAAAAAAAAAGTACTCTGCGTTGTTACTCGAGCTTAAGGGCGAATTC Translation:
MQTAYWVMVMMMVGITAPLSEGRKLNDAIRGLVPNDLTPQLLQSLVSRRHRVFHLDN (SEQ ID NO: 134)
TYLKIPICAWKVCPPTPWRRRDLKKRNK Toxin Sequence:
His-Arg-Val-Phe-His-Leu-Asp-Asn-Thr-Xaa5-Leu-Lys-Ile-Xaa3-Ile- (SEQ ID NO: 135)
Cys-Ala-Xaa4-Lys-Val-Cys-Xaa3-Xaa3-Thr-Xaa3-Xaa4-Arg-Arg-Arg-
Asp-Leu-Lys-Lys-Arg-Asn-Lys- Name: Ls14.1

Species: *loroisii*

Cloned: Yes

DNA Sequence:
GAATTCGCCCTTATGGATCCATGCAGACGGCCTACTGGGTGATGGTGATGATGATG (SEQ ID NO: 136)
GTGTGGATTAAAGGCCCTGTGTCTGAAGGTGGTAAATTGAACGACGTAATTCGGGG
TTTGGTGCCAGACGACTTAACCCCACAGCTTATCTTGCAAAGTCTGATGTCCCGTCG
TCGTTCTGACAGCGATGTTCGGGAGGTGTACATATTATGCATCTGGAAGATATGTCC
ACCATTGCCATGAAGACGACATGATCTTAAGGAAAAGGATAAACGACGTCAGACAA
CCGCTACAACTGTAGTACGACATCGTTAATACGACTTCAGCAAATATTTGAACATCA
CTGTGGTTGTGAAGAAATCAGTTGCTTTAAACGATTGGATTTTTCCTTAAGAGTTGC
ACTGATATCAGCTCTGCACTATGAAATAAAGCTGATGTGACTACCAAAAAAAAAAA
AAAAAAAAAGTACTNTGCGTTGTTACTCGAGCTTAAGGGCGAATTC Translation:
MQTAYWVMVMMMVWIKGPVSEGGKLNDVIRGLVPDDLTPQLILQSLMSRRRSDSDVR (SEQ ID NO: 137)
EVYILCIWKICPPLP Toxin Sequence:
Arg-Ser-Asp-Ser-Asp-Val-Arg-Xaa1-Val-Xaa5-Ile-Leu-Cys-Ile- (SEQ ID NO: 138)
Xaa4-Lys-Ile-Cys-Xaa3-Xaa3-Leu-Xaa3-

TABLE 1-continued

Sequences of β-Superfamily Conotoxins

Name: M14.2

Species: *magus*

Cloned: Yes

DNA Sequence:
GAATTCGCCCTTATGGATCCATGCAGACGGCCTACTGGGTGATGGTGATGATGATG (SEQ ID NO: 139)
GTGTGGATTACAGCCCCTCTGTCTGAAGGTGGTAAATTGAACGACGTAATTCGGGGT
TTGGTGCCACACTCCTTAACCCCACAGCATATCTTGCAAAGTCTGACTTCCCGTAAT
GGTTCTGGCAGCAGCAATCAGAAAGAAGCACAACTATGCATCTGGAAGGTATGTCC
ACCATCCCCATGGAGATGACCACAAGGAAAAAGATGAACGGCGTCAGACAACCGC
CACAACTGTAGTGGGACATCGTTGATACGACTTCAACAAATATTTTAACATCACTGT
GGTTGTAAAGAAATCAGTTGCTTTAAAAGATTGGATTTTTCCTTGTTTAAGAGTTGT
ACTGATATCAGCTCTGCACTATGAAATAAAGCTGATGTGACAAACAAAAAAAAAAA
AAAAAAAGTACTCTGCGTTGTTACTCGAGCTTAAGGGCGAATTC Translation:
MQTAYWVMVMMMVWITAPLSEGGKLNDVIRGLVPHSLTPQHILQSLTSRNGSGSSNQK (SEQ ID NO: 140)
EAQLCIWKVCPPSPWR Toxin Sequence:
Asn-Gly-Ser-Gly-Ser-Ser-Asn-Gln-Lys-Xaa1-Ala-Gln-Leu-Cys-Ile- (SEQ ID NO: 141)
Xaa4-Lys-Val-Cys-Xaa3-Xaa3-Ser-Xaa3-Xaa4-Arg- Name: Mi14.3

Species: *miles*

Cloned: Yes

DNA Sequence:
GAATTCGCCCTTATGGATCCATGCAGACGGCCTACTGGGTGATGATGATGGTGGTG (SEQ ID NO: 142)
ATGATGGTGGGGGTTACTGTCGCTGGCTCCCTGCCTGTGTTTGATGACGACAACGAC
TCTGACCCCGCTGTCAAGCGCGCTATCACGTGGTCCCGCATCCTGGGCGTGTCTCCA
GCCTTCCTGGCACAGCAGCGAGCGCTGGTTCCCTTCGCCAACCGATTCATCAGTGAG
CAGAAACGTTTCCGACCCGCCATGCAGAGCCGATCAGGAGGAATGTCGCTGTGCCT
ATGGAAAGTGTGTCCTGCAGCCCCCTGGCTGGTCGCCAAACGTAAACAGGAAACCA
GCGACTACTGACGTCATACCTCTAAAGACCCACTCATGACGTCAACGCTGAACTGA
CGTCACCGACAGCTCCAACGTCACAGCAGGAGCGAGAGAGAGGCTGGAGCATTTCT
CTTTCTTTTGGTTTTTCGAGTTGAAGTGTGATCAGCTGGGCTGGTGAAAAAATTGTTG
AGTAAAGTTGAATGAAAATCAAAAAAAAAAAAAAAAAAAGTACTCTGCGTTGGTA
CTCGAGGCTTAAAGGCGNAATTC Translation:
MQTAYWVMMMVVMMVGVTVAGSLPVFDDDNDSDPAVKRAITWSRILGVSPAFLAQQ (SEQ ID NO: 143)
RALVPFANRFISEQKRFRPAMQSRSGGMSLCLWKVCPAAPWLVAKRKQETSDY Toxin Sequence:
Phe-Arg-Xaa3-Ala-Met-Gln-Ser-Arg-Ser-Gly-Gly-Met-Ser-Leu-Cys- (SEQ ID NO: 144)
Leu-Xaa4-Lys-Val-Cys-Xaa3-Ala-Ala-Xaa3-Xaa4-Leu-Val-Ala-Lys-
Arg-Lys-Gln-Xaa1-Thr-Ser-Asp-Xaa5-

Name: Mi14.4

Species: *miles*

Cloned: Yes

DNA Sequence:
GAATTCGCCCTTATGGATCCATGCAGACGGCCTACTGGGTGATGGTGATGATGATG (SEQ ID NO: 145)
GTGGTGGGTTCACCGTCGGGAGTCACGTCCATCGGTCTCACAGTCCTACGTCGCGCA
ACCATGGTGATGACTCCATTCATGACAAGACGATTCATCAACATCTGTTTGCCCGTC
TTCCTCTGGAGAACAACGACGACCATCGTTCTGTGGATCTTCCTGCAGTGTATGCGC
CGGGCCAGGCACGTGTGCGTTCTACTTTTGTTCTTGACCTCATTGCAGATAGGGGTT
GGTGCAGACGACATGAAACTACAGCGCCAAAGACGTCAAGGTTTCTGTTGCGTCGT
TATCCCGATTCTTTGGTTCTGTTGTGGGGGTTACCGCACAAATGGCACTGCACTGGC
CGATTGAAAGAACTGCAATAAACGGAATGGCAAGAAGGAATAAAAAAAAAAAAA
AAAAAAAAAAGTACTCTGCGTTGTTACTCGAGCTTAAGGGCGAATTC Translation:
MQTAYWVMVMMMVVGSPSGVTSIGLTVLRRATMVMTPFMTRRFINICLPVFLWRTTT (SEQ ID NO: 146)
TIVLWIFLQCMRRARHVCVLLLFLTSLQIGVGADDMKLQRQRRQGFCCVVIPILWFCCG
GYRTNGTALAD Toxin Sequence:

TABLE 1-continued
Sequences of β-Superfamily Conotoxins

Xaa2-Gly-Phe-Cys-Cys-Val-Val-Ile-Xaa3-Ile-Leu-Xaa4-Phe-Cys-Cys-Gly-Gly-Xaa5-Arg-Thr-Asn-Gly-Thr-Ala-Leu-Ala-Asp- (SEQ ID NO: 147)

Name: Mu14.1

Species: *muriculatus*

Cloned: Yes

DNA Sequence:
ATGCAGACGGCCTACTGGGTGATGGTGATGATGATGGTGTGGATTACAGCCCCTTTG (SEQ ID NO: 148)
TCTGAAGGTGGTAAACTGAACGATGTAATTCGGGGTTTCGCGCTAGATGACTTAGCC
CAAAGCCGTATTATGCAAAGTCTGGTTTTCAGTCATCAGCCTCTTCCAACGGCATCC
ATATGTATCTGGAAGATATGTCCACCAGACCCATGGAGACGACATGATCTTCAGAA
AAGTAACAAATGACGTCAGACAACCGCCACAACTTGAATACAACATCATTAATACG
ACTTCAGCAAATATTTTAACATCACTGTGATTGTTCGGAAGTCAGTTGCTTTAAAGG
ATTGGATTTGTCCCTGTTGTATTGATGTCAACTCTGCACTATGAAATAAAGCTGATG
TGACAAACAAGAAAAAAAAAAAAAAAAAAAAAGTACTCTGCGTTGTTACTCGAG Translation:
MQTAYWVMVMMMVWITAPLSEGGKLNDVIRGFALDDLAQSRIMQSLVFSHQPLPTASI (SEQ ID NO: 149)
CIWKICPPDPWRRHDLQKSNK Toxin Sequence:
Ile-Met-Gln-Ser-Leu-Val-Phe-Ser-His-Gln-Xaa3-Leu-Xaa3-Thr-Ala- (SEQ ID NO: 150)
Ser-Ile-Cys-Ile-Xaa4-Lys-Ile-Cys-Xaa3-Xaa3-Asp-Xaa3-Xaa4-Arg-
Arg-His-Asp-Leu-Gln-Lys-Ser-Asn-Lys- Name: Ms14.1

Species: *musicus*

Cloned: Yes

DNA Sequence:
ATGCAGACGGCCTACTGGGTGATGATGATGACGATGATGGTGTGGATGACAGCCCC (SEQ ID NO: 151)
TCTGTCTGAAGGTCGTCCACTGAGCGACGAAGTTCGGGGTATGGTGCCAGGCGACT
TGGTCCTACAGTATCTGTTCCCAAGTCTGGCTTTCAGTCCTCCGGACATATGTACGT
GGAAGGTATGTCCACCACCCCCATGGAGACGACCAAAAAAAATAACAGACGTCAG
ACAGCCGCCACAACTGTAGTACGACATCGTTGATACGGCTTCAGCAAATATTTTCAA
CATCACTGCGGTTGTGAAGAAATCAGTTGCTTTAAAATGTTGGATTTTTCCTTGTTTA
AAAGAGCTGTACTGATGTCAGCCCTGCATTACGAAATAAAGCTGATGTGACAAACA
AAAAAAAAAAAAAAAAAAAAGTACTCTGCGTTGTTACTCGAG Translation:
MQTAYWVMMMTMMMVWMTAPLSEGRPLSDEVRGMVPGDLVLQYLFPSLAFSPPDICT (SEQ ID NO: 152)
WKVCPPPPWRRPKKITDVRQPPQL Toxin Sequence:
Gly-Met-Val-Xaa3-Gly-Asp-Leu-Val-Leu-Gln-Xaa5-Leu-Phe-Xaa3- (SEQ ID NO: 153)
Ser-Leu-Ala-Phe-Ser-Xaa3-Xaa3-Asp-Ile-Cys-Thr-Xaa4-Lys-Val-
Cys-Xaa3-Xaa3-Xaa3-Xaa3-Xaa4-Arg-Arg-Xaa3-Lys-Lys-Ile-Thr-Asp-
Val-Arg-Gln-Xaa3-Xaa3-Gln-Leu- Name: Ms14.2

Species: *musicus*

Cloned: Yes

DNA Sequence:
ATGCAGACGGCCTACTGGGTGATGATGATGATGATGATGGTGTGGATGACAGCCCC (SEQ ID NO: 154)
TCTGTCTGAAGGTCGTAAACTGATCGACAAAGTTCGGGGTATGGGGCCAGGCGACT
TATCCCTACAGAAAATGTTCCCAAGTCTGGCTTTAGGTCCTGGGGGAGACGTAATAT
GTAGGTGGAAGGTATGTCCACCAACCCCATGGAAACGACTAATAAAATAACTGACG
TCAGACAGCCGCCACAACTGTAGTACGACATCGTTGATACGACTTCAGCAAATATTT
CAACATCACTGCGGTTGTGAAGAAATCAGTTGCTTTAAAAGATTGGATTTTTCCTTG
TTTAAAGAGTTGTACTGATATCAGCTCTGCATTACGAAATAAAGCTGATGTGACAAA
CAAAAAAAAAAAAAAAAAAAAGTACTCTGCGTTGTTACTCGAG Translation:
MQTAYWVMMMMMVWMTAPLSEGRKLIDKVRGMGPGDLSLQKMFPSLALGPGGD (SEQ ID NO: 155)
VICRWKVCPPTPWKRLIK Toxin Sequence:
Gly-Met-Gly-Xaa3-Gly-Asp-Leu-Ser-Leu-Gln-Lys-Met-Phe-Xaa3-Ser- (SEQ ID NO: 156)
Leu-Ala-Leu-Gly-Xaa3-Gly-Gly-Asp-Val-Ile-Cys-Arg-Xaa4-Lys-Val-

TABLE 1-continued
Sequences of β-Superfamily Conotoxins

Cys-Xaa3-Xaa3-Thr-Xaa3-Xaa4-Lys-Arg-Leu-Ile-Lys-

Name: Ms14.3

Species: *musicus*

Cloned: Yes

DNA Sequence:
ATGCAGACGGCCTACTGGGTGATGATGATGATGACGATGATGGTGTGGATGACAGC (SEQ ID NO: 157)
CCCTCTGTCTGAAGGTCGTCCACTGAGCGACAAAGTTCGGGGTATGGTGCCAGGCG
ACTTAGCCCTGCAGTATCTGTTCCCAAGTCTGGCTTTCAATCCCCCGGACATATGTA
CGTGGAAGGTATGTCCACCACCCCCATGGAGACGACCAAAAAAAATAACTGACGTC
GGACAGCCGCCACAACTGTAGTACGACATCGTTGATACGACTTCAGCAAATATTTTC
AACATCACTGCGGTTGTGAAGAAATCAGTTGTTTTAAAAGGTTGGATTTTTCCTTGT
TTAAAAGAGCTGTACTGATGTCAGCTCTGCATTACGAAATAAAGCTGATGTGACAA
ACGAAAAAAAAAAAAAAAAAAAAAAAAAAAAAGTACTCTGCGTTGTTACTCGAG Translation:
MQTAYWVMMMMTMMVWMTAPLSEGRPLSDKVRGMVPGDLALQYLFPSLAFNPPDIC (SEQ ID NO: 158)
TWKVCPPPPWRRPKKITDVGQPPQL Toxin Sequence:
Gly-Met-Val-Xaa3-Gly-Asp-Leu-Ala-Leu-Gln-Xaa5-Leu-Phe-Xaa3- (SEQ ID NO: 159)
Ser-Leu-Ala-Phe-Asn-Xaa3-Xaa3-Asp-Ile-Cys-Thr-Xaa4-Lys-Val-
Cys-Xaa3-Xaa3-Xaa3-Xaa3-Xaa4-Arg-Arg-Xaa3-Lys-Lys-Ile-Thr-Asp-
Val-Gly-Gln-Xaa3-Xaa3-Gln-Leu- Name: Ms14.4

Species: *musicus*

Cloned: Yes

DNA Sequence:
ATGCAGACGGCCTACTGGGTGATGATGATGACGATGATGGTGTGGATGACAGCCCC (SEQ ID NO: 160)
TCTGTCTGAAGGTCGTCCACTGAGCGACAAAGTTCGGGGTATGGTGCCAGGCGACT
TAGTCCTGCAGTATCTGTTCCCAAGTCTGGCTTTCAATCCTCCGGACATATGTACGT
GGAAGGTATGTCCACCACCCCCATGGAGACGACCAAAAAAAATAACTGACGTCAGA
CAGCCGCCACAACTGTAGTACGACATCGTTGATACGACTTCAGCAAATATTTTCAAC
ATCACTGCGGTTGTGAAGAAATCAGTTGTTTTAAAAGGTTGGATTTTTCCTTGTTTAA
AAGAGCTGTACTGATGTCAGCTCTGCATTACGAAATAAAGCTGATGTGACAAGCAA
AAAAAAAAAAAAAAAAAGTACTCTGCGTTGTTACTCGAG Translation:
MQTAYWVMMMTMMVWMTAPLSEGRPLSDKVRGMVPGDLVLQYLFPSLAFNPPDICT (SEQ ID NO: 161)
WKVCPPPPWRRPKKIDVRQPPQL Toxin Sequence:
Gly-Met-Val-Xaa3-Gly-Asp-Leu-Val-Leu-Gln-Xaa5-Leu-Phe-Xaa3- (SEQ ID NO: 162)
Ser-Leu-Ala-Phe-Asn-Xaa3-Xaa3-Asp-Ile-Cys-Thr-Xaa4-Lys-Val-
Cys-Xaa3-Xaa3-Xaa3-Xaa3-Xaa4-Arg-Arg-Xaa3-Lys-Lys-Ile-Thr-Asp-
Val-Arg-Gln-Xaa3-Xaa3-Gln-Leu- Name: Mt14.2

Species: *mustelinus*

Cloned: Yes

DNA Sequence:
ATGCAGACGGCCTACTGGGTGATGGTGATGATGATGGCGTGGTATACAACCCCTGT (SEQ ID NO: 163)
GTCTGAATGTGGGAAATTGAACAACGTAATTCGGGGTTTTGTGCCAAAGGACTGGA
CCCCAATGCTTCCCTGGCGTCGTCTAGTTTCCCATACCAGCAGCAAGTATCCAGGTG
TGACTTTTTGTCCATGGAAGGTGTGTCCGCCAGCGCCATGGAGAATACTTGGGGTCT
AACGCAAAAAAATACATGACGTCAGACAACCGCCACCGCTTTAGTACGACATCGTT
CATACGTCTCCAGCAAGTATTTTAACATCACTGTGGTTGTGAAGAAGTCAGTAGCTT
TAAAAGATTGGATTTTTTCCTTGTTTAAGAGTTGTACTGACATGAGTTCTGCACTATG
AAATAAAGTTGATGTGACGAACGAAAAAAAAAAAAAAAAAAAAGTACTCTGCGTT
GTTACTCGAG Translation:
MQTAYWVMVMMMAWYTTPVSECGKLNNVIRGFVPKDWTPMLPWRRLVSHTSSKYP (SEQ ID NO: 164)
GVTFCPWKVCPPAPWRILGV Toxin Sequence:
Leu-Val-Ser-His-Thr-Ser-Ser-Lys-Xaa5-Xaa3-Gly-Val-Thr-Phe-Cys- (SEQ ID NO: 165)

TABLE 1-continued

Sequences of β-Superfamily Conotoxins

Xaa3-Xaa4-Lys-Val-Cys-Xaa3-Xaa3-Ala-Xaa-Xaa4-Arg-Ile-Leu-Gly-
Val-

Name:    Nb14.1

Species: *nobilis*

Cloned:  Yes

DNA Sequence:
GAATTCGCCCTTATGGATCCATGCAGACGGCCTACTGGGTGATGATGATGGTGGTG         (SEQ ID NO: 166)
GTGATGATGGTGGGGGTTACTGTCGCTGGCTCACTGTCTGTGTTTGATGATGACAAC
GACTCTGACCCAGCTGTCAAGCGCGCCATCACGTGGTCTCGATTCCTGGGCGCGTCT
CCAGCCTTCCTGGCACAGCAGCGAGCGCTGGCTCCCTTCGCCAACCGACCCATCAAT
GAGCAGAAACGTTTCCGACCTGCCGTGAAGAGCCGATCACGACGAGCGCCGCCGTG
CGTGTGGAAGGTGTGTCCCGCTCCCCCCTGGCTGGTCACCAAACGTAAACAGGAAA
CCAGCGACTACTGACGTCATACCTCAATAGACCGACTCATGACTTCAACGCTGAATT
GACGTCACCGAGAGCTCCAACGTCACAGCAGGAGCGAGAGAGAGAGAGAGAGA
GAGAAAGAGAGAGAGAAAGGCTGGAGTATTTCTCTTTCTTTTGGTTTTTCGTGTTGA
AGTGTGATCAGCTGGGCTGGTTCAAAATTGTTGAATAAAGTTGAATGAAAATCAAA
AAAAAAAAAAAAAAAAAAAGTACTCTGCGTTGTTACTCGAGCTTAAGGGCGAATTC Translation:
MQTAYWVMMMVVVMMVGVTVAGSLSVFDDDNDSDPAVKRAITWSRFLGASPAFLA        (SEQ ID NO: 167)
QQRALAPFANRPINEQKRFRPAVKSRSRRAPPCVWKVCPAPPWLVTKRKQETSDY Toxin Sequence:
Phe-Arg-Xaa3-Ala-Val-Lys-Ser-Arg-Ser-Arg-Arg-Ala-Xaa3-Xaa3-     (SEQ ID NO: 168)
Cys-Val-Xaa4-Lys-Val-Cys-Xaa3-Ala-Xaa3-Xaa3-Xaa4-Leu-Val-Thr-
Lys-Arg-Lys-Gln-Xaa1-Thr-Ser-Asp-Xaa5-

Name:    Nb14.2

Species: *nobilis*

Cloned:  Yes

DNA Sequence:
GAATTCGCCCTTATGGATCCATGCAGACGGCCTACTGGGTGATGGTGATGATGATG        (SEQ ID NO: 169)
GTGTGGATTACAGCCCCTCTGTCTGAAGGTGGTAAATTGAACGACGTAATTCGGGGT
TTGGTGCCACACTTCTTAACCCCACAGCATATCTTGCAAAGTCTGACTTCCCGTAAT
GGTTCTGGCAGCAGTAATCAGAAAGAAGCGCAACTATGCATCTGGAAGGTATGTCC
ACCAACCCCATGGAGATGATCACAAGGAAAAAGATGAACGGCGTCAGACAACCGC
CACAACTGTAGTGGGACATCGTTGATACGACTTCAGCAAATATTTTAACATCACTGT
GGTTGTGAAGAAATCAGTTGTTTTAAAAGATTGGATTTTTCCTTGTTTAAGAGTTGT
ACTGATATCAGCTCTGCACTATGAAATAAAGCTGATGTGACAAGCAAAAAAAAAAA
AAAAAAGTACTCTGCGTTGTTACTCGAGCTTAAGGGCGAATTC Translation:
MQTAYWVMVMMMVWITAPLSEGGKLNDVIRGLVPHFLTPQHILQSLTSRNGSGSSNQK     (SEQ ID NO: 170)
EAQLCIWKVCPPTPWR Toxin Sequence:
Asn-Gly-Ser-Gly-Ser-Ser-Asn-Gln-Lys-Xaa1-Ala-Gln-Leu-Cys-Ile-    (SEQ ID NO: 171)
Xaa4-Lys-Val-Cys-Xaa3-Xaa3-Thr-Xaa3-Xaa4-Arg- Name:    Nb14.3

Species: *nobilis*

Cloned:  Yes

DNA Sequence:
GAATTCGCCCTTATGGATCCATGCAGACGGCCTACTGGGTGATGATGATGGTGGTG        (SEQ ID NO: 172)
GTGATGATGGTGGGGGTTACTGTCGCTGGCTCACTGTCTGTGTTTGATGACGACAAT
GACTCTGACCCAGCTGTCAAGCGCGCCATCACGTGGTCTCGATTCCTGGGCGCGTCT
CCAGCCTTCCTGGCACAGCAGCGAGCGCTGGCTCCCTTCGCCAACCGACCCATCAAT
GAGCAGAAACGTTTCCGACCTGCCGTGAAGAGCCGATCACGACGAGCGCCGCCGTG
CGTATGGAAGGTGTGTCCCGCTCCCCCCTGGCTGGTCACCAAACGTAAACAGGAAA
CCAGCGACTACTGACGTCATACCTCAATAGACCGACTCATGACTTCAACGCTGAATT
GACCTCACCGAGAGCTCCAACGTCACAGCAGGAGCGAGAGAGAGAGAGAGAGA
GAGAGAGAGAAAGGCTGGAGTATTTCTCTTTCTTTCGGTTTTTCGTGTTGAAGTGTG
ATCAGCTGGGCTGGTTCAAAATTGTTGAATAAAGTTGAATAAAAAAAAAAAAAAAA
AAAGTACTCTGCGTTGTTACTCGAGCTTAAGGGCGAATTC Translation:
MQTAYWVMMVVVMMVGVTVAGSLSVFDDDNDSDPAVKRAITWSRFLGASPAFLA         (SEQ ID NO: 173)

TABLE 1-continued

Sequences of β-Superfamily Conotoxins

QQRALAPFANRPINEQKRLFRPAVKSRSRRAPPCVWKVCPAPPWLVTKRKQETSDY

Toxin Sequence:
Phe-Arg-Xaa3-Ala-Val-Lys-Ser-Arg-Ser-Arg-Ala-Xaa3-Xaa3-Cys- (SEQ ID NO: 174)
Val-Xaa4-Lys-Val-Cys-Xaa3-Ala-Xaa3-Xaa3-Xaa4-Leu-Val-Thr-Lys-
Arg-Lys-Gln-Xaa1-Thr-Ser-Asp-Xaa5-^

Name:  Pr14.1

Species: *parius*

Cloned: Yes

DNA Sequence:
GAATTCGCCCTTATGGATCCATGCAGACGGCCTACTGGGTGATGGTGATGATGATG           (SEQ ID NO: 175)
GTGGTGTGGATTACAGCCCCTTTGTCTGAAGGTGGTAAACCGAAGCACGCAATTCG
GGGTTTGGTGCCAGACGACTTAACCCCACAGCTTATCTTGCGAAGTCTGATTTCCCG
TCGTAGTTCTTTCGGCAAGGATGCGAAACCCCCCTTTAGTTGTTCAGGCCTCCGAGG
GGGTTGCGTCCTACCTCCCAATCTCAGGCCAAAGTTCAACAAAGGTGGATAACAAA
CCCAAGCGTTCCTAGTTATACGAATGCCAGCAAATAAAAGCAGTTTGATTGTGAAA
AAAAAAAAAAAAAAAAAGTACTCTGCGTTGTTACTCGAGCTTAAGGGCGAATTC Translation:
MQTAYWVMVMMMVVWITAPLSEGGKPKHAIRGLVPDDLTPQLILRSLISRRSSFGKDA        (SEQ ID NO: 176)
KPPFSCSGLRGGCVLPPNLRPKFNKGG Toxin Sequence:
Xaa3-Xaa3-Phe-Ser-Cys-Ser-Gly-Leu-Arg-Gly-Gly-Cys-Val-Leu-         (SEQ ID NO: 177)
Xaa3-Xaa3-Asn-Leu-Arg-Xaa3-Lys-Phe-Asn-Lys-Gly-#

Name:  Pr14.2

Species: *parius*

Cloned: Yes

DNA Sequence:
GAATTCGCCCTTGGATCCATGCAGACGGCCTACTGGGTGATGGTGATGATGATGGT         (SEQ ID NO: 178)
GATGTGGATTACAGCCCCTCTGTCTGAAGGTGGTAAACCGAAGCTCATAATTCGGG
GTTTGGTGCCAAACGACTTAACCCCACAGCTATCTTGCGAAGTCTGATTTCCGGGC
GTACTTATGGCATCTATGATGCGAAACCCCCCTTTAGTTGTGCAGGCCTCCGAGGGG
GTTGCGTCCTACCTCCCAATCTCAGGCCAAAGTTCAAGGAAGGTCGATAAAAAACC
CAAGCGTTCCTAGTTATACGAATGCCAGCAAATAAAAGCAGTTTGATTGCGAAAAA
AAAAAAAAAAAAAAAAGTACTCTGCGTTGTTACTCGAGCTTAAGGGCGAATTC Translation:
MQTAYWVMVMMMVMWITAPLSEGGKPKLIIRGLVPNDLTPQRILRSLISGRTYGIYDA        (SEQ ID NO: 179)
KPPFSCAGLRGGCVLPPNLRPKFKEGR Toxin Sequence:
Xaa3-Xaa3-Phe-Ser-Cys-Ala-Gly-Leu-Arg-Gly-Gly-Cys-Val-Leu-         (SEQ ID NO: 180)
Xaa3-Xaa3-Asn-Leu-Arg-Xaa3-Lys-Phe-Lys-Xaa1-#

Name:  Pl14.1

Species: *planorbis*

Cloned: Yes

DNA Sequence:
GAATTCGCCCTTATGGATCCATGCAGACGGCCTACTGGGTGATGATGATGATGATG          (SEQ ID NO: 181)
GTGTGGATTACAGGCCATCTGTCTGAAGGTGGCAAATTGAAGGATGCAATTAGGGG
TTTGGTGCCAGACGACTTGACCTCAATGTTTGCGTTGCATCTTCCGGTTTCCCATTCT
CGGTCTAGCAGCAATGGTCTGAAGAGAGCTGACCTATGTATCCACAAGATTTGTCC
ACCACGGTATCACCAAAGCCAACAATAAAAGACGTCAGACAACCACCACAACTTTA
GTATGACATCGTTAATAGGACTTCAGCAAGTATTTTAACATCACTGTGGTTGTGATG
AAATCAGTCGCCTTAAAAGATTGGCTTTTTCCTTGTTTAAGAGTTGTACTTGTATCAG
CTTTGCACTTCGAAATAAAGTTGATGTGATGAACCAAAAAAAAAAAAAAAAAAAAG
TACTCTGCGTTGTTACTCGAGCTTAAGGGCGAATTC Translation:
MQTAYWVMMMMVWITGHLSEGGKLKDAIRGLVPDDLTSMFALHLPVSHSRSSSNGL          (SEQ ID NO: 182)
KRADLCIHKICPPRYHQSQQ Toxin Sequence:
Ser-Ser-Ser-Asn-Gly-Leu-Lys-Arg-Ala-Asp-Leu-Cys-Ile-His-Lys-       (SEQ ID NO: 183)
Ile-Cys-Xaa3-Xaa3-Arg-Xaa5-His-Gln-Ser-Gln-Gln-^

TABLE 1-continued

Sequences of β-Superfamily Conotoxins

Name: Pu14.1

Species: *pulicarius*

Cloned: Yes

DNA Sequence:
ATGCAGACGGCCTACTGGGTGATGGTGATGATGATGATGGTGTGGGTTACAGCGCC (SEQ ID NO: 184)
TGTGTCTGAAGGTGGTAAATTGAGCGACGTAATTCGGGGTTTGGTGCCAGACGACA
TAACCCCACAGATTATTTTGCAAAGTCTGAATGCCAGTCGTCATGCTTACAGACGTG
TTCGTCTGAGAGGACAGATATGTATCTGGAAGGTATGTCCACCACTACTACAATGG
ATACATCCATTAGTAAAAAGATGAATGACATCAGACAACCGCCACAACTGTAGTAC
GACATCGTTAACACGACTTCAGCAAATATTCTAACATCACAGTGGTTGTGAAGAN
ATCGGGTTGGCTTTAAAAAAAANAATGGGGGNTTTTCCCCNTGGGTTTAAAAAAAN
NTNGGNNCCGGGNAANNNCCCNNNNTNNNCCCCCCCCCNNTGGGAGAAAAAAAA
ANNCCNNTNNNGGGGGGNNINNCNAAAAAAAAAAAAAAAAAAAAAAAAAAAAAAN
CCCCNGGGGGGNTGNTTTNNCCCCCNCCCCNGGGGGGGGGGGNGNTTTNNCCCCC
CCCCCGNGGGGGGGGGGGNTTTTNNTTTNNGGGGNGCCCCCCCCCCCCCCNNNCN
NNNNAANAANNNNGGGGGGGGGAANAAAAANANNNNNNNNNNNNNNNNNNTT
TTNTCNNTCNNCCGNGNNGNNAAAAAAAAAAANTTNATTTNTNNANNNCNNCNNNCC
NNCNNCNNACCCNNCCCCNNCCNCNNCANNCNNAGANNANGAGGGGGGGNGNN
NNGGNGNANNNNNANNNNNNGAANNNGAGGNGNGNNNCNCGNCNNCGCNCNNG
NC Translation:
MQTAYWVMVMMMMVWVTAPVSEGGKLSDVIRGLVPDDITPQIILQSLNASRHAYRRV (SEQ ID NO: 185)
RLRGQICIWKVCPPLLQWIHPLVKR Toxin Sequence:
Val-Arg-Leu-Arg-Gly-Gln-Ile-Cys-Ile-Xaa4-Lys-Val-Cys-Xaa3- (SEQ ID NO: 186)
Xaa3-Leu-Leu-Gln-Xaa4-Ile-His-Xaa3-Leu-Val-Lys-Arg- Name: Pu14.2

Species: *pulicarius*

Cloned: Yes

DNA Sequence:
ATGCAGACGGCCTACTGGGTGATGGTGATGATGATGATGGTGTGGGTTACAGCGCC (SEQ ID NO: 187)
TGTGTCTGAAGGTGGTAAATTGAGCGACGTAATTCGGGGTTTGGTGCCAGACGACTT
AACCCCACAGATTATCTTGCAAAGTCTGAATGCCAGTCGTCATGCTTACAGACGTGT
TCGTCCGAGAGGACAGATATGTATCTGGAAGGTATGTCCACCACTACTACAATGGA
TACATCCATTAGTAAAAAGATGAATGACATCAGACAACCGCCACAACTGTAGTACG
GCATCGTTAACACGACTTCAGCAAATATTTTAACATCACAGTGGTTGTGAAGAAATC
GGTTGCTTTAAAAAAAGATTGGGTTTTTCCTTGTTTAAGAGTTGTACTGATATCAGTT
CTGCACTATGAAATAAAGCTGATGTGACGAACAAAAAAAAAAAAAAAAAAAAGTA
CTCTGCGTTGTTACTCGAG Translation:
MQTAYWVMVMMMMVWVTAPVSEGGKLSDVIRGLVPDDLTPQIILQSLNASRHAYRR (SEQ ID NO: 188)
VRPRGQICIWKVCPPLLQWIHPLVKR Toxin Sequence:
Val-Arg-Xaa3-Arg-Gly-Gln-Ile-Cys-Ile-Xaa4-Lys-Val-Cys-Xaa3- (SEQ ID NO: 189)
Xaa3-Leu-Leu-Gln-Xaa4-Ile-His-Xaa3-Leu-Val-Lys-Arg- Name: Pu14.3

Species: *pulicarius*

Cloned: Yes

DNA Sequence:
ATGCAGACGGCCTACTGGGTGATGGTGATGATGATGATGGTGTGGGTTACAGCGCC (SEQ ID NO: 190)
TGTGTCTGAAGGTGGTAAATTGAGCGACGTAATTCGGGGTTTGGTGCCAGACGACA
TAACCCCACAGATTATCTTGCAAAGTCTGAATGCCAGTCGTCATGCTTACAGACCTG
TTCGTCTGAGAGGACAGATATGTATCTGGAAGGTATGTCCACCACTACTACAATGG
ATACATCCATTAGTAAAAAGATGAATGACATCAGACAACCGCCACAACTGTAGTAC
GACATCGTTAACACGACTTCAGCAAATATTTTAACATCACAGTGGTTGTGAAGAAT
CGGTTGCTTTAAAAAAAGATTGGGTTTTTCCTTGTTTAAGAGTTGTACTGATATCAGT
TCTGCACTATGAAATAAAGCTGATGTGACGAACAAAAAAAAAAAAAAAAAAAAGT
ACTCTGCGTTGTTACTCGAG Translation:
MQTAYWVMVMMMMVWVTAPVSEGGKLSDVIRGLVPDDITPQIILQSLNASRHAYRPV (SEQ ID NO: 191)

TABLE 1-continued

Sequences of β-Superfamily Conotoxins

RLRGQICIWKVCPPLLQWIHPLVKR

Toxin Sequence:
Xaa3-Val-Arg-Leu-Arg-Gly-Gln-Ile-Cys-Ile-Xaa4-Lys-Val-Cys-     (SEQ ID NO: 192)
Xaa3-Xaa3-Leu-Leu-Gln-Xaa4-Ile-His-Xaa3-Leu-Val-Lys-Arg-^

Name: Ra14.1

Species: *rattus*

Cloned: Yes

DNA Sequence:
ATGCAGACGGCCTACTGGGTGATGGTGATGATGGTGGTGGTGGGGTTCACCGTCGG        (SEQ ID NO: 193)
GGGTCACGTCCATCAATCTCACAGTCCTACATCGCGCAGCCATGGTGATGACTCCAT
TCATGACAAGACGATTCATCAACATCTGTTTGCCCGTCTTCCTCTGGAGAACAACGA
CGACCATCGTTCTGTGGATCTTCCTGCAGGGACCAGCGCAGGCGACATGAAACCAC
AACGCCAAAGACGTCTCTGCTGCATCTTTGCCATTCTTTGGTTCTGTTGTCTCGGTTA
ACAGTACAAATTGCAATGCACTGGCCGATTGAAAGAACTGCAATAAACGGAAAAA
AAAAAAAAAAAAAAAGTACTCTGCGTTGTTACTCGAG Translation:
MQTAYWVMVMMVVVGFTVGGHVHQSHSPTSRSHGDDSIHDKTIHQHLFARLPLENND      (SEQ ID NO: 194)
DHRSVDLPAGTSAGDMKPQRQRRLCCIFAILWFCCLG Toxin Sequence:
Leu-Cys-Cys-Ile-Phe-Ala-Ile-Leu-Xaa4-Phe-Cys-Cys-Leu-#         (SEQ ID NO: 195)

Name: S14.2

Species: *striatus*

Cloned: Yes

DNA Sequence:
GAATTCGCCCTTATGGATCCATGCAGACGGCCTACTGGGTGATGGTGATGATGATG       (SEQ ID NO: 196)
GTGTGGATTACAGCCCCTCTGTCTGAAGGTGGTAAATTGAACGACGTAATTCGGGGT
TTGGTGCCACACATCTTAACCCCACAGCATATCTTGCAAAGTCTGATTTCCCTCTTC
GTTCTAACAACGGTCGTTCGAGTGGAGCACAAATATGCATCTGGAAGGTATGTCCA
CCATCCCCATGGAGACAACCACAAGAAATGATGAATGACATCAGACAACCGCCACA
ACTGTAGTACGACATCGTTGATACGACTTTAGCAAATATTTTAACATCACTGTGGTT
GTGAAGAAATCAGTTGCTTTAAAAGATTGGATTTTTCCTTGTTTAAGAGTTGTACTG
ATATCAGCTCTGCACTATGAAATAAAGCTGATGTGACAAACAAAAAAAAAAAAAAA
AAAAGTACTCTGCGTTGTTACTCGAGCTTAAGGGCGAATTC Translation:
MQTAYWVMVMMMVWITAPLSEGGKLNDVIRGLVPHILTPQHILQSLISPLRSNNGRSSG    (SEQ ID NO: 197)
AQICIWKVCPPSPWRQPQEMMNDIRQPPQL Toxin Sequence:
Ser-Asn-Asn-Gly-Arg-Ser-Ser-Gly-Ala-Gln-Ile-Cys-Ile-Xaa4-Lys- (SEQ ID NO: 198)
Val-Cys-Xaa3-Xaa3-Ser-Xaa3-Xaa4-Arg-Gln-Xaa3-Gln-Xaa1-Met-Met-
Asn-Asp-Ile-Arg-Gln-Xaa3-Xaa3-Gln-Leu-^

Name: Sx14.1

Species: *striolatus*

Cloned: Yes

DNA Sequence:
ATGCAGACGGCCTACTGGGTGATGGTGATGATGATGGTGTGGATTACAGACCCTCT       (SEQ ID NO: 199)
GTCTGAAGGTGGTAAATTGAACGACGTAATTCGGGGTTTGGTGCCACGCATCTTAAC
CCCACAGCATACCTTGCGAAGTCCGACTTCCCTTCTTCGTTCTAACACCGGTGGTTC
GAGTGGAGCACAAATATGCATCTGGAAGGTATGTCCACCATCCCCATGGAGACGAT
CACAAGGAAAAAGATGAATGACGTCAGACAAGCGCCACAACTGTAGTACGACATC
GTTGATACGACTTCAGCAAGTATTTTAACATCACTGTGGTTGTGAAGAAATCAGTTG
CTTTAAAAGATTGGATTTTTCCTTGTTTAAGAGTTGTACTGATATCAGCTCTGCCCTG
TGAAATAAAGCTGATG Translation:
MQTAYWVMVMMMVWITDPLSEGGKLNDVIRGLVPRILTPQHTLRSPTSLLRSNTGGSS     (SEQ ID NO: 200)
GAQICIWKVCPPSPWRRSQGKR Toxin Sequence:
Ser-Asn-Thr-Gly-Gly-Ser-Ser-Gly-Ala-Gln-Ile-Cys-Ile-Xaa4-Lys- (SEQ ID NO: 201)
Val-Cys-Xaa3-Xaa3-Ser-Xaa3-Xaa4-Arg-Arg-Ser-Gln-#

TABLE 1-continued

Sequences of β-Superfamily Conotoxins

Name: Sx14.2

Species: *striolatus*

Cloned: Yes

DNA Sequence:
ATGCAGACGGCCTACTGGGTGATGGTGATGATGATGGTGTGGATTACAGCCCCTCT (SEQ ID NO: 202)
GTCTGAAGGTGGTAAATTGAACGACGTAATTCGGGGTTTGGTGCCACACATCTTAAC
CCCACAGCATATCTTGCAAAGTCTGATTTCCCCTCTTCGTTCTAACAACGGTCGTTC
GAGTGGAGCACAAATATGCATCTGGAAGGTATGTCCACCATCCCCATGGAGACGAT
CACAAGGAAAAAGATGAATGACGTCAGACAAGCGCCACAACTGTAGTACGACATC
GTTGATACGACTTCAGCAAGTATTTTAACATCACTGTGGTTGTGAAGAAATCAGTTG
CTTTAAAAGATTGGATTTTTCCTTGTTTAAGAGTTGTACTGATATCAGCTCTGCACTG
TGAAATAAAGCTGATG Translation:
MQTAYWVMVMMMVWITAPLSEGGKLNDVIRGLVPHILTPQHILQSLISPLRSNNGRSSG (SEQ ID NO: 203)
AQICIWKVCPPSPWRRSQGKR Toxin Sequence:
Ser-Asn-Asn-Gly-Arg-Ser-Ser-Gly-Ala-Gln-Ile-Cys-Ile-Xaa4-Lys- (SEQ ID NO: 204)
Val-Cys-Xaa3-Xaa3-Ser-Xaa3-Xaa4-Arg-Arg-Ser-Gln-#

Name: Sx14.3

Species: *striolatus*

Cloned: Yes

DNA Sequence:
GAATTCGCCCTTATGGATCCATGCAGACGGCCTACTGGGTGATGGTGATGATGATG (SEQ ID NO: 205)
GTGTGGATTAAAGACCCTCTGTCTGAAGGTGGTAAATTGAACGACGTAATTCGGGG
TTTGGTGCCACACATCTTAACCCCACAGCATATCTTGCAAAGTCTGATTTCCCCTCTT
CGTTCTAACAACGGTCGTTCGAGTGGAGCACAAATATGCAACTGGAAGGTATGTCC
ACCATCCCCATGGAGACGACCACGAGGAAAATGATGAATGACATCAGACAACCGCC
ACAACTGTAGTACGACTTCGTTGATACGACTTTAGCAAATATTTTAACATCACTGTG
GTTGTGAAGAAATCAGTTGCTTTAAAAGATTGGATTTTTCCTTGTTTAAGAGTTGTA
CTGATATCAGCTCTGCACTATGAAATAAAGCTGATGTGACAAACAAAAAAAAAAAA
AAAAAAAGTACTCTGCGTTGTTACTCGAGCTTAAGGGCGAATTC Translation:
MQTAYWVMVMMMVWIKDPLSEGGKLNDVIRGLVPHILTPQHILQSLISPLRSNNGRSSG (SEQ ID NO: 206)
AQICNWKVCPPSPWRRPRGK Toxin Sequence:
Ser-Asn-Asn-Gly-Arg-Ser-Ser-Gly-Ala-Gln-Ile-Cys-Asn-Xaa4-Lys- (SEQ ID NO: 207)
Val-Cys-Xaa3-Xaa3-Ser-Xaa3-Xaa4-Arg-Arg-Xaa3-Arg-#

Name: Sx14.4

Species: *striolatus*

Cloned: Yes

DNA Sequence:
GAATTCGCCCTTATGGATCCATGCAGACGGCCTACTGGGTGATGGTGATGATGATG (SEQ ID NO: 208)
GTGTGGATTACAGCCCCTCTGTCTGAAGGTGGTAAATTGAACGACGTAATTCGGGGT
TTGGTGCCACACATCTTAACCCCACAGCATATCTTGCAAAGTCTGATTTCCCCTCTTC
GTTCTAACAACGGTCGTTCGAGTGGAGCACAAATATGCATCTGGAAGGTATGTCCA
CCATCCCCATGGAGACAACCACAAGAAATGATGAATGACATCAGACAACCGCCACA
ACTGTAGTACGACATCGTTGATACGACTTTAGCAAATATTTTAACATCACTGTGGTT
GTGAAGAAATCAGTTGCTTTAAAAGATTGGATTTTTCCTTGTTTAAGAGTTGTACTG
ATATCAGCTCTGCACTATGAAATAAAGCTGATGTGACAAACGAAAAAAAAAAAAAA
AAAAAGTACTCTGCGTTGTTACTCGAGCTTAAGGGCGAATTC Translation:
MQTAYWVMVMMMVWITAPLSEGGKLNDVIRGLVPHILTPQHILQSLISPLRSNNGRSSG (SEQ ID NO: 209)
AQICIWKVCPPSPWRQPQEMMNDIRQPPQL Toxin Sequence:
Ser-Asn-Asn-Gly-Arg-Ser-Ser-Gly-Ala-Gln-Ile-Cys-Ile-Xaa4-Lys- (SEQ ID NO: 210)
Val-Cys-Xaa3-Xaa3-Ser-Xaa3-Xaa4-Arg-Gln-Xaa3-Gln-Xaa1-Met-Met-
Asn-Asp-Ile-Arg-Gln-Xaa3-Xaa3-Gln-Leu-^

Name: Sl14.1

TABLE 1-continued

Sequences of β-Superfamily Conotoxins

Species: *sulcatus*

Cloned: Yes

DNA Sequence:
ATGCAGACGGCCTACTGGGTGATGGTGATGATGATGGTGTGGATTACAGCCTCTCTG  (SEQ ID NO: 211)
TCTGAAGGTGGTAAACCGAACGACGTCATTCGGGGTTTTGTGCCAGACGACTTAAC
CCCACAGCTTATCTTGCGAAGTCTGATTTCCCGTCGTCGTTCTGACAAGGATGTTGG
GAAGAGAATGGAATGTTACTGGAAGGCATGTAGACCCACGCTATCGAGACGACATG
ATCTTGGGTAAAAGATGAATGACGTCAGACAACAGCCACAACTATAGTATGACATC
GTTAATACGACTTCAGCAAATATTTTAACATCACTGTGGTTGTGAAGAAATCAGTTG
CTTTAAAAGATTGGATTTTTCCGTGTTTAAGAGTTGTACTGATATCAGCTCTGCCCTG
TGAAATAAAGCTGATG Translation:
MQTAYWVMVMMMVWITASLSEGGKPNDVIRGFVPDDLTPQLILRSLISRRRSDKDVGK  (SEQ ID NO: 212)
RMECYWKACRPTLSRRHDLG Toxin Sequence:
Arg-Ser-Asp-Lys-Asp-Val-Gly-Lys-Arg-Met-Xaa1-Cys-Xaa5-Xaa4-  (SEQ ID NO: 213)
Lys-Ala-Cys-Arg-Xaa3-Thr-Leu-Ser-Arg-Arg-His-Asp-Leu-#

Name: Tr14.1

Species: *terebra*

Cloned: Yes

DNA Sequence:
ATGCAGACGGCCTACTGGGTGATGGTGATGATGATGGTGTGGATTACAGCCCCTCT  (SEQ ID NO: 214)
GTCTGAAGGTGATAAATTGAACGACGTAATTCGGGGTTTGGTGCCAGATAACTTAG
CCCCACAGCTTGTTTTGCAAAGTCTGGATTCCCGTCGTCATCCTCACGGCATTCGTC
AGGATGGAGCCCAAATATGTATCTGGAAGATATGTCCACCATCCCCATGAAACGA
CTTGGATCTTAAGAAAAGAAACAATTGACGTCAGACAACCGCCACATCTTGAGTAC
GACATCGTTAATACAACTTCAGCAAATATGAAATTTTCAGCATCACTGTGGTTGTGA
AGAAATCAGTTGCTTTAAAAGATTGGATTTGTCCTTGTTTAAGAGTTGTACTGATGT
CATCTCTGCACTGTGAAATAAAGCTGATGTGACAAACAAAAAAAAAAAAAAAAAA
GTACTCTGCGTTGTTACTCGAG Translation:
MQTAYWVMVMMMVWITAPLSEGDKLNDVIRGLVPDNLAPQLVLQSLDSRRHPHGIRQ  (SEQ ID NO: 215)
DGAQICIWKICPPSPWKRLGS Toxin Sequence:
His-Xaa3-His-Gly-Ile-Arg-Gln-Asp-Gly-Ala-Gln-Ile-Cys-Ile-Xaa4-  (SEQ ID NO: 216)
Lys-Ile-Cys-Xaa3-Xaa3-Ser-Xaa3-Xaa4-Lys-Arg-Leu-Gly-Ser-^

Name: Tr14.2

Species: *terebra*

Cloned: Yes

DNA Sequence:
ATGCAGACGGCCTACTGGGTGATGGTGATGATGATGGTGTGGATTACAGCCCCTCT  (SEQ ID NO: 217)
GTCTGAAGGTGATAAATTGAACGACGTAATTCGGGGTTTGGTGCCAGATAACTTAG
CCCCACAGCTTGTTTTGCATAGTCTGGATTCCCGTCGTCATCCTCACGGCATTCGTCA
GGATGGAGCCCAAATATGTATCTGGAAGATATGTCCACCATCCCCATGGAGACGAC
TTGGATCTTAAGAAAAGAAACAATTGACGTCAGACAACCGCCACATCTTGAGTACG
ACATCGTTAATACGACTTCAGCAAATATGAAATTTTCAGCATCACTGTGGTTGTGAA
GAAATCAGTTGCCTTAAAAGATTGGATTTGTCCTTGTTTAAGAGTTGTACTGATGTC
ATCTCTGCACTATGAAATAAAGCTGATGTGACAAACAAAAAAAAAAAAAAAAAA
AGTACTCTGCGTTGTTACTCGAG Translation:
MQTAYWVMVMMMVWITAPLSEGDKLNDVIRGLVPDNLAPQLVLHSLDSRRHPHGIRQ  (SEQ ID NO: 218)
DGAQICIWKICPPSPWRRLGS Toxin Sequence:
His-Xaa3-His-Gly-Ile-Arg-Gln-Asp-Gly-Ala-Gln-Ile-Cys-Ile-Xaa4-  (SEQ ID NO: 219)
Lys-Ile-Cys-Xaa3-Xaa3-Ser-Xaa3-Xaa4-Arg-Arg-Leu-Gly-Ser-^

Name: Vx14.1

Species: *vexillum*

TABLE 1-continued

Sequences of β-Superfamily Conotoxins

Cloned: Yes

DNA Sequence:
GAATTCGCCCTTATGGATCCATGCAGATGGCCTACTGGGTGATGGTGATGATGATGG (SEQ ID NO: 220)
TGTGGATTAAAGGCCCTGTGTCCGAAGGTGGTAAATTGAACGACGTAATTCGGGGT
TTGGTGCCAGACGACTTGACCCCAGTGTCTGCCTTGCATCATCCGGTTTCCCATCGT
CGGTCTCACAGCAGTAGTTTGTGGTGTGTATGTCCATTCAGGGTGTGTCCACCATGC
CATGGAAGATGACCTGGTCCCAAACCAACAAAATAACGTCAGACAACCGCCACAAC
TTTAGTACGACATCCCTTAATACGACTTCAGCAAGTATTTTAACATCACTATGGTGT
GATGAAATCAGTTGCTTTAAAAGATTGGATTTTTCCTTGTTTAAGAGTTGCACTGAT
AACAGCCCAGCAGTATGAAATAAAGTTGATGTGGCAAAAAAAAAAAAAAAAGTAC
TCTGCGTTGTTACTCGAGCTTAAGGGCGAATTC Translation:
MQMAYWVMVMMMVWIKGPVSEGGKLNDVIRGLVPDDLTPVSALHHPVSHRRSHSSS (SEQ ID NO: 221)
LWCVCPFRVCPPCHGR Toxin Sequence:
Ser-His-Ser-Ser-Ser-Leu-Xaa4-Cys-Val-Cys-Xaa3-Phe-Arg-Val-Cys- (SEQ ID NO: 222)
Xaa3-Xaa3-Cys-His-#

Name: Vx14.2

Species: *vexillum*

Cloned: Yes

DNA Sequence:
GAATTCGCCCTTATGGATCCATGCAGACGGCCTACTGGGTGATGGTGATGATGATG (SEQ ID NO: 223)
GTGTGGATTACAGCCCCTTTGTCTGAAGGTGGTAAACTGAACGATGTAATTCGGGGT
TTCGCGCTAGATGACTTAGCCCAAAGCCGTATTATGCAAAGTCTGGTTTTCAGTCAT
CAGCCTCTTCCAACGGCATCCATATGTATCTGGAAGATATGTCCACCAGACCCATGG
AGACGACATGATCTTCAGAAAAGTAACAAATGACGTCAGACAACCGCCACAACTTG
AATACAACATCATTAATACGACTTCAGCAAATATTTTAGCATCACTGTGATTGTTCG
GAAGTCAGTTGCTTTAAAAGATTGGATTTGTCCCTGTTGTATTGATGTCAACTCTGC
ACTATGAAATAAAGCTGATGTGACAAGCAAAAAAAAAAAAAAAAAAAAGTACTCTG
CGTTGTTACTCGAGCTTAAGGGCGAATTC Translation:
MQTAYWVMVMMMVWITAPLSEGGKLNDVIRGFALDDLAQSRIMQSLVFSHQPLPTASI (SEQ ID NO: 224)
CIWKICPPDPWRRHDLQKSNK Toxin Sequence:
Ile-Met-Gln-Ser-Leu-Val-Phe-Ser-His-Gln-Xaa3-Leu-Xaa3-Thr-Ala- (SEQ ID NO: 225)
Ser-Ile-Cys-Ile-Xaa4-Lys-Ile-Cys-Xaa3-Xaa3-Asp-Xaa3-Xaa4-Arg-
Arg-His-Asp-Leu-Gln-Lys-Ser-Asn-Lys-^

Name: Vx14.3

Species: *vexillum*

Cloned: Yes

DNA Sequence:
ATGCAGACGGCCTACTGGGTGATGGTGATGATGATGGTGGTGGGGTTCACCGTCGA (SEQ ID NO: 226)
GAGTCACGTCCATCAGTCTCACAGTCCTACATCGCGCAGCCATGGTGATGACTCCAT
TCATGACAAGACGATTCATCAACATCTGTTTGCCCGTCTTCCTCTGGAGAACAACGA
CGACCATCGTTCTGTGGATCTTCCTGCAGGGACTAGCGCAGGCGACATGAAACCAC
AACGCCAGAAACGTTTCTGCTGCATCTTTGCCCCGATTCTTTTGTTCTGTTGTTTCGG
TTAACAGCACAAATTACACTGCACTGGCCGATTGAAAGAACTGCAATAAACGGTAA
AGCAAAAAAAAAAAAAAAAAAAGTACTCTGCGTTGTTACTCGAG Translation:
MQTAYWVMVMMMVVGFTVESHVHQSHSPTSRSHGDDSIHDKTIHQHLFARLPLENND (SEQ ID NO: 227)
DHRSVDLPAGTSAGDMKPQRQKRFCCIFAPILLFCCFG Toxin Sequence:
Phe-Cys-Cys-Ile-Phe-Ala-Xaa3-Ile-Leu-Leu-Phe-Cys-Cys-Phe-# (SEQ ID NO: 228)

Xaa1 is Glu or γ-carboxy-Glu
Xaa2 is Gln or pyro-Glu
Xaa3 is Pro or hydroxy-Pro
Xaa4 is Trp, D-Trp or 6-bromo-[D or L] Trp
Xaa5 is Tyr, $^{125}$I-Tyr, mono-iodo-Tyr, di-iodo-Tyr, O-sulpho-Tyr or O-phospho-Tyr
^ is free carboxyl or amidated C-terminus, preferably free carboxyl
# is free carboxyl or amidated C-terminus, preferably amidated
? is free carboxyl or amidated C-terminus

TABLE 2

| Alignment of β-Superfamily Conotoxins (SEQ ID NO:)* |
|---|

```
Type 2:
T14.2    tulipa           ----ZTDVLLEATLLTTPAPEQRLFCFWKSCWPRPYPWRRRDLN#        (229)

M14.1    magus            ----ZTDVLLDATLLTTPAPEQRLFCFWKSCWPRPYPWRRRNLN#        (230)

G14.2    geographus       ----ZTDVLLEATLLTTPAPEQRLFCFWKSCTWRPYPWRRRDLN#        (231)

T14.2    tulipa           ----------------------LFCFWKSCWPRPYPWRRRDLN#        (232)

M14.1    magus            ----------------------LFCFWKSCWPRPYPWRRRNLN#        (233)

G14.2    geographus       ----------------------LFCFWKSCTWRPYPWRRRDLN#        (234)

Type 3:
Ge14.1   generalis        ----------------SHSSSLWCVCPFRVCPPCH#                 (235)

Vx14.1   vexillum         ----------------SHSSSLWCVCPFRVCPPCH#                 (236)

Type 4:
Fd14.1   flavidus         ---HDHGIRPKR----------VDTCNWRICAPNPLRRHDLKKGNN^     (237)

Em14.1   emaciatus        ---HTHGTRPKG----------DGTCIWKVCPPDPWRRHRLKKRNN^     (238)

A14.1    aurisiacus       ---HTHGIRPKG----------DGTCTWKVCPPDPWRRHHLKKRNN^     (239)

Tr14.1   terebra          ---HPHGIRQDG----------AQICIWKTCPPSPWKRLGS^          (240)

Tr14.2   terebra          ---HPHGTRQDG----------AQICIWKTCPPSPWRRLGS^          (241)

Ly14.2   litoglyphus      ---HPHGTRQDG----------AQICIWKICPPSPWKRLGS^          (242)

Ly14.1   litoglyphus      ---HPHGTRQDG----------AQICIWKTCPPSPWRRLGS^          (243)

Type 5:
Cn14.1   consors          ---DRSDNGGSSG---------AQICIWKVCPPSP^                (244)

Cn14.5   consors          ---DRSDNGGSSG---------AQICIWKVCPPSPWK^              (245)

Cn14.2   consors          ---ARSDNGGSSG---------AQICIWKVCPPSPWRRPQ#           (246)

Sx14.1   striolatus       -----SNTGGSSG---------AQTCIWKVCPPSPWRRSQ#           (247)

Sx14.3   striolatus       -----SNNGRSSG---------AQICNWKVCPPSPWRRPR#           (248)

Sx14.2   striolatus       -----SNNGRSSG---------AQICIWKVCPPSPWRRSQ#           (249)

Sx14.4   striolatus       -----SNNGRSSG---------AQICTWKVCPPSPWRQPQEMMNDIRQPPQL^ (250)

S14.2    striatus         -----SNNGRSSG---------AQICIWKVCPPSPWRQPQEMMNDIRQPPQL^ (251)

A14.3    aurisiacus       ---LHSDSSDQKG---------AQICIWKVCPPPPWR^              (252)

A14.2    aurisiacus       ---LHSDSSDQKGGMNAWTGAGAQICIWKVCPPPPWR^              (253)

A14.4    aurisiacus       ---LRSDSSDQKGGMNASTGAGAQICIWKVCPPSPWRRTQ#           (254)

Cr14.1   circumcisus      ---LRSDSSGQKG---------AQICIWKVCPLSPWRRPQ#           (255)

Cr14.2   circumcisus      ---LRSDSSGQKG---------AQTCIWKVCPLSPWRRPQGKDE^       (256)

Ac14.1   achatinus        ---LRSDNGGSSG---------AQTCIWKVCPPSPWRRPQ#           (257)

Sm14.1   stercusmuscarum  ---LGIGSSDQN----------AQTCIWKVCPPSP^                (258)

Cn14.3   consors          ---NGSGSSNQKE---------AQLCIWKVCPPSPWR^              (259)

Cn14.4   consors          ---NGSGSSNQKE---------AQLCIWKVCPPTPWR^              (260)

M14.2    magus            ---NGSGSSNQKE---------AQLCIWKVCPPSPWR^              (261)

Nb14.2   nobilis          ---NGSGSSNQKE---------AQLCIWKVCPPTPWR^              (262)

Type 6:
Sl14.1   sulcatus         -------------RSDKDVGKRME-CYWKACRPTLSRRHDL#          (263)

Bk14.1   bocki            -------------RSDKDDPGGQE-CYWNVCAPNQGDHMILRKKMNDDRQPPQL^ (264)
```

TABLE 2-continued

Alignment of β-Superfamily Conotoxins (SEQ ID NO:)*

| | | |
|---|---|---|
| Bt14.1 | *betulinus* | --------------RSDSDVREV-PVCSWKICPP^ (265) |
| Ls14.1 | *loroisii* | --------------RSDSDVREVYILCIWKICPPLP^ (266) |

Type 7:

| | | |
|---|---|---|
| Gd14.1 | *gladiator* | ---------------HPANVRQQGKICVWKVCPPWPVRSPGPQPKNK^ (267) |
| Gd14.2 | *gladiator* | ---------------HPANVRQQGKICVWKVCPPSPVRSPGPLPKNK^ (268) |

Type 8:

| | | |
|---|---|---|
| Ms14.2 | *musicus* | GMGPGDLSLQKMFPSLALGPGGDVICRWKVCPPTPWKRLIK^ (269) |
| Ms14.3 | *musicus* | GMVPGDLALQYLFPSLAFNP-PD-ICTWKVCPPPPWRRPKKITDVGQPPQL^ (270) |
| Ms14.1 | *musicus* | GMVPGDLVLQYLFPSLAFSP-PD-TCTWKVCPPPPWRRPKKITDVRQPPQL^ (271) |
| Ms14.4 | *musicus* | GMVPGDLVLQYLFPSLAFNP-PD-TCTWKVCPPPPWRRPKKITDVRQPPQL^ (272) |

Type 9:

| | | |
|---|---|---|
| Mi14.1 | *miles* | ZQDQSPHVVCCAIGPVLPFCCVSWLHKLH^ (273) |
| Mi14.2 | *miles* | --------LCCTFAPILWFCCH# (274) |
| Ra14.1 | *rattus* | --------LCCIFA-ILWFCCL# (275) |
| Cp14.1 | *capitaneus* | -------GFCCDFPPIFWFCCI# (276) |
| Mi14.4 | *miles* | ------ZGFCCVVIPILWFCCGGYRTNGTALAD^ (277) |
| Vx14.3 | *vexillum* | --------FCCIFAPILLFCCF# (278) |

Type 10:

| | | |
|---|---|---|
| Sl14.2 | *sulcatus* | --------------ZSGCRVPFELKCIWKFCTIYPSRPFASLEEKDECQTVTTTVTWDF^ (279) |
| Ci14.1 | *cinereus* | --------------SSGCSVSLGFKCFWKSCTVTPVRPFVSLEEENECQKVQTSAVWGP^ (280) |

Type 11:

| | | |
|---|---|---|
| Pr14.1 | *parius* | --------------------PPFSCSGLRGGCVLPPNLRPKFNKG# (281) |
| Pr14.2 | *parius* | --------------------PPFSCAGLRGGCVLPPNLRPKFE# (282) |

Type 12:

| | | |
|---|---|---|
| Wi14.1 | *wittigi* | --------------SSDGSDPKAKKQCMWKRCTPDQSR---L-EEDE^ (283) |
| Ci14.4 | *cinereus* | --------------SSDG---KAKKQCAWKTCVPTQWRRRDLKEKDE^ (284) |
| Ci14.3 | *cinereus* | --------------SSDG---KAKRNCFWKACVPEQWRQRDPKEKDE^ (285) |
| Ci14.2 | *cinereus* | --------------SSDG---KAKRNCFWKACVPEQWRQRDLKEKDE^ (286) |

Type 13:

| | | |
|---|---|---|
| Nb14.1 | *nobilis victor* | -----------FRPAVKSRSRRAPPCVWKVCPAPPWLVTKRKQETSDY^ (287) |
| Nb14.3 | *nobilis skinneri* | -----------FRPAVKSRSRRAPPCVWKVCPAPPWLVTKRKQETSDY^ (288) |
| Mi14.3 | *miles* | -----------FRPAMQSRSGGMSLCLWKVCPAAPWLVAKRKQETSDY^ (289) |

Miscellaneous:

| | | |
|---|---|---|
| T14.1 | *tulipa* | --------------HFNSVVPTVYTCMWKVCPPSP^ (290) |
| P14.2 | *purpurascens* | -----------------ZSEEEKICLWKICPPPPWRRS^ (291) |
| P14.1 | *purpurascens* | -----------------ESNGVEICMWKVCPPSPWRRS^ (292) |
| Vx14.2 | *vexillum* | --------IMQSLVFSHQPLPTASTCIWKICPPDPWRRHDLQKSNK^ (293) |
| Mu14.1 | *muriculatus* | --------IMQSLVFSHQPLPTASICIWKICPPDPWRRHDLQKSNK^ (294) |
| Pu14.1 | *pulicarius* | -----------------VRLRGQICTWKVCPPLLQWTHPLVKR^ (295) |
| Pu14.2 | *pulicarius* | -----------------VRPRGQTCTWKVCPPLLQWIHPLVKR^ (296) |
| Pu14.3 | *pulicarius* | -----------------PVRLRGQICIWKVCPPLLQWIHPLVKR^ (297) |
| Mt14.2 | *mustelinus* | -----------LVSHTSSKYPGVTFCPWKVCPPAPWRILGV^ (298) |

TABLE 2-continued

Alignment of β-Superfamily Conotoxins (SEQ ID NO:)*

| | | |
|---|---|---|
| Ba14.1 | baileyi | ---------------HSDSTILRGLCIWKVCEPPPQR^ (299) |
| Pl14.1 | planorbis | --------------SSSNGLKRADLCIHKICPPRYHQSQQ^ (300) |
| Lt14.2 | litteratus | ----------HRVFHLDNTYLKIPICAWKVCPPTPWRRRDLKKRNK^ (301) |
| Lt14.1 | litteratus | ----SPVSTPYPEFHLDEPYLKIPVCIWKTCPPNLLRRRDLKKRNKVRQTTATT^ (302) |
| Ct14.1 | coronatus | --------------LSDGRDWTGYTCIWKACPRPPWIPPK# (303) |
| Cd14.2 | chaldaeus | --------------LSEGRNSTVHTCMWKVCPPPPWRRPHGQR^ (304) |
| Cd14.1 | chaldaeus | --------------LSEGRNSTVHICTWKVCPPPPWRRPHGQR^ (305) |
| Eb14.1 | ebraeus | --------------LSGGTYSRVDTCTWKVCPQSP^ (340) |

*The W or F in the β-turn motif may be in the D or L configuration. Additionally, the K or F in the backbone may also be in the D or L configuration.

TABLE 3

Analogs and Truncations of β-Superfamily Conotoxins (SEQ ID NO:)

| | |
|---|---|
| Q663 | ZCMWKRCIPDQSR^ (306) |
| F531 | VDICNWRTCAPNPLR^ (307) |
| βG-C1325 | LCFX1KSCRPYPWR^ (308) |
| βM1 | LFCFX1WKSCWPRPYWR^ (309) |
| βM2 | LFCFX1KSCWPRPYWR^ (310) |
| βM3 | LX2CFWKSCWPRPYWR^ (311) |
| βM4 | LX2CFX1KSCWPRPYWR^ (312) |
| βM5 | LX2CFWKSCWPR^ (313) |
| βM6 | LFCFX1KSCWPR^ (314) |
| βM7 | LX2CFX1KSCWPR^ (315) |
| βM8 | LX2CFWKSCW^ (316) |
| βM9 | LFCFX1KSCW^ (317) |
| βM10 | LX2CFX1KSCW< (318) |
| βM11 | FCFX1KSCWPR^ (319) |
| βM12 | FCFWX3SCWPR^ (320) |
| βM13 | FCFX1FSCWPR^ (321) |
| βM14 | FCFWKSCWPR^ (322) |
| βP2 | ESNGVEICMX1KVCPPSPWRRS^ (323) |
| βS1 | MECYX1KACRPTLSR^ (324) |
| βS12 | FELKCIX1KFCTIYPSR^ (325) |
| βS12b | FELKCTX1KFCTIYPSRPF^ (326) |
| βT | TVYICMX1KVCPPSP^ (327) |
| βA-CTL03 | SDSSDQKAQICIX1KVCPPPPWR^ (328) |
| βCn2 | GAQICTX1KVCPPSPWR^ (329) |
| βMs14.5 | MFPSLALGPGGDVICRX1KVCPPTPWKRLIK^ (330) |
| βFd-F531 | VDICNX1RTCAPNPLRRHDLKKGNN^ (331) |
| βF531-dW | VDTCNX1RICAPNPLR^ (332) |
| βG14.1 | RLFCFX1KSCTWRPYPWRRRDLN# (333) |
| βD919 β[1-4] | SLWCVCPFRVCPPCHGR^ (334) |
| βD919 β[2-4] | SLWCVCPFRVCPPCHGR^ (335) |
| βGe [1-4] | SLWCVCPX2RVCPPCH# (336) |
| BGe [2-4] | SLWCVCPX2RVCPPCH# (337) |

X1 is D-Trp or L-Trp
X2 is D-Phe or L-Phe
X2 is D-Lys or L-Lys

Example 2

Activity of Type 2 β-Superfamily Conopeptide on Tumor Cell Lines

Test Substance and Concentration: A β-M14.1 derivative, β-M14.1-D1 (LFCFXKSCWPRPYPWR (SEQ ID NO:309, where X is dW) was used for in vitro anti-tumor studies. The test compound was dissolved and diluted with sterile distilled water to obtain initial working solutions of 10000, 1000, 100, 10, and 1 μM. In testing, 100-fold dilution was made in culture media to get final assay concentrations of 100, 10, 1, 0.1, and 0.01 μM.

Cell Culture Media: The culture medium used for the MCF-7 cell line was Minimum Essential Medium, 90%; Fetal Bovine Serum, 10%. The culture medium used for the MIA PaCa-2 cell line was Dulbecco's Modified Eagle's Medium, 90%; Fetal Bovine Serum, 10%. All media were supplemented with 1% Antibiotic-Antimycotic.

Cell Lines: The cell line MCF-7, which is a breast adenocarcinoma, pleural effusion, human, was obtained from the American Type Culture Collection (ATCC HTB-22). The cell line MIA PaCa-2, which is a pancreatic carcinoma, human, was obtained form the American Type culture Collection (ATCC CRL-1420). The tumor cells were incubated in an air atmosphere of 5% $CO_2$ at 3° C.

Chemicals: The sources of the chemicals were as follows: AlamarBlue (Biosource, USA), Antibiotic-Antimycotic (GIBCO BRL, USA), Dulbecco's Modified Eagle's Medium (GIBCO BRL, USA), Fetal Bovine Serum (HyClone, USA), Minimum Essential medium (GIBCO BRL, USA) and Mitomycin (Kyowa, Japan).

Equipment: Centrifuge 5810R (Eppendorf, Germany), $CO_2$ Incubator (Forma Scientific Inc., USA), Hemacytometer(Hausser Scientific Horsharn, USA), Inverted Microscope CK-40 (Olympus, Japan), Spectrafluor Plus (Tecan, Austria), System Microscope E-400 (Nikon, Japan) and Vertical Laminar Flow (Tsao-Hsin, Taiwan).

Reference Methods: Ahmed et al. (1994), Boyd et al. (1989), Boyd et al. (1992).

Aliquots of 100 µl of cell suspension (about $2.5 \times 10^3$/well) were placed in 96-well microtiter plates in an air atmosphere of 5% $CO_2$ at 37° C. After 24 hours, 100 µl of growth medium and 2 µl of test solution, or mitomycin or vehicle (sterile distilled water), were added respectively per well in duplicate for an additional 72-hour incubation. The test compound, β-M14.1 derivative, was evaluated at concentrations of 100, 10, 1, 0.1 and 0.01 µM. At the end of incubation, the media in microplate were all removed, and then 200 µl of fresh media and 20 µl of 90% alamarBlue reagent were added to each well for another 6-hour incubation before detection of cell viability by fluorescent intensity. Fluorescent intensity was measured using a Spectraflour Plus plate reader with excitation at 530 nm and emission at 590 nm.

The measured results was calculated by the following formula:

$PG(\%) = 100 \times (\text{Mean } F_{test} - \text{Mean } F_{time0})/(\text{Mean } F_{ctrl} - \text{Mean } F_{time0})$ If (Mean $F_{test}$ − Mean $F_{time}0$) < 0, then $PG(\%) = 100 \times (\text{Mean } F_{test} - \text{Mean } F_{time0})/(\text{Mean } F_{time0} - \text{Mean } F_{blank})$ Where:
  PG: percent growth
  Mean $F_{time0}$ = The average of 2 measured fluorescent intensities of reduced alamarBlue at the time just before exposure of cells to the test substance.
  Mean $F_{test}$ = The average of 2 measured fluorescent intensities of alamarBlue after 72-hour exposure of cells to the test substance.
  Mean $F_{ctrl}$ = The average of 2 measured fluorescent intensities of alamarBlue after 72-hour incubation without the test substance.
  Mean $F_{blank}$ = The average of 2 measured fluorescent intensities of alamarBlue in medium without cells after 72-hour incubation.

A decrease of 50% or more (≧50%) in fluorescent intensity relative to vehicle-treated control indicated significant growth inhibition, cytostatic or cytotoxic activity, and a semi-quantitative $IC_{50}$, TGI and $LC_{50}$ were then determined by nonlinear regression using GraphPad Prism (GraphPad Software, USA).

The assays were used to detect changes in cell proliferation based on the ability of viable cells to cause alamarBlue to change from its oxidized (non-fluorescent, blue) to a reduced (fluorescent, red) form. With the results obtained from the alamarBlue reaction, cell proliferation can be quantified and metabolic activity of viable cells can be examined. The β-M14.1-D1 was tested for its effect upon the proliferation of 2 different human tumor cell lines, MCF-7 (breast) and MIA PaCa-2 (pancreas), at five final assay concentrations from 0.01 to 100 µM through serial 10-fold dilutions.

Based on the results obtained, the β-M14.1-D1 exhibited significant growth inhibition (≧50%) relative to the respective vehicle treated control group at concentrations between 10 µM to 100 µM in the 2 human tumor cells lines (Table 4). Significant activity was observed for the concurrently tested standard reference agent Mitomycin at <10 µM (Table 1). Consequently, semi-quantitative determinations of estimated $IC_{50}$ (50% inhibition concentration), TGI (total growth inhibition) and $LC_{50}$ (50% lethal concentration) by nonlinear regression analysis were calculated (Table 5).

TABLE 4

Effect of Test Substance Tumor Cells

Percent Growth (Mean ± SEM, n = 2)

| Treatment | Assay Name | Blank | Time₀ | Vehicle | Concentration (µM) | | | | |
|---|---|---|---|---|---|---|---|---|---|
| | | | | | 100 | 10 | 1 | 0.1 | 0.01 | 0.001 |
| PT# 1018911-ADD β-M14.1-D1 | 370000 Breast, MCF-7 | −100 | 0 | 100 | −43 ± 11 | 102 ± 14 | 87 ± 9 | 88 ± 12 | 100 ± 8 | [a]— |
| Mitomycin | 370000 Breast, MCF-7 | −100 | 0 | 100 | — | −96 ± 0 | −38 ± 16 | 5 ± 12 | 88 ± 8 | 95 ± 7 |
| PT# 1018911-ADD β-M14.1-D1 | 371700 Pancreas, MIA PaCa-2 | −100 | 0 | 100 | −14 ± 9 | 109 ± 2 | 100 ± 4 | 102 ± 6 | 102 ± 3 | — |
| Mitomycin | 371700 Pancreas, MIA PaCa-2 | −100 | 0 | 100 | — | −93 ± 2 | −44 ± 16 | 1 ± 6 | 76 ± 5 | 105 ± 10 |

[a]—: Not tested

TABLE 5

Estimated $IC_{50}$, TGI and $LC_{50}$ Values

| Treatment | Prot. # | Assay Name | $^aIC_{50}$ | $^bTGI$ | $^cLC_{50}$ |
|---|---|---|---|---|---|
| PT# 1018911-ADD β-M14.1-D1 | 370000 | Tumor, Breast, MCF-7 | 62 μM | 81 μM | >100 μM |
| Mitomycin | 370000 | Tumor, Breast, MCF-7 | 0.035 μM | 0.18 μM | 0.93 μM |
| PT# 1018911-ADD β-M14.1-D1 | 371700 | Tumor Pancreas, MIA PaCa-2 | 79 μM | 95 μM | >100 μM |
| Mitomycin | 371700 | Tumor Pancreas, MIA PaCa-2 | 0.028 μM | 0.15 μM | 0.78 μM |

$^a$$IC_{50}$ (50% Inhibition Concentration): Test compound concentration where the increase from time0 in the number or mass of treated cells was only 50% as much as the corresponding increase in the vehicle-control at the end of experiment.
$^b$TGI (Total Growth Inhibition): Test compound concentration where the number or mass of treated cells at the end of experiment was equal to that at time$_0$.
$^c$$LC_{50}$ (50% Lethal Concentration): Test compound concentration where the number or mass of treated cells at the end of experiment was half that at time$_0$.

Example 3

In Vitro Functional Activity of Type 2 β-Superfamily Conopeptide

The in vitro functional activity of β-M14.1-D1 with respect to somatostatin $sst_2$ and $sst_5$ was tested using the following assays.

Somatostatin $sst_2$ (Feniuk et al., 1993)

| | |
|---|---|
| Tissue: | Duncan Hartley Guinea pig 325 ± 25 g |
| Vehicle: | 0.1 mL Distilled Water |
| Incubation Time/Temp: | 5 minutes @ 32° C. |
| Incubation Buffer: | Krebs, pH 7.4 |
| Administration Volume: | 10 μL |
| Bath Volume: | 10 mL |
| Time of Assessment: | 5 minutes |
| Quantitation Method: | Isometric (gram changes) |
| Significance Criteria - Ag: | ≧50% Inhibition of contraction relative to somatostatin$_{28}$-responses |
| Significance Criteria - Ant: | ≧50% Inhibition of somatostatin$_{28}$ relaxant response |

Somatostatin $sst_5$ (Feniuk et al., 1993)

| | |
|---|---|
| Tissue: | Duncan Hartley Guinea pig 325 ± 25 g |
| Vehicle: | 0.1 mL Distilled Water |
| Incubation Time/Temp: | 5 minutes @ 32° C. |
| Incubation Buffer: | Krebs, pH 7.4 |
| Administration Volume: | 10 μL |
| Bath Volume: | 10 mL |
| Time of Assessment: | 5 minutes |
| Quantitation Method: | Isometric (gram changes) |
| Significance Criteria - Ag: | ≧50% Inhibition of contraction relative to somatostatin$_{28}$-responses |
| Significance Criteria - Ant: | ≧50% Inhibition of somatostatin$_{28}$ relaxant response |

Biochemical assay results are presented as the percent inhibition of specific binding or activity. All other results are expressed in terms of that assay's quantitation method. For primary assays, only the lowest concentration with a significant response judged by the assays' criteria, is shown. Primary screening in duplicate with quantitative data are shown where applicable for individual assays. Significant responses were noted in the primary assays shown in Table 6.

TABLE 6

Primary Tests$^a$

| Primary Tissue Assay | Tissue, gp | Conc. | Criteria | AG | ANT | $EC_{50}/IC_{50}$ |
|---|---|---|---|---|---|---|
| Somatostatin $sst_2$ | ileum | 1 μM | ≧50% | 68% | ND | 0.49 μM |
| Somatostatin $sst_5$ | vas deferens | 1 μM | ≧50% | 61% | ND | 0.59 μM |

$^a$A standard error of the mean is presented where results are based on multiple. independent determinations.
Gp = guinea pig;
AG = Agonist;
ANT = Antagonist;
ND = Assay Test Not Done Example 4

Radioligand Binding Assay of Type 2 β-Superfamily Conopeptide

The radioligand binding activity of β-M14.1-D1 with respect to somatostatin $sst_1$, $sst_2$, $sst_3$ and $sst_4$ and $sst_5$ was tested using the following assays.

Somatostatin $sst_1$ (Liapakis et al., 1996; Patel and Srikant, 1994)

| | |
|---|---|
| Source: | Human recombinant CHO-K1 |
| Ligand: | 0.1 nM $^{125}$I Somatostatin-14 |
| Vehicle: | 0.4% DMSO |
| Incubation Time/Temp: | 2 hours @ 25° C. |
| Incubation Buffer: | 25 mM Hepes, pH 7.4, 5 mM MgCl$_2$, 1 mM CaCl$_2$, 0.5% BSA |
| NonSpecific Ligand: | 1 μM Somatostatin-14 |
| $K_d$: | 1.9 nM (historical value) |
| $B_{max}$: | 0.5 pmol/mg Protein (historical value) |
| Specific Binding: | 60% (historical value) |
| Quantitation Method: | Radioligand Binding |
| Significance Criteria: | ≧50% of max stimulation or inhibition |

Somatostatin $sst_2$ (Patel and Srikant, 1994)

| | |
|---|---|
| Source: | Human recombinant CHO-K1 |
| Ligand: | 0.03 nM $^{125}$I Somatostatin-14 |
| Vehicle: | 1% H$_2$O |

-continued

| | |
|---|---|
| Incubation Time/Temp: | 4 hours @ 25° C. |
| Incubation Buffer: | 25 mM Hepes, pH 7.4, 5 mM MgCl$_2$, 1 mM CaCl$_2$, 0.5% BSA |
| NonSpecific Ligand: | 1 µM Somatostatin-14 |
| K$_d$: | 0.034 nM (historical value) |
| B$_{max}$: | 11 pmol/mg Protein (historical value) |
| Specific Binding: | 90% (historical value) |
| Quantitation Method: | Radioligand Binding |
| Significance Criteria: | ≧50% of max stimulation or inhibition |

Somatostatin sst$_3$ (Liapakis et al., 1996; Patel and Srikant, 1994)

| | |
|---|---|
| Source: | Human recombinant CHO-K1 |
| Ligand: | 0.1 nM $^{125}$I Somatostatin-14 |
| Vehicle: | 0.4% DMSO |
| Incubation Time/Temp: | 2 hours @ 25° C. |
| Incubation Buffer: | 25 mM Hepes, pH 7.4, 5 mM MgCl$_2$, 1 mM CaCl$_2$, 0.5% BSA |
| NonSpecific Ligand: | 1 µM Somatostatin-14 |
| K$_d$: | 0.79 nM (historical value) |
| B$_{max}$: | 1.1 pmol/mg Protein (historical value) |
| Specific Binding: | 78% (historical value) |
| Quantitation Method: | Radioligand Binding |
| Significance Criteria: | ≧50% of max stimulation or inhibition |

Somatostatin sst$_4$ (Patel and Srikant, 1994)

| | |
|---|---|
| Source: | Human recombinant CHO-K1 |
| Ligand: | 0.12 nM $^{125}$I Somatostatin-14 |
| Vehicle: | 0.4% DMSO |
| Incubation Time/Temp: | 2 hours @ 25° C. |
| Incubation Buffer: | 25 mM Hepes, pH 7.4, 5 mM MgCl$_2$, 1 mM CaCl$_2$, 0.5% BSA |
| NonSpecific Ligand: | 1 µM Somatostatin-14 |
| K$_d$: | 0.87 nM (historical value) |
| B$_{max}$: | 0.5 pmol/mg Protein (historical value) |
| Specific Binding: | 60% (historical value) |
| Quantitation Method: | Radioligand Binding |
| Significance Criteria: | ≧50% of max stimulation or inhibition |

Somatostatin sst$_5$ (Greenwood et al., 1997; Patel and Srikant, 1994)

| | |
|---|---|
| Source: | Human recombinant HEK-293 EBNA cells |
| Ligand: | 0.1 nM $^{125}$I Somatostatin-14 |
| Vehicle: | 1% H$_2$O |
| Incubation Time/Temp: | 60 minutes @ 37° C. |
| Incubation Buffer: | 50 mM Hepes, pH 7.4, 5 mM MgCl$_2$, 1 mM CaCl$_2$, 0.5% BSA |
| NonSpecific Ligand: | 1 µM Somatostatin-14 |
| K$_d$: | 0.5 nM (historical value) |
| B$_{max}$: | 1.2 pmol/mg Protein (historical value) |
| Specific Binding: | 94% (historical value) |
| Quantitation Method: | Radioligand Binding |
| Significance Criteria: | ≧50% of max stimulation or inhibition |

Biochemical assay results are presented as the percent inhibition of specific binding or activity. All other results are expressed in terms of that assay's quantitation method. For primary assays, only the lowest concentration with a significant response judged by the assays' criteria, is shown. Primary screening in duplicate with quantitative data (e.g., IC$_{50}$±SEM, K$_i$±SEM and nH) are shown where applicable for individual assays. In screening packages, primary screening in duplicate with semi-quantitative data (e.g., estimated IC$_{50}$, K$_i$ and nH) are shown where applicable (concentration range of 4 log units). Significant responses were noted in the primary assays shown in Table 7.

TABLE 7

Primary Test

| Primary Biochemical Assay | Species | Conc. | % Inh. | IC$_{50}$ | K$_i$ | n$_h$ |
|---|---|---|---|---|---|---|
| Somatostatin sst$_1$ | hum | 0.1 µM | 61 | 0.053 µM | 0.05 µM | 0.736 |
| Somatostatin sst$_2$ | hum | 0.1 µM | 90 | 0.018 µM | 9.35 nM | 1.24 |
| Somatostatin sst$_3$ | hum | 10 nM | 61 | 6.14 nM | 5.45 nM | 0.714 |
| Somatostatin sst$_4$ | hum | 10 µM | 67 | 5.63 µM | 4.95 µM | 1.26 |
| Somatostatin sst$_5$ | hum | 0.1 µM | 61 | 0.082 µM | 0.068 µM | 0.961 | hum = human

Example 5

Radioligand Binding Assay of β-Superfamily Conopeptides

The radioligand binding activity of truncations of β-M14.1-D1 and other β-superfamily conopeptides with respect to somatostatin sst$_1$, sst$_2$, sst$_3$ and sst$_4$ and sst$_5$ was tested as described in Example 4. The peptides which were tested are set forth in Table 8. The significant responders (≧50% inhibition or stimulation) are set forth in Table 9.

TABLE 8

| Conopeptide | Type | Sequence (SEQ ID NO:)[a] |
|---|---|---|
| β-M14.1-6 | 2 | LFCFX$_1$KSCWPR^ (314) |
| β-M14.1-9 | 2 | LFCFX$_1$KSCW^ (317) |
| β-M14.1-10 | 2 | LX$_2$CFX$_1$KSCW^ (318) |
| β-T14.1-D1 | Misc | TVYICMX$_1$KVCPPSP^ (327) |
| β-Sl14.1-D1 | 6 | MECYX$_1$KACRPTLSR^ (324) |
| β-Cn14.2-D1 | 5 | GAQICIX$_1$KVCPPSPWR^ (329) |

[a] X$_1$ is dW and X$_2$ is dF

TABLE 9

Primary Test

| Primary Biochemical Assay | Species | Peptide | Conc. | % Inh. |
|---|---|---|---|---|
| Somatostatin sst$_1$ | hum | β-Cn14.2-D1 | 10 µM | 61 |
| Somatostatin sst$_3$ | hum | β-M14.1-6 | 0.1 µM | 63 |
| Somatostatin sst$_3$ | hum | β-M14.1-9 | 0.1 µM | 72 |
| Somatostatin sst$_3$ | hum | β-Sl14.1-D1 | 10 µM | 82 |
| Somatostatin sst$_3$ | hum | β-Cn14.2-D1 | 10 µM | 84 |
| Somatostatin sst$_4$ | hum | β-Cn14.2-D1 | 10 µM | 60 |
| Somatostatin sst$_5$ | hum | β-M14.1-6 | 0.1 µM | 57 |
| Somatostatin sst$_5$ | hum | β-M14.1-9 | 0.1 µM | 55 |
| Somatostatin sst$_5$ | hum | β-M14.1-10 | 0.1 µM | 65 |
| Somatostatin sst$_5$ | hum | β-T14.1-D1 | 10 µM | 65 |
| Somatostatin sst$_5$ | hum | β-Sl14.1-D1 | 10 µM | 86 |
| Somatostatin sst$_5$ | hum | β-Cn14.2-D1 | 10 µM | 56 | hum = human

Example 6

Radioligand Binding Assay of Type 3 β-Superfamily Conopeptide

The radioligand binding activity of β-Ge14.1 D1 (SL-WCVCPFRVCPPCH#; SEQ ID NO:335 with 1–3 fold), D919 (with 1–4 fold, SEQ ID NO:334) and D919 (with 2–4 fold, SEQ ID NO:335) with respect to melanocortin $MC_3$, $MC_4$, $MC_5$ and MCH (h) was tested using the following assays.

Melanocortin $MC_3$ (Schioth et al., 1995)

| | |
|---|---|
| Source: | Human recombinant HEK-293 cells |
| Ligand: | 0.035 nM $^{125}$I NDP-αMSH |
| Vehicle: | 0.4% DMSO |
| Incubation Time/Temp: | 60 min @ 37° C. |
| Incubation Buffer: | 25 mM HEPES-KOH, 0.2% BSA, pH 7.0, 100 mM NaCl, 1 mM 1,10-phenanthroline, 1.5 mM CaCl2, 1 mM MgSO4, and one complete protease inhibitor tablet/100 ml |
| NonSpecific Ligand: | 3 μM NDP-αMSH |
| $K_d$: | 0.53 nM (historical value) |
| $B_{max}$: | 6 pmol/mg Protein (historical value) |
| Specific Binding: | 85% (historical value) |
| Quantitation Method: | Radioligand Binding |
| Significance Criteria: | ≧50% of max stimulation or inhibition |

Melanocortin $MC_4$ (Schioth et al., 1995)

| | |
|---|---|
| Source: | Human recombinant HEK-293 cells |
| Ligand: | 0.02 nM $^{125}$I NDP-αMSH |
| Vehicle: | 01% $H_2O$ |
| Incubation Time/Temp: | 2 hours @ 37° C. |
| Incubation Buffer: | 25 mM HEPES-KOH, 0.2% BSA, pH 7.0, 100 mM NaCl, 1 mM 1,10-phenanthroline, 1.5 mM CaCl2, 1 mM MgSO4, and one complete protease inhibitor tablet/100 ml |
| NonSpecific Ligand: | 3 μM NDP-αMSH |
| $K_d$: | 0.5 nM (historical value) |
| $B_{max}$: | 3.9 pmol/mg Protein (historical value) |
| Specific Binding: | 90% (historical value) |
| Quantitation Method: | Radioligand Binding |
| Significance Criteria: | ≧50% of max stimulation or inhibition |

Melanocortin $MC_5$ (Schioth et al., 1995)

| | |
|---|---|
| Source: | Human recombinant HEK-293 cells |
| Ligand: | 0.035 nM $^{125}$I NDP-αMSH |
| Vehicle: | 1% $H_2O$ |
| Incubation Time/Temp: | 2 hours @ 37° C. |
| Incubation Buffer: | 25 mM HEPES-KOH, 0.2% BSA, pH 7.0, 100 mM NaCl, 1 mM 1,10-phenanthroline, 1.5 mM CaCl2, 1 mM MgSO4, and one complete protease inhibitor tablet/100 ml |
| NonSpecific Ligand: | 3 μM NDP-αMSH |
| $K_d$: | 0.53 nM (historical value) |
| $B_{max}$: | 6 pmol/mg Protein (historical value) |
| Specific Binding: | 85% (historical value) |
| Quantitation Method: | Radioligand Binding |
| Significance Criteria: | ≧50% of max stimulation or inhibition |

MCH (h) (Chambers et al., 1999)

| | |
|---|---|
| Source: | Human recombinant CHO cells |
| Ligand: | 0.1 nM $^{125}$I [Phe$^{13}$, Tyr$^{19}$]-MCH |
| Incubation Time/Temp: | 60 min @ 22° C. |
| NonSpecific Ligand: | 1 μM NDP-αMSH |
| $K_d$: | 0.05 nM (historical value) |
| Quantitation Method: | Radioligand Binding |
| Significance Criteria: | ≧50% of max stimulation or inhibition |

Melanocortin $MC_1$ (Siegrist et al., 1988)

| | |
|---|---|
| Source: | Human recombinant CHO cells |
| Ligand: | 0.05 nM $^{125}$I NDP-αMSH |
| Incubation Time/Temp: | 90 min @ 22° C. |
| NonSpecific Ligand: | 0.1 μM MCH |
| $K_d$: | 0.62 nM (historical value) |
| Quantitation Method: | Radioligand Binding |
| Significance Criteria: | ≧50% of max stimulation or inhibition |

Biochemical assay results are presented as the percent inhibition of specific binding or activity. All other results are expressed in terms of that assay's quantitation method. For primary assays, only the lowest concentration with a significant response judged by the assays' criteria, is shown. Primary screening in duplicate with quantitative data (e.g., $IC_{50}$±SEM, $K_i$±SEM and nH) are shown where applicable for individual assays. In screening packages, primary screening in duplicate with semi-quantitative data (e.g., estimated $IC_{50}$, $K_i$ and nH) are shown where applicable (concentration range of 4 log units). Significant responses were noted in the primary assays shown in Tables 10 and 11.

TABLE 10

Primary Test for β-Ge14.1-D1

| Primary Biochemical Assay | Species | Conc. | % Inh. | $IC_{50}$ | $K_i$ | $n_h$ |
|---|---|---|---|---|---|---|
| Melanocortin $MC_5$ | hum | 1 μM | 71 | 0.294 μM | 0.276 μM | 0.762 | hum = human

TABLE 11

Primary Test

| Primary Biochemical Assay | Species | Peptide | Conc. | % Inh. |
|---|---|---|---|---|
| Melanocortin $MC_3$ | hum | D919 [2,4] | 10 μM | 67 |
| Melanocortin $MC_4$ | hum | D919 [2,4] | 10 μM | 67 |
| Melanocortin $MC_4$ | hum | D919 [1,4] | 10 μM | 58 |
| Melanocortin $MC_5$ | hum | D919 [2,4] | 10 μM | 96 |
| Melanocortin $MC_5$ | hum | D919 [1,4] | 10 μM | 89 |
| Melanocortin $MC_1$ | hum | D919 [2,4] | 10 μM | 60 |
| Melanocortin $MC_1$ | hum | D919 [1,4] | 10 μM | 66 |
| MCH (h) | hum | D919 [2,4] | 10 μM | 83 |
| MCH (h) | hum | D919 [1,4] | 10 μM | 65 | hum = human

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

BIBLIOGRAPHY

Abiko, H. et al. (1986). *Brain Res.* 38:328–335.
Ahmed, S. A. et al. (1994). *J Immunol Methods* 170: 211–224.
Aldrete, J. A. et al. (1979). *Crit. Care Med.* 7:466–470.
Barnay, G. et al. (2000). *J. Med. Chem.*
Beeley, N. R. A. (2000). *Drug Disc Today* 5:454.
Bitan, G. et al. (1997). *J. Peptide Res.* 49:421–426.

Bodansky et al. (1966). *Chem. Ind.* 38:1597–98.
Boyd, M. R. et al. (1989). *Principles and Practices of Oncology Updates* 3:1–12
Boyd, M. R. et al. (1992). Data display and analysis strategies for the NCI disease-oriented in vitro antitumor drug screen. In *Cytotoxic anti-cancer drugs: models and concepts for drug discovery and development*, Kluwer Academic, Boston, pp. 11–34.
Bulbring, W. and Wajda, J. (1945). *J. Pharmacol. Exp. Ther.* 85:78–84.
Cartier, G. E. et al. (1996). *J. Biol. Chem.* 271:7522–7528.
Chambers, J. et al. (1999). *Nature* 400:261–265.
Chandler, P. et al. (1993). *J. Biol. Chem.* 268:17173–17178.
Chaplan S. R. (1994). *J Neuroscience Methods* 53:55–63.
Chaplan S. R. (1997). *J Pharmacol. Exp. Ther.* 280:829–838.
Civelli, O. et. al. (2001). *Trends Neurosci* 24:230–7.
Clark, C. et al. (1981). *Toxicon* 19:691–699.
Codere, T. J. (1993). *Eur. J. Neurosci.* 5:390–393.
Craig, A. G. et al. (1997). *J. Biol. Chem* 272:4689–4698.
Cruz, L. J. at al. (1976). *Verliger* 18:302–308.
Cruz, L. J. et al. (1987). *J. Biol. Chem.* 262:15821–15824.
Dorr et al. (1994). Cancer Chemotherapy Handbook, 2d Ed., pp. 15–34, Appleton & Lange, Connecticut.
Ettinger, L. J. et al. (1978). *Cancer* 41:1270–1273.
Fainzilber, M. et al. (1998). *Biochemistry* 37:1470–1477.
Feniuk, W. et al. (1993). *Br. J. Pharmacol* 110:1156–1164.
Golebiowski, Q. et al. (2001). *Curr Opin Drug Disc Dev* 4:428–434.
Greenwood, M. T. et al. (1997). *Pharmacol Exp Ther* 52:807–814.
*Goodman and Gilman's The Pharmacological Basis of Therapeutics*, Seventh Ed., Gilman, A. G. et al., eds., Macmillan Publishing Co., New York (1985).
Hammerland et al. (1992). *Eur. J. Pharmacol.* 226:239–244.
Heading, C. (1999). *Curr. Opin. CPNS Invest. Drugs* 1:153–166.
Hopkins, C. et al. (1995). *J. Biol. Chem.* 270:22361–22367.
Horiki, K. et al. (1978). *Chemistry Letters* 165–68.
Horwell, D. C. (1996). *Bioorg Med Chem.* 4:1573–1576.
Horwell, D. C. (2000). *Drug Discovery Today,*
Hubry, V. et al. (1994). *Reactive Polymers* 22:231–241.
Hylden, J. L. K. and Wilcox, G. (1980). *Eur. J. Pharmacol.* 67:313–316.
Jacobsen, R. et al. (1997). *J. Biol. Chem.* 272:22531–22537.
Jimenez, E. C. et al. (1996). *J. Biol. Chem.* 271:28002–28005.
Kaiser et al. (1970). *Anal. Biochem.* 34:595.
Kapoor (1970). *J. Pharm. Sci.* 59:1–27.
Kornreich, W. D. et al. (1986). U.S. Pat. No. 4,569,967.
Kruszynski, M. et al. (1990). *Experientia* 46:771–773.
Liapakis, G. et al. (1996). *J Biol Chem* 271:20331–20339.
Luer, M. S. & Hatton, J. (1993). *Annals Pharmcotherapy* 27:912–921.
Liu, H. et al. (1997). *Nature* 386:721–724.
Malmberg, A. B. and Basbaum, A. I. (1998). *Pain* 76:215–222.
Maric, M. et al. (1989). *Physiol. Pharmacol.* 67:1437–1441.
Martinez, J. S. et al. (1995). *Biochem.* 34:14519–14526.
Mayer, E. A. et al. (1994). *Gastroenterology* 107:271–293.
McIntosh, J. M. et al. (1998). *Methods Enzymol.* 294:605–624.
*The Merck Manual of Diagnosis and Therapy*, 16 Ed., Berkow, R. et al., eds., Merck Research Laboratories, Rahway, N.J., pp. 1436–1445 (1992).
*Methoden der Organischen Chemie (Houben-Weyl): Synthese von Peptiden*, E. Wunsch (Ed.), Georg Thieme Verlag, Stuttgart, Ger. (1974).
Murphy, A. J. et al. (1998). *Curr. Opin. Drug Disc. And Devel.* 1:192–199
Nehlig, A. et al. (1990). Effects of phenobarbital in the developing rat brain. In *Neonatal Seizures*, Wasterlain, C. G. and Vertt, P. (eds.), Raven Press, New York, pp. 285–194.
Nishiuchi, Y. et al. (1993). *Int. J. Pept. Protein Res.* 42:533–538.
Okarvi, S. M. (2001). *Eur. J. Nucl. Med* 28:929–938.
Olivera, B. M. et al. (1984). U.S. Pat. No. 4,447,356.
Olivera, B. M. et al. (1985). *Science* 230:1338–1343.
Olivera, B. M. et al. (1990). *Science* 249:257–263.
Olivera, B. M. et al. (1996). U.S. Pat. No. 5,514,774.
Ornstein, et al. (1993). *Biorganic Medicinal Chemistry Letters* 3:43–48.
Patel, Y. C. and Srikant, C. B. (1994). *Endocrinol* 135:2814–1817.
*Remington's Pharmaceutical Sciences*, 18th Ed. (1990, Mack Publishing Co., Easton, Pa.).
Rivier, J. R. et al. (1978). *Biopolymers* 17:1927–38.
Rivier, J. R. et al. (1987). *Biochem.* 26:8508–8512.
Sambrook, J. et al. (1989). *Molecular Cloning: A Laboratory Manual,* 2nd Ed., Cold Spring Harbor Laboratory, Cold Spring Harbor, N.Y.
Schioth, H. B. et al. (1995). *Eur J Pharmacol* 288:311–317.
Shaaban, S. (2001). *Cur. Opin Drug Disc Dev* 4:535–547
Shon, K.-J. et al. (1994). *Biochemistry* 33:11420–11425.
Shon, K.-J. et al. (1997). *Biochemistry* 36:9581–9587.
Siegrist, W. et al. (1988). *J Recep Res* 8:323–343.
Slooter, G. D. et al. (2001). *Br. J. Surg.* 88:31–40.
Stewart and Young, *Solid-Phase Peptide Synthesis*, Freeman & Co., San Francisco, Calif. (1969).
Troupin, A. S. et al. (1986). MK-801. In *New Anticonvulsant Drugs, Current Problems in Epilepsy* 4, Meldrum, B. S. and Porter, R. J. (eds.), John Libbey, London, pp. 191–202.
Vale et al. (1978). U.S. Pat. No. 4,105,603.
Van de Steen, P. et al. (1998). *Critical Rev. in Biochem. and Mol. Biol.* 33:151–208.
Virgolini, I. Q. (2001). *J Nucl Med* 45:153–159.
White, H. S., et al. (1992). *Epilepsy Res.* 12:217–226.
White, H. S., et al. (1995). Experimental Selection, Quantification, and Evaluation of Antiepileptic Drugs. In *Antiepileptic Drugs*, 4th Ed., Levy, R. H., eds., Raven Press, N.Y., pp. 99–110.
Wong, E. H. P. et al. (1986). *Proc. Natl. Acad. Sci. USA* 83:7104–7108.
Zhou L. M., et al. (1996). *J. Neurochem.* 66:620–628.
Zimm, S. et al. (1984). *Cancer Res.* 44:1698–1701.
U.S. Pat. No. 3,842,067.
U.S. Pat. No. 3,862,925.
U.S. Pat. No. 3,972,859.
U.S. Pat. No. 5,514,774.
U.S. Pat. No. 5,550,050.
U.S. Pat. No. 5,670,622.
U.S. Pat. No. 5,719,264.
U.S. Pat. No. 5,844,077.
U.S. Pat. No. 5,889,147.
U.S. Pat. No. 5,969,096.
U.S. Pat. No. 6,077,934.
Published PCT Application WO 92/19195.
Published PCT Application WO 94/25503.
Published PCT Application WO 95/01203.

Published PCT Application WO 95/05452.
Published PCT Application WO 96/02286.
Published PCT Application WO 96/02646.
Published PCT Application WO 96/40871.

Published PCT Application WO 96/40959.
Published PCT Application WO 97/12635.
Published PCT Application WO 98/03189.
Published PCT Application WO 00/23092.

What is claimed is:

1. An isolated peptide comprising the amino acid sequence set forth in SEQ ID NO: 18.

2. The peptide of claim 1, wherein the peptide comprises the amino acid sequence Ser-Ser-Asp-Gly-Ser-Asp-Xaa3-Lys-Ala-Lys-Lys-Gln-Cys-Met-Xaa4-Lys-Arg-Cys-Ile-Xaa3-Asp-Gln-Ser-Arg-Leu-Xaa1-Xaa1-Asp-Xaa1 (SEQ ID NO: 18).

3. The peptide of claim 2, wherein Xaa1 is Glu or .gamma.-carboxy-Glu, Xaa2 is Gln or pyro-Glu, Xaa3 is Pro or trans-4-hydroxy-Pro, Xaa4 is D or L Trp or D or L 6-bromo-Trp, and Xaa5 is Tyr, mono-iodo-Tyr, .sup.125I-Tyr, di-iodo-Tyr, O-sulpho-Tyr or O-phospho-Tyr.

4. The peptide of claim 2, wherein Xaa1 is Glu, Xaa3 is Pro and Xaa4 is D-Trp or L-Trp.

5. The peptide of claim 1 comprising any one or more of the following alterations: Arg residues may be substituted by Lys, ornithine, homoarginine, nor-Lys, N-methyl-Lys, N,N-dimethyl-Lys, N,N,N-trimethyl-Lys or any synthetic basic amino acid; the Lys residues may be substituted by Arg, ornithine, homoarginine, nor-Lys, or any synthetic basic amino acid; the Ser residues may be substituted with Thr or any synthetic hydroxylated amino acid; the Trp residues may be substituted with Trp (D), neo-Trp, 6-halo-Trp (D or L), or any aromatic synthetic amino acid; the Asn or Ser residues may be substituted with a glycan; the halogen may be Iodo, chloro, fluoro or bromo; the acidic amino acid residues may be substituted with any synthetic acidic amino acid; the Leu may be substituted with Leu (D); the Glu residues may be substituted with Gla or Asp; the N-terminal Gln may be substituted with pyro-glutamate (Z); the aliphatic amino acids may be substituted by synthetic derivatives bearing non-natural aliphatic branched or linear side chains $C_nH_{2n+2}$ up to and including n=8; the Met residues may be substituted with nor-leucine (Nle); the Cys residues may be in D or L configuration and may optionally be substituted with homocysteine (D or L); basic residues in the backbone may be D or L configuration; pairs of Cys residues may be replaced pairwise with isoteric lactam or ester-thioether replacements; and individual Cys residues may be replaced with homoCys, seleno-Cys or penicillamine, so that disulfide bridges may be formed between Cys-homoCys or Cys-penicillamine, or homoCys-penicillamine.

6. The peptide of claim 5 wherein, when the Trp residues are substituted, they are substituted with 6-halo.

7. The peptide of claim 5 wherein the acidic amino acid residues are substituted with tetrazolyl derivatives of Gly and Ala.

8. The peptide of claim 5 wherein the central Trp residue within the beta-turn is epimerized to the D-form.

9. The peptide of claim 5 wherein, when pairs of Cys residues are replaced pairwise with isoteric lactam or ester-thioether replacements, they are replaced with Ser/(Glu or Asp), Lys/(Glu or Asp), Cys/(Glu or Asp) or Cys/Ala combinations.

10. The peptide of claim 5, wherein the glycan is any N-, S- or O-linked mono-, di-, tri-, poly- or oligosaccharide that can be attached to any hydroxy, amino or thiol group of natural or modified amino, wherein the monosaccharides making up the glycan can be unmodified or modified D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose, wherein the glycosidic linkage is beta and 1–4 or 1–3, and wherein the linkage between the glycan and the amino acid may be alpha or beta.

11. The peptide of claim 10, wherein the modification may include one or more O-sulfate, O-phosphate, O-acetyl or acidic groups, and combinations thereof.

12. The peptide of claim 10, wherein the glycan may also include similar polyhydroxy groups or polypropylene glycol derivatives.

13. The peptide of claim 1, wherein the peptide is tagged with a radiolabel.

14. The peptide of claim 1 in which a basic or aromatic amino acid in the beta turn is a D-isomer.

15. The peptide of claim 14, wherein the peptide is tagged with a radiolabel.

16. An isolated β-superfamily conopeptide propeptide comprising the amino acid sequence set forth in SEQ ID NO: 17.

17. The propeptide of claim 16, wherein the propeptide comprises the amino acid sequence MMLVWITAPLPEG-GKLKHVIRGLVPDDLTPQLILRSLIS-RRSSDGSDPKAKKQCMWKRCJPDQSRLEEDE (SEQ ID NO:17).

18. The peptide of claim 10 wherein the glycosidic linkage is 1–3.

19. The peptide of claim 10 wherein the linkage between the glycan and the amino acid is alpha and is 1-.

20. The peptide of claim 12 wherein the similar polyhydroxy groups are D-penicillamine 2,5 and halogenated derivatives thereof.

* * * * *